United States Patent
Soloveychik et al.

(10) Patent No.: US 11,840,743 B2
(45) Date of Patent: Dec. 12, 2023

(54) SELECTIVE MODULATION OF PROTEIN-PROTEIN INTERACTIONS

(71) Applicant: SyntheX, Inc., San Francisco, CA (US)

(72) Inventors: Maria Soloveychik, San Francisco, CA (US); Charly Chahwan, San Francisco, CA (US)

(73) Assignee: SYNTHEX, INC., San Francisco, CA (US)

( * ) Notice: Subject to any disclaimer, the term of this patent is extended or adjusted under 35 U.S.C. 154(b) by 494 days.

(21) Appl. No.: 15/931,295

(22) Filed: May 13, 2020

(65) Prior Publication Data

US 2020/0347462 A1 Nov. 5, 2020

Related U.S. Application Data

(63) Continuation of application No. PCT/US2018/061292, filed on Nov. 15, 2018.

(60) Provisional application No. 62/590,147, filed on Nov. 22, 2017, provisional application No. 62/587,269, filed on Nov. 16, 2017.

(51) Int. Cl.
*C07K 14/72* (2006.01)
*C12Q 1/6897* (2018.01)
*C12N 15/10* (2006.01)
*C12N 15/80* (2006.01)
*C12N 15/81* (2006.01)

(52) U.S. Cl.
CPC ....... *C12Q 1/6897* (2013.01); *C12N 15/1055* (2013.01); *C12N 15/1093* (2013.01); *C12N 15/80* (2013.01); *C12N 15/81* (2013.01); *C12N 15/815* (2013.01); *C12Q 2521/50* (2013.01); *C12Q 2600/158* (2013.01)

(58) Field of Classification Search
CPC ............................... C07K 14/72; C07K 14/61
See application file for complete search history.

(56) References Cited

U.S. PATENT DOCUMENTS

| | | | |
|---|---|---|---|
| 6,673,540 B1 * | 1/2004 | Young | C07K 14/72 435/7.1 |
| 2002/0004242 A1 | 1/2002 | McVey et al. | |
| 2004/0265791 A1 | 12/2004 | Tetsu et al. | |
| 2006/0223089 A1 | 10/2006 | Vidal et al. | |
| 2006/0292656 A1 | 12/2006 | Singh et al. | |
| 2008/0261819 A1 | 10/2008 | Lorens et al. | |
| 2009/0130676 A1 | 5/2009 | Brent et al. | |
| 2017/0010277 A1 | 1/2017 | Watanabe et al. | |
| 2017/0240883 A1 | 8/2017 | Christiansen et al. | |
| 2017/0266306 A1 | 9/2017 | Eckert et al. | |

FOREIGN PATENT DOCUMENTS

| | | |
|---|---|---|
| WO | WO-9849338 A1 | 11/1998 |
| WO | WO-2017031399 A1 | 2/2017 |
| WO | WO-2017053706 A1 | 3/2017 |
| WO | WO-2017075335 A1 | 5/2017 |
| WO | WO-2017205852 A2 | 11/2017 |
| WO | WO-2019099678 A1 | 5/2019 |

OTHER PUBLICATIONS

Vidal et al. Prospects for drug screening using the reverse two-hybrid system. TIBTECH, vol. 17, pp. 374-381 (Sep. 1999).
Akada et al. Screening and identification of yeast sequences that cause growth inhibition when overexpressed. Mol Gen Genet. Apr. 16, 1997;254(3):267-74.doi: 10.1007/s004380050415.
GenBank Accession No. ADN19205. Version No. ADN19205.1. prolyl oligopeptidase [Amanita bisporigera]. Record created Sep. 20, 2010. 1 page. Retrieved Jul. 30, 2020 at URL: https://www.ncbi.nlm.nih.gov/protein/ADN19205.1/.
GenBank Accession No. GAW09065. Version No. GAW09065.1. prolyl oligopeptidase [Lentinula edodes]. Record created Feb. 2, 2017. 2 pages. Retrieved Jul. 30, 2020 at URL: https://www.ncbi.nlm.nih.gov/protein/GAW09065.1/.
GenBank Accession No. GAW09067. Version No. GAW09067.1. tetrapyrrole methylase [Lentinula edodes]. Record created Feb. 2, 2017. 2 pages. Retrieved Jul. 30, 2020 at URL: https://www.ncbi.nlm.nih.gov/protein/GAW09067.1/.
GenBank Accession No. HQ225840. Version No. HQ225840.1. Amanita bisporigera prolyl oligopeptidase (POPA) mRNA, complete cds. Record created Sep. 20, 2010. 2 pages. Retrieved Jul. 30, 2020 at URL: https://www.ncbi.nlm.nih.gov/nuccore/HQ225840.1/.
GenBank Accession No. HQ225841. Version No. HQ225841.1. Amanita bisporigera prolyl oligopeptidase (POPB) mRNA, complete cds. Record created Sep. 20, 2010. 2 pages. Retrieved Jul. 30, 2020 at URL: https://www.ncbi.nlm.nih.gov/nuccore/HQ225841.1/.
GenBank Accession No. JN827313. Version No. JN827313.2. Galerina marginata prolyl oligopeptidase (POPA) mRNA, complete cds. Record created Jan. 10, 2012. 2 pages. Retrieved Jul. 30, 2020 at URL: https://www.ncbi.nlm.nih.gov/nuccore/JN827313.2/.
GenBank Accession No. JN827314. Version No. JN827314.2. Galerina marginata prolyl oligopeptidase (POPB) mRNA, complete cds. Record created Jan. 10, 2012. 2 pages. Retrieved Jul. 30, 2020 at URL: https://www.ncbi.nlm.nih.gov/nuccore/JN827314.2/.
GenBank Accession No. KDR68385. Version No. KDR68385.1. hypothetical protein GALMADRAFT_104945 [Galerina marginata CBS 339.88]. Record created Jun. 6, 2014. 2 pages. Retrieved Jul. 30, 2020 at URL: https://www.ncbi.nlm.nih.gov/protein/KDR68385.1.

(Continued)

*Primary Examiner* — Tekchand Saidha
(74) *Attorney, Agent, or Firm* — Wilson Sonsini Goodrich & Rosati

(57) ABSTRACT

The present disclosure provides methods to identify peptides and small molecule moieties that are able to modulate protein-protein interactions (PPIs). Some moieties can disrupt specific PPIs within a complex, or disrupt variant-specific PPIs. Some moieties can alternatively bridge between two proteins in a protein-specific or a variant-specific manner. The methods described enable generation of compounds able to modulate PPI networks within cells with implications for drug development for pathological conditions.

20 Claims, 17 Drawing Sheets

Specification includes a Sequence Listing.

(56) References Cited

OTHER PUBLICATIONS

GenBank Accession No. KDR68475. Version No. KDR68475.1. hypothetical protein GALMADRAFT_78538 [Galerina marginata CBS 339.88]. Record created Jun. 6, 2014. 2 pages. Retrieved Jul. 30, 2020 at URL: https://www.ncbi.nlm.nih.gov/protein/KDR68475.1/.

GenBank Accession No. KDR73903. Version No. KDR73903.1. hypothetical protein GALMADRAFT_141673 [Galerina marginata CBS 339.88]. Record created Jun. 6, 2014. 2 pages. Retrieved Jul. 30, 2020 at URL: https://www.ncbi.nlm.nih.gov/protein/KDR73903.1/.

GenBank Accession No. KDR74877. Version No. KDR74877.1. hypothetical protein GALMADRAFT_99137 [Galerina marginata CBS 339.88]. Record created Jun. 6, 2014. 2 pages. Retrieved Jul. 30, 2020 at URL: https://www.ncbi.nlm.nih.gov/protein/KDR74877.1/.

GenBank Accession No. KDR80488. Version No. KDR80488.1. hypothetical protein GALMADRAFT_136963 [Galerina marginata CBS 339.88]. Record created Jun. 6, 2014. 2 pages. Retrieved Jul. 30, 2020 at URL: https://www.ncbi.nlm.nih.gov/protein/KDR80488.1/.

GenBank Accession No. KDR84981. Version No. KDR84981.1. hypothetical protein GALMADRAFT_260690 [Galerina marginata CBS 339.88]. Record created Jun. 6, 2014. 2 pages. Retrieved Jul. 30, 2020 at URL: https://www.ncbi.nlm.nih.gov/protein/KDR84981.1/.

GenBank Accession No. OAX31299. Version No. OAX31299.1. tetrapyrrole methylase [Rhizopogon vinicolor AM-OR11-026]. Record created Jun. 7, 2016. 1 page. Retrieved Jul. 30, 2020 at URL: https://www.ncbi.nlm.nih.gov/protein/OAX31299.1/.

GenBank Accession No. OAX32862. Version No. OAX32862.1. tetrapyrrole methylase [Rhizopogon vinicolor AM-OR11-026]. Record created Jun. 7, 2016. 1 page. Retrieved Jul. 30, 2020 at URL: https://www.ncbi.nlm.nih.gov/protein/OAX32862.1/.

GenBank Accession No. OAX32863. Version No. OAX32863.1. beta-lactamase/transpeptidase-like protein [Rhizopogon vinicolor AM-OR11-026]. Record created Jun. 7, 2016. 2 pages. Retrieved Jul. 30, 2020 at URL: https://www.ncbi.nlm.nih.gov/protein/OAX32863.1/.

GenBank Accession No. OAX34183. Version No. OAX34183.1. beta-lactamase/transpeptidase-like protein [Rhizopogon vinicolor AM-OR11-026]. Record created Jun. 7, 2016. 2 pages. Retrieved Jul. 30, 2020 at URL: https://www.ncbi.nlm.nih.gov/protein/OAX34183.1/.

GenBank Accession No. OAX34185. Version No. OAX34185.1. FAD/NAD(P)-binding domain-containing protein [Rhizopogon vinicolor AM-OR11-026]. Record created Jun. 7, 2016. 2 pages. Retrieved Jul. 30, 2020 at URL: https://www.ncbi.nlm.nih.gov/protein/OAX34185.1/.

GenBank Accession No. XP_567292. Version No. XP 567292. conserved hypothetical protein [*Cryptococcus neoformans* var. neoformans JEC21]. Record created Jan. 28, 2005. 2 pages. Retrieved Jul. 30, 2020 at URL: https://www.ncbi.nlm.nih.gov/protein/XP_567292.1/.

Kawahata et al., A positive selection for plasmid loss in *Saccharomyces cerevisiae* using galactose-inducible growth inhibitory sequences. Yeast 15(1):1-10 (1999).

Luo et al., Peptide macrocyclization catalyzed by a prolyl oligopeptidase involved in α-amanitin biosynthesis. Chemistry and Biology 21(12):1610-1617 (2014).

PCT/US2018/061292 International Search Report and Written Opinion dated Feb. 5, 2019.

Pooggin et al., Role of a short open reading frame in ribosome shunt on the cauliflower mosaic virus RNA leader. Journal of Biological Chemistry 275(23):17288-17296 (2000).

Pulman et al. Expansion and diversification of the MSDIN family of cyclic peptide genes in the poisonous agarics Amanita phalloides and A. bisporigera. BMC Genomics. 2016; 17: 1038. Published online Dec. 15, 2016. doi: 10.1186/s12864-016-3378-7.14 pages.

Varshavsky, 1996, The N-end rule: Functions, mysteries, uses. Proc. Nat. Acad. Sci. USA, 93:12142-12149.

* cited by examiner

Disruption of specific complex components

Allele specific interaction disruption

Step 1.

Step 2.

Step 3.

Step 4.

SELECTIVE MODULATION OF PROTEIN-PROTEIN INTERACTIONS

CROSS-REFERENCE

This application is a continuation application of International Application No. PCT/US2018/061292, filed Nov. 15, 2018, which claims the benefit of U.S. Provisional Application No. 62/587,269 titled SELECTIVE DISRUPTION OF PROTEIN-PROTEIN INTERACTIONS, filed on Nov. 16, 2017 and U.S. Provisional Application No. 62/590,147 titled CYCLIC AND BICYCLIC PEPTIDES AND METHODS OF MAKING AND USING THEREOF, filed on Nov. 22, 2017, which are incorporated herein by reference.

SEQUENCE LISTING

The instant application contains a Sequence Listing which has been submitted electronically in ASCII format and is hereby incorporated by reference in its entirety. Said ASCII copy created on May 13, 2020, is named 50607703301_SL.txt and is 2,446,912 bytes in size.

BACKGROUND

Disruption of protein-protein interactions in a precise manner can be a key for controlling cellular functions. Many pathological conditions are characterized by aberrant functions of cellular pathways, either because of precocious protein complex formation or the incorporation of malfunctional variants. Thus, compounds that can specifically and precisely prevent the formation of such protein complexes or the malfunction of faulty variants could be beneficial to treating various ailments. The selective disruption of precise protein-protein interactions is difficult to achieve using the traditional enzyme active-site/inhibitor-based drug development scheme. Accordingly, there is a need for development of methods and compositions that target protein-protein interactions in precise and selective ways.

SUMMARY

Disclosed herein, in certain embodiments, is a method for identifying a molecule that selectively disrupts an interaction between a first test protein and a second test protein in a host cell, comprising: expressing in the host cell a first fusion protein comprising the first test protein and a DNA-binding moiety; expressing in the host cell a second fusion protein comprising the second test protein and a gene activating moiety; expressing in the host cell a third fusion protein comprising the third test protein and a different DNA-binding moiety; and delivering a molecule from a library to the host cell, wherein a sequence of gene for expressing a death agent is disposed within the host cell and operably linked a promoter DNA sequence specific for the DNA binding moiety of the first fusion protein, wherein a positive selection reporter is disposed within the host and operably linked to a promoter DNA sequence specific for the DNA binding moiety of the third fusion protein, and wherein, in the absence of the molecule, the interaction between the first test protein and the second test protein causes the gene activating moiety to activate expression of the death agent, while the interaction between the second test protein and the third test protein causes the gene activating moiety to activate the expression of the positive selection reporter. In some embodiments, the molecule from the library is delivered exogenously. In some embodiments, the host cell comprises more than one sequence for expressing a positive control reporter that is activated by a promoter DNA sequence specific for a DNA binding moiety. In some embodiments, the host cell comprises more than one sequence for expressing a death agent that is activated by a promoter DNA sequence specific for a DNA binding moiety. In some embodiments, the host cell comprises an integrated DNA encoding the first fusion protein, an integrated DNA encoding the second fusion protein, an integrated DNA encoding the third fusion protein; a plasmid DNA encoding the death agent; and a plasmid DNA encoding a positive selection reporter. In some embodiments, the first test protein is a variation of KRAS. In some embodiments, the third test protein is KRAS. In some embodiments, the second test protein is c-Raf. In some embodiments, the first test protein is YAP or TAZ. In some embodiments, the third test protein is VGLL4. In some embodiments, the second test protein is TEAD. In some embodiments, the DNA binding moiety is derived from LexA, cI, Gli-1, YY1, Glucocorticoid receptor, TetR, or Ume6. In some embodiments, the gene activating moiety is derived from VP16, GAL4, NF-κB, B42, BP64, VP64, or p65. In some embodiments, the death agent is an overexpressed product of genetic element selected from DNA or RNA. In some embodiments, the genetic element is a Growth Inhibitory (GIN) sequence such as GIN11. In some embodiments, the death agent is a ribosomally encoded xenobiotic agent, a ribosomally encoded poison, a ribosomally encoded endogenous or exogenous gene that results in severe growth defects upon mild overexpression, a ribosomally encoded recombinase that excises an essential gene for viability, a limiting factor involved in the synthesis of a toxic secondary metabolite, or any combination thereof. In some embodiments, the death agent is Cholera toxin, SpvB toxin, CARDS toxin, SpyA Toxin, HopU1, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, or any combination thereof. In some embodiments, the host cell is a fungus or bacteria. In some embodiments, the fungus is *Aspergillus*. In some embodiments, the fungus is *Pichia pastoris*. In some embodiments, the fungus is *S. cerevisiae*. In some embodiments, the molecule is small molecule. In some embodiments, the small molecule is peptidomimetic. In some embodiments, the molecule is peptide or protein. In some embodiments, the peptide or protein is derived from naturally occurring protein product. In certain embodiments, the peptide or protein is synthesized protein product. In some embodiments, the peptide or protein is product of recombinant genes. In some embodiments, the molecule is a peptide or protein expressed from test DNA molecule inserted into the host cell, wherein the test DNA molecule comprises DNA sequences that encodes polypeptides, forming the library. In some embodiments, the library comprises polypeptides 60 or fewer amino acids in length. In some embodiments, the DNA sequence encodes a 3'UTR of mRNA. In some embodiments, the 3'UTR is the 3'UTR of sORF1. In some embodiments, the polypeptides comprise a common N-terminal sequence of Methionine-Valine-Asparagine. In some embodiments, the polypeptides in the library are processed into cyclic or bicyclic peptides in the host cell.

Disclosed herein, in certain embodiments, is a plasmid vector, comprising the components of PLASMID 1, or any combination of the components of PLASMID 1. In some embodiments, the plasmid vector comprises a DNA sequence encoding a first polypeptide inserted in frame with Gal4-DNA binding domain ("DBD"), a DNA sequence encoding a second polypeptide inserted in frame with LexA-DBD, and a DNA sequence encoding a third polypeptide inserted in frame with Dofl-AD. In certain embodiments, a host cell comprises the plasmid vectors.

Disclosed herein, in certain embodiments, is a library of plasmid vectors, each plasmid vector comprising: a DNA sequence encoding a different peptide sequence operably linked to a first switchable promoter; a DNA sequence encoding a death agent under control of a second switchable promoter; and a DNA sequence encoding a positive selection reporter under control of a third switchable promoter. In some embodiments, the different peptide sequence encodes a common N-terminal stabilization sequence. In some embodiments, the DNA sequence encodes a mRNA sequence comprising a 3'UTR. In some embodiments, the different peptide sequence is 60 amino acids or fewer in length. In some embodiments, the different peptide sequences are random. In some embodiments, the different peptide sequences are pre-enriched for binding to a target. In some embodiments is a library of host cells, each comprises a library of the plasmid vectors.

Disclosed herein, in certain embodiments, is a host cell configured to express: a first fusion protein comprising a DNA-binding moiety; a second fusion protein comprising a gene activating moiety; a third fusion protein comprising a different DNA-binding moiety; a death agent, wherein the expression of the death agent is under control of a promoter DNA sequence specific for one of the DNA-binding moiety; a positive selection reporter, wherein the expression of the positive reporter is under control of a promoter DNA sequence specific for the other DNA-binding moiety; and a polypeptide of 60 or fewer amino acids, wherein the polypeptide modulates an interaction between the first test protein and the second test protein; wherein the host cell optionally has a mutant background enabling uptake of small molecules; and wherein the host cell optionally has a mutant background enabling increased transformation efficiency. In some embodiments, the polypeptide encodes an N-terminal sequence for peptide stabilization. In some embodiments, the polypeptide is an encoded product of an mRNA, wherein the mRNA comprises a 3'UTR. In some embodiments, the mRNA is an encoded product of a DNA molecule, wherein the DNA molecule is delivered into the host cell exogenously. In some embodiments, synthetic compound libraries can be tested. In some embodiments, the host cell is a eukaryote or a prokaryote. In some embodiments, the host cell is animal, plant, a fungus, or bacteria. In some embodiments, the host cell is a haploid yeast cell. In some embodiments, the host cell is a diploid yeast cell. In some embodiments, the diploid yeast cell is produced by mating a first host cell comprising DNA sequences encoding the first chimeric gene, the second chimeric gene, and the third chimeric gene, to a second host cell comprising DNA sequences encoding the death agent, positive selection reporter, and the mRNA comprising a nucleotide sequence encoding a polypeptide. In some embodiments, the fungus is *Aspergillus*. In some embodiments, the fungus is *Pichia pastoris*. In some embodiments, the fungus is *S. cerevisiae*. In some embodiments is a kit, comprising: the plasmid vector and the library of plasmid vectors.

Disclosed herein, in certain embodiments, is a method for identifying a molecule that selectively facilitates an interaction between a first test protein and a second test protein, comprising: expressing in the host cell a first fusion protein comprising the first test protein and a DNA-binding moiety; expressing in the host cell a second fusion protein comprising the second test protein and a gene activating moiety; expressing in the host cell a third fusion protein comprising the third test protein and a different DNA-binding moiety; and delivering a molecule from a library to the host cell such that the molecule forms a bridging interaction between the first test protein and the second test protein; wherein a sequence of a gene for expressing a death agent is disposed within the host cell and operably linked a promoter DNA sequence specific for the DNA binding moiety of the third fusion protein; wherein a positive selection reporter is disposed within the host cell and operably linked to a promoter DNA sequence specific for the DNA binding moiety of the first fusion protein; and wherein the first test protein and second test protein to form a functional transcription factor that activates expression of the death agent when the molecule from the library forms the bridging interaction. In some embodiments, the molecule from the library is delivered exogenously. In some embodiments, the host cell comprises more than one sequence for expressing a death agent that is activated by the promoter DNA sequence specific for a DNA binding moiety. In some embodiments, the host cell comprises more than one sequence for expressing a positive control reporter that is activated by a promoter DNA sequence specific for a DNA binding moiety. In some embodiments, the host cell comprises an integrated DNA encoding the first fusion protein, an integrated DNA encoding the second fusion protein, an integrated DNA encoding the third fusion protein; a plasmid DNA encoding the death agent; and a plasmid DNA encoding a positive selection reporter. In some embodiments, the DNA binding moiety is derived from LexA, cI, Gli-1, YY1, Glucocorticoid receptor, TetR, or Ume6. In some embodiments, the gene activating moiety is derived from VP16, Gal4, NF-κB, B42, BP64, VP64, or p65. In some embodiments, the death agent is a genetic element wherein overexpression of genetic material results in growth inhibition of the host cell. In some embodiments, the death agent is an overexpressed product of DNA. In some embodiments, the death agent is an overexpressed product of RNA. In some embodiments, the sequence of the gene for expressing the death agent is a Growth Inhibitory (GIN) sequence such as GIN11. In some embodiments, the death agent is a ribosomally encoded xenobiotic agent, a ribosomally-encoded poison, a ribosomally-encoded endogenous or exogenous gene that results in severe growth defects upon mild overexpression, a ribosomally-encoded recombinase that excises an essential gene for viability, a limiting factor involved in the synthesis of a toxic secondary metabolite, or any combination thereof. In some embodiments, the death agent is Cholera toxin, SpvB toxin, CARDS toxin, SpyA Toxin, HopU1, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, or any combination thereof. In some embodiments, the first test protein is a variation of KRAS. In some embodiments, the third test protein is KRAS. In some embodiments, the second test protein is c-Raf. In some embodiments, the first test protein is YAP or TAZ. In some embodiments, the third test protein is VGLL4. In some embodiments, the second test protein is TEAD. In some embodiments, the molecule is small molecule. In some embodiments, the small molecule is peptidomimetic. In some embodiments, the molecule is peptide or protein. In some embodiments, the peptide or protein is derived from naturally occurring protein product. In some embodiments, the peptide or protein is synthesized protein product. In some embodiments, the peptide or protein is product of recombinant genes. In some embodiments, the peptide or protein is expressed product of test DNA molecule inserted into the host cell, wherein the test DNA molecule comprises of DNA sequences that encodes polypeptides, forming the library. In some embodiments, the library comprises of sixty or fewer amino acids. In some embodiments, the peptide or protein is a product of post-translational modification. In some embodiments, the post-translational modification includes cleavage. In some embodiments, the post-translational modification includes cyclization. In some embodiments, the post-translational modification includes bi-cyclization. In some embodiments, the cyclization comprises reacting with prolyl endopeptidase. In some embodiments, the cyclization comprises reacting with beta-lactamase. In some embodiments, the bicyclization comprises reacting with hydroxylase and dehydratase. In some embodiments, the bicyclization is formed by a tryptathionine bridge. In some embodiments, the post-translational modification includes methylation. In some embodiments, the methylation comprises reacting with N-methyltransferase. In some embodiments, the post-translational modification includes halogenation. In some embodiments, the post-translational modification includes glycosylation. In some embodiments, the post-translational modification includes acylation. In some embodiments, the post-translational modification includes phosphorylation. In some embodiments, the post-translational modification includes acetylation. In some embodiments, the test DNA molecule comprises of gene sequence expressing modifying enzyme. In some embodiments, the test DNA molecule comprises of a gene sequence expressing N-terminal sequence of methionine-valine-asparagine. In some embodiments, the test DNA molecule comprises of a gene sequence encoding a 3'UTR. In some embodiments, the 3'UTR is 3'UTR of sORF1. In some embodiments, the host cell is a eukaryote or a prokaryote. In some embodiments, the host cell is animal, plant, a fungus, or bacteria. In some embodiments, the fungus is *Aspergillus*. In some embodiments, the fungus is *Pichia pastoris*. In some embodiments, the fungus is *S. cerevisiae*.

Disclosed herein, in certain embodiments, is a method of identifying a molecule that selectively modulates a first test protein and a second test protein in a host cell, comprising: expressing in the host cell a first fusion protein comprising the first test protein and a second fusion protein comprising the second test protein; delivering a first molecule to the host cell; modifying the first molecule while in the host cell via a modifying enzyme; and allowing the first molecule to modulate the interaction between the first test protein and the second test protein, wherein the first molecule is a product of an encoded DNA sequence, wherein the first molecule comprises a library and one or more modifying enzymes, and wherein the one or more modifying enzymes modify the library. In some embodiments, the first molecule is a small molecule. In some embodiments, the small molecule is peptidomimetic. In some embodiments, the first molecule is peptide or protein. In certain embodiments, the peptide or protein is derived from naturally occurring protein product. In some embodiments, the peptide or protein is synthesized protein product. In some embodiments, the first molecule is encoded in the host cell. In some embodiments, the first molecule is delivered exogenously. In some embodiments, the one or more modifying enzymes cause cleavage of the library. In some embodiments, the one or more modifying enzymes cause cyclization of the library. In some embodiments, the one or more modifying enzymes cause bicyclization of the library. In some embodiments, the cyclization comprises reacting with prolyl endopeptidase. In some embodiments, the cyclization comprises reacting with beta-lactamase. In some embodiments, the bicyclization comprises reacting with hydroxylase and dehydratase. In some embodiments, the bicyclization comprises formation of a tryptathionine bridge. In some embodiments, the one or more modifying enzymes cause methylation. In some embodiments, the one or more modifying enzymes is a methyltransferase. In some embodiments, the one or more modifying enzyme is a halogenase. In some embodiments, the one or more modifying enzymes cause glycosylation. In some embodiments, the one or more modifying enzymes cause acylation. In some embodiments, the one or more modifying enzymes cause phosphorylation. In some embodiments, the one or more modifying enzymes cause acetylation. In some embodiments, the library comprises of sixty or fewer amino acids. In some embodiments, the first test protein is KRAS or a variation of KRAS. In some embodiments, the second test protein is c-Raf. In some embodiments, the first test protein is YAP, TAZ, or VGLL4. In some embodiments, the second test protein is TEAD. In some embodiments, the host cell is a eukaryote or a prokaryote. In some embodiments, the host cell is animal, plant, a fungus, or bacteria. In some embodiments, the fungus is *Aspergillus*. In some embodiments, the fungus is *Pichia pastoris*. In some embodiments, the fungus is *S. cerevisiae*.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A illustrates a case where a peptide is unable to disrupt the pairwise interaction of interest (A-C). FIG. 1B illustrates a case where a peptide is able to disrupt the pairwise interaction of interest (A-C) without disrupting another interaction (A-B).

FIG. 2A illustrates a case where a peptide is unable to disrupt the pairwise interaction of interest (A-B'). FIG. 2B illustrates a case where a peptide is able to disrupt the pairwise interaction of interest between one variant (B') and a protein (A) without disrupting the interaction between another variant (B) and the protein (A).

FIG. 3A shows a case where a peptide is able to bridge one variant (B) and a protein (A). FIG. 3B illustrates a case where a peptide is able to bridge the secondary variant (B') and a protein (A).

FIG. 4A illustrates a case where a peptide is unable to disrupt the pairwise interaction of interest. FIG. 4B illustrates a case where a peptide is able to disrupt the Prey and BaitMut interaction by acting on the Prey without disrupting the interaction between BaitWT and Prey.

FIG. 5A illustrates a case where a peptide is unable to disrupt the pairwise interaction of interest. FIG. 5B illustrates a case where a peptide disrupts the Prey-BaitMut interaction by acting on the BaitMut without disrupting the interaction between BaitWT and Prey.

DETAILED DESCRIPTION

Figure 1A:
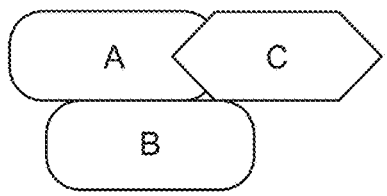
FIGS. 1A and 1B illustrate a platform to identify a compound that specifically disrupts a protein-protein interaction.
Figure 1A:
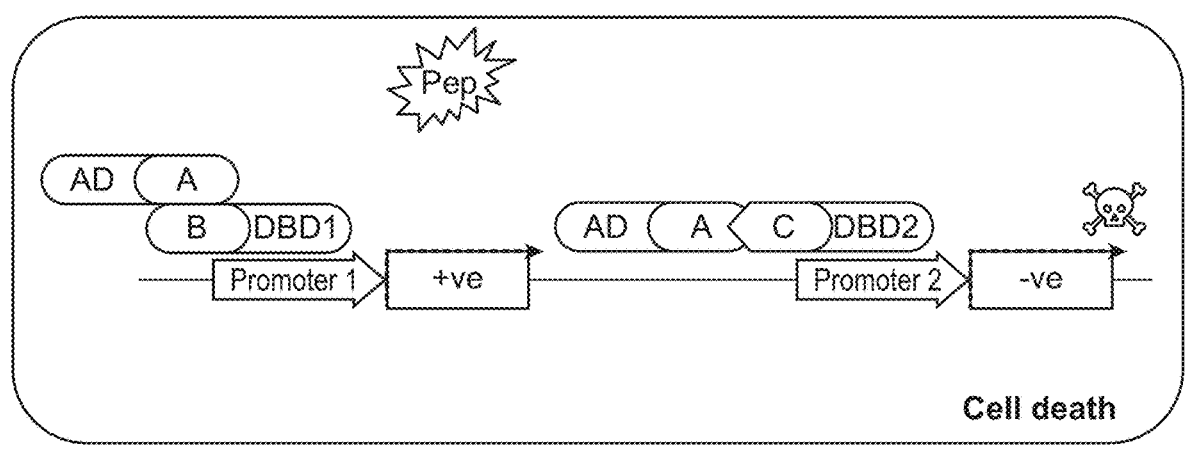

Two-hybrid screening can be used to identify and characterize protein-protein interactions. The two-hybrid system was initially developed using yeast as a host organism. However, bacterial or animal cell two-hybrid systems can also be used to characterize protein-protein interactions. The present disclosure provides a system that can use a unified eukaryotic or prokaryotic two-hybrid system in which bait and prey expression plasmid is used in both organismal contexts. Additionally, an extensive series of leucine zipper fusion proteins of known affinities can be generated to compare the efficiency of interaction detection using both systems. The yeast system can produce a quantitative readout over a dynamic range. "Auto-activation" by baits can be less prevalent in the bacterial system. In addition, modified expression vectors disclosed herein can be used for expression of a protein of interest in both eukaryotes and prokaryotes.

Three-hybrid systems rely on similar principles as two-hybrid systems, but involve an additional factor to bridge a protein-protein interaction to result in a gene expression readout.

The present disclosure also provides a system for delivering molecules across the cell membrane. The cell membrane presents a major challenge in drug discovery, especially for biologics such as peptides, proteins, and nucleic acids. One potential strategy to subvert the membrane barrier and deliver biologics into cells is to attach them to "cell penetrating peptides" (CPPs). Despite three decades of investigation, the fundamental basis for CPP activity remains elusive. CPPs that enter cells via endocytosis generally exit from endocytic vesicles in order to reach the cytosol. Unfortunately, the endosomal membrane has proven to be a significant barrier towards cytoplasmic delivery of these CPPs such that often a negligible fraction of the peptides escapes into the cell interior. What are thus needed are new scaffolds and structures that impart peptides with highly proficient intrinsic cell penetrating ability to various cell types. Several naturally occurring polyketides and peptides exhibit remarkable cell permeability (e.g. cyclosporine and amanitins). These peptides are characterized by specific modifications (e.g., N-methylation of the backbone and cyclization) that can play a crucial role in their cell membrane permeability. The compositions and methods disclosed herein describe methods and approaches that enable the general utilization of similar modifications to generate compositions that may be of high therapeutic value and that may be capable of disrupting select protein-protein interactions with high selectivity.

Definitions

As used herein, "reporter gene" refers to a gene whose expression can be assayed. Such genes include, for example, LacZ, β-glucuronidase (GUS), amino acid biosynthetic genes, the yeast LEU2, HIS3, LYS2, or URA3 genes, nucleic acid biosynthetic genes, the mammalian chloramphenicol transacetylase (CAT) gene, the green fluorescent protein (GFP) or any surface antigen gene for which specific antibodies are available. Reporter genes can result in both positive and negative selection.

An "allele" refers to a DNA sequence of a gene which includes a naturally occurring, or pathogenic variant of a gene. Expression of differing alleles may lead to different protein variants.

A "promoter" is a DNA sequence located proximal to the start of transcription at the 5' end of an operably linked transcribed sequence. The promoter can contain one or more regulatory elements or modules, which interact in modulating transcription of the operably linked gene. Promoters can be switchable or constitutive. Switchable promoters allow for reversible induction or repression of operably linked target genes upon administration of an agent. Examples of switchable promoters include but are not limited to the LexA operator and the alcohol dehydrogenase I (alcA) gene promoter. Examples of constitutive promoters include the human beta-actin gene promoter.

"Operably linked" describes two macromolecular elements arranged such that modulating the activity of the first element induces an effect on the second element. In this manner, modulation of the activity of a promoter element can be used to alter or regulate the expression of an operably-linked coding sequence. For example, the transcription of a coding sequence that is operably-linked to a promoter element can be induced by factors that activate the promoter's activity; transcription of a coding sequence that is operably-linked to a promoter element can be inhibited by factors that repress the promoter's activity. Thus, a promoter region is operably-linked to the coding sequence of a protein if transcription of such coding sequence activity is influenced by the activity of the promoter.

"In frame" as used herein throughout, refers to the proper positioning of a desired sequence of nucleotides within a DNA fragment or coding sequence operably linked to a promoter sequence, thereby permitting transcription and/or translation.

"Fusion construct" refers to recombinant genes that encode fusion proteins.

A "fusion protein" is a hybrid protein, i.e., a protein that has been constructed to contain domains from at least two different proteins. Fusion proteins described herein can be a hybrid proteins that possess both (1) a transcriptional regulatory domain from a transcriptional regulatory protein or a DNA binding domain from a DNA binding protein and (2) a heterologous protein to be assayed for interaction status. The protein that is the source of the transcriptional regulatory domain may different from the protein that is the source of the DNA binding domain. In other words, the two domains may be heterologous to each other.

A transcriptional regulatory domain of a prey fusion protein can either activate or repress transcription of target genes, depending on the biological activity of the domain. Bait proteins of the disclosure may also be fusion proteins, where the fusion protein is encoded by a fusion gene that can encodes for a protein of interest that is operably linked to a DNA binding moiety.

"Bridging interaction" refers to an interaction between a first protein and a second that occurs only when one or both of the first protein and the second protein interact with a molecule, such as a peptide or small molecule from a library. In some cases, the bridging interaction between the first protein and the second protein is direct, while in other cases the bridging interaction between the first protein and the second protein is indirect.

"Expression" is the process by which the information encoded within a gene is revealed. If the gene encodes a protein, then expression involves both transcription of the DNA into mRNA, the processing of mRNA (if necessary) into a mature mRNA product, and translation of the mature mRNA into protein.

As used herein, a "cloning vehicle" is any entity that is capable of delivering a nucleic acid sequence into a host cell for cloning purposes. Examples of cloning vehicles include plasmids or phage genomes. A plasmid that can replicate autonomously in the host cell is especially desired. Alternatively, a nucleic acid molecule that can insert (integrate) into the host cell's chromosomal DNA is useful, especially a molecule that inserts into the host cell's chromosomal DNA in a stable manner, that is, a manner that allows such molecule to be inherited by daughter cells.

Cloning vehicles are often characterized by one or a small number of endonuclease recognition sites at which such DNA sequences may be cut in a determinable fashion without loss of an essential biological function of the vehicle, and into which DNA may be spliced in order to bring about its replication and cloning.

The cloning vehicle can further contain a marker suitable for use in the identification of cells transformed with the cloning vehicle. For example, a marker gene can be a gene that confers resistance to a specific antibiotic on a host cell.

The word "vector" can be used interchangeably with "cloning vehicle."

As used herein, an "expression vehicle" is a vehicle or vector similar to the cloning vehicle that is especially designed to provide an environment that allows the expression of the cloned gene after transformation into the host. One manner of providing such an environment is to include transcriptional and translational regulatory sequences on such expression vehicles, such transcriptional and translational regulatory sequences being capable of being operably linked to the cloned gene. Another manner of providing such an environment is to provide a cloning site or sites on such vehicle, wherein a desired cloned gene and a desired expression regulatory element can be cloned.

In an expression vehicle, the gene to be cloned is usually operably-linked to certain control sequences such as promoter sequences. Expression control sequences will vary depending on whether the vector is designed to express the operably-linked gene in a prokaryotic or eukaryotic host and can additionally contain transcriptional elements such as enhancer elements, termination sequences, tissue-specificity elements, or translational initiation and termination sites.

A "host" refers to any organism that is the recipient of a cloning or expression vehicle. The host may be a yeast cell or a cultured animal cell such as a mammalian or insect cell. The yeast host may be *Saccharomyces cerevisiae*.

A "host cell" as described herein can be a bacterial, fungal, or mammalian cell or from an insect or plant. Examples of bacterial host cells are *E. coli* and *B. subtilis*.

Examples of fungal cells are *S. cerevisiae* and *S. pombe*. Non-limiting examples of mammalian cells are immortalized mammalian cell lines, such as HEK293, A549, HeLa, or CHO cells, or isolated patient primary tissue cells that have been genetically immortalized (such as by transfection with hTERT). Non-limiting example of the plant is *Nicotiana tabacum* or *Physcomitrella patens*. A non-limiting example of insect cell is a sf9 (*Spodoptera frugiperda*) cell.

A "DNA-binding domain (DBD)," or a "DNA-binding moiety" is a moiety that is capable of directing specific polypeptide binding to a particular DNA sequence (i.e., a "protein binding site"). These proteins can be homodimers or monomers that bind DNA in a sequence specific manner. Exemplary DNA-binding domains of the disclosure include LexA, cI, glucocorticoid receptor binding domains, and the Ume6 domain.

A "gene activating moiety" or "activation domain" ("AD") is a moiety that is capable of inducing (albeit in many instances weakly inducing) the expression of a gene to whose control region it is bound (one example is an activation domain from a transcription factor). As used herein, "weakly" is meant below the level of activation effected by GAL4 activation region II and is preferably at or below the level of activation effected by the B42 activation domain. Levels of activation can be measured using any downstream reporter gene system and comparing, in parallel assays, the level of expression stimulated by the GAL4 region II-polypeptide with the level of expression stimulated by the polypeptide to be tested.

Screening for Disruptors to a Protein-Protein Interaction (PPI)

The often large and broad surfaces that can form the contact interface between two proteins can be potential targets of canonical small molecule inhibitors. However, the large and broad surfaces can have size limitations, and evolved resistance can occur readily. The specificity of antibodies can be combined with cell permeability in the form of short peptides, for example, peptides of less than 25 residues. Screening for short peptide disruptors of protein-protein interactions (PPIs) can be performed using technologies such as phage display or mRNA display. However, these screens are performed in vitro and require the purification of one of the interacting proteins of interest. Upon selection of a peptide sequence with affinity toward one of the proteins, secondary screens can be performed to validate that the peptide interferes with the binding interface of the second protein. This secondary screening can further rely upon the proper folding of the proteins and the replication of intracellular biophysical conditions in the assays.

Methods and systems of the disclosure can involve the intracellular selection of peptide disruptors of PPIs. Stated differently, various systems described herein can be used to screen for molecules that selectively disrupt an interaction between two proteins. A model organism, for example *Saccharomyces cerevisiae*, can be employed, and the coexpression of a PPI of interest with a test DNA molecule comprising a DNA sequence that encodes a randomized peptide library can allow for the selection of unbiased peptides that interfere with a specific PPI using selection mechanisms (e.g., a stringent viability readout selection mechanisms). The method can involve a permutation of a yeast two-hybrid system that can rely on the reconstitution of a transcription factor that requires an interaction between one or two test proteins fused to one or two DNA binding domain(s) (DBDs) and a second test protein fused to a transcription activation domain (AD) or gene activating moiety.

Methods and systems of the disclosure can use the reconstitution of a transcription factor mediated by the interaction between a protein fused to an AD, for example, VP16, NF-κB AD, VP64AD, BP64 AD, B42 acidic activation domain (B42AD), or p65 transactivation domain (p65AD) and another protein fused to a DBD, for example, LexA, cI, Gli-1, YY1, glucocorticoid receptor binding domain, or Ume6 domain.

Methods and system of the disclosure can also use two different proteins, or two variants of one protein, fused to different DBDs. These proteins may interact with the same protein fused to an AD to drive two different or identical reporters. The system can identify inhibitors against a specific PPI in a complex without affecting the rest of the complex integrity (see FIGS. 1A and 1B). This system can also be used to identify selective inhibitors that disrupt a PPI between a specific isoform and its binding partner without affecting another variant (see FIGS. 2A and 2B).

An efficient interaction between the two proteins of interest can direct RNA polymerase to a specific genomic site, and allow for the expression of a genetic element. The genetic element can be, for example, a gene that encodes a protein that enables an organism to grow on selection media. The selection media can be specific to, for example, ADE2, URA3, TRP1, KANR, or NATR, and will lack the essential component (Ade, Ura, Trp) or include a drug (G418, NAT). Markers that can detect when an interaction is no longer present (for example when the interaction is disrupted by an external composition) can be referred to as counter-selection markers, such as the URA3 gene, and can be poor or leaky (easily masked by the selection of mutants that escape the selection). This leakiness of the selection marker can lead to a high false positive rate.

Methods and systems of the disclosure can combine a strong negative selection marker with the intracellular stabilization of the production of short peptides to screen for blockers of PPIs. An inducible two-hybrid approach can be employed, which can drive the expression of any one or combination of several cytotoxic reporters (death agents) as well as positive selection markers. A method of the disclosure involving induced expression of a combination of cytotoxic reporters in a two-hybrid system can allow for a multiplicative effect in lowering the false-positive rate of the two-hybrid assay, as all of the cytotoxic reporters must simultaneously be "leaky" to allow for an induced cell to survive.

Disclosed herein, in certain embodiments, is a method for identifying a molecule that selectively disrupts an interaction between a first test protein and a second test protein in a host cell, comprising: expressing in the host cell a first fusion protein comprising the first test protein and a DNA-binding moiety; expressing in the host cell a second fusion protein comprising the second test protein and a gene activating moiety; expressing in the host cell a third fusion protein comprising the third test protein and a different DNA-binding moiety; and delivering a molecule from a library to the host cell; wherein a sequence of gene for expressing a death agent is disposed within the host cell and operably linked a promoter DNA sequence specific for the DNA binding moiety of the first fusion protein, wherein a positive selection reporter is disposed within the host and operably linked to a promoter DNA sequence specific for the DNA binding moiety of the third fusion protein, wherein, in the absence of the molecule, the interaction between the first test protein and the second test protein causes the gene activating moiety to activate expression of the death agent, while the interaction between the second test protein and the third test protein causes the gene activating moiety to activate the expression of the positive selection reporter.

Figure 1B:
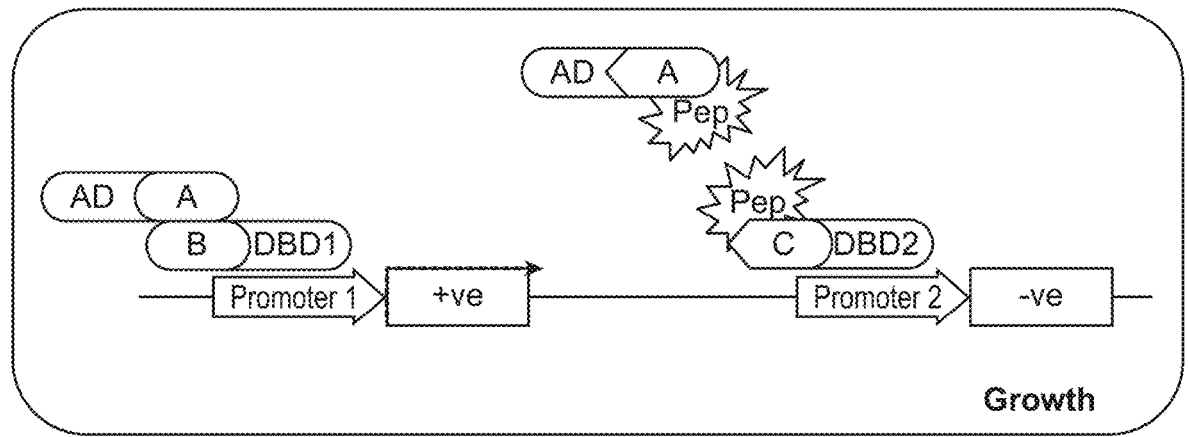

FIGS. 1A and 1B show a platform to identify a compound that disrupts a protein-protein interaction within a complex in a specific manner. DBD1 and DBD2 are promoter specific DNA-binding domains. AD refers to an activation domain. A, B, and C refer to three proteins, wherein B and C each interact with A. Broken arrows indicate active expression of the reporter. +ve refers to positive selection markers, −ve refers to death agents (negative selection markers). Pep refers to a peptide, such as a peptide from a library. In some embodiments, a peptide library may be replaced with a library that includes compounds other than peptides like small molecules. In some embodiments, the small molecules are peptidomimetics. Two scenarios are shown; FIG. 1A illustrates a case where a peptide (e.g., a peptide from a library) is unable to disrupt the pairwise interaction of interest (A-C), and a death agent is expressed, leading to cell death. FIG. 1B illustrates a case where a peptide (e.g., a peptide from a library) is able to disrupt the pairwise interaction of interest (A-C) without disrupting the A-B interaction. Selective peptide disruption activity is assayed by survival due to (1) the absence of expression of the death agent and (2) expression of the positive selection reporter (which provides evidence of selectivity).

Figure 2A:
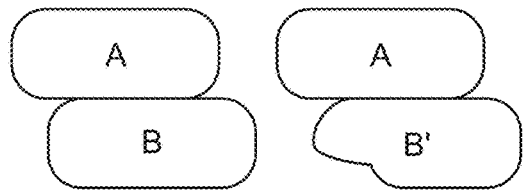
FIGS. 2A and 2B illustrate a platform to identify a compound that disrupts a protein-protein interaction (A-B') in a variant-specific manner.
Figure 2A:
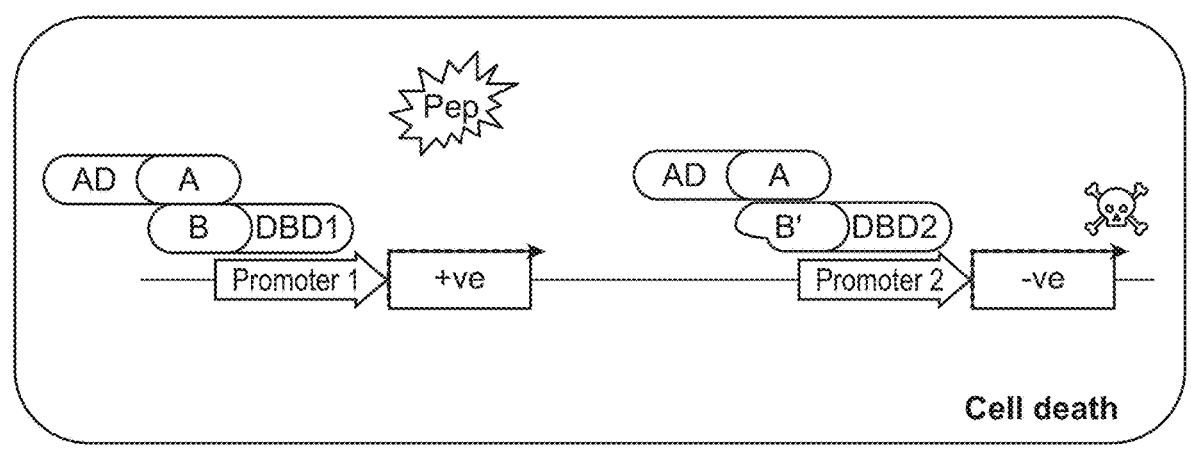
Figure 2B:
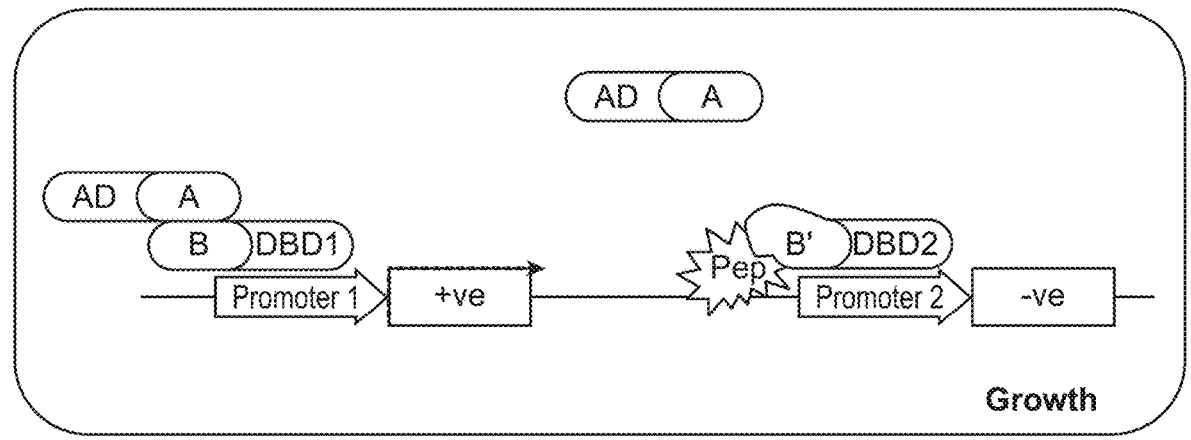

FIGS. 2A and 2B show a platform to identify a compound that disrupts a protein-protein interaction in a variant-specific manner. In other words, in contrast to FIGS. 1A and 1B in which B and C were unrelated protein, FIGS. 2A and 2B describe an analogous assay in which B and B' are related (but different) proteins (e.g., protein variants). As in FIGS. 1A and 1B, DBD1 and DBD2 are promoter-specific DNA-binding domains. AD refers to an activation domain. A, B, and B' refer to three proteins, wherein B and B' are two variants that are configured to interact with A. Broken arrows indicate active expression of the reporter. +ve refers to a positive selection marker, while −ve refers to a death agent. Pep refers to a peptide. Two scenarios are shown; FIG. 2A illustrates a case where a peptide is unable to disrupt the pairwise interaction of interest (A-B'), and a death is expressed, leading to cell death. FIG. 2B illustrates a case where a peptide is able to disrupt the pairwise interaction between the A and B' without disrupting the interaction between the A and B. Selective peptides disruption is assayed by survival due to (1) the absence of expression of the death agent and (2) and expression of the positive selection reporter (which provides evidence of selectivity).

Screening for Facilitators to Protein-Protein Interaction

The system can additionally be used to screen for molecules that "bridge" an interaction between two proteins in a selective manner. In some embodiments, the system can be used to identify molecules which can bind to one isoform, or one protein, and bridge its interaction with another macromolecule, such as a protein, RNA, or DNA. For example, the bridging could occur to link the protein to an E3 ligase to mediate its degradation. For example, bridging can occur between an oncogenic protein such as K-Ras oncogenic alleles, Cyclin D family, Cyclin E family, c-MYC, EGFR, HER2, PDGFR, Raf kinase, VEGF and beta-catenin, or oncogenic variants such as IDH1(R132H, R132S, R132C, R132G, and R132L) or IDH2(R140Q, R172K), and an E3 ligase. An E3 ligase can be chosen from a list including, but not limited to, Cereblon, Skp2, MDM2, FBXW7, DCAF15, VHL, AMFR, ANAPC11, ANKIBL AREL1, ARIH1, ARIH2, BARD1, BFAR, BIRC2, BIRC3, BIRC7, BIRC8, BMI1, BRAP, BRCA1, CBL, CBLB, CBLC, CBLL1, CCDC36, CCNB1IP1, CGRRF1, CHFR, CNOT4, CUL9, CYHR1, DCST1, DTX1, DTX2, DTX3, DTX3L, DTX4, DZIP3, E4F1, FANCL, G2E3, HACE1, HECTD1, HECTD2, HECTD3, HECTD4, HECW1, HECW2, HERC1, HERC2, HERC3, HERC4, HERC5, HERC6, HLTF, HUWE1, IRF2BP1, IRF2BP2, IRF2BPL, Itch, KCMF1, KMT2C, KMT2D, LNX1, LNX2, LONRF1, LONRF2, LONRF3, LRSAM1, LTN1, MAEA, MAP3K1, MARCH1, MARCH10, MARCH11, MARCH2, MARCH3, MARCH4, MARCH5, MARCH6, MARCH7, MARCH8, MARCH9, MDM4, MECOM, MEX3A, MEX3B, MEX3C, MEX3D, MGRN1, MIB1, MIB2, MID1, MID2, MKRN1, MKRN2, MKRN3, MKRN4P, MNAT1, MSL2, MUL1, MYCBP2, MYLIP, NEDD4, NEDD4L, NEURL1, NEURL1B, NEURL3, NFX1, NFXL1, NHLRC1, NOSIP, NSMCE1, PARK2, PCGF1, PCGF2, PCGF3, PCGF5, PCGF6, PDZRN3, PDZRN4, PELI1, PELI2, PELI3, PEX10, PEX12, PEX2, PHF7, PHRF1, PJA1, PJA2, PLAG1, PLAGL1, PML, PPIL2, PRPF19, RAD18, RAG1, RAPSN, RBBP6, RBCK1, RBX1, RC3H1, RC3H2, RCHY1, RFFL, RFPL1, RFPL2, RFPL3, RFPL4A, RFPL4AL1, RFPL4B, RFWD2, RFWD3, RING1, RLF, RLIM, RMND5A, RMND5B, RNF10, RNF103, RNF11, RNF111, RNF112, RNF113A, RNF113B, RNF114, RNF115, RNF121, RNF122, RNF123, RNF125, RNF126, RNF128, RNF13, RNF130, RNF133, RNF135, RNF138, RNF139, RNF14, RNF141, RNF144A, RNF144B, RNF145, RNF146, RNF148, RNF149, RNF150, RNF151, RNF152, RNF157, RNF165, RNF166, RNF167, RNF168, RNF169, RNF17, RNF170, RNF175, RNF180, RNF181, RNF182, RNF183, RNF185, RNF186, RNF187, RNF19A, RNF19B, RNF2, RNF20, RNF207, RNF208, RNF212, RNF212B, RNF213, RNF214, RNF215, RNF216, RNF217, RNF219, RNF220, RNF222, RNF223, RNF224, RNF225, RNF24, RNF25, RNF26, RNF31, RNF32, RNF34, RNF38, RNF39, RNF4, RNF40, RNF41, RNF43, RNF44, RNF5, RNF6, RNF7, RNF8, RNFT1, RNFT2, RSPRY1, SCAF11, SH3RF1, SH3RF2, SH3RF3, SHPRH, SIAH1, SIAH2, SIAH3, SMURF1, SMURF2, STUB1, SYVN1, TMEM129, TOPORS, TRAF2, TRAF3, TRAF4, TRAF5, TRAF6, TRAF7, TRAIP, TRIM10 TRIM11 TRIM13 TRIM15 TRIM17 TRIM2 TRIM21 TRIM22 TRIM23 TRIM24 TRIM25 TRIM26, TRIM27, TRIM28, TRIM3, TRIM31, TRIM32, TRIM33, TRIM34, TRIM35, TRIM36, TRIM37 TRIM38 TRIM39 TRIM4 TRIM40 TRIM41 TRIM42 TRIM43 TRIM43B TRIM45 TRIM46, TRIM47, TRIM48, TRIM49, TRIM49B, TRIM49C, TRIM49D1, TRIM5, TRIM50, TRIM51, TRIM52, TRIM54, TRIM55, TRIM56, TRIM58, TRIM59, TRIM6, TRIM60, TRIM61, TRIM62, TRIM63, TRIM64, TRIM64B, TRIM64C, TRIM65, TRIM67, TRIM68, TRIM69, TRIM7, TRIM71, TRIM72, TRIM73, TRIM74, TRIM75P, TRIM77, TRIM5, TRIM9, TRIML1, TRIML2, TRIP12, TTC3, UBE3A, UBE3B, UBE3C, UBE3D, UBE4A, UBE4B, UBOX5, UBR1, UBR2, UBR3, UBR4, UBR5, UBR7, UHRF1, UHRF2, UNK, UNKL, VPS11, VPS18, VPS41, VPS8, WDR59, WDSUB1, WWP1, WWP2, XIAP, ZBTB12, ZFP91, ZFPL1, ZNF280A, ZNF341, ZNF511, ZNF521, ZNF598, ZNF645, ZNRF1, ZNRF2, ZNRF3, ZNRF4, Zswim2, and ZXDC. The peptide-mediated bridging event can be specific to a mutant variant, or to one member of a complex, without disrupting the integrity of the WT variant or the rest of the complex.

Disclosed herein, in certain embodiments, is a method for identifying a molecule that selectively facilitates an interaction between a first test protein and a second test protein comprising: expressing in the host cell a first fusion protein comprising the first test protein and a DNA-binding moiety;

expressing in the host cell a second fusion protein comprising the second test protein and a gene activating moiety; expressing in the host cell a third fusion protein comprising the third test protein and a different DNA-binding moiety; and delivering a molecule from a library to the host cell such that the molecule forms a bridging interaction between the first test protein and the second test protein; wherein a sequence of a gene for expressing a death agent is disposed within the host cell and operably linked a promoter DNA sequence specific for the DNA binding moiety of the third fusion protein; wherein a positive selection reporter is disposed within the host cell and operably linked to a promoter DNA sequence specific for the DNA binding moiety of the first fusion protein; and wherein the first test protein and second test protein to form a functional transcription factor that activates expression of the death agent when the molecule from the library forms the bridging interaction.

Figure 3A:
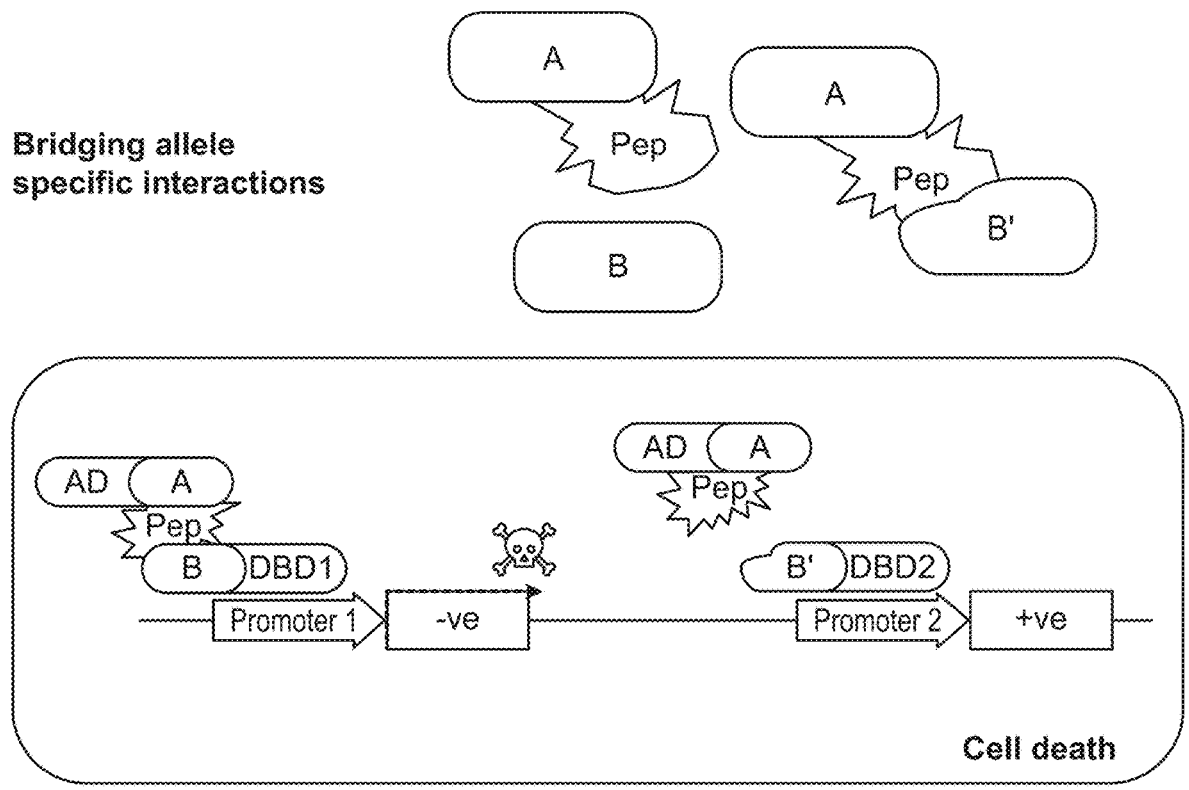
FIGS. 3A and 3B exemplify an embodiment of a platform to identify a compound that bridges two proteins in a variant- or protein-specific manner.
Figure 3B:
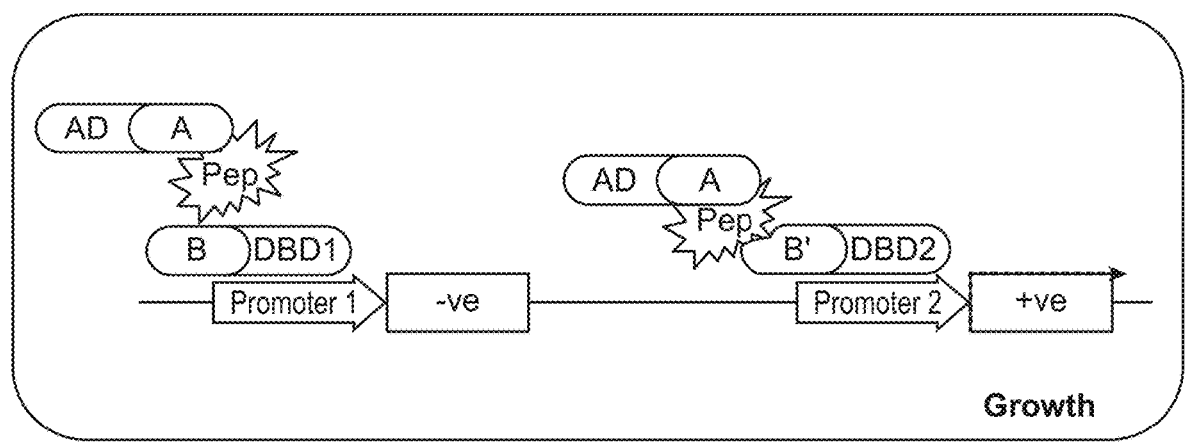

FIGS. 3A and 3B show a platform to identify a compound that bridges a protein-protein interaction in a variant- or protein-specific manner. DBD1 and DBD2 are promoter specific DNA-binding domains. AD refers to an activation domain. A, B, and B' refer to three proteins, wherein B and B' are two variants to be assayed for interaction with A. Broken arrows indicate active expression of the reporter. +ve refers to positive selection markers, −ve refers to death agents. Pep refers to a peptide (e.g., a peptide from a library). Two scenarios are shown; FIG. 3A illustrates a case where a peptide is able to bridge an interaction between one variant (B) and a protein (A). In this case, this is the control variant (B) and it leads to expression of the death and cell death. FIG. 3B illustrates a case where a peptide is able to bridge the secondary variant (B') and a protein (A). In this case, the peptide is bridging the variant of interest (B') and enables its binding to protein A. This combination of results leads to (1) the activation of a positive selection marker and (2) the lack of activation of the death agent (due to the lack of bridging to the unintended variant).

In some embodiments, the host cell disclosed herein further comprises an integrated DNA encoding the first fusion protein, an integrated DNA encoding the second fusion protein, an integrated DNA encoding the third fusion protein; a plasmid DNA encoding the death agent; and a plasmid DNA encoding a positive selection reporter.

Figure 8:
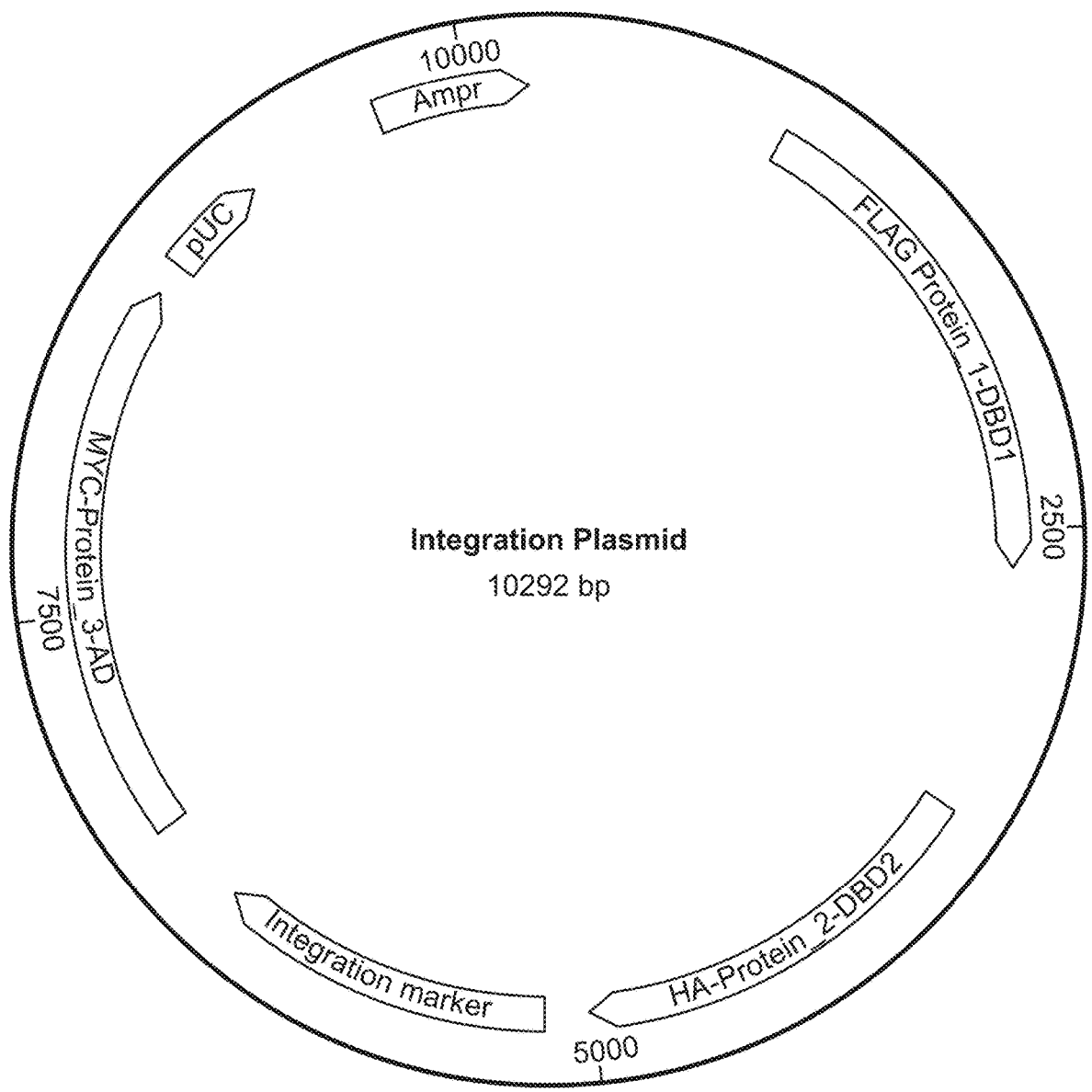
FIG. 8 shows an embodiment of an integration plasmid that encodes two bait proteins, each with its own DNA binding domain ("DBD"), and a prey protein with an activation domain ("AD").
Figure 9:
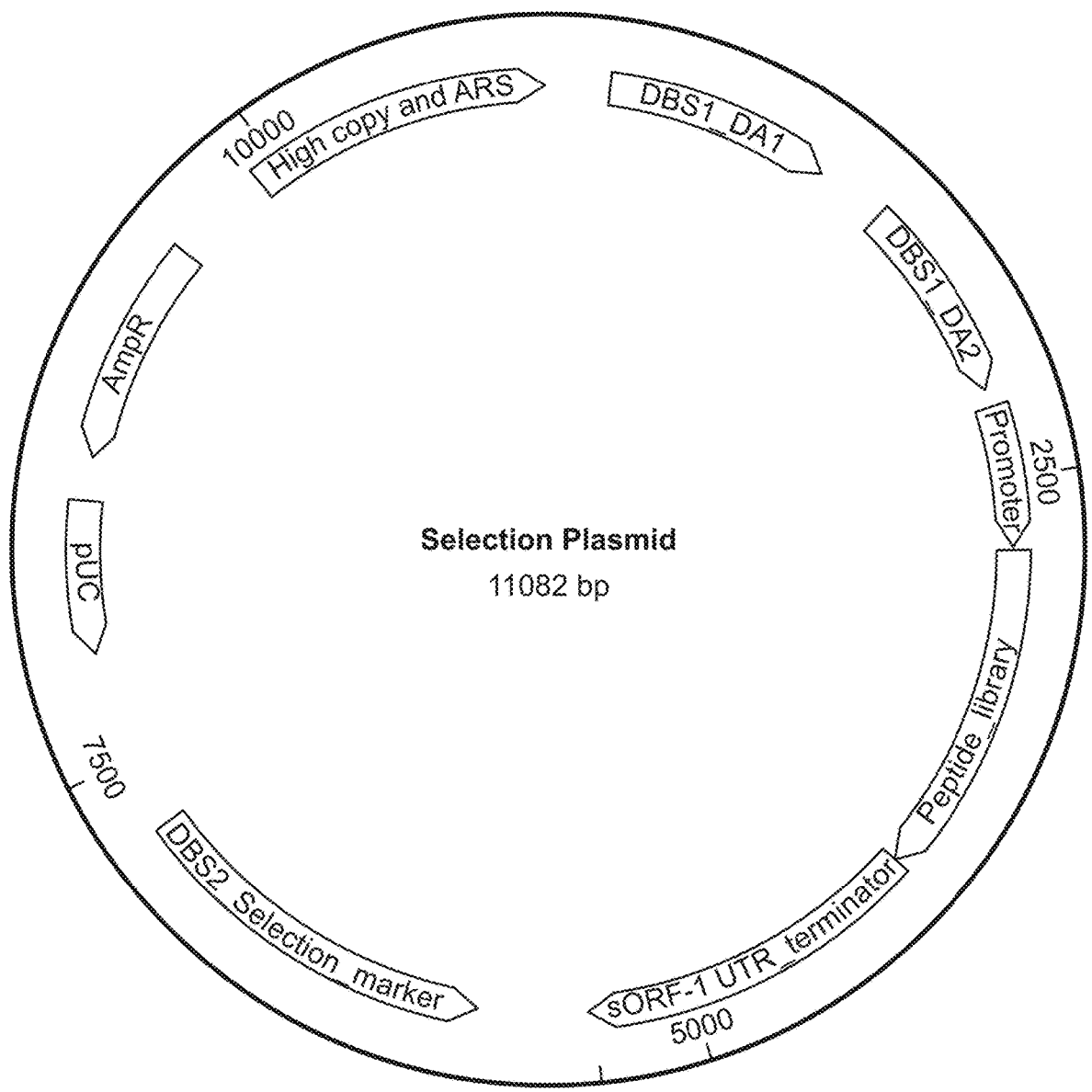
FIG. 9 shows an embodiment of a selection and library plasmid that encodes two death agents, both with the same DNA binding sequence, a positive selection agent driven by another DNA binding sequence and an inducible stabilized peptide library.
Figure 10:
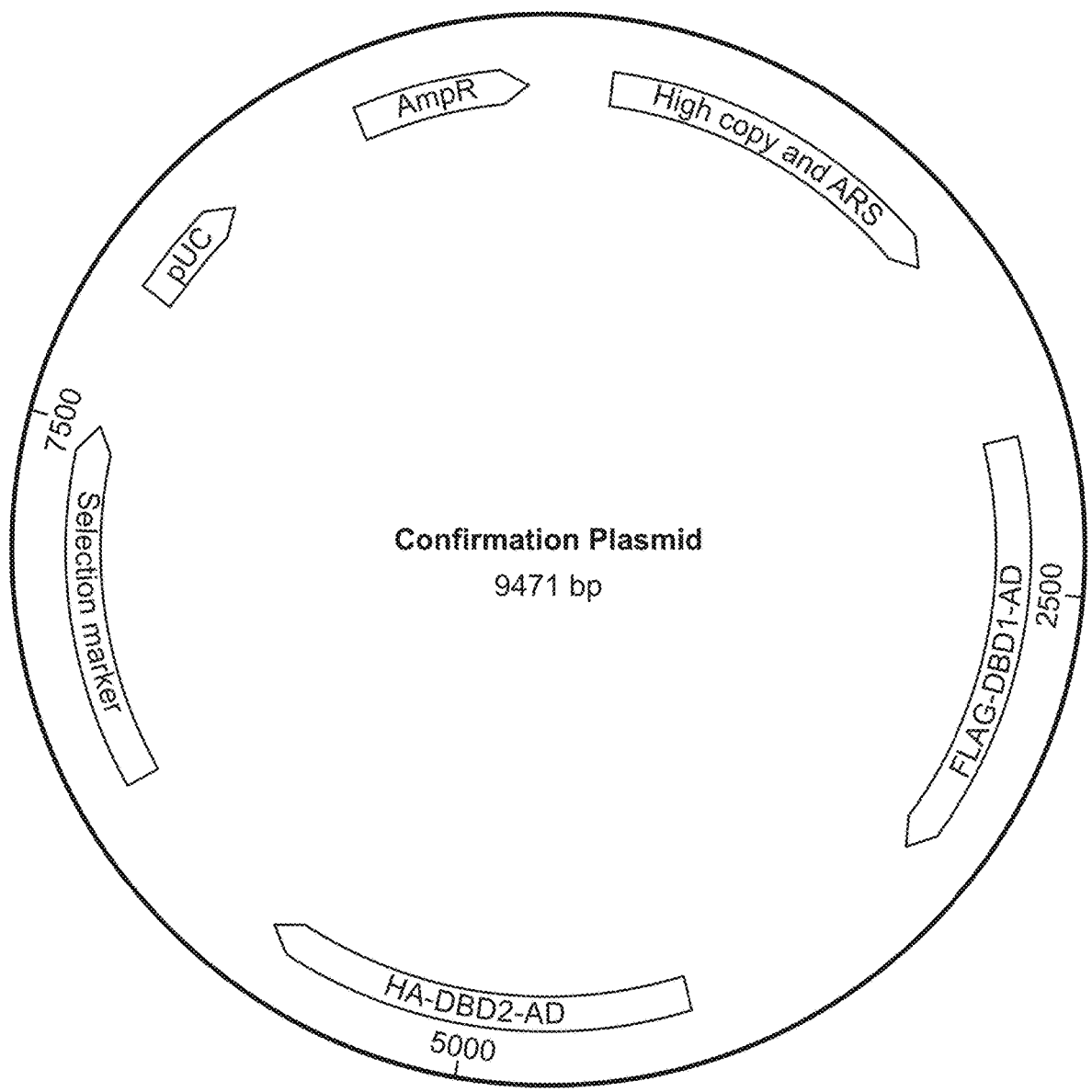
FIG. 10 shows an embodiment of a confirmation plasmid that encodes two bait-prey fusion proteins, each with its own DBD.

To identify peptides that can disrupt or facilitate a PPI, a PPI integration plasmid (PLASMID 1; FIG. 8), a selection and library plasmid (PLASMID 2; FIG. 9), and a confirmation plasmid (PLASMID 3; FIG. 10) can be used. The integration of PLASMID 1 into the genome of the host cell (as confirmed using PLASMID 3) can be followed by transformation of a library of PLASMID 2 encoding random peptides with, for example, NNK or NNN codons.

Expression of Fusion Proteins for PPI

In some embodiments, the host cell disclosed herein comprises a plasmid vector, which comprises the components of PLASMID 1 (FIG. 8), or any combination of the components of PLASMID 1. PLASMID 1 can contain, for example, two restriction sites that enable the integration of two proteins that constitute the PPI of interest. The PPI of interest can involve a pair of domains having known importance for carcinogenesis, such as p53-MDM2, RAS-RASBDPs, and MYC-MAX. The PPI of interest can also involve the interaction of an oncogene (such as Cyclin E family, Cyclin D family, c-MYC, EGFR, HER2, K-Ras, PDGFR, Raf kinase, and VEGF) or a tumor suppressor (such as BRCA1, BRCA2, cyclin-dependent kinase inhibitor 1C, PTEN, p16, p27, p53, p73, and Retinoblastoma protein (pRb)) with a known cellular interaction partner. The PPI of interest can involve the interaction of a protein involved in the DNA repair pathway (such as ATM, ATRX, BRCA1, BRCA2, ERCC1, FANCB, FANCF, FEN1, HMGA1, HMGA1, MDC1, MGMT, MLH1, MSH2, MSH4, Mre11A, NBS1, NEIL1, PARP1, PARP2, PMS2, RAD51, RAD52, RAD54, RAD51AP1, WRN, and XPF) with another cellular factor.

PLASMID 1 can be configured to express two proteins that constitute a PPI and an additional factor, for example, a variant of one of the proteins, such as KRAS (G12D, G12V, G12C, G12S, G13D, Q61K, or Q61L, etc.) and WT KRAS along with BRAF. The additional factor can also be another protein bound to one of the components of the PPI, or as member of a larger complex (such as YAP or TAZ disruption from TEAD without compromising VGLL4 binding to TEAD, or maintaining binding of BAX to BAK but preventing binding of BAX to BCL-2).

In some embodiments, the host cell disclosed herein comprises PLASMID 1, wherein a DNA sequence encoding a first polypeptide is inserted in frame with Gal4-DBD, a second polypeptide is inserted in frame with LexA-DBD, and wherein a DNA sequence encoding a third polypeptide is inserted in frame with VP64-AD.

In some embodiments, the first test protein is a variant of KRAS, the second test protein is c-Raf, and the third test protein is KRAS.

In some embodiments, the first test protein is YAP or TAZ, the second test protein is TEAD, and the third test protein is VGLL4.

PLASMID 1 can encode for the fusion of an activation domain or another gene activating moiety and a DBD to each protein driven by either a strong promoter and terminator (such as ADH1), or by an inducible promoter (such as GAL1). Other exemplary activation domains include those of VP16 and B42AD. In some embodiments, the DNA binding moiety is derived from LexA, TetR, Lad, Gli-1, YY1, glucocorticoid receptor, or Ume6 domain and the gene activating moiety is derived from Gal4, B42, or VP64, Gal4, NF-κB AD, Dofl, BP64, B42, or p65. Each protein fusion can be tagged for subsequent biochemical experiments with, for example, a FLAG, HA, MYC, or His tag. PLASMID 1 can also include bacterial selection and propagation markers (i.e. ori and AmpR), and yeast replication and selection markers (i.e. TRP1 and CEN or 2 um). The plasmid may contain multiple bait proteins fused to different DBDs. The plasmid can also be integrated into the genome at a specified locus.

Disclosed herein, in certain embodiments, is a library of plasmid vectors, each plasmid vector comprising: a DNA sequence encoding a different peptide sequence operably linked to a first switchable promoter; a DNA sequence encoding a death agent under control of a second switchable promoter; and a DNA sequence encoding a positive selection reporter under control of a third switchable promoter.

Expression of Selection Markers

Positive Selection Markers

An efficient interaction between the two test proteins can direct RNA polymerase to a specific genomic site, and allow expression of a protein that enables an organism to grow on selection media. The selection media can be specific to, for example, ADE2, URA3, TRP1, KAN$^R$, or NAT$^R$, and can lack the essential component (Ade, Ura, Trp) or can include a drug (G418, NAT). PLASMID 2 (FIG. 9) can encode for one or more positive selection markers that enable an organism to grow on selection media.

Figure 6:
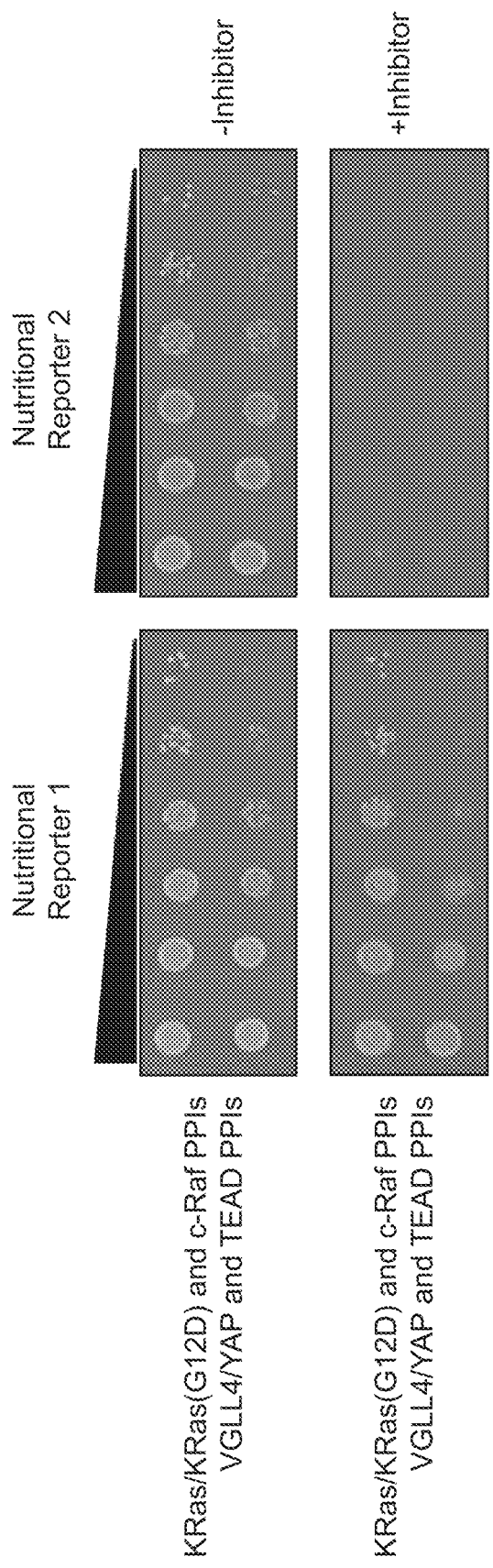
FIG. 6 illustrates two platforms to identify a compound that specifically disrupts a protein-protein interaction in cell culture by selecting for nutritional reporter.

FIG. 6 shows the results of two systems for identifying a compound that specifically disrupts a protein-protein interaction in cell culture using a positive selection marker. In the first platform, KRas and KRas(G12D) fused to DBDs and c-Raf fused to AD were expressed in yeast cells. In the absence of any inhibitors, the DBD fusion protein and AD fusion protein pairs maintain interaction to drive expression of nutritional reporters 1 and 2. A 5-fold dilution series starting at $10^4$ cells were spotted onto selective media with or without inhibitor and visualized after 2 days of growth at 30° C. The results showed that the cells grown on media that selected for nutritional reporter 2 had particularly poor survival rate when the inhibitor was added, illustrating both (1) the specificity of the inhibitor for KRas(G12D) and c-Raf and (2) the validity of the screening assay.

In the second platform, VGLL4 and YAP fused to DBDs and TEAD fused to AD were expressed in cells. In the absence of any inhibitors, the DBD fusion protein and AD fusion protein pairs maintain interaction to drive expression of nutritional reporters 1 and 2. A 5-fold dilution series starting at $10^4$ cells were spotted onto selective media with or without inhibitor and visualized after 2 days of growth at 30° C. The results showed that the cells grown on media that selected for nutritional reporter 2 had particularly poor survival rate when the inhibitor was added, illustrating both (1) the specificity of the inhibitor for the YAP and TEAD interaction and (2) the validity of the screening assay.

Negative Selection Markers

An inducible two-hybrid approach can be employed, which can drive the expression of any one or combination of several cytotoxic reporters (death agents) as well as positive selection markers. A method of the disclosure involving induced expression of a combination of cytotoxic reporters in a two-hybrid system can allow for a multiplicative effect in lowering the false-positive rate of the two-hybrid assay, as all of the cytotoxic reporters must simultaneously be "leaky" to allow for an induced cell to survive. The cytotoxic reporters can be, for example:

TABLE 1

| | | |
|---|---|---|
| Cholera toxin (CtxA) | SEQ ID NO.: 1 | MVKIIFVFFIFLSSFSYANDDKLYRADSRPPDEIKQSGGLMPRGQSEYFDRGTQMN INLYDHARGTQTGFVRHDDGYVSTSISLRSAHLVGQTILSGHSTYYIYVIATAPNM FNVNDVLGAYSPHPDEQEVSALGGIPYSQIYGWYRVHFGVLDEQLHRNRGYRDRYY SNLDIAPAADGYGLAGFPPEHRAWREEPWIHHAPPGCGNAPRSSMSNTCDEKTQSL GVKFLDEYQSKVKRQIFSGYQSDIDTHNRIKDEL |
| SpvB toxin (Salmonella enterica) | SEQ ID NO.: 2 | MLILNGFSSATLALITPPFLPKGGKALSQSGPDGLASITLPLPISAERGFAPALAL HYSSGGGNGPFGVGWSCATMSIARRTSHGVPQYNDSDEFLGPDGEVLVQTLSTGDA PNPVTCFAYGDVSFPQSYTVTRYQPRTESSFYRLEYWVGNSNGDDFWLLHDSNGIL HLLGKTAAARLSDPQAASHTAQWLVEESVTPAGEHIYYSYLAENGDNVDLNGNEAG RDRSAMRYLSKVQYGNATPAADLYLWTSATPAVQWLFTLVFDYGERGVDPQVPPAF TAQNSWLARQDPFSLYNYGFEIRLHRLCRQVLMFHHFPDELGEADTLVSRLLLEYD ENPILTQLCAARTLAYEGDGYRRAPVNNMMPPPPPPPPMMGGNSSRPKSKWAIVE ESKQIQALRYYSAQGYSVINKYLRGDDYPETQAKETLLSRDYLSTNEPSDEEFKNA MSVYINDIAEGLSSLPETDHRVVYRGLKLDKPALSDVLKEYTTIGNIIIDKAFMST SPDKAWINDTILNIYLEKGHKGRILGDVAHFKGEAEMLFPPNTKLKIESIVNCGSQ DFASQLSKLRLSDDATADTNRIKRIINMRVLNS |
| CARDS toxin (Mycoplasma pneumoniae) | SEQ ID NO.: 3 | MSENLYFQGHMPNPVRFVYRVDLRSPEEIFEHGFSTLGDVRNFFEHILSTNFGRSY FISTSETPTAAIRFFGSWLREYVPEHPRRAYLYEIRADQHFYNARATGENLLDLMR QRQVVFDSGDREMAQMGIRALRTSFAYQREWFTDGPIAAANVRSAWLVDAVPVEPG HAHHPAGRVVETTRINEPEMHNPHYQELQTQANDQPWLPTPGIATPVHLSIPQAAS VADVSEGTSASLSFACPDWSPPSSNGENPLDKCIAEKIDNYNLQSLPQYASSVKEL EDTPVYLRGIKTQKTFMLQADPQNNNVFLVEVNPKQKSSFPQTIFFWDVYQRICLK DLTGAQISLSLTAFTTQYAGQLKVHLSVSAVNAVNQKWKMTPQDIAITQFRVSSEL LGQTENGLFWNTKSGGSQHDLYVCPLKNPPSDLEELQIIVDECTTHAQFVTMRAAS TFFVDVQLGWYWRGYYYTPQLSGWSYQMKTPDGQIFYDLKTSKIFFVQDNQNVFFL HNKLNKQTGYSWDWVEWLKHDMNEDKDENFKWYFSRDDLTIPSVEGLNFRHIRCYA DNQQLKVIISGSRWGGWYSTYDKVESNVEDKILVKDGFDRF |
| SpyA Toxin (Streptococcus pyogenes) | SEQ ID NO.: 4 | MLKKRYQLAMILLLSCFSLVWQTEGLVELFVCEHYERAVCEGTPAYFTFSDQKGAE TLIKKRWGKGLVYPRAEQEAMAAYTCQQAGPINTSLDKAKGKLSQLTPELRDQVAQ LDAATHRLVIPWNIVVYRYVYETFLRDIGVSHADLTSYYRNHQFNPHILCKIKLGT RYTKHSFMSTTALKNGAMTHRPVEVRICVKKGAKAAFVEPYSAVPSEVELLFPRGC QLEVVGAYVSQDHKKLHIEAYFKGSL |
| HopU1 (Pseudomonas syringae) | SEQ ID NO.: 5 | MNINRQLPVSGSERLLTPDVGVSRQACSERHYSTGQDRHDFYRFAARLHVDAQCFG LSIDDLMDKFSDKHFRAEHPEYRDVYPEECSAIYMHTAQDYSSHLVRGEIGTPLYR EVNNYLRLQHENSGREAEIDNHDEKLSPHIKMLSSALNRLMDVAAFRGTVYRGIRG DLDTIARLYHLFDTGGRYVEPAFMSTTRIKDSAQVFEPGTPNNIAFQISLKRGADI SGSSQAPSEEEIMLPMMSEFVIEHASALSEGKHLFVLSQI |
| Chelt toxin | SEQ ID NO.: 6 | MKTIISLIFIMFPLFVSAHNGNFYRADSRSPNEIKDLGGLYPRGYYDFFERGTPMS ISLYDHARGAPSGNTRYDDGFVSTTTDIDSAHEIGQNILSGYTEYYIYLIAPAPNL LDVNAVLGRYSPHPQENEYSALGGIPWTQVIGWYVVNNGVLDRNIHRNRQFRADLF NNLSPALPSESYQFAGFEPEHPAWRQEPWINFAPPGCGRNVRLTKHINQQDCSNSQ EELVYKKLQDLRTQFKVDKKLKLVNKTSSNNIIFPNHDFIREWVDLDGNGDLSYCG FTVDSDGSRKRIVCAHNNGNFTYSSINISLSDYGWPKGQRFIDANGDGLVDYCRVQ YVWTHLYCSLSLPGQYFSLDKDAGYLDAGYNNSRAWAKVIGTNKYSFCRLTSNGYI CTDIDSYSTAFKDDDQGWADSRYWMDIDGNGGDDYCRLVYNWTHLRCNLQGKDGLW KRVESKYLDGGYPSLRFKIKMTSNKDNYCRIVRNHRVMECAYVSDNGEFHNYSLNM PFSLYNKNDIQFIDIDGDNRDDICRYNSAPNTMECYLNQDKSFSQNKLVLYLSAKP ISSLGSGSSKIIRTFNSEKNSSAYCYNAGYGTLRCDEFVIY |

TABLE 1-continued

| | | |
|---|---|---|
| Certhrax toxin | SEQ ID NO.: 7 | MKEIIRNLVRLDVRSDVDENSKKTQELVEKLPHEVLELYKNVGGEIYITDKRLTQH EELSDSSHKDMFIVSSEGKSFPLREHFVFAKGGKEPSLIIHAEDYASHLSSVEVYY ELGKAIIRDTFPLNQKELGNPKFINAINEVNQQKEGKGVNAKADEDGRDLLFGKEL KKNLEHGQLVDLDLISGNLSEFQHVFAKSFALYYEPHYKEALKSYAPALFNYMLEL DQMRFKEISDDVKEKNKNVLDFKWYTRKAESWGVQTFKNWKENLTISEKDIITGYT GSKYDPINEYLRKYDGEIIPNIGGDLDKKSKKALEKIENQIKNLDAALQKSKITEN LIVYRRVSELQFGKKYEDYNLRQNGIINEEKVMELESNFKGQTFIQHNYMSTSLVQ DPHQSYSNDRYPILLEITIPEGVHGAYIADMSEYPGQYEMLINRGYTFKYDKFSIV KPTREEDKGKEYLKVNLSIYLGNLNREK |
| EFV toxin | SEQ ID NO.: 8 | MSQLNKWQKELQALQKANYQETDNQLFNVYRQSLIDIKKRLKVYTENAESLSFSTR LEVERLFSVADEINAILQLNSPKVEKTIKGYSAKQAEQGYYGLWYTLEQSQNIALS MPLINHDYIMNLVNAPVAGKRLSKRLYKYRDELAQNVTNNIITGLFEGKSYAEIAR WINEETEASYKQALRIARTEAGRTQSVTTQKGYEEAKELGINIKKKWLATIDKHTR RTHQELDGKEVDVDEEFTIRGHSAKGPRMFGVASEDVNCRCTTIEVVDGISPELRK DNESKEMSEFKSYDEWYADRIRQNESKPKPNFTELDFFGQSDLQDDSDKWVAGLKP EQVNAMKDYTSDAFAKMNKILRNEKYNPREKPYLVNIIQNLDDAISKFKLKHDIIT YRGVSANEYDAILNGNVFKEFKSTSINKKVAEDFLNFTSANKDGRVVKFLIPKGTQ GAYIGTNSSMKKESEFLLNRNLKYTVEIVDNILEVTILG |
| ExoT | SEQ ID NO.: 9 | MHIQSSQQNPSFVAELSQAVAGRLGQVEARQVATPREAQQLAQRQEAPKGEGLLSR LGAALARPFVAIIEWLGKLLGSRAHAATQAPLSRQDAPPAASLSAAEIKQMMLQKA LPLTLGGLGKASELATLTAERLAKDHTRLASGDGALRSLATALVGIRDGSLIEASR TQAARLLEQSVGGIALQQWGTAGGAASQHVLSASPEQLREIAVQLHAVMDKVALLR HAVESEVKGEPVDKALADGLVEHFGLEAEQYLGEHPDGPYSDAEVMALGLYTNGEY QHLNRSLRQGRELDAGQALIDRGMSAAFEKSGPAEQVVKTFRGTQGRDAFEAVKEG QVGHDAGYLSTSRDPSVARSFAGLGTITTLFGRSGIDVSEISIEGDEQEILYDKGT DMRVLLSAKDGQGVTRRVLEEATLGERSGHSEGLLDALDLATGTDRSGKPQEQDLR LRMRGLDLA |
| CdtB | SEQ ID NO.: 10 | MKKIICLFLSFNLAFANLENFNVGTWNLQGSSAATESKWSVSVRQLVSGANPLDIL MIQEAGTLPRTATPTGRHVQQGGTPIDEYEWNLGTLSRPDRVFIYYSRVDVGANRV NLAIVSRMQAEEVIVLPPPTTVSRPIIGIRNGNDAFFNIHALANGGTDVGAIITAV DAHFANMPQVNWMIAGDFNRDPSTITSTVDRELANRIRVVFPTSATQASGGTLDYA ITGNSNRQQTYTPPLLAAILMLASLRSHIVSDHFPVNFRKF |
| Diptheria toxin | SEQ ID NO.: 11 | MSRKLFASILIGALLGIGAPPSAHAGADDVVDSSKSFVMENFSSYHGTKPGYVDSI QKGIQKPKSGTQGNYDDDWKGFYSTDNKYDAAGYSVDNENPLSGKAGGVVKVTYPG LTKVLALKVDNAETIKKELGLSLTEPLMEQVGTEEFIKRFGDGASRVVLSLPFAEG SSSVEYINNWEQAKALSVELEINFETRGKRGQDAMYEYMAQACAGNRVRRSVGSSL SCINLDWDVIRDKTKTKIESLKEHGPIKNKMSESPNKTVSEEKAKQYLEEFHQTAL EHPELSELKTVTGTNPVFAGANYAAWAVNVAQVIDSETADNLEKTTAALSILPGIG SVMGIADGAVHHNTEEIVAQSIALSSLMVAQAIPLVGELVDIGFAAYNFVESIINL FQVVHNSYNRPAYSPGHKTQPFLHDGYAVSWNTVEDSIIRTGFQGESGHDIKITAE NTPLPIAGVLLPTIPGKLDVNKSKTHISVNGRKIRMRCRAIDGDVTFCRPKSPVYV GNGVHANLHVAFHRSSSEKIHSNEISSDSIGVLGYQKTVDHTKVNSKLSLFFEIKS |
| ExoU/VipB | SEQ ID NO.: 12 | MKLAEIMTKSRKLKRNLLEISKTEAGQYSVSAPEHKGLVLSGGGAKGISYLGMIQA LQERGKIKNLTHVSGASAGAMTASILAVGMDIKDIKKLIEGLDITKLLDNSGVGFR ARGDRFRNILDVIYMMQMKKHLESVQQPIPPEQQMNYGILKQKIALYEDKLSRAGI VINNVDDIINLTKSVKDLEKLDKALNSIPTELKGAKGEQLENPRLTLGDLGRLREL LPEENKHLIKNLSVVVTNQTKHELERYSEDTTPQQSIAQVVQWSGAHPVLFVPGRN AKGEYIADGGILDNMPEIEGLDREEVLCVKAEAGTAFEDRVNKAKQSAMEAISWFK ARMDSLVEATIGGKWLHATSSVLNREKVYYNIDNMIYINTGEVTTTNTSPTPEQRA RAVKNGYDQTMQLLDSHKQTFDHPLMAILYIGHDKLKDALIDEKSEKEIFEASAHA QAILHLQEQIVKEMNDGDYSSVQNYLDQIEDILTVDAKMDDIQKEKAFALCIKQVN FLSEGKLETYLNKVEAEAKAAAEPSWATKILNLLWAPIEWVVSLFKGPAQDFKVEV QPEPVKVSTSENQETVSNQKDINPAVEYRKIIAEVRREHTDPSPSLQEKERVGLST TFGGH |
| HopPtoE | SEQ ID NO.: 13 | MNRVSGSSSATWQAVNDLVEQVSERTTLSTTGYQTAMGRLNKPEKSDADALMTMRR AQQYTDSAKRTYISETLMNLADLQQRKIYRTNSGNLRGAIEMTPTQLTDCVQKCRE EGFSNCDIQALEIGLHLRHKLGISDFTIYSNRKLSHNYVVIHPSNAFPKGAIVDSW TGQGVVELDFKTRLKFKHREENYAVNANMHEWIERYGQAHVID |
| HopPtoF | SEQ ID NO.: 14 | MGNICGTSGSRHVYSPSHTQRITSAPSTSTHVGGDTLTSIHQLSHSQREQFLNMHD PMRVMGLDHDTELFRTTDSRYIKNDKLAGNPQSMASILMHEELRPNRFASHTGAQP HEARAYVPKRIKATDLGVPSLNVMTGSLARDGIRAYDHMSDNQVSVKMRLGDFLER GGKVYADASSVADDGETSQALIVTLPKGQKVPVERV |
| HopPtoG | SEQ ID NO.: 15 | MQIKNSHLYSASRMVQNTFNASPKMEVTNAIAKNNEPAALSATQTAKTHEGDSKGQ SSNNSKLPFRAMRYAAYLAGSAYLYDKTANNFFLSTTSLHDGKGGFTSDARLNDAQ DKARKRYQNNHSSTLENKNSLLSPLRLCGENQFLTMIDYRAATKIYLSDLVDTEQA HTSILKNIMCLKGELTNEEAIKKLNPEKTPKDYDLTNSEAYISKNKYSLTGVKNEE TGSTGYTSRSITKPFVEKGLKHFIKATHGEKALTPKQCMETLDNLLRKSITLNSDS QFAAGQALLVFRQVYAGEDAWGDAERVILKSHYNRGTVLQDEADKIELSRPFSEQD LAKNMFKRNTSIAGPVLYHAYIYIQEKIFKLPPDKIEDLKHKSMADLKNLPLTHVK LSNSGVGFEDASGLGDSFTALNATSCVNHARIMSGEPPLSKDDVVILIGCLNAVYD NSSGIRHSLREIARGCFVGAGFTVQDGDDFYKQICKNASKQFYNG |

| | | |
|---|---|---|
| VopF | SEQ ID NO.: 16 | MFKISVSQQANVMSTSDTAQRSSLKISIKSICNKSLSKKLHTLAEKCRRFSQELKE HTASKKQIVEQATTTVRESSLTKSDSELGSSRSLLTSDVLSSSSSHEDLTAVNLED NDSVFVTIESSSELIVKQDGSIPPAPPLPGNIPPAPPLPSAGNIPTAPGLPKQAT TESVAQTSDNRSKLMEEIRQGVKLRATPKSSSTEKSASDPHSKLMKELINHGAKLK KVSTSDIPVPPPLPAAFASKPTDGRSALLSEIAGESKDRLRKAGSSETLNVSQPTV AESSIPEAYDLLLSDEMFNLSPKLSETELNTLADSLADYLFKAADIDWMQVIAEQT KGSTQATSLKSQLEQAPEYVKAFCDEILKFPDCYKSADVASPESPKAGPSSVIDVA LKRLQAGRNRLFSTIDAKGTNELKKGEAILESAINAARSVMTAEQKSALLSSNVKS ATFKVFSELPCMEGFAEQNGKAAFNALRLAFYSSIQSGDTAQQDIARFMKENLATG FSGYSYLGLTSRVAQLEAQLAALTTK |
| YopJ | SEQ ID NO.: 17 | MIGPISQINISGGLSEKETSSLISNEELKNIITQLETDISDGSWFHKNYSRMDVEV MPALVIQANNKYPEMNLNLVTSPLDLSIEIKNVIENGVRSSRFIINMGEGGIHFSV IDYKHINGKTSLILFEPANFNSMGPAMLAIRTKTAIERYQLPDCHFSMVEMDIQRS SSECGIFSFALAKKLYIERDSLLKIHEDNIKGILSDGENPLPHDKLDPYLPVTFYK HTQGKKRLNEYLNTNPQGVGTVVNKKNETIVNREDNNKSIVDGKELSVSVHKKRIA EYKTLLKV |
| AvrPtoB | SEQ ID NO.: 18 | MAGINGAGPSGAYFVGHTDPEPASGGAHGSSSGASSSNSPRLPAPPDAPASQARDR REMLLRARPLSRQTREWVAQGMPPTAEAGVPIRPQESAEAAAPQARAEERHTPEAD AAASHVRTEGGRTPQALAGTSPRHTGAVPHANRIVQQLVDAGADLAGINTMIDNAM RRHAIALPSRTVQSILIEHFPHLLAGELISGSELATAFRAALRREVRQQEASAPPR TAARSSVRTPERSTVPPTSTESSSGSNQRTLLGRFAGLMTPNQRRPSSASNASASQ RPVDRSPPRVNQVPTGANRVVMRNHGNNEADAALQGLAQQGVDMEDLRAALERHIL HRRPIPMDIAYALQGVGIAPSIDTGESLMENPLMNLSVALHRALGPRPARAQAPRP AVPVAPATVSRRPDSARATRLQVIPAREDYENNVAYGVRLLSLNPGAGVRETVAAF VNNRYERQAVVADIRAALNLSKQFNKLRTVSKADAASNKPGFKDLADHPDDATQCL FGEELSLTSSVQQVIGLAGKATDMSESYSREANKDLVFMDMKKLAQFLAGKPEHPM TRETLNAENIAKYAFRIVP |
| SdbA | SEQ ID NO.: 19 | MHKKYNYYSLEKEKKTFWQHILDILKAPFRLPGWVVSFFLARNITHVALNPNNIPQ QRLIHLTKTSNRPEDDIVVINFKKRPPHKWENDTLIKIANTIAALPFVTPRLRTRL HYDNENDINHVNKLLAEIDALVQGKSKQKYCKGRAFDWSKIHLKGLEFLDPKMRGY VYEQLHEKYGYVSYTTKRKPNIEFFTLKTPDGSELDSVQVTGEDEEKKPMGERKFI ITCIARDQNFINWIKDLNYTAKNLGATAISFNYRGVDYSRGLVWTENNLVDDILAQ VQRLISLGADPKNICLDGMCIGGAVATIAAAKLHEKGMKVKLNNERSFTSLSSLVF GFIVPELQTANWWSPLTYGRFLLAGVVYALLTPLIWLAGWPVDVTKAWNRIPAQDK MYSVVRDKDNGLYDGVIHDHFCSIASLVDSQINSILYKLSTDQPLTEEEKQILCDD QFSHHFKPSQSVLKNPKYKGPHFISRQDLVAELGHREEYTNHDYFLDRLREKFQLD RATRPVALAEDGEKDIDGISSQLSNNKERPLIIASSGGTGHISATHGIINDLQSKT DNVVITQHHAELYKNKPFSITSVLIRIGVWFTSLPILEDILKGVMRFIGYPVLPSS SIFWDQMSKIQQSETKKENGIETGRTRPYVDMLLDIYPEGYEYTAFNNATHLTSSI EDIQTMISFKGHVEEDNRNIVYQNILQRLMHAAKQNTPYTRLISTQALSLGAICDA VKYYNTVFLPVYNAERGTSYQPIAIDQYMTDLPSLGCIHFMNNLEELTSEQRQLME IHAVNMSEPPKEAHFGKEQGFKAVHNIDPRNNPMIRNAFKDPSLTKYLDKTQSFDL HFNVYKKEKQNALPVLNGKEKITIKPHAKIASIMIGSLAANASADYAKYLLNQGYE HIFLFGGLNDSIAARIDQIINSYPAPTRDEIRKKIILLGNQSDVEMAPIMTRSNCV VIRGGGLSVMEQMAMPIMDDKIVLLHHEDNEEGPLTSGLSWEDGNSDKLIEYLSEK GAYAKKTSPGLCSGHLHEAEKSFEKKYHGQLKSTETKKKVDLTIPQQETYSLKKEW DRKTGYTESGHILSHQHRFENTIPEVREPFCSKEDLHHNELSSQSLVSVSAG |
| SidG | SEQ ID NO.: 20 | MSRSKDEVLEANDSLFGITVQTWGTNDRPSNGMMNFADQQFFGGDVGHASINMKLP VTDKTKQWIEKYCYSQTYDQFKKVKGNEDKTYEEYLKTAKRLIPVELKTQVTRKAQ YDSNGNLVTTHEKAYEQIYFDIDWSWWPGRLQNTEDDMVWEREGKHFEYDEKWKEY LQPEQRVHRGKLGSRKMDYAPTSIIHQRDIPTSELEKITRDHKIHTIEEKLNVVKL LQSKIDEMPHTKMSPSMELMFKNLGINVEKLLDETKDNGVDPTNLEAMREYLTNRL TERKLELETELSEAKKEVDSTQVKNKVEDVYYDFEYKLNQVRKKMEEVNSQLEKMD SLLHKLEGNTSGPIPYTAEIDELMSVLPFLKEELELENGTLSPKSIENLIDHIDEL KNELASKQEKKNERNLNLIKKYEELCEQYKDDEEGLEEALWEEGIDVEEVNSAKKD ISKPAPEIQKLTDLQEQLRNHKESGVKLSSELEETLNSSVKMWKTKIDSPCQVISE SSVKALVSKINSTRPELVKEKEQLPEQEESLSKEAKKAQEELIKIQEFSQFYSENS SAYMVIGLPPHHQVSLPLAVNGKRGLHPEAMLKKMHELVAGPEKKEENLHTNNCSL TSIEVLSAGAQHDPLLHSIMGTRALGFFGTPQQVLENAKLTSKTINEGKKSNIFTP LVTASPLDRALGYAMSIYMDPEASKAKQNAGLALGVLVGLAKTPGIIGSLLNPKQ GFNDILNTLNLVYSRNSTGLKVGLTLMALPAMIVLAPLAAIQKGVEVIAETIAKPF KLIANLFKQKPESTDEITVSVGSKKVAEKEGSYSNTALAGLVNSKIKSKIDENTIT VEFQKSPQKMIEEFESQLKENPGKVVVLSEKAHNAVLKFVSKSDDEALKQKFYDCC NQSVARSQKFAPKTRDEIDELVEEVTSTDKTELTTSPRQEPSMSSTIDEEENIDSE HQIETGTESTMRI |
| VpdA | SEQ ID NO.: 21 | MKTKQEVSQQDKLKDSKSSTPLQTKETWFISDALNITFDPYDFSISVTEQAPMPYR IVESGGGSRILAHIGALDELTRHGLKFTEFSGSSAGAMVAAFAYLGYNCSEIKQII SWFNEDKLLDSPLIFNFNNIKQIFNKGGLSSAKLMRQAANYVILKKVMDIISDEKF KTRFAKFQNFLEENIYRCPENITFQTLARIKEICPECELGEKLFITGTNLSTQKHE VFSIDTTPSMALADAIIISANLPIAFERICYQGNVYSDGGISNNLPAHCFSEKGHK TTFLKHKDDVDFSVLALQFDNGLEENALYSQNPIPKWSWLSNTFYSLITGHPNVTE NWYEDLQILRRHAHQSILIKTPTIALTNLTISQDTKKALVESGRTAAKTYLELHEF YTDDYGNIRHNECLHEKFQKPEELLDYCVLHSHFELLKKIKQAISCSQYLEKGYKH YLCELCDNLLPPQLKCPNEGSGTEQPEIKLEKDTIICEKNNNSGLTFSMTFFGVPS |

TABLE 1-continued

| | | |
|---|---|---|
| | | PLVKTLNQDSPELKIKLFTGLYPILIQNWQNLCPVSGISGILNSIRMSFVEISSTD<br>TCIKTLIDKLNEIEIGHFLIFVFKAALKNYDKHDFILLLKNLKHLHHSIELIRNKP<br>FHSDDRFYGQWSFEGHDPKRILEFIKSDDISGLMTILEDKKALPNNKPN |
| Lpg0969 | SEQ ID<br>NO.: 22 | MVSLEHIQKLISECRKLGKDGLDNGTNGLIPELEIDVVPPSAFLGVGNNPAIFVNS<br>KTYKLMRTTHEKWVENKTIVEKSYLLSQPAIKIIGAIVHETGHAFNVAAKIPNTEA<br>NACIFEIEVLMRLFQVKSPLLLGCTELDMQSYFKSRLTDYNKCVKDCQCLAEMVEF<br>ITHQFKLDEVSISEKENQIPLLSISNKWPGLFAKKQIAPDMDKLLTSPVTITPEVK<br>ILFYQLVKEHFHSPETEIKLDI |
| Lpg1978 | SEQ ID<br>NO.: 23 | MYKIYSYLGWRIDMKTENLPQAGQEAQIDKKIHFIWVGHIMPQKNIQVVSEWAEKN<br>PGYETIIWVDKKIAPAKELDLFILDMKSKGITVKDINEEGVCRDSIRHELDQESPN<br>YGMVSDMLRLNILAAEGGIYLDSDILCSAPFPDEIYAPFGFLLSPWSQGANNTLCN<br>DIILCSKGNQIIQQLADAIEQSYIARDSFEFTHEYASMKETKGERIAKTLGVTGPG<br>FLFHQLKKMGILNDKSEMEAIHWELQDQRYLIDGSVKEPDYFYVPQNNTNDASWVP<br>SIKRPGIENMSFQERLENAVQLIAFDIQKTGLFNLDHYANELKVKQNSWCIAAETS<br>PELKPDSYLLIRPRDKTGEWTLYYVDEDKKLNPVTLPVIKGAIKLSEVSDPLRKFH<br>TLLSQVSDPVNPTAHELKQIGRALIELKPRQDEWHCKNKWSGAEEIAQELWQRITS<br>NETLRAQIKQCFTQFESLKPRVAELGLTRASGAGTEVEAHESTVKEQEIISQNTVG<br>EEGTKEKNSVQLASENSSDEKIKTAHDLIDEIIQDVIQLDGKLGLLGGNTRQLEDG<br>RVINIPNGAAMIFDDYKKYKQGELTAESALESMIKIAKLSNQLNRHTFFNQRQPET<br>GQFYKKVAAIDLQTTIAAEYDNNHGLRI |
| YopE | SEQ ID<br>NO.: 24 | MKISSFISTSLPLPTSVSGSSSVGEMSGRSVSQQTSDQYANNLAGRTESPQGSSLA<br>SRIIERLSSVAHSVIGFIQRMFSEGSHKPVVTPAPTPAQMPSPTSFSDSIKQLAAE<br>TLPKYMQQLNSLDAEMLQKNHDQFATGSGPLRGSITQCQGLMQFCGGELQAEASAI<br>LNTPVCGIPFSQWGTIGGAASAYVASGVDLTQAANEIKGLAQQMQKLLSLM |
| SptP | SEQ ID<br>NO.: 25 | MLKYEERKLNNLTLSSFSKVGVSNDARLYIAKENTDKAYVAPEKFSSKVLTWLGKM<br>PLFKNTEVVQKHTENIRVQDQKILQTFLHALTEKYGETAVNDALLMSRINMNKPLT<br>QRLAVQITECVKAADEGFINLIKSKDNVGVRNAALVIKGGDTKVAEKNNDVGAESK<br>QPLLDIALKGLKRTLPQLEQMDGNSLRENFQEMASGNGPLRSLMTNLQNLNKIPEA<br>KQLNDYVTTLTNIQVGVARFSQWGTCGGEVERWVDKASTHELTQAVKKIHVIAKEL<br>KNVTAELEKIEAGAPMPQTMSGPTLGLARFAVSSIPINQQTQVKLSDGMPVPVNTL<br>TFDGKPVALAGSYPKNTPDALEAHMKMLLEKECSCLVVLTSEDQMQAKQLPPYFRG<br>SYTFGEVHTNSQKVSSASQGEAIDQYNMQLSCGEKRYTIPVLHVKNWPDHQPLPST<br>DQLEYLADRVKNSNQNGAPGRSSSDKHLPMIHCLGGVGRTGTMAAALVLKDNPHSN<br>LEQVRADFRDSRNNRMLEDASQFVQLKAMQAQLLMTTAS |
| SopE2 | SEQ ID<br>NO.: 26 | MTNITLSTQHYRIHRSDVEPVKEKTTEKDIFAKSITAVRNSFISLSTSLSDRFSLH<br>QQTDIPTTHFHRGNASEGRAVLTSKTVKDFMLQKLNSLDIKGNASKDPAYARQTCE<br>AILSAVYSNNKDQCCKLLISKGVSITPFLKEIGEAAQNAGLPGEIKNGVFTPGGAG<br>ANPFVVPLIASASIKYPHMFINHNQQVSFKAYAEKIVMKEVTPLFNKGTMPTPQQF<br>QLTIENIANKYLQNAS |
| SopB/SigD | SEQ ID<br>NO.: 27 | MQIQSFYHSASLKTQEAFKSLQKTLYNGMQILSGQGKAPAKAPDARPEIIVLREPG<br>ATWGNYLQHQKASNHSLHNLYNLQRDLLTVAATVLGKQDPVLTSMANQMELAKVKA<br>DRPATKQEEAAAKALKKNLIELIAARTQQQDGLPAKEAHRFAAVAFRDAQVKQLNN<br>QPWQTIKNTLTHNGHHYTNTQLPAAEMKIGAKDIFPSAYEGKGVCSWDTKNIHHAN<br>NLWMSTVSVHEDGKDKTLFCGIRHGVLSPYHEKDPLLRHVGAENKAKEVLTAALFS<br>KPELLNKALAGEAVSLKLVSVGLLTASNIFGKEGTMVEDQMRAWQSLTQPGKMIHL<br>KIRNKDGDLQTVKIKPDVAAFNVGVNELALKLGFGLKASDSYNAEALHQLLGNDLR<br>PEARPGGWVGEWLAQYPDNYEVVNTLARQIKDIWKNNQHHKDGGEPYKLAQRLAML<br>AHEIDAVPAWNCKSGKDRTGMMDSEIKREIISLHQTHMLSAPGSLPDSGGQKIFQK<br>VLLNSGNLEIQKQNTGGAGNKVMKNLSPEVLNLSYQKRVGDENIWQSVKGISSLIT<br>S |
| SipA | SEQ ID<br>NO.: 28 | MVTSVRTQPPVIMPGMQTEIKTQATNLAANLSAVRESATTTLSGEIKGPQLEDFPA<br>LIKQASLDALFKCGKDAEALKEVFTNSNNVAGKKAIMEFAGLFRSALNATSDSPEA<br>KTLLMKVGAEYTAQIIKDGLKEKSAFGPWLPETKKAEAKLENLEKQLLDIIKNNTG<br>GELSKLSTNLVMQEVMPYIASCIEHNFGCTLDPLTRSNLTHLVDKAAAKAVEALDM<br>CHQKLTQEQGTSVGREARHLEMQTLIPLLLRNVFAQIPADKLPDPKIPEPAAGPVP<br>DGGKKAEPTGINININIDSSNHSVDNSKHINNSRSHVDNSQRHIDNSNHDNSRKTI<br>DNSRTFIDNSQRNGESHHSTNSSNVSHSHSRVDSTTHQTETAHSASTGAIDHGIAG<br>KIDVTAHATAEAVTNASSESKDGKVVTSEKGTTGETTSFDEVDGVTSKSIIGKPVQ<br>ATVHGVDDNKQQSQTAEIVNVKPLASQLAGVENVKTDTLQSDTTVITGNKAGTTDN<br>DNSQTDKTGPFSGLKFKQNSFLSTVPSVTNMHSMHFDARETFLGVIRKALEPDTST<br>PFPVRRAFDGLRAEILPNDTIKSAALKAQCSDIDKHPELKAKMETLKEVITHHPQK<br>EKLAEIALQFAREAGLTRLKGETDYVLSNVLDGLIGDGSWRAGPAYESYLNKPGVD<br>RVITTVDGLHMQR |
| YpkA | SEQ ID<br>NO.: 29 | MKSVKIMGTMPPSISLAKAHERISQHWQNPVGELNIGGKRYRIIDNQVLRLNPHSG<br>FSLFREGVGKIFSGKMFNFSIARNLTDTLHAAQKTTSQELRSDIPNALSNLFGAKP<br>QTELPLGWKGEPLSGAPDLEGMRVAETDKFAEGESHISIIETKDKQRLVAKIERSI<br>AEGHLFAELEAYKHIYKTAGKHPNLANVHGMAVVPYGNRKEEALLMDEVDGWRCSD<br>TLRTLADSWKQGKINSEAYWGTIKFIAHRLLDVTNHLAKAGVVHNDIKPGNVVFDR<br>ASGEPVVIDLGLHSRSGEQPKGFTESFKAPELGVGNLGASEKSDVFLVVSTLLHCI<br>EGFEKNPEIKPNQGLRFITSEPAHVMDENGYPIHRPGIAGVETAYTRFITDILGVS<br>ADSRPDSNEARLHEFLSDGTIDEESAKQILKDTLTGEMSPLSTDVRRITPKKLREL<br>SDLLRTHLSSAATKQLDMGGVLSDLDTMLVALDKAEREGGVDKDQLKSFNSLILKT |

TABLE 1-continued

| | | |
|---|---|---|
| | | YRVIEDYVKGREGDTKNSSTEVSPYHRSNFMLSIVEPSLQRIQKHLDQTHSFSDIG<br>SLVRAHKHLETLLEVLVTLSQQGQPVSSETYGFLNRLAEAKITLSQQLNTLQQQQE<br>SAKAQLSILINRSGSWADVARQSLQRFDSTRPVVKFGTEQYTAIHRQMMAAHAAIT<br>LQEVSEFTDDMRNFTVDSIPLLIQLGRSSLMDEHLVEQREKLRELTTIAERLNRLE<br>REWM |
| YopM | SEQ ID<br>NO.: 30 | MFINPRNVSNTFLQEPLRHSSNLTEMPVEAENVKSKTEYYNAWSEWERNAPPGNGE<br>QREMAVSRLRDCLDRQAHELELNNLGLSSLPELPPHLESLVASCNSLTELPELPQS<br>LKSLQVENNNLKALPDLPPSLKKLHVRENDLTDLPELPQSLESLRVDNNNLKALSD<br>LPPSLEYLTASSNKLEELPELQNLPFLAAIYADNNLLETLPDLPPSLKKLHVREND<br>LTDLPELPQSLESLQVDNNNLKALSDLPPSLEYLTASSNKLEELPELQNLPFLAAI<br>YADNNLLETLPDLPPHLEILVASYNSLTELPELPQSLKSLRVDNNNLKALSDLPPS<br>LEYLTASSNKLEELPELQNLPFLAAIYADNNLLETLPDLPPSLKKLHVRENDLTDL<br>PELPQSLTFLDVSDNNISGLSELPPNLYYLDASSNEIRSLCDLPPSLVDLNVKSNQ<br>LSELPALPPHLERLIASFNYLAEVPELPQNLKQLHVEQNALREFPDIPESLEELEM<br>DSERVVDPYEFAHETTDKLEDDVFE |
| Amatoxin | SEQ ID<br>NO.: 31 | MSDINATRLPIWGIGCNPCVGDDVTTLLTRGEALC |
| Phallacidin | SEQ ID<br>NO.: 32 | MSDINATRLPAWLVDCPCVGDDVNRLLTRGESLC |
| Killer toxin<br>KP1 | SEQ ID<br>NO.: 33 | MIKPERSILTILIGILCLLAYVLANGEPHDGDNEWSSYCSDQGFRRSDDGLVTTPD<br>VGQESIGKNSINGSELVDYLQCLKVRLNGQKQVVSNDGWLLLLVQEPSVNVTQKAM<br>SECNYNVSSGHKAGSYIQVTNTPADYKVISRRGSYEGDQLPEDVKPYFGVQKTSDY<br>RPISKRINPNLTLRQLAYNFAALNMCSLWCNSCISRSCPYYIAELTVHVNNIHHGT<br>VWLHHFCRNASPQGGNLYSTLTISHKDTAYYVGTGWWKVRSTAATTNDVAGDWYPA<br>SWNQYWCGPHY |
| Killer toxin<br>KP6 | SEQ ID<br>NO.: 34 | MLIFSVLMYLGLLLAGASALPNGLSPRNNAFCAGFGLSCKWECWCTAHGTGNELRY<br>ATAAGCGDHLSKSYYDARAGHCLFSDDLRNQFYSHCSSLNNNMSCRSLSKRTIQDS<br>ATDTVDLGAELHRDDPPPTASDIGKRGKRPRPVMCQCVDTTNGGVRLDAVTRAACS<br>IDSFIDGYYTEKDGFCRAKYSWDLFTSGQFYQACLRYSHAGTNCQPDPQYE |
| Killer Toxin<br>K1 | SEQ ID<br>NO.: 35 | MTKPTQVLVRSVSILFFITLLHLVVALNDVAGPAETAPVSLLPREAPWYDKIWEVK<br>DWLLQRATDGNWGKSITWGSFVASDAGVVIFGINVCKNCVGERKDDISTDCGKQTL<br>ALLVSIFVAVTSGHHLIWGGNRPVSQSDPNGATVARRDISTVADGDIPLDFSALND<br>ILNEHGISILPANASQYVKRSDTAEHTTSFVVTNNYTSLHTDLIHHGNGTYTTFTT<br>PHIPAVAKRYVYPMCEHGIKASYCMALNDAMVSANGNLYGLAEKLFSEDEGQWETN<br>YYKLYWSTGQWIMSMKFIEESIDNANNDFEGCDTGH |
| Killer Toxin<br>K28 (KHR) | SEQ ID<br>NO.: 36 | MGHLAILFSIIAVLNIATAVASSDSIYLKGHRVGQDIDSLYRVYDNGTMYPVTFNE<br>WLNDLTGMNDLATNNATILKRDSSDVSCVTETCQYVDYHVDDEGVITIDISTYRIP<br>VEWDSGSAGNASYGVSKRDTKYETFCKKKICGINVSGFCNAYDFAVHAFDEGGSVY<br>NPVSGITDRIKEATKRDKTECLGYELDHVRIDPAVDWSISISTWKQGSANCDTQAS<br>ADSLKCAAQKALESEHNHQKTAFCIHLDNGGSFNLDIRLISELSFSKYNPWALPCP<br>KYKGSNSWQVVSDCFQ |
| Killer Toxin<br>K28 (KHS) | SEQ ID<br>NO.: 37 | MPRFAIIFALLIAYSLFLSTLFTGSIPDRANTVTSNAPCQVVIWDWIRTRRICNCC<br>SRLCYSLLGRSNLSRTAKRGVCTIAGAVLATAAVIVAAVLVGKSSGSATKRGLTKT<br>ISVLNHTIPFTDHILNGQTLSNGTGSNFVTIGFSGYAVHATIKRASTTDIISWVIP<br>ESMEPTLARVASYVSSSSINLAAVPDTGGNASALSFQNAVQEFATSWVSMTYDQSY<br>GDLRNVANDEGGEEILILMRKRSYRISFQVIETGSTALLLRTRRVVSQLITMTYLV<br>TVQARVGIQIGDIFQHYGGIDNYVMTSISVLRTLEDKAFHENKLLIVREPPNKSNQ<br>DANQSYRLRPFSANDLIQNLKSVDIGFLAFCSFFDKYAHYPEIIMMKITIFISKGN<br>LWSIIYVIQARYVRKRVMKVRGQMPGGLLTNMESLLNIVSTPNLNISEFHIQTHSM<br>SQSKPMYFQKQCYSSQNNIIYIYNSIHITCGAVYVIVHDVRTPSVFVLIELRNCKP<br>LKNSWCETTKTSPRDTKIKKNEYNETVCRRAGALLDGRVRTIRFLMMRTHWSRVKG<br>VSCNTANRLSRFCNHVVSYYPSQNATIHLLPTSLRAESLEQQYTTRPLSSSNNRFC<br>CLKSIFINNCKKACESPSLVSCNLQQTAELLMVYYLYICEACYVSRNHDLLSKQCM<br>STVRAVYVARMRLPKERSTFPCMPRLCWLVNGVVVV |
| Anthrax<br>lethal factor<br>endopeptidase | SEQ ID<br>NO.: 38 | MHVKEKEKNKDENKRKDEERNKTQEEHLKEIMKHIVKIEVKGEEAVKKEAAEKLLE<br>KVPSDVLEMYKAIGGKIYIVDGDITKHISLEALSEDKKKIKDIYGKDALLHEHYVI<br>AKEGYEPVLVIQSSEDYVENTEKALNVYYEIGKILSRDILSKINQPYQKFLDVLNT<br>IKNASDSDGQDLLFTNQLKEHPTDFSVEFLEQNSNEVQEVFAKAFAYYIEPQHRDV<br>LQLYAPEAFNYMDKFNEQEINLSLEELKDQRMLSRYEKWEKIKQHYQHWSDSLSEE<br>GRGLLKKLQIPIEPKKDDIIHSLSQEEKELLKRIQIDSSDELSTEEKEFLKKLQID<br>IRDSLSEEEKELLNRIQVDSSNPLSEKEKEFLKKLKLDIQPYDINQRLQDTGGLID<br>SPSINLDVRKQYKRDIQNIDALLHQSIGSTLYNKIYLYENMNINNLTATLGADLVD<br>STDNTKINRGIFNEFKKNFKYSISSNYMIVDINERPALDNERLKWRIQLSPDTRAG<br>YLENGKLILQRNIGLEIKDVQIIKQSEKEYIRIDAKVVPKSKIDTKIQEAQLNINQ<br>EWNKALGLPKYTKLITFNVHNRYASNIVESAYLILNEWKNNIQSDLIKKVTNYLVD<br>GNGRFVFTDITLPNIAEQYTHQDEIYEQVHSKGLYVPESRSILLHGPSKGVELRND<br>SEGFIHEFGHAVDDYAGYLLDKNQSDLVTNSKKFIDIFKEEGSNLTSYGRTNEAEF<br>FAEAFRLMHSTDHAERLKVQKNAPKTFQFINDQIKFIINS |

TABLE 1-continued

| | | |
|---|---|---|
| Shiga Toxin | SEQ ID NO.: 39 | MKCILLKWVLCLLLGFSSVSYSREFTIDFSTQQSYVSSLNSIRTEISTPLEHISQG<br>TTSVSVINHTPPGSYFAVDIRGLDVYQARFDHLRLIIEQNNLYVAGFVNTATNTFY<br>RFSDFAHISVPGVTTVSMTTDSSYTTLQRVAALERSGMQISRHSLVSSYLALMEFS<br>GNTMTRDASRAVLRFVIVTAEALRFRQIQREFRQALSETAPVYTMTPGDVDLTLNW<br>GRISNVLPEYRGEDGVRVGRISFNNISAILGTVAVILNCHHQGARSVRAVNEESQP<br>ECQITGDRPVIKINNTLWESNTAAAFLNRKSQSLYTTGE |
| Saporin Toxin | SEQ ID NO.: 40 | MKSWIMLVVTWLIILQTTVTAVIIYELNLQGTTKAQYSTFLKQLRDDIKDPNLHYG<br>GTNLPVIKRPVGPPKFLRVNLKASTGTVSLAVQRSNLYVAAYLAKNNNKQFRAYYF<br>KGFQITTNQLNNLFPEATGVSNQQELGYGESYPQIQNAAGVTRQQAGLGIKKLAES<br>MTKVNGVARVEKDEALFLLIVVQMVGEAARFKYIENLVLNNFDTAKEVEPVPDRVI<br>ILENNWGLLSRAAKTANNGVFQTPLVLTSYAVPGVEWRVTTVAEVEIGIFLNVDNN<br>GLPSIIYNNIISGAFGDTY |
| Ricin Toxin | SEQ ID NO.: 41 | MYAVATWLCFGSTSGWSFTLEDNNIFPKQYPIINFTTAGATVQSYTNFIRAVRGRL<br>TTGADVRHDIPVLPNRVGLPINQRFILVELSNHAELSVTLALDVTNAYVVGYRAGN<br>SAYFFHPDNQEDAEAITHLFTDVQNRYTFAFGGNYDRLEQLAGNLRENIELGNGPL<br>EEAISALYYYSTGGTQLPTLARSFIICIQMISEAARFQYIEGEMRTRIRYNRRSAP<br>DPSVITLENSWGRLSTAIQESNQGAFASPIQLQRRNGSKFSVYDVSILIPIIALMV<br>YRCAPPPSSQFSLLIRPVVPNFNADVCMDPEPIVRIVGRNGLCVDVRDGRFHNGNA<br>IQLWPCKSNTDANQLWTLKRDNTIRSNGKCLTTYGYSPGVYVMIYDCNTAATDATR<br>WQIWDNGTIINPRSSLVLAATSGNSGTTLTVQTNIYAVSQGWLPTNNTQPFVTTIV<br>GLYGLCLQANSGQVWIEDCSSEKAEQQWALYADGSIRPQQNRDNCLTSDSNIRETV<br>VKILSCGPASSGQRWMFKNDGTILNLYSGLVLDVRRSDPSLKQIILYPLHGDPNQI<br>WLPLF |

In some embodiments, the death agent is an overexpressed product of genetic element selected from DNA or RNA. In some embodiments, the genetic element is a Growth Inhibitory (GIN) sequence such as GIN11.

In some embodiments, the death agent is a ribosomally encoded xenobiotic agent, a ribosomally encoded poison, a ribosomally encoded endogenous or exogenous gene that results in severe growth defects upon mild overexpression, a ribosomally encoded recombinase that excises an essential gene for viability, a limiting factor involved in the synthesis of a toxic secondary metabolite, or any combination thereof. In some embodiments, the ribosomally encoded death agent is Cholera toxin, SpvB toxin, CARDS toxin, SpyA Toxin, HopU1, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, or any combination thereof.

Along with one or more positive selection markers, a plasmid (such as PLASMID 2) can also include one or more negative selection markers under control of a different DNA binding sequence to enable binary selection. The plasmid (e.g., PLASMID 2) can encode for one or more of negative selection markers in Table 1 driven by a promoter which depends on the DBD present in the PPI integration plasmid—DNA Binding Sequence (DBS), for example, the LexAop sequence (DBS) which can become bound by LexA (DBD). In some embodiments, to ensure repression of the 'death agents,' the plasmid (e.g., PLASMID 2) can include a silencing construct such as a TetR'-Tup11 fusion driven by a strong promoter (such as ADH1) to bind the DBD and silence transcription in the presence of doxycycline. The plasmid (e.g., PLASMID 2) can comprise bacterial selection and propagation markers (i.e. on/and AmpR), and yeast replication and selection markers (i.e. LEU2 and CEN or 2 um) as well.

Figure 7:
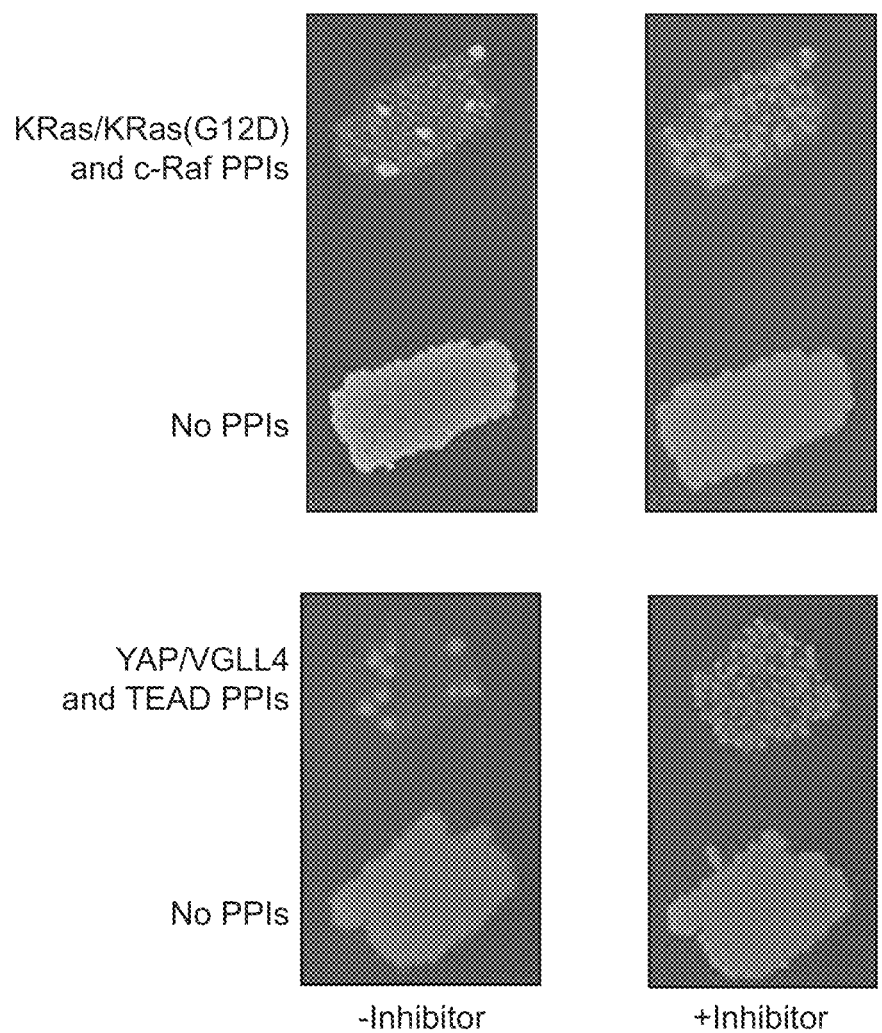
FIG. 7 illustrates two platforms to identify a compound that specifically disrupts a protein-protein interaction in cell culture by selecting for cytotoxic reporter.

FIG. 7 shows two platforms to identify a disrupting compound in cell culture using both a negative and a positive selection marker. In the first platform, KRas and KRas(G12D) fused to DBDs and c-Raf fused to AD were expressed in yeast cells. In the absence of inhibitors, the KRas(G12D) and c-Raf maintain an interaction to drive expression of a cytotoxic reporter, resulting in a low amount of cell growth/survival. A nutritional reporter was controlled by KRas and c-Raf interaction. The cells were patched onto selective media for a nutritional marker with or without inhibitor and visualized after 4 days of growth at 30° C. In cell populations with KRas(G12D) and c-Raf interaction, only those with the inhibitor showed enhanced cell viability, illustrating the specificity of the inhibitor for the KRas (G12D) and c-Raf interaction.

In the second platform, VGLL4 and YAP fused to DBDs and TEAD fused to AD were expressed in cells. In the absence of inhibitors, the YAP and TEAD maintain an interaction to drive expression of cytotoxic reporter. A nutritional reporter was controlled by VGLL4 and TEAD interaction. The cells were patched onto selective media for a nutritional marker with or without inhibitor and visualized after 4 days of growth at 30° C. In cell populations with YAP and TEAD interaction, only those with the inhibitor showed enhanced cell viability, illustrating the specificity of the disruptor to YAP and TEAD interaction.

In some embodiments, the host cell can further comprises more than one sequence for expressing a positive control reporter that is activated by a promoter DNA sequence specific for a DNA binding moiety. In some embodiments, the host cell further comprises more than one sequence for expressing a death agent that is activated by a promoter DNA sequence specific for a DNA binding moiety.

Figure 4A:
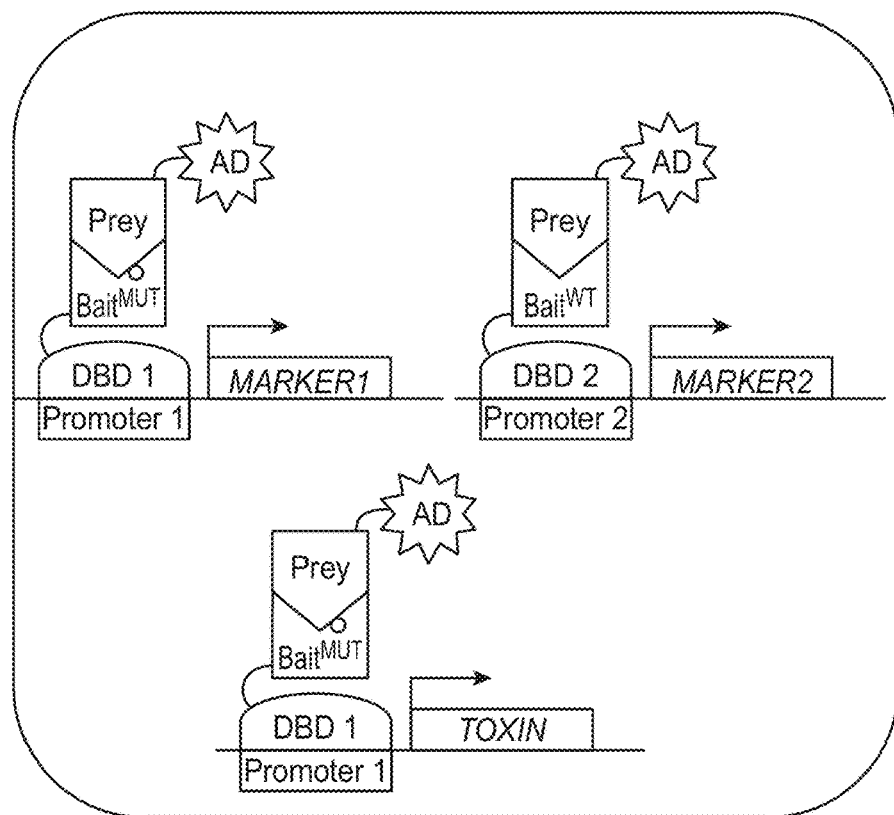
FIGS. 4A and 4B show an embodiment of a platform to identify a compound that specifically disrupts a protein-protein interaction, where the platform includes two positive selection markers and a negative selection markers. In these figures, the compound may interact with the prey to disrupt the prey-bait interaction.
Figure 4B:
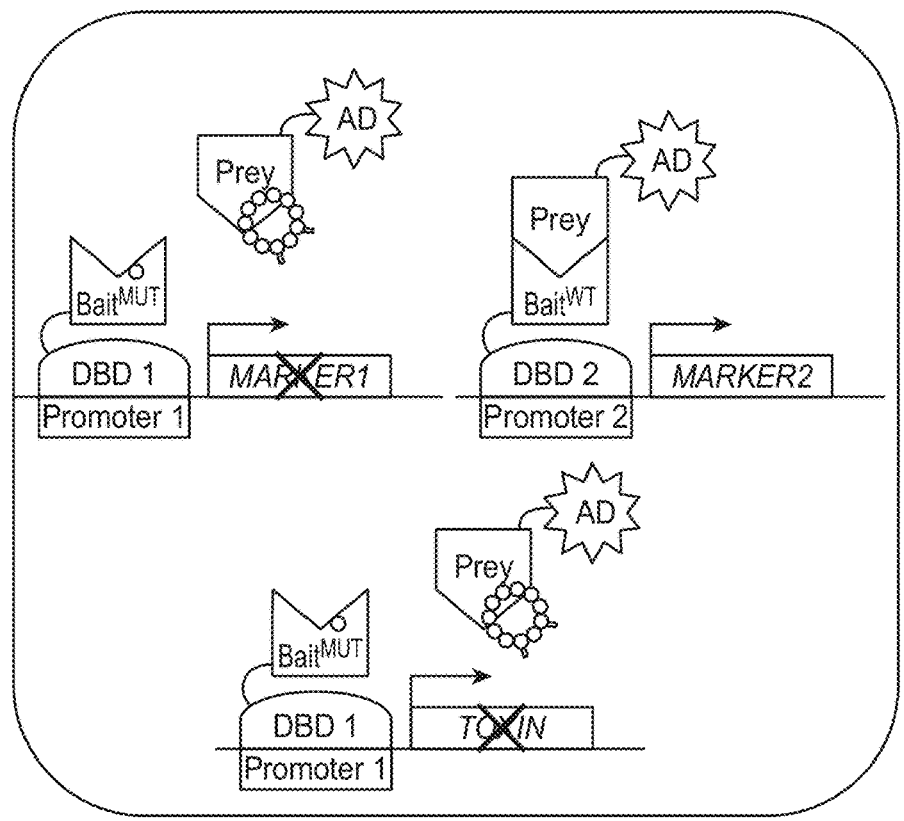

FIGS. 4A and 4B illustrate a platform with more than one positive selection markers and a negative selection marker for identifying a compound that disrupts a protein-protein interaction within a complex in a specific manner. The multiple selection markers can reduce false positive rate due to mutations that leads to avoidance of selection. DBD land DBD2 are promoter specific DNA-binding domains. AD refers to an activation domain. Prey, BaitWT, and BaitMut refer to three proteins, wherein BaitWT and BaitMut each interacts with Prey. Broken arrows indicate active expression of the reporter. Markers land 2 refer to positive selection markers, toxins refers to death agent. The ring comprising smaller circular items illustrates a potential inhibitor (e.g., a randomly produced peptide). Two scenarios are shown; FIG. 4A illustrates a case where a peptide is unable to disrupt the pairwise interaction of interest, and death agent is expressed, leading to cell death. FIG. 4B illustrates a case where a peptide is able to disrupt the Prey and BaitMut interaction by acting on the Prey without disrupting the BaitWT and Prey interaction. Peptide disruption activity is assayed by survival, and specificity is assayed by growth on the expressed positive selection reporter, marker 2.

Figure 5A:
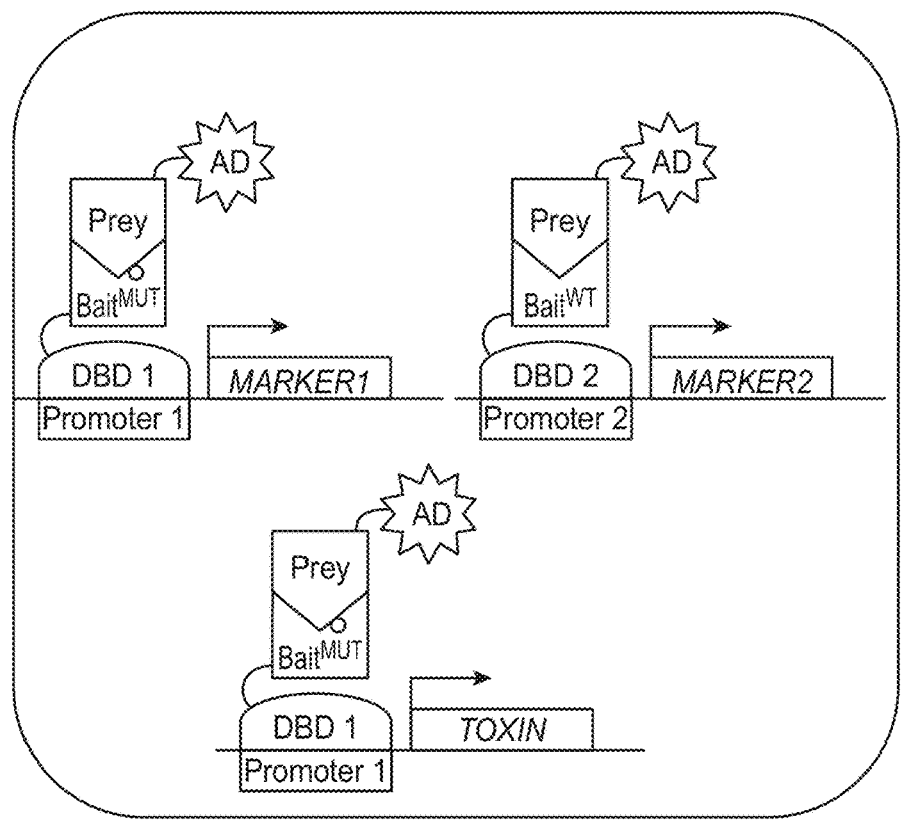
FIGS. 5A and 5B show an embodiment of a platform to identify a compound that specifically disrupts a protein-protein interaction in a system with two positive selections and a negative selection. In contrast with FIGS. 4A and 4B, in these figures, the compound may act on the bait (rather than the prey) to disrupt the prey-bait interaction.
Figure 5B:
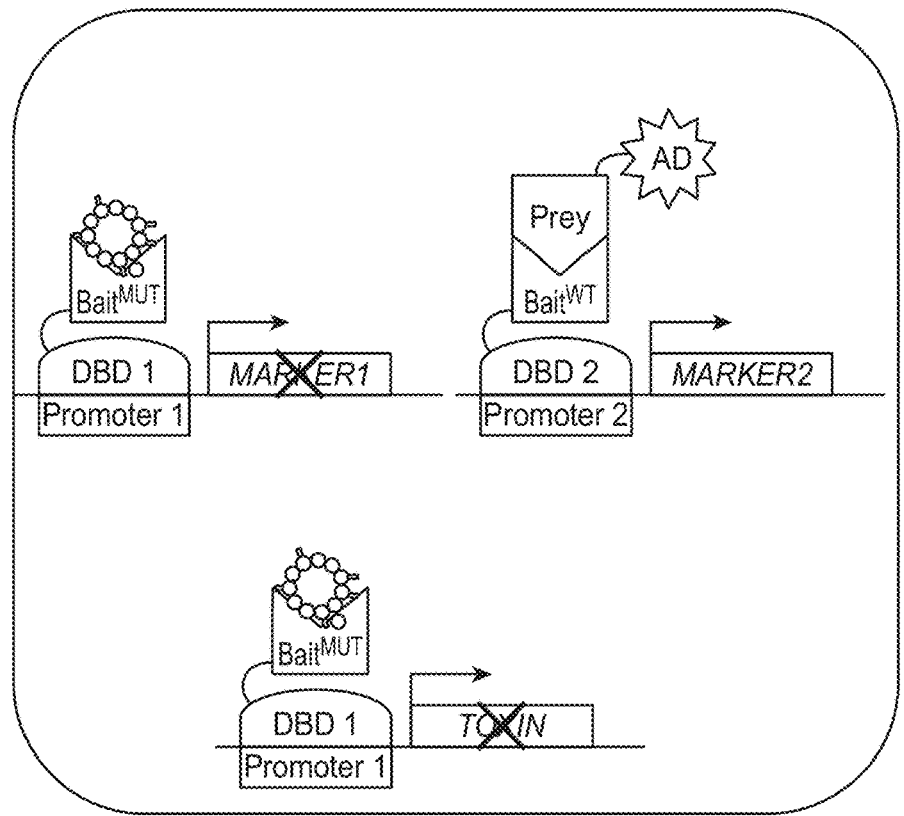

FIGS. 5A and 5B show a platform that is analogous to the platform of FIGS. 4A and 4B, where the inhibitor binds to the bait instead of the prey. More specifically, the platform of FIGS. 5A and 5B has more than one positive selection marker and one negative selection marker for identifying a compound that disrupts a protein-protein interaction within a complex in a specific manner. The multiple selection markers can reduce false positive rate due to mutations that leads to avoidance of selection. DBD1 and DBD2 are promoter specific DNA-binding domains. AD refers to an activation domain. Prey, BaitWT, and BaitMut refer to three proteins, wherein BaitWT and BaitMut each interacts with Prey. Broken arrows indicate active expression of the reporter. Markers 1 and 2 refers to positive selection markers, toxins refers to death agent. The ring comprising smaller circular items illustrates a randomly produced peptide. Two scenarios are shown; FIG. 5A illustrates a case where a peptide is unable to disrupt the pairwise interaction of interest, and death agent is expressed, leading to cell death. FIG. 5B illustrates a case where a peptide is able to disrupt the Prey and BaitMut interaction by acting on the BaitMut without disrupting the BaitWT and Prey interaction, and peptide disruption activity is assayed by survival and specificity is assayed by growth on the expressed positive selection reporter, marker 2.

A plasmid (e.g., PLASMID 3) can be used to confirm expression of the reporters and the successful construction of the strains. PLASMID 3 can include a direct fusion between the AD and one or multiple DBDs. The plasmid (e.g., PLASMID 3) can further include bacterial selection and propagation markers (i.e. ori and AmpR), and yeast replication and selection markers (i.e. TRP1 and CEN or 2 um).

FIG. 10 illustrates a confirmation plasmid. The depicted plasmid show the integration of two bait-prey fusion proteins, each with its own DBD. Protein tags may be included to enable detection of the proteins. The plasmid may also include propagation and selection markers for growth in hosts.

Disclosed herein, in certain embodiments, is a library of plasmid vectors, each plasmid vector comprising a DNA sequence encoding a different peptide sequence operably linked to a first switchable promoter; a DNA sequence encoding a death agent under control of a second switchable promoter; and a DNA sequence encoding a positive selection reporter under control of a third switchable promoter.

Addition or Expression of Modulators

A molecule from a library that can selectively disrupt or facilitate PPI of interest can be screened by via use of positive and/or negative selection markers in a host cell.

In some embodiments, the molecule is small molecule. In some embodiments, the small molecule is peptidomimetic. The host cell can be made to become permeabilized to small molecules, for example by deletion of drug efflux pumps, such as PDR5, ERG6, or 12geneΔ0HSR (Chinen, 2011), to enable a small molecule screening approach. The host cell can additionally carry mutations to enable more efficient transformation with vectors and/or more efficient uptake small molecules.

In other embodiments, the molecule is peptide or protein. In some embodiments, the peptide or protein is derived from naturally occurring protein product. In another embodiment, the peptide or protein is synthesized protein product. In other embodiments, the peptide or protein is a product of recombinant genes.

In some embodiments, the molecule is introduced to the host cell exogenously. In other embodiments, the molecule is the expression product of test DNA inserted into the host cell, wherein the test DNA comprises of DNA sequences that encodes a polypeptide. Libraries can be formed by delivery of a plurality of test DNA molecules into host cells. In some embodiments, the peptide sequences of the polypeptides in the library are random. In some embodiments, the different peptide sequences are pre-enriched for binding to a target.

To screen for peptides that selectively disrupt or facilitate a PPI of interest, peptides from a randomized peptide library can be applied to the host cell. PLASMID 2 can be further used to express a randomized peptide library (such as a randomized NNK 60-mer sequences). PLASMID 2 can include a restriction site for integration of a randomized peptide library driven by a strong promoter (such as the ADH1 promoter) or an inducible promoter (such as the GAL1 promoter).

In some embodiments, the randomized peptide library is about 60-mer. In some embodiments, the randomized peptide library is from about 5-mer to 20-mer. In some embodiments, the randomized peptide library is less than 15-mer.

The library can also initiate with a fixed sequence of, for example, Methionine-Valine-Asparagine (MVN) for N-terminal stabilization and/or another combination of high-half-life N-end residues (see, for e.g., Varshaysky. Proc. Natl. Acad. Sci. USA. 93:12142-12149 (1996)) to maximize the half-life of the peptide, and terminate with the 3'UTR of a short protein (such as sORF1). The peptide can also be tagged with a protein tag such as Myc. In some embodiments, N-terminal residues of the peptide comprise Met, Gly, Ala, Ser, Thr, Val, or Pro or any combination thereof to minimize proteolysis.

The plurality of different short peptide sequences can be randomly generated by any method (e.g. NNK or NNN nucleotide randomization). The plurality of different short peptide sequences can also be preselected, either by previous experiments selecting for binding to a target, or from existing data sets in the scientific literature that have reported rationally-designed peptide libraries.

In some embodiments, the library comprises polypeptides about 60 amino acids or fewer in length. In another embodiment, the library comprises polypeptides about 30 or fewer amino acids in length. In another embodiment, the library comprises polypeptides about 20 or fewer amino acids in length.

Modification of Disrupting or Facilitating Peptides

The peptide that disrupts or facilitates PPI can also be a product of post-translational modification. The post-translational modification can include any one or combination of cleavage, cyclization, bi-cyclization, methylation, halogenation, glycosylation, acylation, phosphorylation, and acetylation. In some embodiments, the methylation comprises reacting with an N-methyltransferase. In some embodiments, the post-translational modification is done by naturally occurring enzymes. In some embodiments, the post-translational modification is done by synthetic enzymes. In some embodiments, the synthetic enzymes are chimeric.

The peptide can be ribosomally synthesized and post-translationally modified peptide (RiPP) whereby the core peptide is flanked by prepropeptide sequence comprising a leader peptide and recognition sequences which signal for the recruitment of maturation, cleavage, and/or modifying enzymes such as excision or cyclization enzymes including, for example, lanthipeptides maturation enzymes from *Lactococcus lactis* (LanB, LanC, LanM, LanP) patellamide biosynthesis factors from cyanobacteria (PatD, PatG), butelase 1 from *Clitoria ternatea*, and POPB from *Galerina marginata, Lentinula edodes, Omphalotacae olearis, Dendrothele bispora,* or *Amanita bisporigera*, or other species. In some embodiments, the cyclization or bicyclization enzymes are synthetic chimeras.

Figure 11:
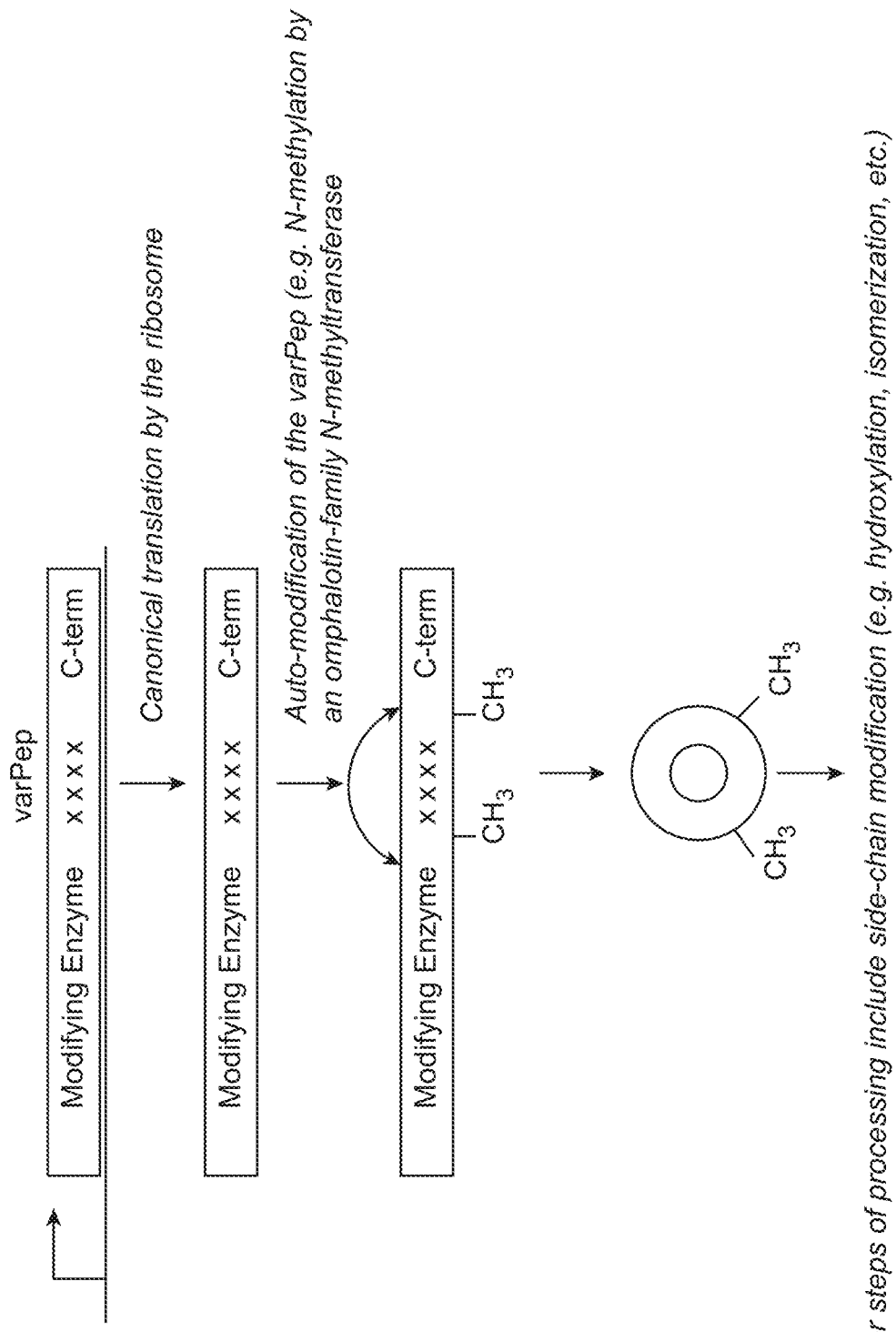
FIG. 11 illustrates a cyclization process of families of RiPP scaffolds that lead to the generation of N-to-C cyclized, backbone N-methylated macrocycles by the action of (1) prolyl oligopeptidases belonging to the PopB family and (2) N-methyltransferases belonging to the omphalotin methyltransferase family. The variable peptide library region is embedded within the primary sequence of the modifying enzyme. N- and C-term sequences refer to consensus binding and processing recognition elements. The N-terminus comprises the enzymatic N-methyltransferase domain, a linker region, and the processing enzymes binding sites.

In one example, as illustrated in FIG. 11, the variable peptide library region is embedded within the primary sequence of a modifying enzyme (e.g., the homolog of the omphalotin N-methyltransferase enzyme from *Dendrothele bispora, Marasmius fiardii, Lentinula edodes, Fomitiporia mediterranea, Omphalotus olearius* or other) and contains random residues, some of which may be post-translationally decorated by additional modifications like hydroxylation, halogenation, glycosylation, acylation, phosphorylation, methylation, acetylation. This diversified variable region is excised and modified to form N-to-C cyclized, optionally backbone N-methylated macrocycles by the action of a prolyl endopeptidase belonging to the PopB family and N-methyltransferases belonging to the omphalotin methyltransferase family. An exemplary list of prolyl endopeptidases is shown in Table 2. An exemplary list of N-methyltransferases is shown in Table 3.

TABLE 2

| | | Amino acid sequences of prolyl endopeptidase type cyclizing enzymes |
|---|---|---|
| *Galerina marginata* CBS 339.88 | SEQ ID NO.: 42 KDR68475.1 hypothetical protein GALMADR AFT_78538 | MSSVTWAPGNYPSTRRSDHVDTYQSASKGEVPVPDPYQWLEESTDEVDKW TTAQADLAQSYLDQNADIQKLAEKFRASRNYAKFSAPTLLDDGHWYWFYN RGLQSQSVLYRSKEPALPDFSKGDDNVGDVFFDPNVLAADGSAGMVLCKF SDGKFFAYAVSHLGGDYSTIYVRSTSSPLSQASVAQGVDGRLSDEVKWF KFSTIIWTKDSKGFLYQRYPARERHEGTRSDRNAMMCYHKVGTTQEEDII VYQDNEHPEWIYGADTSEDGKYLYLYQFKDTSKKNLLWVAELDEDGVKSG IHWRKVVNEYAADYNIITNHGSLVYIKTNLNAPQYKVITIDLSKDEPEIR DFIPEEKDAKLAQVNCANEEYFVAIYKRNVKDEIYLYSKAGVQLTRLAPD FVGAASIANRQKQTHFFLTLSGFNTPGTIARYDFTAPETQRFSILRTTKV NELDPDDFESTQVWYESKDGTKIPMFIVRHKSTKFDGTAAAIQYGYGGFA TSADPFFSPIILTFLQTYGAIFAVPSIRGGGEFGEEWHKGGRRETKVNTF DDFIAAAQFLVKNKYAAPGKVAINGASNGGLLVMGSIVRAPEGTFGAAVP EGGVADLLKFHKFTGGQAWISEYGNPSIPEEFDYIYPLSPVHNVRTDKVM PATLITVNIGDGRVVPMHSFKFIATLQHNVPQNPHPLLIKIDKSWLGHGM GKPTDKNVKDAADKWGFIARALGLELKTVE |
| *Amanita bisporigera* | SEQ ID NO.: 43 ADN19205.1 prolyl oligopeptidase | MPPTPWAPHSYPPTRRSDHVDVYQSASRGEVPVPDPYQWLEENSNEVDEW TTAQTAFTQGYLDKNADRQKLEEKFRASKDYVKFSAPTLLDSGHWYWFYN SGVQSQAVLYRSKKPVLPDFQRGTRKVGEVYFDPNVLSADGTAIMGTCRF SPSGEYFAYAVSHLGVDYFTIYVRPTSSSLSQAPEAEGGDGRLSDGVKWC KFTTIIWTKDSKGFLYQRYPARESLVAKDRDKDAMVCYHRVGTTQLEDII VQQDKENPDWTYGTDASEDGKYIYLVVYKDASKQNLLWVAEFDKDGVKPE IPWRKVINEFGADYHVITNHGSLIYVKTNVNAPQYKVVTIDLSTGEPEIR DFIPEQKDAKLTQVKCVNKGYFVAIYKRNVKDEIYLYSKAGDQLSRLASD FIGVASITNREKQPHSFLTFSGFNTPGTISRYDFTAPDTQRLSILRTTKL NGLNADDFESTQVWYKSKDGTKVPMFIVRHKSTKFDGTAPAIQNGYGGFA ITADPFFSPIMLTFMQTYGAILAVPNIRGGGEFGGEWHKAGRRETKGNTF DDFIAAAQFLVKNKYAAPGKVAITGASNGGFLVCGSVVRAPEGTFGAAVS EGGVADLLKFNKFTGGMAWTSEYGNPFIKEDFDFVQALSPVHNVPKDRVL PATLLMTNAGDDRVVPMHSLKFVANLQYNVPQNPHPLLIRVDKSWLGHGF GKTTDKHTKDAADKWSFVAQSLGLEWKTVD |
| *Hypsizygus marmoreus*] | SEQ ID NO.: 44 KYQ30898.1 Prolyl endopeptidase | MAISPTPWTPNTYPPTRRSSHVDIYKSATRGEVRVADPYQWLEENTEETD KWTTAQEEFTRSYLDKNTDRQRLEDAFRTSTDYAKFSSPTLYEDGRWYWF YNSGLQPQPLIYRSKGKTLPDFSQDDNVVGEVFFDPNLLSDDGTAALSIY DFSDCGKYFAYGISFSGSDFSTIYVRSTESPLAKKNSGSTDDDRLSDEIK HVKFSAVTWTKDSKGFFYQRYPAHENAKEGIETGGDVDAMIYYHVIGTSQ SEDILVHSDKSNPEWMWSIDITEDGKYLILYTMKDSSRKNLMWIAELSKN EIGPNIQWNKIIDVFDAEYHLITNDGPILYVKTNADAPQYKLVTMDISGD KDISRDLIPEDKNANLVQVDCVNRDTFAVIYKRNVKDEIYLYSKTGIQLS RLASDFVGAASISSSREKQPHFFVTMTGFSTPGTVARYDFGAPEEQRWSIY RSVKVNGLNPDDFESKQVWYESKDGTKIPMFIVRHKATKFDGTAPAIQYG YGGFSISINPFFSPTILTFLQTYGAVLAVPNIRGGAEFGEDWHKAGTREK KGNVFDDFVAATQYLVKNKYAGEGKVAINGGSNGGLLVGACINRAPEGTF GAAVAEVGVMDLLKFSKFTIGKAWTSDYGDPDDPKDFDFICPLSPLHNIP TDRVLPPTMLLTADHDDRVVPMHSFKHAATLQYTLPHNPHPLVIRIDKKA GHGAGKSTEKRIKESADKWGFVAQSLGLVWQEPA |
| *Conocybe apala* | SEQ ID NO.: 45 ACQ65797.1 prolyl oligopeptidase | MPPSTPNEYPPTRRSDDVLTYRSEKNGEVVVPDPYQWLEHNTEETDKWTT AQAAFTRAHLDKNPKRNALEEAFTAANDYAKFSAPQLHDDGRWYWYYNTG LQAQTCLWRTRDDTIPDFSKQLDEDVGEIFFDPNALSKDGTAALSTYRFS RDGKYFAYAIAQSGSDFNTIYVRPTDSPLTKRDESGRDPSRLADEVKFVK FSGITWAPNSEGFFYQRYPHIDGATLEEGGIATRRDLHAMVYYHRVGTPQ SEDILIHRDPANPEWMFGVNVTDNGEYIELYISKDSSRKNMLWVANFAMN KIGEQFQWRKVINDFAAEYDVITNHGPVYYFRTDDGAPKHKILSINIDTN ERKLLVPESEDAALFSTVCVNKNYMALIYKRNVKDEVHLYTLEGKPVRRL AEDFVGACTISGKEKQPWFFVTMSGFTSPSTVGRYNFQIPEEENRWSIFR |

TABLE 2-continued

Amino acid sequences of prolyl endopeptidase type cyclizing enzymes

| | | |
|---|---|---|
| | | AAKIKNLNPNDFEASQVWYKSKDGTNVPMFIVRHKSTQFDGTAPALQYGY<br>GGFSISIDPFFSASILTFLKVYGAILVVPSIRGGNEFGEEWHRGGMKQNK<br>VNCFDDFIAATNHLVEHKYAAPGKVAINGGSNGGLLVAACINRAPEGTFG<br>AAIAEVGVHDMLKFHKFTIGKAWTSDYGNPDDPHDFDYIYPISPVHNVPT<br>DKILPPTLLLTADHDDRVVPMHTFKLAATLQHTLPHNPHPLLLRVDKKAG<br>HGAGKPLQLKIREQADKWGFVAQSFQLVWRDGV |
| *Amanita bisporigera* | SEQ ID<br>NO.: 46<br>GenBank<br>HQ225841.1<br>POPB | MPPTPWAPHSYPPTRRSDHVDVYQSASRGEVPVPDPYQWLEENSNEVDEW<br>TTAQTAFTQGYLDKNADRQKLEEKFRASKDYVKFSAPTLLDSGHWYWFYN<br>SGVQSQAVLYRSKKPVLPDFQRGTRKVGEVYFDPNVLSADGTAIMGTCRF<br>SPSGEYFAYAVSHLGVDYFTIYVRPTSSSLSQAPEAEGGDGRLSDGVKWC<br>KFTTITWTKDSKGFLYQRYPARESLVAKDRDKDAMVCYHRVGTTQLEDII<br>VQQDKENPDWTYGTDASEDGKYIYLVVYKDASKQNLLWVAEFDKDGVKPE<br>IPWRKVINEFGADYHVITNHGSLIYVKTNVNAPQYKVVTIDLSTGEPEIR<br>DFIPEQKDAKLTQVKCVNKGYFVAIYKRNVKDEIYLYSKAGDQLSRLASD<br>FIGVASITNREKQPHSFLTFSGFNTPGTISRYDFTAPDTQRLSILRTTKL<br>NGLNADDFESTQVWYKSKDGTKVPMFIVRHKSTKFDGTAPAIQNGYGGFA<br>ITADPFFSPIMLTFMQTYGAILAVPNIRGGGEFGGEWHKAGRRETKGNTF<br>DDFIAAAQFLVKNKYAAPGKVAITGASNGGFLVCGSVVRAPEGTFGAAVS<br>EGGVADLLKFNKFTGGMAWTSEYGNPFIKEDFDFVQALSPVHNVPKDRVL<br>PATLLMTNAGDDRVVPMHSLKFVANLQYNVPQNPHPLLIRVDKSWLGHGF<br>GKTTDKHTKDAADKWSFVAQSLGLEWKTVD |
| *Lentinula edodes* | SEQ ID<br>NO.: 47<br>GenBank<br>GAW09065.1<br>The DOE<br>Joint<br>Genome<br>Institute<br>(JGI)<br>011197;<br>LENED_011197) | MFSATQESPTMSVPQWDPYPPVSRDETSAITYQSKLCGSVTVRDPYSALE<br>VPFDDSEETKAFVHAQRKFARTYLDEIPDRETWLQTLKESWNYRRFTVPK<br>RESDGYTYFEYNDGLQSQMSLRRVKVSEEDTILTESGPGGELFFDPNLLS<br>LDGNAALTGSMMSPCGKYWAYGVSEHGSDWMTTYVRKTSSPHMPSQEKGK<br>DPGRMDDVIRYSRFFIVYWSSDSKGFFYSRYPPEDDEGKGNTPAQNCMVY<br>YHRLGEKQEKDTLVYEDPEHPFWLWALQLSPSGRYALLTASRDASHTQLA<br>KIADIGTSDIQNGIQWLTIHDQWQARFVIIGDDDSTIYFMTNLEAKNYLV<br>ATLDIRHSEAGVKTLVAENPDALLISASILSTDKLVLVYLHNARHEIHVH<br>DLNTGKPIRQIFDNLIGQFSLSGRRDDNDMFVFHSGFTSPGTIYRFRLNE<br>DSNKGTLFRAVQVPGLNLSDFTTESVFYPSKDGTPIHMFITRLKDTPVDG<br>TAPVYIYGYGGFALAMLPTFSVSTLLFCKIYRAMYVVPNIRGGSEFGESW<br>HREGMLDKKQNVFDDFNAATKWLVANKYANKYNVAIRGGSNGGVLTTACA<br>NQAPELYRCVITIGGIIDMLRFPKFTFGALWRSEYGDPEDPEDFDFIYKY<br>SPYHNIPSGDVVLPAMLFFTAAYDDRVSPLHSFKHVAALQYNFPNGPNPV<br>LMRIDLNTGHFAGKSTQKMLEETADEYRCDLLCCNLQL |
| *Omphalotacae olearis* | SEQ ID<br>NO.: 48<br>The DOE<br>Joint<br>Genome<br>Institute<br>(JGI) 2090;<br>OMPOL1_2090 | MSFPGWGPYPPVERDETSAITYSSKLHGSVTVRDPYSQLEVPFEDSEETK<br>AFVHSQRKFARTYLDENPDREAWLETLKKSWNYRRFSALKPESDGHYYFE<br>YNDGLQSQLSLYRVRMGEEDTVLTESGPGGELFFNPNLLSLDGNAALTGF<br>VMSPCGNYWAYGVSEHGSDWMSIYVRKTSSPHLPSQERGKDPGRMNDKIR<br>HVRFFIVSWTSDSKGFFYSRYPPEDDEGKGNAPAMNCMVYYHRIGEDQES<br>DVLVHEDPEHPFWISSVQLTPSGRYILFAASRDASHTQLVKIADLHENDI<br>GTNMKWKNLHDPWEARFTIVGDEGSKIYFMTNLKAKNYKVATFDANHPDE<br>GLTTLIAEDPNAFLVSASIHAQDKLLLVYLRNASHEIHIRDLTTGKPLGR<br>IFEDLLGQFMVSGRRQDNDIFVLFSSFLSPGTVYRYTFGEEKGHSSLFRA<br>ISIPGLNLDDFMTESVFYPSKDGTSVHMFITRPKDVLLDGTSPVLQYGYG<br>GFSLAMLPTFSLSTLLFCKIYRAIYAIPNIRGGSEYGESWHREGMLDKKQ<br>NVFDDFNAATEWLIANKYASKDRIAIRGGSNGGVLTTACANQAPGLYRCV<br>ITIEGIIDMLRFPKFTFGASWRSEYGDPEDPEDFDFIFKYSPYHNIPPPG<br>DTIMPAMLFFTAAYDDRVSPLHTFKHVAALQHNFPKGPNPCLMRIDLNSG<br>HFAGKSTQEMLEETADEYRLKVQ |

TABLE 3

Amino acid sequences of N-methyltransferases

| | | |
|---|---|---|
| *Lentinula edodes* | SEQ ID<br>NO.: 49<br>GenBank<br>GAW09067.1<br>The DOE<br>Joint<br>Genome<br>Institute<br>(JGI)<br>011194;<br>LENED_011194) | METPTLNKSGSLTIVGTGIESIGQMTLQTLSYIEAADKVFYCVIDPATEAF<br>ILTKNKDCVDLYQYYDNGKSRMDTYTQMSEVMLREVRKGLDVVGVFYGHPG<br>VFFVNPSLRALAIAKSEGFKARMLPGVSAEDCLYADLCIDPSNPGCLTYEAS<br>DFLIRERPTNIYSHFILFQVGCVGIADFNFTGFENSKFGILVDRLEKEYGA<br>EHPVVHYIAAMLPHEDPVTDQWTIGQLREPEFYKRVGGVSTFYIPPKERKE<br>INVDIIRELKFLPEGKVPDTRTQIYPPNQWEPEVPTVPAYGSNEHAAIAQL<br>DTHTPPEQYQPLATSKAMTDVMTKLALDPKALAEYKADHRAFAQSVPDLTA<br>NERTALEIGDSWAFRCAMKEMPISLLDNAKQSMEEASEQGFPWIIVVGVVG<br>VVGSVVSSA |
| *Omphalotacae olearis* | SEQ ID<br>NO.: 50<br>The DOE<br>Joint | METSTQTKAGSLTIVGTGIESIGQMTLQALSYIEAAAKVFYCVIDPATEAF<br>ILTKNKNCVDLYQYYDNGKSRLNTYTQMSELMVREVRKGLDVVGVFYGHPG<br>VFVNPSHRALAIAKSEGYRARMLPGVSAEDCLFADLCIDPSNPGCLTYEAS<br>DFLIRDRPVSIHSHLVLFQVGCVGIADFNFTGFDNNKFGVLVDRLEQEYGA |

TABLE 3-continued

Amino acid sequences of N-methyltransferases

| | | |
|---|---|---|
| | Genome Institute (JGI) 2087; OMPOL1_2087 | EHPVVHYIAAMMPHQDPVTDKYTVAQLREPEIAKRVGGVSTFYIPPKARKA SNLDIIRRLELLPAGQVPDKKARIYPANQWEPDVPEVEPYRPSDQAAIAQL ADHAPPEQYQPLATSKAMSDVMTKLALDPKALADYKADHRAFAQSVPDLTP QERAALELGDSWAIRCAMKNMPSSLLDAARESGEEASQNGFPWVIVVGVIG VIGSVMSTE |
| *Dendrothele bispora* | SEQ ID NO.: 51 The DOE Joint Genome Institute (JGI) 765759 | MESSTQTKPGSLIVVGTGIESIGQMTLQALSYIEAASKVFYCVIDPATEAF ILTKNKNCVDLYQYYDNGKSRMDTYTQMAELMLKEVRNGLDVVGVFYGHPG VFVNPSHRALAIARSEGYQARMLPGVSAEDCLFADLCIDPSNPGCLTYEAS DELIRERPVNVHSHLILFQVGCVGIADFNFSGFDNSKFTILVDRLEQEYGP DHTVVHYIAAMMPHQDPVTDKFTIGQLREPEIAKRVGGVSTFYIPPKARKD INTDIIRLLEFLPAGKVPDKHTQIYPPNQWEPDVPTLPPYGQNEQAAITRL EAHAPPEEYQPLATSKAMTDVMTKLALDPKALAEYKADHRAFAQSVPDLTP QERAALELGDSWAIRCAMKNMPSSLLEAASQSVEEASMNGFPWVIVTGIVG VIGSVVSSA |
| *Rhizopogon vinicolor* | SEQ ID NO.: 52 GenBank AM-OR11-026; OAX31299.1 | MTTDTKRGTLTIAGSGIASIAHITLETLSYIKESDKLFYLVCDPVTEAFIQ DNATGDFFDLSVFYDKNKSRYDSYIQMCEIMLRAVRAGHSVLGIFYGHPGV FVSPSHRAIAVAREEGYKARMLPGVSAEDYMFADLEFDPSQSTCNTYEATE LLLRDRPLDPAIQNIIWQVGSVGVVDMEFEKSKFHLLVDRLEQDFGPDHKV VHYIGAVLPQSTTTMDIFTISDLRKENVAKQFGTISTLYIPPRDEGPVSSS MTQAFDFKAGAMVYSPVKWAGPKLNIVSALSPYERDVISQIDTHVAPEGYK ILHTSAAMNKFMTDLSLKPKFLEEYKLYPEAVVESAEGLSNLEKFGLKFGS DGAVYILMKATESDIASGRQLTEDEIAKAHKSVGFPTVLVILPTVIVVLIG RE |
| *Rhizopogon vinicolor* | SEQ ID NO.: 53 GenBank AM-OR11-026; OAX32862.1 | MSTKRGTLTIAGSGIASVGHITLGTLSYIKESDKIFYLVCDPVTEAFIYDN STADCFDLSVFYDKTKGRYDSYIQMCEVMLKAVRAGHDVLGVFYGHPGVFV SPSHRAIAVARQEGYKAKMLPGISAEDYMFADLEFDPSVSGCKTCEATEIL LRDKPLDPTIQNIIWQVGSVGVVDMEFSKSKFQLLVDRLEKDFGPDHKVVH YIGAVLPQSTTTMDTFTIADLRKEDVAKQFGTISTLYIPPRDEGHVNLSMA KVFGGPGASVKLNDSIKWAGPKLNIVSANDPHERDVIAQVDTHVAPEGHKK LRVSAAMKKFMTDLALKPKFLEEYKLDPVAVVESAEGLSNLERFGLKFARS GPADALMKATESDIASGRQLTEEEIAQGTGPVGLQTALALLVLLGLGVAIV TRPDD |

Figure 12:
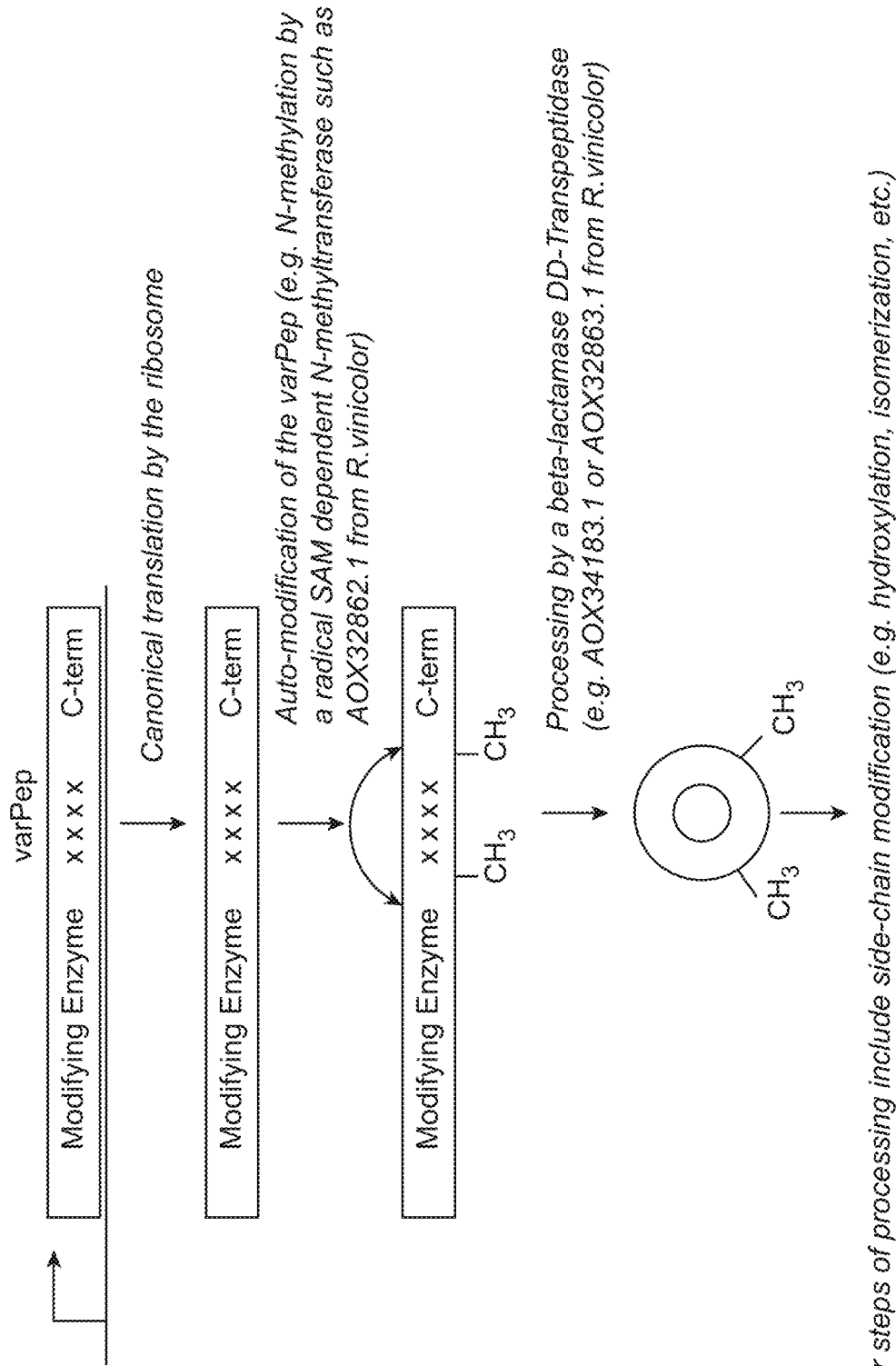
FIG. 12 illustrates a cyclization process of different families of RiPP scaffolds that lead to the generation of N-to-C cyclized, backbone N-methylated macrocycles by the action of a beta-lactamase (alanyl-alanine transpeptidase) and an N-methyltransferase. The variable peptide library region is embedded within the primary sequence of the modifying enzyme. N- and C-term sequences refer to consensus binding and processing recognition elements. The N-terminus comprises the enzymatic N-methyltransferase domain, a linker region, and the processing enzymes binding sites.

In other embodiments, the cyclization comprises reacting with beta-lactamase (FIG. 12). As shown in FIG. 12, a variable region is excised and end-to-end cyclized by the actions of an N-methyltransferase and a beta-lactamase family member. Table 4 shows an exemplary list of lactamase and amino acid sequences of the processed cyclic peptides. In some embodiments, some of the sidechains of the randomized residues are subsequently isomerized from the L- to D-configuration or decorated with additional modifications like hydroxylation, halogenation, glycosylation, acylation, phosphorylation, methylation, and acetylation.

TABLE 4

Amino acid sequences of the N-methyltransferase and beta-lactamase processed cyclic peptides

| | | |
|---|---|---|
| *Rhizophogun vinicolor* | SEQ ID NO.: 54 GenBank OAX32863.1 hypothetical protein beta-lactamase (transpeptidase) | MAKVFGLVLGFLSQTFTYPSQVWFSPVGANNGQVITPELSNSIQETLDVWN ITGLSVAIIPKSGEPEYHSWGDRTEDGESVTQDTLFHMASVSKAFCVSALG ILMDDFEHGRNVTPLPPALTEFNWHTSIQDLLPGEWQLMDEWASRKANMKD ILSHVSGLPRHDFAFGPYESPKEAVSRLRYLRPAFELREQWSYNNQMFMVA GHIVETYSGKTYTSFVEDRIFTPLGMSSSTESPAKAAKTGKFTQGWTSSGR LLPELFPEDMVMLMAGAGGVISSAVDMSKWVALWLNKGVYDNVTVIPSSVY GNASQSYAVSISTPVDSEHSIQGYGLGWFQNSYLGHNVVYHSGSIPGLSML VSFLPDDDVGFVVFANGGDKAAPVMNISNSIIDAALHLRSGPAPPIMPEKK AVTSPSEDIVNLELPLEEFSGTYTDPGYGTFTFCSPSSSSSYCQQVMTDFT AVDSVHPSAPSPLQLLAAWPRMGSSHIRAVHQSGNKFLLLCTALFPEGYGR DSTPFETAEIGTPGATAEFVVEDGKVVGEGLEGLVDQVTERERTQTTVKDR AEVWFDKV |
| *Rhizophogun vinicolor* | SEQ ID NO.: 55 GenBank OAX34183.1 hypothetical protein beta-lactamase (transpeptidase) | MIMAKVFGLVLGFLSQTFTYPSQIRLSPVGVNNGQVITPELSNSIQETLDV WNITGLSVAIIPKSGEPEYHSWGDRTEDGESVTQDTLFHMASVSKAFCVSA LGILMDDFEHGRNVTPLPPALTEFNWHTSIQDLLPGEWQLMDEWASRKANV KDILSHVSGLPSHHFAFGPYESPKEVVSRLRYLRPAFELREQWSYNNQMFT VAGHIVETYSGKTYTSFVEDRIFTPLGMFSSTFSPAKAVKTGKFTQGWTSS GRLLPEFFQEDMIMPMAGPGGVISSAVDMSKWVALWLNKGVHDNVTIIPSS VYGNASQSYAVSISTPVDSEHSILGYGLGWFRNSYLGHDVVYHSGSIPGLS TLVSFLPDDDVGFVVFANGDNKAAPVMNISNRIIDAALHLRSGPAPPIMPE KKAVTSPSEDIVNLELPLEEFSGTYTDPGYGTFTFCSPSSSSPYCQQVIAN FTTVDSVRPSAPSSLQLLAAWPRVGSSHIRTVHQSGNKPMLLPTALFPEGY GRDSTPFETAEIGTRGAPVEFVVEDGRVVGFGLFGLVGQVTERERTQTTVK DRAGVWFDKV |

TABLE 4-continued

Amino acid sequences of the N-methyltransferase and beta-lactamase processed cyclic peptides

| | | |
|---|---|---|
| *Rhizophogun vinicolor* | SEQ ID NO.: 56 GenBank OAX32862.1 hypothetical N-methyltransferase | MSTKRGTLTIAGSGIASVGHITLGTLSYIKESDKIFYLVCDPVTEAFIYDN STADCFDLSVFYDKTKGRYDSYIQMCEVMLKAVRAGHDVLGVFYGHPGVFV SPSHRAIAVARQEGYKAKMLPGISAEDYMFADLEFDPSVSGCKTCEATEIL LRDKPLDPTIQNIIWQVGSVGVVDMEFSKSKFQLLVDRLEKDFGPDHKVVH YIGAVLPQSTTTMDTFTIADLRKEDVAKQFGTISTLYIPPRDEGHVNLSMA KVFGGPGASVKLNDSIKWAGPKLNIVSANDPHERDVIAQVDTHVAPEGHKK LRVSAAMKKFMTDLALKPKFLEEYKLDPVAVVESAEGLSNLERFGLKFARS GPADALMKATESDIASGRQLTEEEIAQGTGPVGLQTALALLVLLGLGVAIV TRPDD |
| *Rhizophogun vinicolor* | SEQ ID NO.: 57 GenBank OAX34185.1 hypothetical protein FAD/NAD(P)-dependent oxidoreductase, D-amino acid dehydrogenase | MTSDNLQPEVISANWLKSLEAASSTGDTASFVSHFLPDGWFRDMLCFTWNF RTLSGQEKIHGFISEVVDGQSRLSYSHLHDFKLDDHSVNAPSPFKLPGPPD IEGVQGAFTFSITKPAAYGRGFFRLTQDVHGNWKALTLFTNMQDLVGHEES SADEYDPHEKANPTVVIVIKVGGGQSGLICAARLGKLGIRALVIDKNARVG DIWRQRYAEALPSFAVLSRQETQVPEPYAAYSQISKLLPYPSNFPKYLPKG KLANFLESYAINQELCIWLSSTVSPSPVYDSFSARWTVEVEHENRKVILHP KHLVLATGHGRPRIPTWNGMDDFQGTLYHSDFHRDAEKFRGKCVVVIGAGN ASGDICEDFVAQGAAEVTIVQRSATCVVSSATADAFVFKLPFSDKTPIEEL DFRHNSMPLAFVLQLMKSGGTQHMKAHDKEHHEGLRKAGFNLTWEPSPGSG EVGLLGFVFERAGSGTMIDTGFGKLIVEGTVKVKQGQNISHFDKEGITFKD GSKLPADVIVAATGNELTMDAIRAVLGDTIAEQLPPKVWGLDAEGELNQMY RPSGHPGLWFAVGSLGMTRFCSKHLGLQILAQEVGIA |

Figure 15:
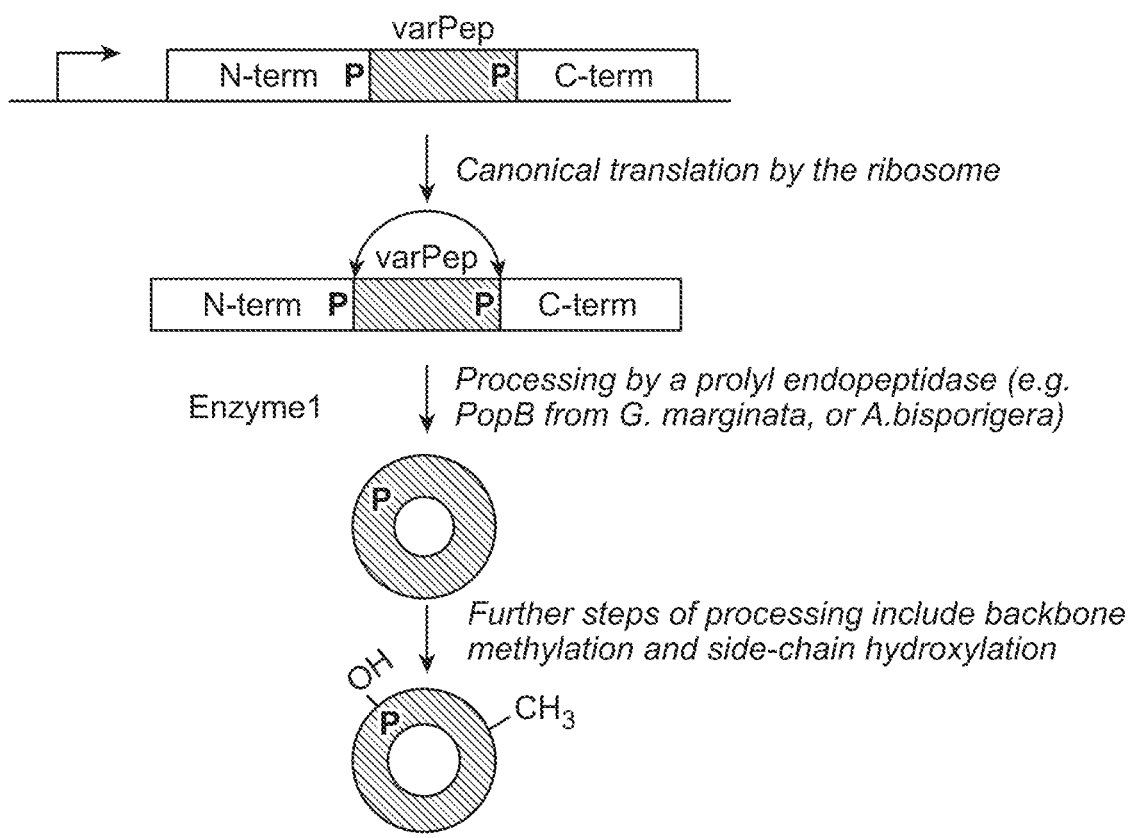
FIG. 15 illustrates a cyclization process for members of the MSDIN family of RiPPs that leads to the generation of N-to-C cyclized macrocycles by the action of prolyl oligopeptidases belonging to the PopB family.
Figure 16:
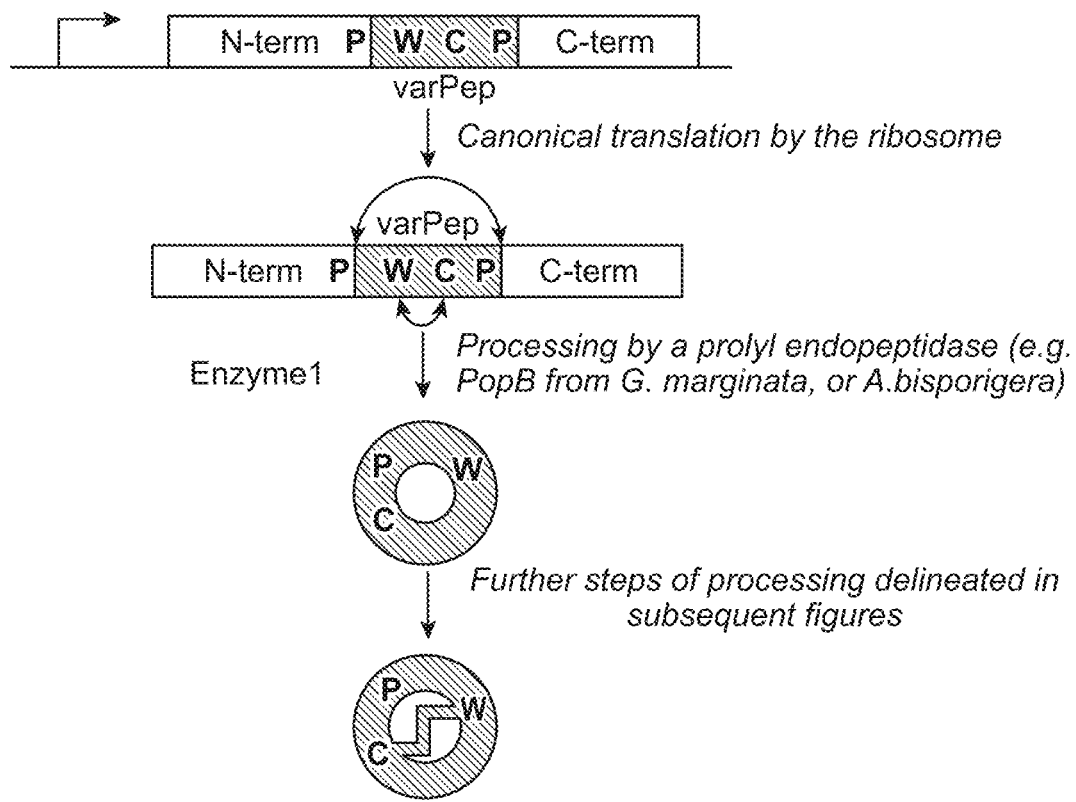
FIG. 16 illustrates a bicyclization process for members of the MSDIN family of RiPPs that leads to the generation of N-to-C cyclized macrocycles and bicyclic macrocycles internally bridged via a tryptathionine bridge.
Figure 17:
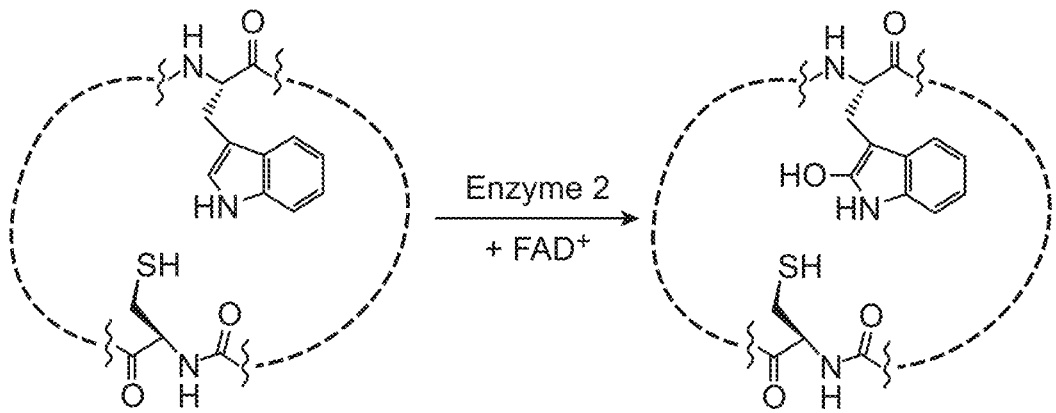
FIG. 17 illustrates biochemical steps to create a tryptathionine bridge of a bicyclic ring.
Figure 17:
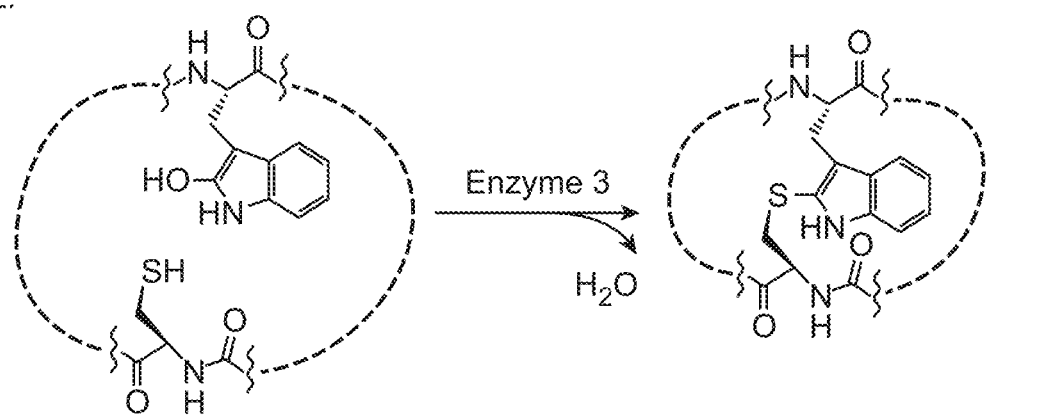
Figure 17:
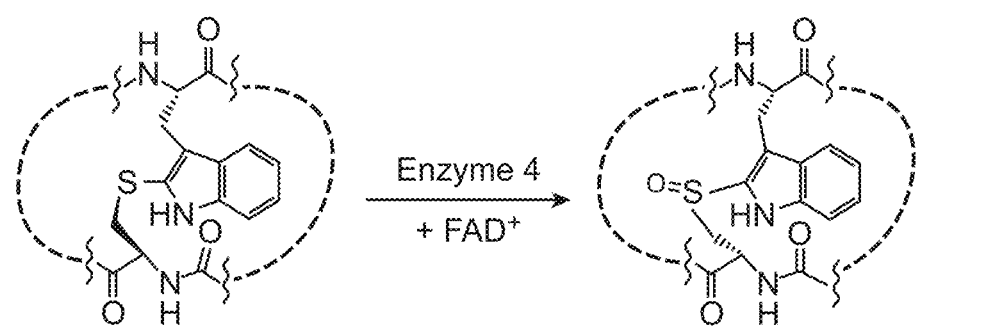
Figure 17:
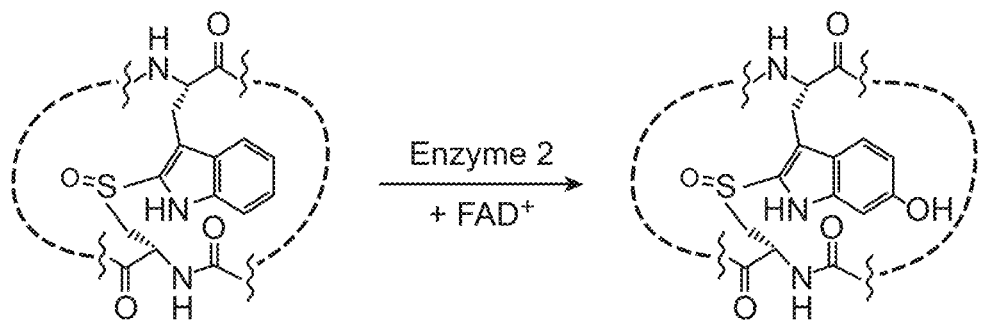

In some embodiments, the cyclization comprises reacting with a prolyl endopeptidase, an N-methyltransferase, and a hydroxylase (FIG. 15). In some embodiments, the bicyclization comprises further modification of the indicated anchored residues on the cyclized peptide, forming an internal tryptathionine bridge (FIG. 16). FIG. 17 illustrates a biochemical steps to create the tryptathionine bridge with hydroxylase and dehydratase. Step 1 involves hydroxylation of the 2-position of the indole ring of the tryptophan residue by a hydroxylase belonging to the cytochrome P450 family of oxygenases (FIG. 17). An example of such hydroxylase is shown in TABLE 5.

TABLE 5

Amino acid sequences of a hydroxylase

| | | |
|---|---|---|
| *Galerina marginata* CBS 339.88 | SEQ ID NO.: 58 KDR84981.1 hypothetical protein GALMADRAFT_260690 | MGKMAYHTVLDDIALYLLGSAALVIFYRSFFYPYFLSGRRLAPGPTKGELS KELKQFNNEINVHFLRHMVKEYGPIFRLVGAPMIPGPGLVVCTPTAQQRIL VSNSINYGQPRLAFFRWVTGGLFTLPEREHRGMRKILDPVFSFRNLISTTG VYYNTVQSLITIFRSKIDGENGAKDGDVILVYEWLARLAIDNVSEAILGFK LDTLHDPNNELITTLDELSRIPTAAFELLVRVPGFLRLVTFDSVRHSTLWQ RRVPGRLGVFFTFMRCLSTIRKNALAIKATILQEDSANRDLNVISVLQHMQ SSDETANADIAGNIIMLWMSGRATIATRISWLLWLLAKDQQCQQQLRDEIA PLFSRDPRPDYRSLDKLQWLDSVIMESIRLFLFGPNIRVALNDDYIDGVFV PKGTVVVIPLDLFTRGDIWGEDPDQFKPARWLDSTKRYKISPPFLSFLTGP HRCIAKGMAIMQTKIVIASLIANFEFKPAYEGQHVEGNPSIIGHGMPLHVK PIRPS |

Step 2 involves the formation of a tryptathionine bridge between the 2'-hydroxyl position on tryptophan and the thiol group from the cysteine residue. This condensation reaction is catalyzed by a novel family of dehydratases. Examples of the dehydratases are shown in TABLE 6.

TABLE 6

Amino acid sequences of dehydratases

| | | |
|---|---|---|
| *Galerina marginata* CBS 339.88 | SEQ ID NO.: 59 KDR80488.1 hypothetical protein GALMADRAFT_136963 | MPYVPDPKYFEHREQSSGATLYYCLVCRDGRERQPHHIKTHEASQAHRTAL SVFDSQAESSSQQTHGNPTQPGYFDPVIDDAVRALLVSGSGDPHQPLYPAG HPNVYGEPNFTDSRRRTSPVTGIDWDQFEAQEDTHAVPSAQDQLRADICQA TLDWLNDDISDDDEREPSEVDSVDSDAESDREPIPDDQPRKRARTNRDNPI SEDWYPWQDKITCTLDILMHLPRSVFSRKQLDLFLWLLRVNNVDDVPTGKS MKMLNKILQGMCGIETIAYEGKLGHNYHVNNIAQILAQELCNPKVGPHIYF YPEDSGDNLAEARQAARWLHELRPEETTPMIHLPSGDYYIYEPAMLSNRSF CIPFRWFTRNGKFHARAWSLETGVVDNTLGWIVHKENEVEISEDDLLKDFT RFSSDCEAYNVPHPSRILGVSCADSGNLLPWNHTNPVLGNRWRQLAKGHRT LCLPLWMYCDDTSGNTSKKWNEHNSFLFTLAGLPREHTAKEYNIHFLCTSN LAPPLEMMDGVVSQIEAAQQNGIWAWDCVRKEPVLIFPTILALLGDNPMHS EFACHIGLRGKFFCRTCWVKGSDAQDDANIVTPGLHETPENSPAPSPAPSP APSPAPSPAPSPALSMAPQSQPPTPSEPSMQVPAPPSTAAPTKARGKKKET MSAMLNRITAFIKPGRLRNKSETQKTLQNFKEQAQTIGAKTKLKTARTETG |

TABLE 6-continued

Amino acid sequences of dehydratases

| | | |
|---|---|---|
| | | IKDTVQEFFFEKLFSSYKNKRGPQAKQEALDQAVNQLPSDITSPVWRLKGL<br>DPHQDTPVEILHVVLLGFIKYFWRDLVQNQINDDQKQTLIQRLNSFDVTGL<br>GITQLGGETLVNYAGSLTGRDFRAVAQVAPFVIYDMVPADVFDAWLALSKL<br>VPLVWQPYIENVAQYLTTLEHEIHVFLLRTARWTTGWFNKSKFHIILHLPS<br>HIRRFGPAILFATEAFESFNAVIRAKSVHSNRQAPSRDIALAFAQGNRIRH<br>LLSGGHFLSADTHMVVDPDQPQLGQYERLARGRWRSVGPGPGHLVSAEPIL<br>PSYLGIPPQSTTSSAGLCKRTKTPPQTFLQTLTGLKLPNVSRPGARELWQT<br>CSEVYLLNDDKCLIGHHVIVQRQSEQASFVSPPFIARIGEILQKVGSANHA<br>HDKPDGILVQTLKSSEVADKFQMPRLVPQNEWSFVPLADILCTVNAQHDCD<br>RNGCTASGFRYVYQERIQTNDQRPVVEHVNQPEDFILNTAQMRDALHLQKF<br>RIRSRSLDEQTIIHESVARTINQRKAQDNSSSGTGGAGVSGRGRGRGRGRG<br>GGVEGPSTSRGRGGGIEGRGASSSSGNGRGRGRGARSAQSVPF |
| Galerina<br>marginata<br>CBS 339.88 | SEQ ID<br>NO.: 60<br>KDR74877.1<br>hypothetical<br>protein<br>GALMADRAFT_99137 | MPRKKPAPECFETDEASKMIRCLICKENDTVQQGTWIKHGSASQHIETNAH<br>KLAVARREQLLQVQQEEERRLQEIYGGNTIPLSGNAQLYPTYPRANMYGNQ<br>DAVDTDMDNQNSPPQAYMLCDADIPDLGIKPIERPDPSQERERLRQQVEQL<br>LLQAEHEDEFGSPDDPDDLTSTNIAQAFADLDLEEMLDEEEVEDYFNQVSP<br>EHDYYPYPNKTTMLLDIDLNLPRLRMSSNQLRLILWLLKQTGVSNVPSFSG<br>FRNMQTHLRNMCGTTPKQHVSSLGNIFYSNNIGESVMRDFANPEVAKHLHL<br>YPEETEGPISEVWQAERWKEFAPSELTPMFSQGHRQFFIDEVAQLQDGQYV<br>IPRNWVMRKGKLTSDCHIVTVNPVRFSKLHGSLVLVLKQCFQSGWTLLSET<br>QIFHADDFQFNYFDVVSRIRGPISWSEGTEVPAMPNNLRELAGDDDLVVIM<br>VPLWCDDVSGNKSKQYNKHINVYMANSNIPGRLLQQEYFVRFVSTSPNATS<br>PEQFSALKDQINETQKKPIQCYNAHTNKKTRAILRVPGLPADNPQQSEESC<br>HMGGNANCKCRKCHVGGPHEKKESNEGYHEHYLTGIKRSAEETRLELEKQI<br>KLAMYGVEKPINETQTNTGTKDKVAQHWIDILLAKSRELKSANPSRSVEEI<br>AQELQTWFDEQPGDKINPLLSIAGLDPTQDTPVEILHTILLGIVKYAWHHL<br>HSNWTEAEQNLFTVRLQSTDIDGLSVPPIRVAYMMQYRNGLIGKHFKTLMQ<br>TLPFHVHGTVSDAQFKLVKAIGELGSVLWVHEIGDMEKYLSDLEILIGNVL<br>DAFAEIDPSTAMYARFIYEPMPVPSKIIVKLKLHMLPHLIEDIKRFGPAIR<br>NSTEVFECFNAIFRLCSILSNHQAASRDIALKFASMDRLKHMLSGGYWLSE<br>VEEGKFEWIRAGENVRNILQSEPTIQRHLGWAPSAKFQSGRKRTPPTSWEN<br>TKASQFMDSEETAAIGFPNPRLLSWRKGVTTTAQSGDRCSTGSWVVARNHK<br>VCYILASHYCSIAKNDQGESCIGRIHEIIGPDEKSASSTGIITLECFQLGK<br>EHHPDFGLPTLQRPQADLPKYILKAWQDPLFIFSAHHDCHTASCQATALQP<br>QLQERQLTSRMNKLIAHNDSDHFIINLYGLHNAILLREFLPRELTAPQPLH<br>QDRKAFHYEVAAKLRVQQAEKRAKTNARRKATRAANKAKQVERQKQNPDHE<br>QESEQEMDERPNSENGSDIELGGDDDIEVETRRKRRRN |
| Hypsizygus<br>marmoreus | SEQ ID<br>NO.: 61<br>KYQ37095.1<br>hypothetical<br>protein<br>Hypma_08924 | MGRRAEELPAYVELSEDGTLVRCNLCLMHNRLDYSKEWIQRKGWRSHKGSG<br>IHDRSEAKQRVLDDAAMDLQEPASAEVEVVTFNDILIINAPKTPTGNMQSE<br>EQAMWDHFDAGSFTLEAGEDPNHSSQRLYQDLARKADAYGAWDGTEALPEY<br>RDLDDVSQFLDEDEEEDLLSEILRGLGLEEEHEDSSDRNPAEELNSPWYPY<br>GSKLMFLLDTIDNLPRLRISGAMMRVFLWLLREVGVRQVPSFDKLRKIQRK<br>LREGSGVPTVHWMSPKGNAYSFNDPAVIVANDWASPITRPHLRRYPVIPKD<br>GVITEVYHAEKWHREINRHFLTPMYDDGFRHYFIDELAQLKDGRYAVPVRW<br>LEDVDGRIVADAWRVELEDDNRATIIDTATVRIHSQELALNFEEIIESNLM<br>PEWSDTTTEAGHPSRMPNPDRALAEGDPIYTSFIDIFGDDVSGNRSKSWNK<br>HWNMYISHRNLPRKLLHQQYHTHFVSTSTFASIPEQFVGVKEAIESTHSKP<br>VKVRDADTGKQIRLKIYCNCGPGDNPSQSETSGHIGGNGNYPCRKCHTGGT<br>QKSKETDEGFYKMFTAGEARSSKETLAEVKSQVEAACTGVAKTVADAQSDT<br>GVKDAYTQYWIDAIIEKARAMQKENPGMPTTTIQATLIKWVYDHEEAIYNS<br>FLTLDGFDASRDTPVEILHTILLGIVKYLWHRSHTSWNAAQKKIYSTRLQG<br>TNTQGLSIHHIRANYIMQYANSLIGRQLKTLAQVNVFHVYDLVDPLRFLFT<br>KATGELCALLWFTEIRDLEEYLSDVDIAAANVLDIAAVIDPSKIVSKIKYH<br>LLSHLREDIIRFGPLVGVATEVFECFNAVERYCSILSNHLAPSRDIAYKLA<br>AQETMKHFLSGGWWHVKDSVDLQGNPKWVQPGPSVRTFMASNPVLHTLCGW<br>TRNNDSTPGTVKSEPRKRGPDKQTLLPLVRLAWLETQGSRALNNTSPNNET<br>QWQRCKYVIAETQDQCNVGSWVFARSPLLENIPIPGRIVEILQDTSASPSA<br>FVVIDVFQVSATRDEVEGMPVLLRRFNECCLHVIPASSVIFDFNAQHDCRY<br>AKCEATGEQPLIQERVPSGVTENFVVHKAIDRYLINIHALHNAHLIRATLP<br>RDLTAPIPYAPNREAHHSAIAAELRSAQDTKRAKTAAKTAANAAAKKAEAA<br>LKDTTSGPAAKRRRVDDEGSGEEDNRDVDMVSV |
| Galerina<br>marginata<br>CBS 339.88 | SEQ ID<br>NO.: 62<br>KDR73903.1<br>hypothetical<br>protein<br>GALMADRAFT_141673 | MAKGRKLNNPLPDFIEISNDGLQVRCTLCLAARQHNGSGWIKRGSVSNHLK<br>SDNHTNSLEAHEMKKSAEKAEGRSVQEEIAMEEGMDFVILSSKIQPEITAP<br>ARAPRRSNEEQEMWDRYTLGGEVFDAGVDHTLVEAEEERKRLEREATDFDLW<br>HGADFLPEEDPNDGELLLDELEQDDILSELLRNAHLNAPDAADVLTEEPRA<br>AADPRICDAWSPYESKMMFLLDTLDNLPRLRISNSLMNVFLWILREGGARD<br>VPSLYHLRQVQTTLRKSTGVPTTQHKSPKGNVYSMNDPRTLVAMDWANPVI<br>CDHIRRYPVIPRNGVISEVYHAQKWRKDVDPHTLSPMYDAGNCHYYIDEVA<br>RLKNGTFIIPVRWLEDEDRNVCADAYVVQFDDQFIASVVDGETIIVQASDL<br>QNNFLDLKDMGLLPTWGNQTIESGHPARMPNPDRALAEGDPLYTSWIDVFG<br>DDVSGNRSKNWNKHWNIYISHRNLPRKLLQQEFHTHFVSTSPVASVTEQFH<br>GIKQVIELTHKSPVKVRHGTSGAQIRFKINVNCGPGDNPAQSEVCGHIGVN<br>GNKLCRKCHTGGTHEVKESDEGFNSLFEPGDARSAQEIVADVESQVQLACL<br>GIAQHVQNQQTKNGIKDAYTQYWIDYLINRARTLRKEQPRRTTADIQSELL<br>VWVQEHKDEIYNPFLKLDGFDAAVDTPVEILHTILLGIVKYLWHGSHTSWT |

TABLE 6-continued

Amino acid sequences of dehydratases

```
AIQKQTYSVRLQSTDTSGLSIHAIRANYIMQYANSLIGRQFKTIAQVNVFH
VYDLVDTTQFLLTKAVGELTALLWIPEIANMEEYLLDVEAAAANVLDLFAL
IDPSKMTNKLKLHLLVHLKADILRFGPLVGVATETFECFNAIFRFCSIYSN
HLAPSRDIAFQLASQEVLKYRLTGGWWPASDGEWKRPGPSVRNFIHDHPTL
QALLGWTKEEKLVNGSFRLEPLKRDASQKIESRKHLPWLQTQGAKAVNSSE
DNDSKWTACRFAVANSGDKCSVGSWVFATSPFNSNQSVTGRIVEVLAESEG
KRAVVVLDIFEVCSTRHKIFGMPMLARRHEEPVYAVIASTNIEFLYNVQHD
CPLAKCTASGKQPLIQERVESGLFKTYIEHKPIEREVINTHAFHNAHRLRA
VLQRSLVVPIPLYPPEIRKTKHAEFAHNLQATQKVKLEARAAQKAKEIITP
ADKTDSTIPKKRTRSEMETETDDTAIATQADVFFNAQGCP
```

Step 3 describes S-oxygenation of the tryptathionine thiol by a flavin-monoxygenase enzyme that converts it to a sulfinyl form. Examples of such monoxygenase are shown in TABLE 7. Step 4 describes potential future modification steps such as hydroxylation of side chains on the peptide such as the hydroxylation of position 6 on the indole ring of the tryptathionine-forming tryptophan residue by a P450 family monoxygenase.

TABLE 7

Amino acid sequences of monoxygenases

| | | |
|---|---|---|
| Galerina marginata CBS 339.88 | SEQ ID NO.: 63 KDR68385.1 hypothetical protein GALMADRAFT_104945 | MVQIKRLLLGFLSSPSQTPLESNHGPVPSKSIAVVGAGSAGLAMLRTLVEL EAFSRNNWEVVLYEERESVGGIWLPDNNDVFPPEIPKTPLYPLLRTNTPVP SMTYPGFPFPPSTPLYPRHDHVEAYHLRYARRHNLLDFIKFDTMVEKAFWN GTPEEGYWNLTLSSKEGRMRYKTEDHLVVATGNNHIPHIPVWKGQEDWLAS PANHSRKIIHSVYYRGPEAFSNQTVLIVGNGGSGRDAATQILGYASQTFMS IRRSYGPVDDGVIVKPDISHFTEAGVVEVDGTILDPDVILLGTGYEMQKPL LSEGGELSFDPTAKDNSSVRGILVTNGHYIFPLHRHIFSLSPRYPPNALAF IGLLSFIASCPSDIAQSLFAAHAILDPSILPPRHLLLEELASYEDKARRQG LDPYLKGPIMLNNTSNDYQDELVEYLKQKNAIPDDGKKFVEEWRREILAYH YLQRGWSRIEKLGMGPAWTEGVKTEAQWFDLMTRVNEWQKNWETENGIAFR VDLDLTG |

Figure 13:
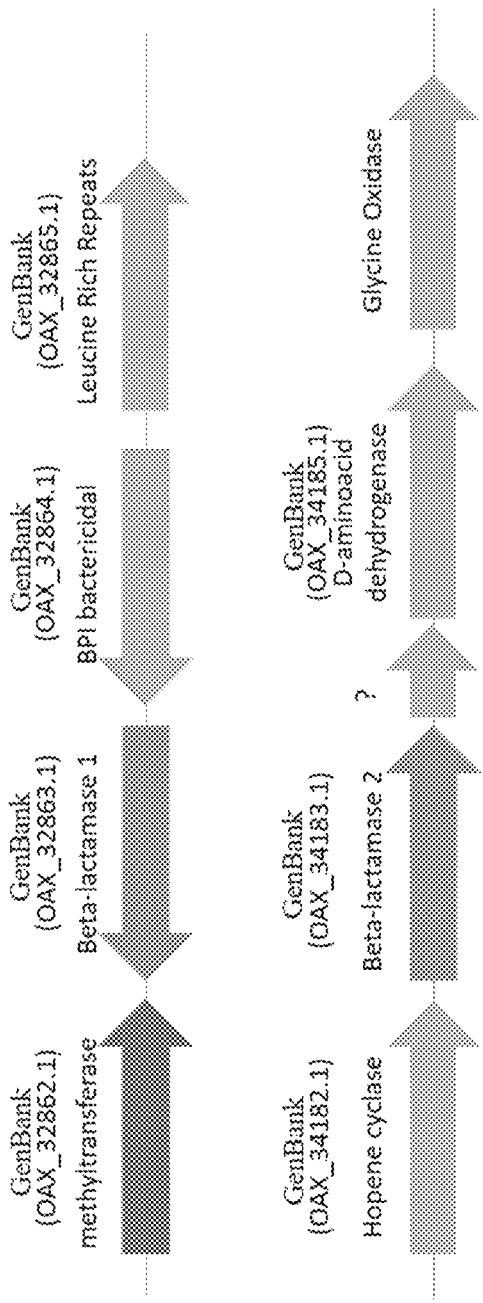
FIG. 13 shows a gene organization within two sets exemplary loci from *Rhizopogon vinicolor* that encode for modifying enzymes that could be used in the schematic depicted in FIG. 12.

A gene organization within two exemplary loci in *Rhizopogon vinicolor* that encode for methyltransferase, beta-lactamase, hopene cyclase, beta-lactamase 2, dehydrogenase, and glycine oxidase is shown in FIG. 13.

Figure 14:
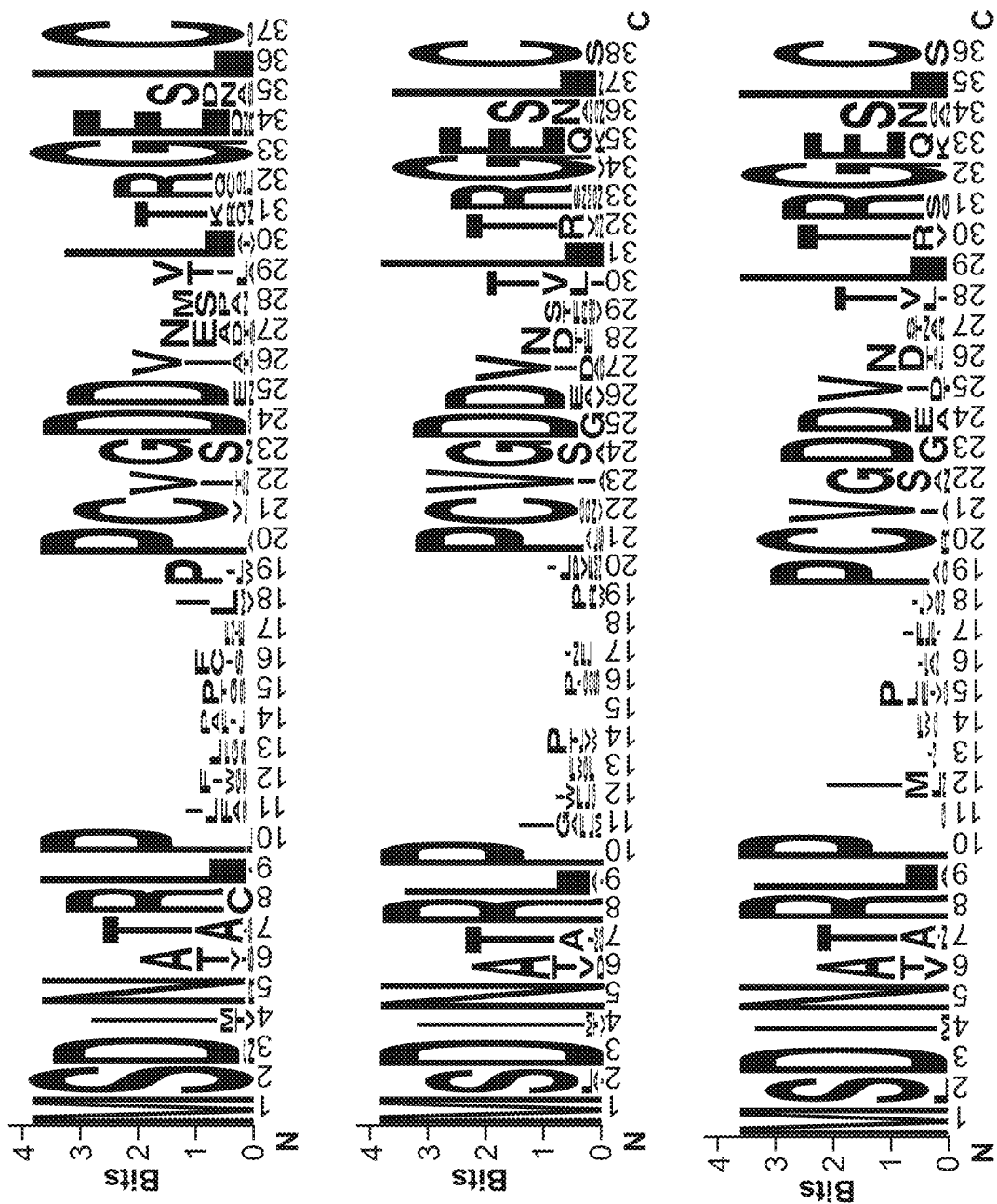
FIG. 14 shows WebLogo alignments of a large variety of MSDIN family genes (toxin preproprotein sequences) identified in the genomes of *Amanita bisporigera* and *Amanita phalloides*. See Pulman, Jane A., et al. "Expansion and Diversification of the MSDIN Family of Cyclic Peptide Genes in the Poisonous Agarics *Amanita phalloides* and *A. Bisporigera*." BMC Genomics, vol. 17, no. 1, 15 Dec. 2016, p. 1038, doi:10.1186/s12864-016-3378-7.

The sequence which flanks the encoded random peptide library can be, for example, as shown in FIG. 14, by using N-term and C-term flanks from the MSDIN family genes (toxin preproprotein sequences) identified in the genomes of *Amanita bisporigera* and *Amanita phalloides*. The low consensus central regions indicate areas where a random peptide library could be inserted to facilitate post-translational processing into a cyclic peptide. See Pulman, Jane A., et al. "Expansion and Diversification of the MSDIN Family of Cyclic Peptide Genes in the Poisonous Agarics *Amanita phalloides* and *A. Bisporigera*." BMC Genomics, vol. 17, no. 1, 15 Dec. 2016, p. 1038, doi:10.1186/s12864-016-3378-7.

The enzymes can additionally be targeted to a specific cellular compartment to increase peptide synthesis efficiency and increase yield for peptide production purposes.

Disclosed herein, in certain embodiments, is a method of detecting interaction between a first test protein and a second test protein in a host cell, comprising: expressing in the host cell a first fusion protein comprising the first test protein and a second fusion protein comprising the second test protein; delivering a first molecule to the host cell; modifying the first molecule while in the host cell via a modifying enzyme; and allowing the first molecule to modulate the interaction between the first test protein and the second test protein, wherein the first molecule is a product of an encoded DNA sequence, wherein the first molecule comprises a randomized polypeptide library and one or more modifying enzymes, wherein the one or more modifying enzymes modify the randomized polypeptide library.

Host Cells

In some embodiments, the host cell is a eukaryote or a prokaryote. In some embodiments, the host cell is from animal, plant, a fungus, or bacteria. In some embodiments, the fungus is *Aspergillus, S. cerevisiae,* or *Pichia pastoris*. In some embodiments, the host cell is a haploid yeast cell. In other embodiments, the host cell is a diploid yeast cell. In some embodiments, the diploid yeast cell is produced by mating a first host cell comprising DNA sequences encoding the first chimeric gene, the second chimeric gene, and the third chimeric gene, to a second host cell comprising DNA sequences encoding the death agent, positive selection reporter, and the mRNA comprising a nucleotide sequence encoding a polypeptide. In some embodiments, the plant is *Nicotiana tabacum* or *Physcomilrella patens*. In some embodiments, the host cell is a sf9 (*Spodoptera frupperda*) insect cell.

Disclosed herein, in certain embodiments, is a host cell configured to express a first fusion protein comprising a DNA-binding moiety; a second fusion protein comprising a gene activating moiety; a third fusion protein comprising a different DNA-binding moiety; a death agent, wherein the expression of the death agent is under control of a promoter DNA sequence specific for one of the DNA-binding moiety; a positive selection reporter, wherein the expression of the positive reporter is under control of a promoter DNA sequence specific for the other DNA-binding moiety; and a polypeptide of 60 or fewer amino acids, wherein the polypeptide modulates an interaction between the first test protein and the second test protein; wherein the host cell optionally has a mutant background enabling uptake of small molecules; and wherein the host cell optionally has a mutant background enabling increased transformation efficiency.

Disclosed herein, in certain embodiments, is a host cell comprising a plasmid vector which comprises the components of PLASMID 1, or any combination of the components of PLASMID 1; or the plasmid vector, wherein a DNA sequence encoding a first polypeptide is inserted in frame with Gal4-DBD, a second polypeptide is inserted in frame with LexA-DBD, and wherein a DNA sequence encoding a third polypeptide is inserted in frame with VP64-AD.

Disclosed herein, in certain embodiments, is a kit comprising PLASMID 1, PLASMID 2, and PLASMID 3; and transfectable host cells compatible with PLASMIDS 1-3, or any combination thereof. In some embodiments, the provided host cells are already transfected with PLASMID 1 or 2. In some embodiments, the kit includes selectable agents for use with host cells transfected with PLASMIDS 1-3. In some embodiments a library of variants of PLASMID 1 are provided, wherein more than a single pair of Y2H interactors are represented. Such a library can be used to, for example, screen for protein-protein interactions that are inhibited by a defined agent. In some embodiments a library of variants of PLASMID 2 are provided, wherein a plurality of different short test polypeptide sequences for screening are represented. The plurality of different short peptide sequences can be randomly generated by any method (e.g. NNK or NNN nucleotide randomization). The plurality of different short peptide sequences can also be preselected, either by previous experiments selecting for binding to a target, or from existing data sets in the scientific literature that have reported rationally-designed peptide libraries.

The host cell can additionally be made to be permeable to small molecules, for example by deletion of drug efflux pumps, such as PDR5, ERG6, or 12geneΔ0HSR (Chinen, 2011), to enable a small molecule screening approach.

The host cell can additionally carry mutations to enable more efficient transformation with vectors and/or more efficient uptake small molecules.

PLASMIDS 1, 2, and 3 can be used in various permutations. In some embodiments, integration of PLASMID 1 into the genome of the host cell (as confirmed using PLASMID 3) is followed by transformation of a library of PLASMID 2 with randomly encoded peptides using, for example, NNK or NNN codons.

In some embodiments, to perform a screen to identify a peptide that can disrupt a PPI, the host cell is propagated in selection media to ensure the presence of PLASMID 1 and a proper PPI (e.g. on media lacking the positive selection marker for yeast, or in media containing antibiotic for human or bacterial cells). This host cell is then be transformed with PLASMID 2, and immediately transferred to selection media to ensure all components are present (i.e. on media lacking both plasmid selection markers for yeast, or antibiotics for bacterial or mammalian cells), and are inducing expression of any inducible component (e.g. with Gal, doxycycline, etc).

In other embodiments, the plasmids are used as a 'plug and play platform' utilizing the yeast mating type system, where the 2 or more plasmids (or the genetic elements therein) are introduced into the same cell by cell fusion or cell fusion followed by meiosis instead of transfection. This cell fusion involves two different yeast host cells bearing different genetic elements. In this embodiment, yeast host cell 1 is one of MATa or MATalpha and includes an integration of PLASMID 1. In this embodiment, yeast host cell 1 strain can be propagated on positive selection media to ensure a proper PPI is present. In this embodiment, the yeast host cell 2 can be the opposite mating type. This strain carries (or has integrated) the randomized peptide library and 'death agent' (e.g. cytotoxic reporter) plasmid (PLASMID 2). Yeast host cell 2 can be generated via large batch high efficiency transformation protocols which ensure a highly diversified library variation within the cell culture. Aliquots of this library batch can then be frozen to maintain consistency. In this embodiment, the strains are mated in batch to result in a diploid strain that carries all the markers, the PPI, positive selection, 'death agents' and peptide. This batch culture then can be propagated on solid medium that enables selection of all the system components (i.e. media lacking both positive selection markers), and inducing expression of any inducible component (i.e. with Gal).

Surviving colonies from limiting dilution experiments performed on host cells bearing both the Y2/3H and library/cytotoxic constructs (either introduced to the cell by transfection or mating) can constitute colonies with a specific PPI that has been disrupted by a peptide and no longer triggers the death cascade triggered by the encoded 'death agents' (e.g. cytotoxic reporters) while maintaining a differential PPI driving a positive selection marker. The peptide sequence can be obtained by DNA sequencing the peptide-encoding region of PLASMID 2 in each surviving colony.

To ensure that survival is due to inhibition of the PPI rather than stochastic chance or faulty gene expression, an inducible promoter can be used to inactivate the production of either the PPI or the peptide and confirm specificity. In some embodiments, cell survival is observed only on media with galactose wherein all the components are expressed; and no survival is observed on media without galactose when expression of the peptide is lost.

The plasmids can also be isolated and re-transformed into a fresh host cell to confirm specificity. Biochemical fractionation of the viable host cells which contain the PPI, peptide, positive selection and 'death agent' followed by pull-down experiments can confirm an interaction between the peptide sequence and either PPI partner using the encoded tags (e.g. Myc-tag, HA-tag, His-tag). This is also helpful to perform SAR to determine the binding interface.

The peptides to be used in screening assay can be derived from a complex library that involves post-translational modifying enzymes. The modified peptides can be analyzed by methods such as mass spectrometry, in addition being sequenced to ID the primary sequence. The peptides can also be tested for inherent membrane permeability by reapplying them onto the host cells exogenously (from a lysate) and observing for reporter inactivation or activation.

Once enough surviving host cell colonies are sequenced, highly conserved sequence patterns can emerge and can be readily identified using a multiple-sequence alignment. Any such pattern can be used to 'anchor' residues within the library peptide insert sequence and permute the variable residues to generate diversity and achieve tighter binding. In some embodiments, this can also be done using an algorithm developed for pattern recognition and library design. Upon convergence, the disrupting peptide pattern, as identified through sequencing, can be used to define a peptide disruptor sequence. Convergence is defined by the lack of retrieval of any new sequences in the last iteration relative to the penultimate one.

EXAMPLES

Example 1: Method for Identifying a Disruptor of a Protein-Protein Interaction

This is an example of a system that uses two variants of one protein, fused to different DBDs to identify inhibitors against a specific PPI. The PPI integration plasmid (PLASMID 1; FIG. 8) is used to integrate into *Saccharomyces cerevisiae* three proteins that constitute the binary PPIs of interest. The plasmid encodes for the fusion of an AD (VP16) with c-Raf, a DBD (LexA) with KRas(G12D), and a DBD (Gal4BD) with KRas, driven by a strong promoter and terminator ADH1. Fusion proteins VP16—c-Raf, LexA—KRas(G12D), and Gal4BD—KRas are tagged with MYC, FLAG, and HA, respectively. The plasmid further includes bacterial selection and propagation markers (ori and AmpR), and yeast replication and selection markers (TRP1 and CEN). The plasmid also has sites for integration into the genome at a specified locus.

*Saccharomyces cerevisiae* is co-transformed with the selection and library plasmid (PLASMID 2; FIG. 9) for the expression of a randomized peptide library (NNK 20-mer sequences). The plasmid is driven by a strong promoter, ADH1. The initiation sequence of the selection and library plasmid is a fixed sequence of methionine-valine-asparagine (MVN) to maximize the half-life of the peptide, and terminated with an untranslated region (UTR) of a short protein (sORF1). The selection and library plasmid also comprises a sequence that encodes a His-tag. The translated protein has the N-terminus of methionine to minimize proteolysis.

The selection and library plasmid additionally comprises a LexAop sequence, which induces 'death agents' (cytotoxic reporter expression) when bound by a functional transcriptional factor that is formed by LexA—KRas(G12D) fusion protein and VP64—c-Raf fusion protein, unless interrupted by a disrupter peptide. The selection and library plasmid also contains a positive selection marker, ADE2 which is under control of Gal4BD-KRas. The plasmid further includes bacterial selection and propagation markers (ori and AmpR), and yeast replication and selection markers (TRP1 and CEN).

To confirm expression of the reporters and the successful construction of the strains, *Saccharomyces cerevisiae* is transformed with a confirmation plasmid (PLASMID 3; FIG. 10). The confirmation plasmid includes a direct fusion between the AD fusion protein (VP64-c-Raf) and DBD fusion proteins (LexA—KRas(G12D) or Gal4BD—KRas). The confirmation plasmid includes yeast replication and selection markers (TRP1 and CEN). The confirmation plasmid is used to confirm integration of LexAop promoter before the ADE2 gene. Transformation with the confirmation plasmid allows for the activation of ADE2 only if the promoter is properly integrated. Also, confirmation of death agents is enabled by inducible expression of the confirmation fusion construct.

The screen is performed by mating the strains in a batch to result in a diploid strain, which carries all the markers, the PPIs, the positive selection, the death agents, and the peptide. This batch culture is then propagated on solid medium, which enables selection of all the system components (media lacking two nutritional components) and induces expression of any inducible component with Gal.

Surviving colonies constitute colonies with a specific PPI (KRas—c-Raf) that have been disrupted by a peptide and no longer trigger the death cascade induced by the encoded death agents and maintain positive selection of the remaining PPI.

The peptide sequence that disrupts the death agent-driving PPI is obtained by DNA sequencing the peptide-encoding region of the selection and library plasmid in each surviving colony.

To confirm specificity, the inducible marker is used to inactivate the production of the PPI and confirm specificity. The plasmid is then isolated and re-transformed into a fresh parental strain to confirm specificity.

Biochemical fractionation of the viable strain that contained the PPI, peptide, selection marker, and death agent, followed by pull-down experiments is done to confirm an interaction between the peptide sequence and either PPI partner using the encoded tags.

An alternative example can be made by switching LexA with TetR. In another alternative example, fusion proteins in the PPI integration plasmid and the randomized peptide library in selection and library plasmid are driven by an inducible promoter, GAL1, instead of ADH1 promoter. In another example, yeast selection marker 2 um is included in the PPI integration plasmid and selection and library plasmid, instead of CEN. Similarly, yeast selection marker LEU2 can be used alternatively in another example. In yet another example, the N-terminus of the peptide translated from the selection and library plasmid can alternatively be glycine, alanine, serine, threonine, valine, or proline. In other examples, the genetic reporter in the confirmation plasmid is HIS3 or URA3, in place of ADE2. Either mating types of *Saccharomyces cerevisiae* haploid state can be used as background strain in alternative examples. In other examples, background strains also express the enzymes for the cyclization and methylation of peptides like lanthipeptides maturation enzymes from *Lactococcus lactis* (LanB, LanC, LanM, LanP), patellamide biosynthesis factors from cyanobacteria (PatD, PatG), butelase 1 from *Clitoria ternatea*, and GmPOPB from *Galerina marginata* or other species.

Example 2: Method for Identifying Protein-Protein Interaction Disruptor

This is an example of system that uses two different proteins, fused to different DBDs to identify inhibitors against a specific PPI. The PPI integration plasmid (PLASMID 1; FIG. 8) is used to integrate into *Saccharomyces cerevisiae* three proteins that constitute the binary PPIs of interest. The plasmid encode for the fusion of an AD (VP64) with TEAD, a DBD (LexA) with YAP, and a DBD (Gal4BD) with VGLL4, each associated with ADH1 promoter. Three protein fusion sequences are tagged with either FLAG, MYC or HA. The plasmid further includes yeast replication and selection markers (TRP1 and CEN). The plasmid also has sites for integration into the genome at a specified locus.

The *Saccharomyces cerevisiae* is co-transformed with the selection and library plasmid (PLASMID 2; FIG. 9) for the expression of a randomized peptide library (NNK 20-mer sequences). The selection plasmid is driven by a strong promoter, ADH1. The selection and library plasmid also comprises a sequence that encodes a His-tag.

The selection and library plasmid additionally comprises a LexAop sequence, which induces 'death agent' (cytotoxic reporter expression) when bound by a functional transcriptional factor that is formed by LexA—YAP fusion protein and VP64—TEAD fusion protein, unless interrupted by a disrupter peptide. The selection and library plasmid also contains a positive selection marker, ADE2 which is under control of Gal4BD—VGLL4 and VP64—TEAD. The plasmid further includes yeast replication and selection markers (TRP1 and CEN).

To confirm expression of the reporters and the successful construction of the strains, *Saccharomyces cerevisiae* is transformed with a confirmation plasmid (PLASMID 3; FIG. 10). The confirmation plasmid includes a direct fusion between the AD fusion protein (VP64—TEAD) and DBD fusion proteins (LexA—YAP or Gal4BD—VGLL4). The confirmation plasmid includes yeast replication and selection markers (TRP1 and CEN). The confirmation plasmid is used to confirm integration of LexAop promoter before the ADE2 gene. Transformation with the confirmation plasmid allows for the activation of ADE2 only if the promoter is properly integrated. Also, confirmation of death agents is enabled by inducible expression of the confirmation fusion construct.

The screen is performed by propagating the parental strain on selection media to ensure the presence of the PPI Integration plasmid, and that a proper PPI has occurred, which is confirmed via use of the confirmation plasmid. The strain is cultured on media lacking nutrient markers against positive selection markers to ensure selection of colonies where the desired interaction occurred. The strain is then transformed with the selection and library plasmid, and is immediately plated on selection media to ensure all components are present (on media lacking the two nutritional markers) and is induced expression of any inducible component (with Gal).

Surviving colonies constitute colonies with a specific PPI (YAP-TEAD) that has been disrupted by a peptide and no longer triggers the death cascade induced by the encoded death agents and maintain positive selection of the remaining PPI.

The peptide sequence that disrupts the death agent-driving PPI is obtained by DNA sequencing the peptide-encoding region of the selection and library plasmid in each surviving colony.

To confirm specificity, the inducible marker is used to inactivate the production of the PPI and confirm specificity. The plasmid is then isolated and re-transformed into a fresh parental strain to confirm specificity.

Biochemical fractionation of the viable strain that contained the PPI, peptide, selection marker, and death agent is followed by pull-down experiments to confirm an interaction between the peptide sequence and either PPI partner using the encoded tags.

An alternative example can be made by switching LexA with TetR. In another alternative example, fusion proteins in the PPI integration plasmid and the randomized peptide library in selection and library plasmid are driven by an inducible promoter, GAL1, instead of ADH1 promoter. In another example, yeast selection marker 2 um is included in the PPI integration plasmid and selection and library plasmid, instead of CEN. Similarly, yeast selection marker LEU2 can be used alternatively in another example. In yet another example, the N-terminus of the peptide translated from the selection and library plasmid can alternatively be glycine, alanine, serine, threonine, valine, or proline. In other examples, the genetic reporter in the confirmation plasmid is HIS3 or URA3, in place of ADE2. Either mating types of *Saccharomyces cerevisiae* haploid state can be used as background strain in alternative examples. In other examples, background strains also express the enzymes for the cyclization and methylation of peptides like lanthipeptides maturation enzymes from *Lactococcus lactis* (LanB, LanC, LanM, LanP), patellamide biosynthesis factors from cyanobacteria (PatD, PatG), butelase 1 from *Clitoria ternatea*, and GmPOPB from *Galerina marginata* or other species.

Example 3: Method for Identifying Protein-Protein Interaction Facilitator

This is an example of system that uses two variants of one protein, fused to different DBDs to identify facilitator for a specific PPI. The PPI integration plasmid (PLASMID 1; FIG. 8) is used to integrate into *Saccharomyces cerevisiae* three proteins that constitute the binary PPIs of interest. The plasmid encodes for the fusion of an AD (VP64) with Mdm2, a DBDs (LexA) with KRas, and a DBD (Gal4BD) with KRas(G12D). DBD-KRas, each driven by ADH1 promoter. Three protein fusion sequences are tagged with either FLAG, MYC or HA. The plasmid further includes yeast replication and selection markers (TRP1 and CEN). The plasmid also has sites for integration into the genome at a specified locus.

The *Saccharomyces cerevisiae* is co-transformed with the selection and library plasmid (PLASMID 2; FIG. 9) for the expression of a randomized peptide library, NNK 20-mer sequences. The selection plasmid is driven by a strong promoter, ADH1. The selection and library plasmid also comprises a sequence that encodes a HIS tag.

The selection and library plasmid additionally comprises a LexAop sequence, which induces 'death agents' (cytotoxic reporter expression) when bound by a functional transcriptional factor that is formed by LexA—KRas fusion protein and VP64—Mdm2 fusion protein, when mediated by a facilitator peptide. The selection and library plasmid also contains a positive selection marker, ADE2 which is under control of Gal4BD-KRas(G12D) fusion protein and VP64—Mdm2 fusion protein and leading to expression of the positive selection marker when the fusion proteins are mediated by a facilitator. The plasmid further includes yeast replication and selection markers (TRP1 and CEN).

To confirm expression of the reporters and the successful construction of the strains, *Saccharomyces cerevisiae* is transformed with confirmation plasmid (PLASMID 3; FIG. 10). The confirmation plasmid includes a direct fusion between the AD fusion protein (VP64—Mdm2) and DBD fusion proteins (LexA—KRas or Gal4BD—KRas(G12D)). The confirmation plasmid includes yeast replication and selection markers (TRP1 and CEN). The confirmation plasmid is used to confirm integration of LexAop promoter before the ADE2 gene. Transformation with the confirmation plasmid allows for the activation of ADE2 only if the promoter is properly integrated. Also, confirmation of death agents is enabled by inducible expression of the confirmation fusion construct.

The screen is performed by mating the strains in a batch to result in a diploid strain, which carries all the markers, the PPIs, the positive selection, the death agents, and the peptide. This batch culture is then propagated on solid medium, which enable selection of all the system components (media lacking two nutritional components) and induce expression of any inducible component with Gal.

Surviving colonies constitute colonies with a specific PPI (KRas(G12D)—Mdm2) that has been facilitated by a peptide and do not have nonspecific PPI (KRas—Mdm2) that can trigger the death cascade induced by the encoded death agents and maintain positive selection of the remaining PPI.

The peptide sequence that is able to facilitate a specific PPI is obtained by DNA sequencing the peptide-encoding region of the selection and library plasmid in each surviving colony.

To confirm specificity, the inducible marker is used to inactivate the production of the PPI and confirm specificity. The plasmid is then isolated and re-transformed into a fresh parental strain to confirm specificity.

Biochemical fractionation of the viable strain that contained the PPI, peptide, selection marker, and death agent is followed by pull-down experiments to confirm an interaction between the peptide sequence and either PPI partner using the encoded tags.

An alternative example can be made by switching LexA with TetR. In another alternative example, fusion proteins in the PPI integration plasmid and the randomized peptide library in selection and library plasmid are driven by an inducible promoter, GAL1, instead of ADH1 promoter. In another example, yeast selection marker 2 um is included in the PPI integration plasmid and selection and library plasmid, instead of CEN. Similarly, yeast selection marker LEU2 can be used alternatively in another example. In yet another example, the N-terminus of the peptide translated from the selection and library plasmid can alternatively be glycine, alanine, serine, threonine, valine, or proline. In other examples, the genetic reporter in the confirmation plasmid is HIS3 or URA3, in place of ADE2. Either mating types of *Saccharomyces cerevisiae* haploid state can be used as background strain in alternative examples. In other examples, background strains also express the enzymes for the cyclization and methylation of peptides like lanthipeptides maturation enzymes from *Lactococcus lactis* (LanB, LanC, LanM, LanP), patellamide biosynthesis factors from cyanobacteria (PatD, PatG), butelase 1 from *Clitoria ternatea*, and GmPOPB from *Galerina marginata* or other species.

Example 4: Reversible Induction of a Nutritional Reporter by Protein-Protein Interaction This is an example of two platforms that either used two variants or two different proteins, fused to different DBDs to identify inhibitor by nutrient based selection. In the first platform, KRas and KRas(G12D) fused to DBDs and c-Raf fused to AD were expressed in *Saccharomyces cerevisiae* cells using an integration plasmid (FIG. 6). In the absence of any inhibitors, the DBD fusion protein and AD fusion protein pairs maintained their interaction to drive expression of Nutritional reporters 1 and 2. A 5-fold dilution series starting at $10^4$ cells were spotted onto selective media with or without inhibitor and visualized after 2 days of growth at 30° C. The results showed that the cells grown on media that selected for Nutritional reporter 2 had poor survival rate when added the inhibitor, illustrating the specificity of the inhibitor for KRas(G12D) and c-Raf interaction.

In the second platform, VGLL4 or YAP fused to DBD and TEAD fused to AD were expressed in *Saccharomyces cerevisiae* cells with an integration plasmid (FIG. 6). In the absence of any inhibitors, the DBD fusion protein and AD fusion protein pairs maintained their interaction to drive expression of Nutritional reporters 1 and 2. A 5-fold dilution series starting at $10^4$ cells were spotted onto selective media with or without inhibitor and visualized after 2 days of growth at 30 C. The results showed that the cells grown on media that selected for Nutritional reporter 2 had particularly poor survival rate when added the inhibitor, illustrating the specificity of the inhibitor for YAP and TEAD.

Example 5: Reversible Induction of a Cytotoxic Reporter by Protein-Protein Interaction This is an example of two platforms that used either two variants or two different proteins, fused to different DBDs to identify inhibitor by toxicity based selection. In the first platform, KRas and KRas(G12D) fused to DBDs and c-Raf fused to AD were expressed in *Saccharomyces cerevisiae* cells with an integration plasmid. In the absence of inhibitors, the KRas(G12D) and c-Raf maintained an interaction to drive expression of cytotoxic reporter. A nutritional reporter was controlled by KRas and c-Raf interaction. The cells were patched onto selective media for a nutritional marker with or without inhibitor and visualized after 4 days of growth at 30° C. In cell populations with KRas(G12D) and c-Raf interaction, only those with the inhibitor showed enhanced cell viability, illustrating the specificity of the inhibitor to KRas(G12D) and c-Raf interaction. In the second platform, VGLL4 or YAP fused to DBD and TEAD fused to AD were expressed in *Saccharomyces cerevisiae* cells with an integration plasmid. In the absence of inhibitors, the YAP and TEAD maintained their interaction to drive expression of cytotoxic reporter. A nutritional reporter was controlled by VGLL4 and TEAD interaction. The cells were patched onto selective media for a nutritional marker with or without inhibitor and visualized after 4 days of growth at 30 C. In cell populations with YAP and TEAD interaction, only those with the inhibitor showed enhanced cell viability, illustrating the specificity of the inhibitor to YAP and TEAD interaction.

Example 6: Cyclization of Peptides

This is an example of a system that induces cyclization of randomized peptides in a complex to achieve enhanced cell permeability and peptide stability. The *Saccharomyces cerevisiae* is transformed with the selection and library plasmid (PLASMID 2; FIG. 9) for the expression of a randomized peptide library, NNK 60-mer sequences. The selection plasmid is driven by a strong promoter, ADH1. The initiation sequence of the selection and library plasmid is a fixed sequence that encodes Methionine Valine Asparagine (MVN) at N-terminus of peptide to maximize the half-life of the peptide, and terminate with sequence that encodes the UTR of a short protein (sORF1). The peptide is also tagged with a HIS tag.

The variable peptide library region of the selection and library plasmid is embedded within primary sequence of modifying enzyme, a homolog of N-methyltransferase from *Rhizophogun vinicolor* and contains randomized residues. The diversified variable region is excised and end-to-end cyclized by the action of a beta-lactamase DD-transpeptidase from *R. vinicolor*. Some of the side chains of the randomized residues are subsequently post-translationally isomerized from L- to D-configuration and hydroxylated.

Example 7: Cyclization of Peptides

This is an example of a system that induces cyclization of randomized peptides in a complex to achieve enhanced cell permeability and peptide stability. The *Saccharomyces cerevisiae* is transformed with the selection and library plasmid (PLASMID 2; FIG. 9) for the expression of a randomized peptide library, NNK 60-mer sequences. The selection plasmid is driven by a strong promoter, ADH1. The initiation sequence of the selection and library plasmid is a fixed sequence that encodes Methionine Valine Asparagine (MVN) at N-terminus of peptide to maximize the half-life of the peptide, and terminate with sequence that encodes the UTR of a short protein (sORF1). The peptide is also tagged with a HIS tag.

The variable peptide library region of the selection and library plasmid is embedded within primary sequence of modifying enzyme, a homolog of prolyl endopeptidases belonging to the PopB family and contains randomized residues. A post-translational processing of the variable peptide by the co-expressed prolyl endopeptidases leads to the generation of N-to-C cyclized macrocycles.

Example 8: Bicyclization of Peptides

This is an example of a system that induces cyclization of randomized peptides in a complex to achieve enhanced cell permeability and peptide stability. The *Saccharomyces cerevisiae* is transformed with the selection and library plasmid (PLASMID 2; FIG. 9) for the expression of a randomized peptide library, NNK 60-mer sequences. The selection plasmid is driven by a strong promoter, ADH1. The initiation sequence of the selection and library plasmid is a fixed sequence that encodes Methionine Valine Asparagine (MVN) at N-terminus of peptide to maximize the half-life of the peptide, and terminated with sequence that encodes the UTR of a short protein (sORF1). The peptide is also tagged with a HIS tag.

The variable peptide library region of the selection and library plasmid is embedded within primary sequence of modifying enzyme, a homolog of prolyl endopeptidases belonging to the PopB family and contains randomized residues. A post-translational processing of the variable peptide by the co-expressed prolyl endopeptidases leads to the generation of N-to-C cyclized macrocycles.

The macrocycles is then hydroxylated at the 2-position of the indole ring of the tryptophan residue by a hydroxylase belonging to the Cytochrome P450 family of oxygenases. A condensation reaction is followed catalyzed by dehydratase to form a tryptathionine bridge between the 2'-hydroxyl position on tryptophan and the thiol group from the cysteine residue. A flavin-monooxygenase enzyme converts the intermediate product to a sulfinyl form by S-oxygenation of the tryptathionine thiol. Some of the side chains of the peptide are subsequently hydroxylated at position 6 on the indole ring of the tryptathionine-forming tryptophan residue by a P450 family monoxygenase. The resulting bicyclized macrocycles comprises a tryptathionine bridge.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A method of screening for a molecule that disrupts an interaction between a first test protein and a second test protein in a host cell, while not disrupting an interaction between a third test protein and a second protein in the host cell, the method comprising:

expressing in the host cell a first fusion protein comprising the first test protein and a first DNA-binding moiety;

expressing in the host cell a second fusion protein comprising the second test protein and a gene activating moiety;

expressing in the host cell a third fusion protein comprising a third test protein and a second DNA-binding moiety, wherein the second DNA-binding moiety is different from the first DNA-binding moiety; and delivering a molecule to the host cell to test for disruption of the interaction of the first test protein and the second test protein without disrupting the interaction between the third test protein and the second protein;

wherein a plurality of death agent genes are disposed within the host cell, each operably linked to a promoter DNA sequence specific for the first DNA-binding moiety, wherein a positive selection reporter is disposed within the host cell and operably linked to a promoter DNA sequence specific for the second DNA binding moiety, and wherein, when the molecule does not disrupt the interaction between the first test protein and the second test protein and does not disrupt the interaction between the second test protein and the third test protein, an interaction between the first test protein and the second test protein causes the gene activating moiety to activate expression of the death agent genes, while an interaction between the second test protein and the third test protein causes the gene activating moiety to activate expression of the positive selection reporter; and wherein, when the molecule disrupts the interaction between the first test protein and the second test protein but not the third test protein and the second test protein, (1) an interaction between the second test protein and the third test protein causes the gene activating moiety to activate expression of the positive selection reporter; and (2) disruption of the interaction between the first test protein and the second test moiety does not activate expression of the death agents;

wherein the host cell is a fungal cell.

2. The method of claim 1, wherein the host cell comprises an integrated DNA encoding the first fusion protein, an integrated DNA encoding the second fusion protein, an integrated DNA encoding the third fusion protein, a plasmid DNA encoding death agents produced by the death agent genes, and a plasmid DNA encoding the positive selection reporter.

3. The method of claim 1, wherein the first test protein is a Ras variant, the second test protein is a Raf kinase, and the third test protein is Ras.

4. The method of claim 1, wherein the first DNA-binding moiety, the second DNA-binding moiety, or both, is a LexA, cI, Gli-1, YY1, Glucocorticoid receptor, TetR, or Ume6 DNA binding moiety.

5. The method of claim 1, wherein the gene activating moiety is a VP16, GAL4, NF-κB, B42, BP64, VP64, or p65 gene activating moiety.

6. The method of claim 1, wherein death agent(s) encoded by the death agent genes are selected from the group consisting of: a ribosomally encoded xenobiotic agent, a ribosomally encoded poison, a ribosomally encoded endogenous or exogenous gene that results in severe growth defects upon mild overexpression, a ribosomally encoded recombinase that excises an essential gene for viability, a limiting factor involved in the synthesis of a toxic secondary metabolite, and any combination thereof.

7. The method of claim 1, wherein death agent(s) encoded by the death agent genes are selected from the group consisting of: Cholera toxin, SpvB toxin, CARDS toxin, SpyA Toxin, HopU1, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, and any combination thereof.

8. The method of claim 1, wherein the fungal cell is selected from the group consisting of: *Aspergillus, Pichia pastoris*, and *Saccharomyces cerevisiae*.

9. The method of claim 1, wherein the molecule is a small molecule.

10. The method of claim 9, wherein the small molecule is a peptidomimetic.

11. The method of claim 1, wherein the molecule is a peptide or a protein.

12. The method of claim 11, wherein the peptide or the protein is a naturally occurring protein product, is a synthesized protein product, or is produced by expression of a recombinant gene.

13. The method of claim 11, wherein the peptide or protein is expressed from a library comprising test DNA molecules comprising DNA sequences that encode polypeptides, and wherein the peptide or the protein is expressed from the test DNA molecules.

14. The method of claim 13, wherein the polypeptides are 60 or fewer amino acids in length.

15. The method of claim 14, wherein the polypeptides are processed into cyclic or bicyclic peptides in the host cell.

16. A method of screening for a molecule that disrupts an interaction between a first test protein and a second test protein in a host cell, while not disrupting an interaction between a third test protein and a second test protein in the host cell, the method comprising:
- expressing in the host cell a first fusion protein comprising the first test protein and a first DNA-binding moiety;
- expressing in the host cell a second fusion protein comprising the second test protein and a gene activating moiety;
- expressing in the host cell a third fusion protein comprising a third test protein and a second DNA-binding moiety, wherein the second DNA-binding moiety is different from the first DNA-binding moiety; and
- delivering a molecule to the host cell to test for disruption of the interaction between the first test protein and the second test protein without disrupting the interaction between the third test protein and the second test protein;
- wherein a plurality of death agent genes are disposed within the host cell, each operably linked to a promoter DNA sequence specific for the first DNA-binding moiety,
- wherein a positive selection reporter is disposed within the host cell and operably linked to a promoter DNA sequence specific for the second DNA binding moiety, and
- wherein, when the molecule does not disrupt the interaction between the first test protein and the second test protein and does not disrupt the interaction between the second test protein and the third test protein, an interaction between the first test protein and the second test protein causes the gene activating moiety to activate expression of the death agent genes, while an interaction between the second test protein and the third test protein causes the gene activating moiety to activate expression of the positive selection reporter; and
- wherein, when the molecule disrupts the interaction between the first test protein and the second test protein but not the third test protein and the second test protein, the cell survives in the presence of a positive selection agent;
- wherein the host cell is a fungal cell;
- wherein the first DNA-binding moiety, the second DNA-binding moiety, or both, is a LexA, cI, Gli-1, YY1, Glucocorticoid receptor, TetR, or Ume6 DNA binding moiety;
- wherein the gene activating moiety is a VP16, GAL4, NF-κB, B42, BP64, VP64, or p65 gene activating moiety; and
- wherein death agent(s) encoded by the death agent genes are selected from the group consisting of: a ribosomally encoded xenobiotic agent, a ribosomally encoded poison, a ribosomally encoded endogenous or exogenous gene that results in severe growth defects upon mild overexpression, a ribosomally encoded recombinase that excises an essential gene for viability, a limiting factor involved in the synthesis of a toxic secondary metabolite, and any combination thereof.

17. The method of claim 16, wherein the fungal cell is selected from the group consisting of *Aspergillus, Pichia pastoris*, and *Saccharomyces cerevisiae*.

18. The method of claim 17, wherein the first test protein is YAP or TAZ, the second test protein is TEAD, and the third test protein is VGLL4.

19. The method of claim 17, wherein the first test protein is a Ras variant, the second test protein is a Raf kinase, and the third test protein is Ras.

20. The method of claim 1, wherein the first test protein is YAP or TAZ, the second test protein is TEAD, and the third test protein is VGLL4.

* * * * *

SEQUENCE LISTING

<160> NUMBER OF SEQ ID NOS: 63

<210> SEQ ID NO 1
<211> LENGTH: 258
<212> TYPE: PRT
<213> ORGANISM: Vibrio cholerae

<400> SEQUENCE: 1

Met Val Lys Ile Ile Phe Val Phe Phe Ile Phe Leu Ser Ser Phe Ser
1               5                   10                  15

Tyr Ala Asn Asp Asp Lys Leu Tyr Arg Ala Asp Ser Arg Pro Pro Asp
            20                  25                  30

Glu Ile Lys Gln Ser Gly Gly Leu Met Pro Arg Gly Gln Ser Glu Tyr
        35                  40                  45

Phe Asp Arg Gly Thr Gln Met Asn Ile Asn Leu Tyr Asp His Ala Arg
    50                  55                  60

Gly Thr Gln Thr Gly Phe Val Arg His Asp Asp Gly Tyr Val Ser Thr
65                  70                  75                  80

Ser Ile Ser Leu Arg Ser Ala His Leu Val Gly Gln Thr Ile Leu Ser
                85                  90                  95

Gly His Ser Thr Tyr Tyr Ile Tyr Val Ile Ala Thr Ala Pro Asn Met
            100                 105                 110

Phe Asn Val Asn Asp Val Leu Gly Ala Tyr Ser Pro His Pro Asp Glu
        115                 120                 125

Gln Glu Val Ser Ala Leu Gly Gly Ile Pro Tyr Ser Gln Ile Tyr Gly
    130                 135                 140

Trp Tyr Arg Val His Phe Gly Val Leu Asp Glu Gln Leu His Arg Asn
145                 150                 155                 160

Arg Gly Tyr Arg Asp Arg Tyr Tyr Ser Asn Leu Asp Ile Ala Pro Ala
                165                 170                 175

Ala Asp Gly Tyr Gly Leu Ala Gly Phe Pro Pro Glu His Arg Ala Trp
            180                 185                 190

Arg Glu Glu Pro Trp Ile His His Ala Pro Pro Gly Cys Gly Asn Ala
        195                 200                 205

```
Pro Arg Ser Ser Met Ser Asn Thr Cys Asp Glu Lys Thr Gln Ser Leu
    210                 215                 220

Gly Val Lys Phe Leu Asp Glu Tyr Gln Ser Lys Val Lys Arg Gln Ile
225                 230                 235                 240

Phe Ser Gly Tyr Gln Ser Asp Ile Asp Thr His Asn Arg Ile Lys Asp
                245                 250                 255

Glu Leu

<210> SEQ ID NO 2
<211> LENGTH: 593
<212> TYPE: PRT
<213> ORGANISM: Salmonella enterica

<400> SEQUENCE: 2

Met Leu Ile Leu Asn Gly Phe Ser Ser Ala Thr Leu Ala Leu Ile Thr
1               5                   10                  15

Pro Pro Phe Leu Pro Lys Gly Gly Lys Ala Leu Ser Gln Ser Gly Pro
                20                  25                  30

Asp Gly Leu Ala Ser Ile Thr Leu Pro Leu Pro Ile Ser Ala Glu Arg
            35                  40                  45

Gly Phe Ala Pro Ala Leu Ala Leu His Tyr Ser Ser Gly Gly Gly Asn
50                  55                  60

Gly Pro Phe Gly Val Gly Trp Ser Cys Ala Thr Met Ser Ile Ala Arg
65                  70                  75                  80

Arg Thr Ser His Gly Val Pro Gln Tyr Asn Asp Ser Asp Glu Phe Leu
                85                  90                  95

Gly Pro Asp Gly Glu Val Leu Val Gln Thr Leu Ser Thr Gly Asp Ala
            100                 105                 110

Pro Asn Pro Val Thr Cys Phe Ala Tyr Gly Asp Val Ser Phe Pro Gln
        115                 120                 125

Ser Tyr Thr Val Thr Arg Tyr Gln Pro Arg Thr Glu Ser Ser Phe Tyr
    130                 135                 140

Arg Leu Glu Tyr Trp Val Gly Asn Ser Asn Gly Asp Asp Phe Trp Leu
145                 150                 155                 160

Leu His Asp Ser Asn Gly Ile Leu His Leu Leu Gly Lys Thr Ala Ala
                165                 170                 175

Ala Arg Leu Ser Asp Pro Gln Ala Ala Ser His Thr Ala Gln Trp Leu
            180                 185                 190

Val Glu Glu Ser Val Thr Pro Ala Gly Glu His Ile Tyr Tyr Ser Tyr
        195                 200                 205

Leu Ala Glu Asn Gly Asp Asn Val Asp Leu Asn Gly Asn Glu Ala Gly
    210                 215                 220

Arg Asp Arg Ser Ala Met Arg Tyr Leu Ser Lys Val Gln Tyr Gly Asn
225                 230                 235                 240

Ala Thr Pro Ala Ala Asp Leu Tyr Leu Trp Thr Ser Ala Thr Pro Ala
                245                 250                 255

Val Gln Trp Leu Phe Thr Leu Val Phe Asp Tyr Gly Glu Arg Gly Val
            260                 265                 270

Asp Pro Gln Val Pro Ala Phe Thr Ala Gln Asn Ser Trp Leu Ala
        275                 280                 285

Arg Gln Asp Pro Phe Ser Leu Tyr Asn Tyr Gly Phe Glu Ile Arg Leu
    290                 295                 300

His Arg Leu Cys Arg Gln Val Leu Met Phe His Phe Pro Asp Glu
305                 310                 315                 320
```

Leu Gly Glu Ala Asp Thr Leu Val Ser Arg Leu Leu Glu Tyr Asp
                325                 330                 335

Glu Asn Pro Ile Leu Thr Gln Leu Cys Ala Ala Arg Thr Leu Ala Tyr
            340                 345                 350

Glu Gly Asp Gly Tyr Arg Arg Ala Pro Val Asn Asn Met Met Pro Pro
        355                 360                 365

Pro Pro Pro Pro Pro Pro Met Met Gly Gly Asn Ser Ser Arg Pro
    370                 375                 380

Lys Ser Lys Trp Ala Ile Val Glu Glu Ser Lys Gln Ile Gln Ala Leu
385                 390                 395                 400

Arg Tyr Tyr Ser Ala Gln Gly Tyr Ser Val Ile Asn Lys Tyr Leu Arg
                405                 410                 415

Gly Asp Asp Tyr Pro Glu Thr Gln Ala Lys Glu Thr Leu Leu Ser Arg
            420                 425                 430

Asp Tyr Leu Ser Thr Asn Glu Pro Ser Asp Glu Glu Phe Lys Asn Ala
        435                 440                 445

Met Ser Val Tyr Ile Asn Asp Ile Ala Glu Gly Leu Ser Ser Leu Pro
    450                 455                 460

Glu Thr Asp His Arg Val Val Tyr Arg Gly Leu Lys Leu Asp Lys Pro
465                 470                 475                 480

Ala Leu Ser Asp Val Leu Lys Glu Tyr Thr Thr Ile Gly Asn Ile Ile
                485                 490                 495

Ile Asp Lys Ala Phe Met Ser Thr Ser Pro Asp Lys Ala Trp Ile Asn
            500                 505                 510

Asp Thr Ile Leu Asn Ile Tyr Leu Glu Lys Gly His Lys Gly Arg Ile
        515                 520                 525

Leu Gly Asp Val Ala His Phe Lys Gly Glu Ala Glu Met Leu Phe Pro
    530                 535                 540

Pro Asn Thr Lys Leu Lys Ile Glu Ser Ile Val Asn Cys Gly Ser Gln
545                 550                 555                 560

Asp Phe Ala Ser Gln Leu Ser Lys Leu Arg Leu Ser Asp Asp Ala Thr
                565                 570                 575

Ala Asp Thr Asn Arg Ile Lys Arg Ile Ile Asn Met Arg Val Leu Asn
            580                 585                 590

Ser

<210> SEQ ID NO 3
<211> LENGTH: 601
<212> TYPE: PRT
<213> ORGANISM: Mycoplasma pneumoniae

<400> SEQUENCE: 3

Met Ser Glu Asn Leu Tyr Phe Gln Gly His Met Pro Asn Pro Val Arg
1               5                   10                  15

Phe Val Tyr Arg Val Asp Leu Arg Ser Pro Glu Glu Ile Phe Glu His
                20                  25                  30

Gly Phe Ser Thr Leu Gly Asp Val Arg Asn Phe Phe Glu His Ile Leu
            35                  40                  45

Ser Thr Asn Phe Gly Arg Ser Tyr Phe Ile Ser Thr Ser Glu Thr Pro
        50                  55                  60

Thr Ala Ala Ile Arg Phe Phe Gly Ser Trp Leu Arg Glu Tyr Val Pro
65                  70                  75                  80

Glu His Pro Arg Arg Ala Tyr Leu Tyr Glu Ile Arg Ala Asp Gln His
                85                  90                  95

```
Phe Tyr Asn Ala Arg Ala Thr Gly Glu Asn Leu Leu Asp Leu Met Arg
            100                 105                 110

Gln Arg Gln Val Val Phe Asp Ser Gly Asp Arg Glu Met Ala Gln Met
            115                 120                 125

Gly Ile Arg Ala Leu Arg Thr Ser Phe Ala Tyr Gln Arg Glu Trp Phe
        130                 135                 140

Thr Asp Gly Pro Ile Ala Ala Asn Val Arg Ser Ala Trp Leu Val
145                 150                 155                 160

Asp Ala Val Pro Val Glu Pro Gly His Ala His Pro Ala Gly Arg
                165                 170                 175

Val Val Glu Thr Thr Arg Ile Asn Glu Pro Glu Met His Asn Pro His
            180                 185                 190

Tyr Gln Glu Leu Gln Thr Gln Ala Asn Asp Gln Pro Trp Leu Pro Thr
            195                 200                 205

Pro Gly Ile Ala Thr Pro Val His Leu Ser Ile Pro Gln Ala Ala Ser
    210                 215                 220

Val Ala Asp Val Ser Glu Gly Thr Ser Ala Ser Leu Ser Phe Ala Cys
225                 230                 235                 240

Pro Asp Trp Ser Pro Ser Ser Asn Gly Glu Asn Pro Leu Asp Lys
                245                 250                 255

Cys Ile Ala Glu Lys Ile Asp Asn Tyr Asn Leu Gln Ser Leu Pro Gln
            260                 265                 270

Tyr Ala Ser Ser Val Lys Glu Leu Glu Asp Thr Pro Val Tyr Leu Arg
        275                 280                 285

Gly Ile Lys Thr Gln Lys Thr Phe Met Leu Gln Ala Asp Pro Gln Asn
        290                 295                 300

Asn Asn Val Phe Leu Val Glu Val Asn Pro Lys Gln Lys Ser Ser Phe
305                 310                 315                 320

Pro Gln Thr Ile Phe Phe Trp Asp Val Tyr Gln Arg Ile Cys Leu Lys
            325                 330                 335

Asp Leu Thr Gly Ala Gln Ile Ser Leu Ser Leu Thr Ala Phe Thr Thr
            340                 345                 350

Gln Tyr Ala Gly Gln Leu Lys Val His Leu Ser Val Ser Ala Val Asn
        355                 360                 365

Ala Val Asn Gln Lys Trp Lys Met Thr Pro Gln Asp Ile Ala Ile Thr
    370                 375                 380

Gln Phe Arg Val Ser Ser Glu Leu Leu Gly Gln Thr Glu Asn Gly Leu
385                 390                 395                 400

Phe Trp Asn Thr Lys Ser Gly Gly Ser Gln His Asp Leu Tyr Val Cys
            405                 410                 415

Pro Leu Lys Asn Pro Pro Ser Asp Leu Glu Glu Leu Gln Ile Ile Val
            420                 425                 430

Asp Glu Cys Thr Thr His Ala Gln Phe Val Thr Met Arg Ala Ala Ser
            435                 440                 445

Thr Phe Phe Val Asp Val Gln Leu Gly Trp Tyr Trp Arg Gly Tyr Tyr
        450                 455                 460

Tyr Thr Pro Gln Leu Ser Gly Trp Ser Tyr Gln Met Lys Thr Pro Asp
465                 470                 475                 480

Gly Gln Ile Phe Tyr Asp Leu Lys Thr Ser Lys Ile Phe Phe Val Gln
            485                 490                 495

Asp Asn Gln Asn Val Phe Phe Leu His Asn Lys Leu Asn Lys Gln Thr
            500                 505                 510
```

```
Gly Tyr Ser Trp Asp Trp Val Glu Trp Leu Lys His Asp Met Asn Glu
            515                 520                 525

Asp Lys Asp Glu Asn Phe Lys Trp Tyr Phe Ser Arg Asp Asp Leu Thr
530                 535                 540

Ile Pro Ser Val Glu Gly Leu Asn Phe Arg His Ile Arg Cys Tyr Ala
545                 550                 555                 560

Asp Asn Gln Gln Leu Lys Val Ile Ile Ser Gly Ser Arg Trp Gly Gly
            565                 570                 575

Trp Tyr Ser Thr Tyr Asp Lys Val Glu Ser Asn Val Glu Asp Lys Ile
            580                 585                 590

Leu Val Lys Asp Gly Phe Asp Arg Phe
            595                 600

<210> SEQ ID NO 4
<211> LENGTH: 250
<212> TYPE: PRT
<213> ORGANISM: Streptococcus pyogenes

<400> SEQUENCE: 4

Met Leu Lys Lys Arg Tyr Gln Leu Ala Met Ile Leu Leu Leu Ser Cys
1               5                   10                  15

Phe Ser Leu Val Trp Gln Thr Glu Gly Leu Val Glu Leu Phe Val Cys
                20                  25                  30

Glu His Tyr Glu Arg Ala Val Cys Glu Gly Thr Pro Ala Tyr Phe Thr
            35                  40                  45

Phe Ser Asp Gln Lys Gly Ala Glu Thr Leu Ile Lys Lys Arg Trp Gly
        50                  55                  60

Lys Gly Leu Val Tyr Pro Arg Ala Glu Gln Glu Ala Met Ala Ala Tyr
65                  70                  75                  80

Thr Cys Gln Gln Ala Gly Pro Ile Asn Thr Ser Leu Asp Lys Ala Lys
                85                  90                  95

Gly Lys Leu Ser Gln Leu Thr Pro Glu Leu Arg Asp Gln Val Ala Gln
            100                 105                 110

Leu Asp Ala Ala Thr His Arg Leu Val Ile Pro Trp Asn Ile Val Val
        115                 120                 125

Tyr Arg Tyr Val Tyr Glu Thr Phe Leu Arg Asp Ile Gly Val Ser His
130                 135                 140

Ala Asp Leu Thr Ser Tyr Tyr Arg Asn His Gln Phe Asn Pro His Ile
145                 150                 155                 160

Leu Cys Lys Ile Lys Leu Gly Thr Arg Tyr Thr Lys His Ser Phe Met
                165                 170                 175

Ser Thr Thr Ala Leu Lys Asn Gly Ala Met Thr His Arg Pro Val Glu
            180                 185                 190

Val Arg Ile Cys Val Lys Lys Gly Ala Lys Ala Ala Phe Val Glu Pro
        195                 200                 205

Tyr Ser Ala Val Pro Ser Glu Val Glu Leu Leu Phe Pro Arg Gly Cys
210                 215                 220

Gln Leu Glu Val Val Gly Ala Tyr Val Ser Gln Asp His Lys Lys Leu
225                 230                 235                 240

His Ile Glu Ala Tyr Phe Lys Gly Ser Leu
                245                 250

<210> SEQ ID NO 5
<211> LENGTH: 264
<212> TYPE: PRT
<213> ORGANISM: Pseudomonas syringae
```

<400> SEQUENCE: 5

```
Met Asn Ile Asn Arg Gln Leu Pro Val Ser Gly Ser Glu Arg Leu Leu
1               5                   10                  15

Thr Pro Asp Val Gly Val Ser Arg Gln Ala Cys Ser Glu Arg His Tyr
            20                  25                  30

Ser Thr Gly Gln Asp Arg His Asp Phe Tyr Arg Phe Ala Ala Arg Leu
        35                  40                  45

His Val Asp Ala Gln Cys Phe Gly Leu Ser Ile Asp Asp Leu Met Asp
    50                  55                  60

Lys Phe Ser Asp Lys His Phe Arg Ala Glu His Pro Glu Tyr Arg Asp
65                  70                  75                  80

Val Tyr Pro Glu Glu Cys Ser Ala Ile Tyr Met His Thr Ala Gln Asp
                85                  90                  95

Tyr Ser Ser His Leu Val Arg Gly Glu Ile Gly Thr Pro Leu Tyr Arg
            100                 105                 110

Glu Val Asn Asn Tyr Leu Arg Leu Gln His Glu Asn Ser Gly Arg Glu
        115                 120                 125

Ala Glu Ile Asp Asn His Asp Glu Lys Leu Ser Pro His Ile Lys Met
    130                 135                 140

Leu Ser Ser Ala Leu Asn Arg Leu Met Asp Val Ala Ala Phe Arg Gly
145                 150                 155                 160

Thr Val Tyr Arg Gly Ile Arg Gly Asp Leu Asp Thr Ile Ala Arg Leu
                165                 170                 175

Tyr His Leu Phe Asp Thr Gly Arg Tyr Val Glu Pro Ala Phe Met
            180                 185                 190

Ser Thr Thr Arg Ile Lys Asp Ser Ala Gln Val Phe Glu Pro Gly Thr
        195                 200                 205

Pro Asn Asn Ile Ala Phe Gln Ile Ser Leu Lys Arg Gly Ala Asp Ile
    210                 215                 220

Ser Gly Ser Ser Gln Ala Pro Ser Glu Glu Ile Met Leu Pro Met
225                 230                 235                 240

Met Ser Glu Phe Val Ile Glu His Ala Ser Ala Leu Ser Glu Gly Lys
                245                 250                 255

His Leu Phe Val Leu Ser Gln Ile
            260
```

<210> SEQ ID NO 6
<211> LENGTH: 601
<212> TYPE: PRT
<213> ORGANISM: Vibrio cholerae

<400> SEQUENCE: 6

```
Met Lys Thr Ile Ile Ser Leu Ile Phe Ile Met Phe Pro Leu Phe Val
1               5                   10                  15

Ser Ala His Asn Gly Asn Phe Tyr Arg Ala Asp Ser Arg Ser Pro Asn
            20                  25                  30

Glu Ile Lys Asp Leu Gly Gly Leu Tyr Pro Arg Gly Tyr Tyr Asp Phe
        35                  40                  45

Phe Glu Arg Gly Thr Pro Met Ser Ile Ser Leu Tyr Asp His Ala Arg
    50                  55                  60

Gly Ala Pro Ser Gly Asn Thr Arg Tyr Asp Asp Gly Phe Val Ser Thr
65                  70                  75                  80

Thr Thr Asp Ile Asp Ser Ala His Glu Ile Gly Gln Asn Ile Leu Ser
                85                  90                  95
```

```
Gly Tyr Thr Glu Tyr Tyr Ile Tyr Leu Ile Ala Pro Ala Pro Asn Leu
                100                 105                 110

Leu Asp Val Asn Ala Val Leu Gly Arg Tyr Ser Pro His Pro Gln Glu
            115                 120                 125

Asn Glu Tyr Ser Ala Leu Gly Gly Ile Pro Trp Thr Gln Val Ile Gly
        130                 135                 140

Trp Tyr Val Val Asn Asn Gly Val Leu Asp Arg Asn Ile His Arg Asn
145                 150                 155                 160

Arg Gln Phe Arg Ala Asp Leu Phe Asn Asn Leu Ser Pro Ala Leu Pro
                165                 170                 175

Ser Glu Ser Tyr Gln Phe Ala Gly Phe Glu Pro Glu His Pro Ala Trp
            180                 185                 190

Arg Gln Glu Pro Trp Ile Asn Phe Ala Pro Pro Gly Cys Gly Arg Asn
        195                 200                 205

Val Arg Leu Thr Lys His Ile Asn Gln Gln Asp Cys Ser Asn Ser Gln
        210                 215                 220

Glu Glu Leu Val Tyr Lys Lys Leu Gln Asp Leu Arg Thr Gln Phe Lys
225                 230                 235                 240

Val Asp Lys Lys Leu Lys Leu Val Asn Lys Thr Ser Ser Asn Asn Ile
                245                 250                 255

Ile Phe Pro Asn His Asp Phe Ile Arg Glu Trp Val Asp Leu Asp Gly
            260                 265                 270

Asn Gly Asp Leu Ser Tyr Cys Gly Phe Thr Val Asp Ser Asp Gly Ser
        275                 280                 285

Arg Lys Arg Ile Val Cys Ala His Asn Asn Gly Asn Phe Thr Tyr Ser
        290                 295                 300

Ser Ile Asn Ile Ser Leu Ser Asp Tyr Gly Trp Pro Lys Gly Gln Arg
305                 310                 315                 320

Phe Ile Asp Ala Asn Gly Asp Gly Leu Val Asp Tyr Cys Arg Val Gln
                325                 330                 335

Tyr Val Trp Thr His Leu Tyr Cys Ser Leu Ser Leu Pro Gly Gln Tyr
            340                 345                 350

Phe Ser Leu Asp Lys Asp Ala Gly Tyr Leu Asp Ala Gly Tyr Asn Asn
        355                 360                 365

Ser Arg Ala Trp Ala Lys Val Ile Gly Thr Asn Lys Tyr Ser Phe Cys
        370                 375                 380

Arg Leu Thr Ser Asn Gly Tyr Ile Cys Thr Asp Ile Asp Ser Tyr Ser
385                 390                 395                 400

Thr Ala Phe Lys Asp Asp Asp Gln Gly Trp Ala Asp Ser Arg Tyr Trp
                405                 410                 415

Met Asp Ile Asp Gly Asn Gly Gly Asp Asp Tyr Cys Arg Leu Val Tyr
            420                 425                 430

Asn Trp Thr His Leu Arg Cys Asn Leu Gln Gly Lys Asp Gly Leu Trp
        435                 440                 445

Lys Arg Val Glu Ser Lys Tyr Leu Asp Gly Gly Tyr Pro Ser Leu Arg
        450                 455                 460

Phe Lys Ile Lys Met Thr Ser Asn Lys Asp Asn Tyr Cys Arg Ile Val
465                 470                 475                 480

Arg Asn His Arg Val Met Glu Cys Ala Tyr Val Ser Asp Asn Gly Glu
                485                 490                 495

Phe His Asn Tyr Ser Leu Asn Met Pro Phe Ser Leu Tyr Asn Lys Asn
            500                 505                 510
```

-continued

```
Asp Ile Gln Phe Ile Asp Ile Asp Gly Asp Asn Arg Asp Asp Ile Cys
        515                 520                 525

Arg Tyr Asn Ser Ala Pro Asn Thr Met Glu Cys Tyr Leu Asn Gln Asp
    530                 535                 540

Lys Ser Phe Ser Gln Asn Lys Leu Val Leu Tyr Leu Ser Ala Lys Pro
545                 550                 555                 560

Ile Ser Ser Leu Gly Ser Gly Ser Ser Lys Ile Ile Arg Thr Phe Asn
                565                 570                 575

Ser Glu Lys Asn Ser Ser Ala Tyr Cys Tyr Asn Ala Gly Tyr Gly Thr
            580                 585                 590

Leu Arg Cys Asp Glu Phe Val Ile Tyr
        595                 600

<210> SEQ ID NO 7
<211> LENGTH: 476
<212> TYPE: PRT
<213> ORGANISM: Bacillus cereus

<400> SEQUENCE: 7

Met Lys Glu Ile Ile Arg Asn Leu Val Arg Leu Asp Val Arg Ser Asp
1               5                   10                  15

Val Asp Glu Asn Ser Lys Lys Thr Gln Glu Leu Val Glu Lys Leu Pro
            20                  25                  30

His Glu Val Leu Glu Leu Tyr Lys Asn Val Gly Gly Glu Ile Tyr Ile
        35                  40                  45

Thr Asp Lys Arg Leu Thr Gln His Glu Glu Leu Ser Asp Ser Ser His
    50                  55                  60

Lys Asp Met Phe Ile Val Ser Ser Glu Gly Lys Ser Phe Pro Leu Arg
65                  70                  75                  80

Glu His Phe Val Phe Ala Lys Gly Gly Lys Glu Pro Ser Leu Ile Ile
                85                  90                  95

His Ala Glu Asp Tyr Ala Ser His Leu Ser Ser Val Glu Val Tyr Tyr
            100                 105                 110

Glu Leu Gly Lys Ala Ile Ile Arg Asp Thr Phe Pro Leu Asn Gln Lys
        115                 120                 125

Glu Leu Gly Asn Pro Lys Phe Ile Asn Ala Ile Asn Glu Val Asn Gln
    130                 135                 140

Gln Lys Glu Gly Lys Gly Val Asn Ala Lys Ala Asp Glu Asp Gly Arg
145                 150                 155                 160

Asp Leu Leu Phe Gly Lys Glu Leu Lys Lys Asn Leu Glu His Gly Gln
                165                 170                 175

Leu Val Asp Leu Asp Leu Ile Ser Gly Asn Leu Ser Glu Phe Gln His
            180                 185                 190

Val Phe Ala Lys Ser Phe Ala Leu Tyr Tyr Glu Pro His Tyr Lys Glu
        195                 200                 205

Ala Leu Lys Ser Tyr Ala Pro Ala Leu Phe Asn Tyr Met Leu Glu Leu
    210                 215                 220

Asp Gln Met Arg Phe Lys Glu Ile Ser Asp Asp Val Lys Glu Lys Asn
225                 230                 235                 240

Lys Asn Val Leu Asp Phe Lys Trp Tyr Thr Arg Lys Ala Glu Ser Trp
                245                 250                 255

Gly Val Gln Thr Phe Lys Asn Trp Lys Glu Asn Leu Thr Ile Ser Glu
            260                 265                 270

Lys Asp Ile Ile Thr Gly Tyr Thr Gly Ser Lys Tyr Asp Pro Ile Asn
        275                 280                 285
```

-continued

```
Glu Tyr Leu Arg Lys Tyr Asp Gly Glu Ile Ile Pro Asn Ile Gly Gly
        290                 295                 300

Asp Leu Asp Lys Lys Ser Lys Lys Ala Leu Glu Lys Ile Glu Asn Gln
305                 310                 315                 320

Ile Lys Asn Leu Asp Ala Ala Leu Gln Lys Ser Lys Ile Thr Glu Asn
                325                 330                 335

Leu Ile Val Tyr Arg Arg Val Ser Glu Leu Gln Phe Gly Lys Lys Tyr
            340                 345                 350

Glu Asp Tyr Asn Leu Arg Gln Asn Gly Ile Ile Asn Glu Glu Lys Val
        355                 360                 365

Met Glu Leu Glu Ser Asn Phe Lys Gly Gln Thr Phe Ile Gln His Asn
    370                 375                 380

Tyr Met Ser Thr Ser Leu Val Gln Asp Pro His Gln Ser Tyr Ser Asn
385                 390                 395                 400

Asp Arg Tyr Pro Ile Leu Leu Glu Ile Thr Ile Pro Glu Gly Val His
                405                 410                 415

Gly Ala Tyr Ile Ala Asp Met Ser Glu Tyr Pro Gly Gln Tyr Glu Met
            420                 425                 430

Leu Ile Asn Arg Gly Tyr Thr Phe Lys Tyr Asp Lys Phe Ser Ile Val
        435                 440                 445

Lys Pro Thr Arg Glu Glu Asp Lys Gly Lys Glu Tyr Leu Lys Val Asn
    450                 455                 460

Leu Ser Ile Tyr Leu Gly Asn Leu Asn Arg Glu Lys
465                 470                 475
```

<210> SEQ ID NO 8
<211> LENGTH: 487
<212> TYPE: PRT
<213> ORGANISM: Enterococcus faecalis
<220> FEATURE:
<223> OTHER INFORMATION: strain V583

<400> SEQUENCE: 8

```
Met Ser Gln Leu Asn Lys Trp Gln Lys Glu Leu Gln Ala Leu Gln Lys
1               5                   10                  15

Ala Asn Tyr Gln Glu Thr Asp Asn Gln Leu Phe Asn Val Tyr Arg Gln
                20                  25                  30

Ser Leu Ile Asp Ile Lys Lys Arg Leu Lys Val Tyr Thr Glu Asn Ala
            35                  40                  45

Glu Ser Leu Ser Phe Ser Thr Arg Leu Glu Val Glu Arg Leu Phe Ser
        50                  55                  60

Val Ala Asp Glu Ile Asn Ala Ile Leu Gln Leu Asn Ser Pro Lys Val
65                  70                  75                  80

Glu Lys Thr Ile Lys Gly Tyr Ser Ala Lys Gln Ala Glu Gln Gly Tyr
                85                  90                  95

Tyr Gly Leu Trp Tyr Thr Leu Glu Gln Ser Gln Asn Ile Ala Leu Ser
            100                 105                 110

Met Pro Leu Ile Asn His Asp Tyr Ile Met Asn Leu Val Asn Ala Pro
        115                 120                 125

Val Ala Gly Lys Arg Leu Ser Lys Arg Leu Tyr Lys Tyr Arg Asp Glu
    130                 135                 140

Leu Ala Gln Asn Val Thr Asn Asn Ile Ile Thr Gly Leu Phe Glu Gly
145                 150                 155                 160

Lys Ser Tyr Ala Glu Ile Ala Arg Trp Ile Asn Glu Glu Thr Glu Ala
                165                 170                 175
```

Ser Tyr Lys Gln Ala Leu Arg Ile Ala Arg Thr Glu Ala Gly Arg Thr
                180                 185                 190

Gln Ser Val Thr Thr Gln Lys Gly Tyr Glu Ala Lys Glu Leu Gly
            195                 200                 205

Ile Asn Ile Lys Lys Trp Leu Ala Thr Ile Asp Lys His Thr Arg
210                 215                 220

Arg Thr His Gln Glu Leu Asp Gly Lys Glu Val Asp Val Asp Glu Glu
225                 230                 235                 240

Phe Thr Ile Arg Gly His Ser Ala Lys Gly Pro Arg Met Phe Gly Val
                245                 250                 255

Ala Ser Glu Asp Val Asn Cys Arg Cys Thr Thr Ile Glu Val Val Asp
                260                 265                 270

Gly Ile Ser Pro Glu Leu Arg Lys Asp Asn Glu Ser Lys Glu Met Ser
            275                 280                 285

Glu Phe Lys Ser Tyr Asp Glu Trp Tyr Ala Asp Arg Ile Arg Gln Asn
            290                 295                 300

Glu Ser Lys Pro Lys Pro Asn Phe Thr Glu Leu Asp Phe Phe Gly Gln
305                 310                 315                 320

Ser Asp Leu Gln Asp Asp Ser Asp Lys Trp Val Ala Gly Leu Lys Pro
                325                 330                 335

Glu Gln Val Asn Ala Met Lys Asp Tyr Thr Ser Asp Ala Phe Ala Lys
                340                 345                 350

Met Asn Lys Ile Leu Arg Asn Glu Lys Tyr Asn Pro Arg Glu Lys Pro
            355                 360                 365

Tyr Leu Val Asn Ile Ile Gln Asn Leu Asp Asp Ala Ile Ser Lys Phe
            370                 375                 380

Lys Leu Lys His Asp Ile Ile Thr Tyr Arg Gly Val Ser Ala Asn Glu
385                 390                 395                 400

Tyr Asp Ala Ile Leu Asn Gly Asn Val Phe Lys Glu Phe Lys Ser Thr
                405                 410                 415

Ser Ile Asn Lys Lys Val Ala Glu Asp Phe Leu Asn Phe Thr Ser Ala
            420                 425                 430

Asn Lys Asp Gly Arg Val Val Lys Phe Leu Ile Pro Lys Gly Thr Gln
            435                 440                 445

Gly Ala Tyr Ile Gly Thr Asn Ser Ser Met Lys Lys Glu Ser Glu Phe
450                 455                 460

Leu Leu Asn Arg Asn Leu Lys Tyr Thr Val Glu Ile Val Asp Asn Ile
465                 470                 475                 480

Leu Glu Val Thr Ile Leu Gly
                485

<210> SEQ ID NO 9
<211> LENGTH: 457
<212> TYPE: PRT
<213> ORGANISM: Pseudomonas aeruginosa

<400> SEQUENCE: 9

Met His Ile Gln Ser Ser Gln Gln Asn Pro Ser Phe Val Ala Glu Leu
1               5                   10                  15

Ser Gln Ala Val Ala Gly Arg Leu Gly Gln Val Glu Ala Arg Gln Val
            20                  25                  30

Ala Thr Pro Arg Glu Ala Gln Gln Leu Ala Gln Arg Gln Glu Ala Pro
            35                  40                  45

Lys Gly Glu Gly Leu Leu Ser Arg Leu Gly Ala Ala Leu Ala Arg Pro

```
            50                  55                  60
Phe Val Ala Ile Ile Glu Trp Leu Gly Lys Leu Leu Gly Ser Arg Ala
 65                  70                  75                  80

His Ala Ala Thr Gln Ala Pro Leu Ser Arg Gln Asp Ala Pro Pro Ala
                 85                  90                  95

Ala Ser Leu Ser Ala Ala Glu Ile Lys Gln Met Met Leu Gln Lys Ala
            100                 105                 110

Leu Pro Leu Thr Leu Gly Gly Leu Gly Lys Ala Ser Glu Leu Ala Thr
            115                 120                 125

Leu Thr Ala Glu Arg Leu Ala Lys Asp His Thr Arg Leu Ala Ser Gly
        130                 135                 140

Asp Gly Ala Leu Arg Ser Leu Ala Thr Ala Leu Val Gly Ile Arg Asp
145                 150                 155                 160

Gly Ser Leu Ile Glu Ala Ser Arg Thr Gln Ala Ala Arg Leu Leu Glu
                165                 170                 175

Gln Ser Val Gly Gly Ile Ala Leu Gln Gln Trp Gly Thr Ala Gly Gly
            180                 185                 190

Ala Ala Ser Gln His Val Leu Ser Ala Ser Pro Glu Gln Leu Arg Glu
        195                 200                 205

Ile Ala Val Gln Leu His Ala Val Met Asp Lys Val Ala Leu Leu Arg
210                 215                 220

His Ala Val Glu Ser Glu Val Lys Gly Glu Pro Val Asp Lys Ala Leu
225                 230                 235                 240

Ala Asp Gly Leu Val Glu His Phe Gly Leu Glu Ala Glu Gln Tyr Leu
                245                 250                 255

Gly Glu His Pro Asp Gly Pro Tyr Ser Asp Ala Glu Val Met Ala Leu
            260                 265                 270

Gly Leu Tyr Thr Asn Gly Glu Tyr Gln His Leu Asn Arg Ser Leu Arg
        275                 280                 285

Gln Gly Arg Glu Leu Asp Ala Gly Gln Ala Leu Ile Asp Arg Gly Met
    290                 295                 300

Ser Ala Ala Phe Glu Lys Ser Gly Pro Ala Glu Gln Val Val Lys Thr
305                 310                 315                 320

Phe Arg Gly Thr Gln Gly Arg Asp Ala Phe Glu Ala Val Lys Glu Gly
                325                 330                 335

Gln Val Gly His Asp Ala Gly Tyr Leu Ser Thr Ser Arg Asp Pro Ser
            340                 345                 350

Val Ala Arg Ser Phe Ala Gly Leu Gly Thr Ile Thr Thr Leu Phe Gly
        355                 360                 365

Arg Ser Gly Ile Asp Val Ser Glu Ile Ser Ile Glu Gly Asp Glu Gln
    370                 375                 380

Glu Ile Leu Tyr Asp Lys Gly Thr Asp Met Arg Val Leu Leu Ser Ala
385                 390                 395                 400

Lys Asp Gly Gln Gly Val Thr Arg Arg Val Leu Glu Glu Ala Thr Leu
                405                 410                 415

Gly Glu Arg Ser Gly His Ser Glu Gly Leu Leu Asp Ala Leu Asp Leu
            420                 425                 430

Ala Thr Gly Thr Asp Arg Ser Gly Lys Pro Gln Glu Gln Asp Leu Arg
        435                 440                 445

Leu Arg Met Arg Gly Leu Asp Leu Ala
    450                 455

<210> SEQ ID NO 10
```

<211> LENGTH: 265
<212> TYPE: PRT
<213> ORGANISM: Unknown
<220> FEATURE:
<223> OTHER INFORMATION: Description of Unknown:
CdtB toxin sequence

<400> SEQUENCE: 10

Met Lys Lys Ile Ile Cys Leu Phe Leu Ser Phe Asn Leu Ala Phe Ala
1 5 10 15

Asn Leu Glu Asn Phe Asn Val Gly Thr Trp Asn Leu Gln Gly Ser Ser
20 25 30

Ala Ala Thr Glu Ser Lys Trp Ser Val Ser Val Arg Gln Leu Val Ser
35 40 45

Gly Ala Asn Pro Leu Asp Ile Leu Met Ile Gln Glu Ala Gly Thr Leu
50 55 60

Pro Arg Thr Ala Thr Pro Thr Gly Arg His Val Gln Gln Gly Gly Thr
65 70 75 80

Pro Ile Asp Glu Tyr Glu Trp Asn Leu Gly Thr Leu Ser Arg Pro Asp
85 90 95

Arg Val Phe Ile Tyr Tyr Ser Arg Val Asp Val Gly Ala Asn Arg Val
100 105 110

Asn Leu Ala Ile Val Ser Arg Met Gln Ala Glu Glu Val Ile Val Leu
115 120 125

Pro Pro Pro Thr Thr Val Ser Arg Pro Ile Ile Gly Ile Arg Asn Gly
130 135 140

Asn Asp Ala Phe Phe Asn Ile His Ala Leu Ala Asn Gly Gly Thr Asp
145 150 155 160

Val Gly Ala Ile Ile Thr Ala Val Asp Ala His Phe Ala Asn Met Pro
165 170 175

Gln Val Asn Trp Met Ile Ala Gly Asp Phe Asn Arg Asp Pro Ser Thr
180 185 190

Ile Thr Ser Thr Val Asp Arg Glu Leu Ala Asn Arg Ile Arg Val Val
195 200 205

Phe Pro Thr Ser Ala Thr Gln Ala Ser Gly Gly Thr Leu Asp Tyr Ala
210 215 220

Ile Thr Gly Asn Ser Asn Arg Gln Gln Thr Tyr Thr Pro Pro Leu Leu
225 230 235 240

Ala Ala Ile Leu Met Leu Ala Ser Leu Arg Ser His Ile Val Ser Asp
245 250 255

His Phe Pro Val Asn Phe Arg Lys Phe
260 265

<210> SEQ ID NO 11
<211> LENGTH: 560
<212> TYPE: PRT
<213> ORGANISM: Corynebacterium diphtheriae

<400> SEQUENCE: 11

Met Ser Arg Lys Leu Phe Ala Ser Ile Leu Ile Gly Ala Leu Leu Gly
1 5 10 15

Ile Gly Ala Pro Pro Ser Ala His Ala Gly Ala Asp Asp Val Val Asp
20 25 30

Ser Ser Lys Ser Phe Val Met Glu Asn Phe Ser Ser Tyr His Gly Thr
35 40 45

Lys Pro Gly Tyr Val Asp Ser Ile Gln Lys Gly Ile Gln Lys Pro Lys
50 55 60

```
Ser Gly Thr Gln Gly Asn Tyr Asp Asp Asp Trp Lys Gly Phe Tyr Ser
 65                  70                  75                  80

Thr Asp Asn Lys Tyr Asp Ala Ala Gly Tyr Ser Val Asp Asn Glu Asn
                 85                  90                  95

Pro Leu Ser Gly Lys Ala Gly Val Val Lys Val Thr Tyr Pro Gly
            100                 105                 110

Leu Thr Lys Val Leu Ala Leu Lys Val Asp Asn Ala Glu Thr Ile Lys
            115                 120                 125

Lys Glu Leu Gly Leu Ser Leu Thr Glu Pro Leu Met Glu Gln Val Gly
            130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
            195                 200                 205

Gln Ala Cys Ala Gly Asn Arg Val Arg Arg Ser Val Gly Ser Ser Leu
            210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Lys Ala Lys Gln Tyr Leu
            260                 265                 270

Glu Glu Phe His Gln Thr Ala Leu Glu His Pro Glu Leu Ser Glu Leu
            275                 280                 285

Lys Thr Val Thr Gly Thr Asn Pro Val Phe Ala Gly Ala Asn Tyr Ala
            290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
            355                 360                 365

Ile Pro Leu Val Gly Glu Leu Val Asp Ile Gly Phe Ala Ala Tyr Asn
            370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
            420                 425                 430

Thr Gly Phe Gln Gly Glu Ser Gly His Asp Ile Lys Ile Thr Ala Glu
            435                 440                 445

Asn Thr Pro Leu Pro Ile Ala Gly Val Leu Leu Pro Thr Ile Pro Gly
            450                 455                 460

Lys Leu Asp Val Asn Lys Ser Lys Thr His Ile Ser Val Asn Gly Arg
465                 470                 475                 480
```

```
Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
            500                 505                 510

His Val Ala Phe His Arg Ser Ser Glu Lys Ile His Ser Asn Glu
        515                 520                 525

Ile Ser Ser Asp Ser Ile Gly Val Leu Gly Tyr Gln Lys Thr Val Asp
530                 535                 540

His Thr Lys Val Asn Ser Lys Leu Ser Leu Phe Phe Glu Ile Lys Ser
545                 550                 555                 560

<210> SEQ ID NO 12
<211> LENGTH: 621
<212> TYPE: PRT
<213> ORGANISM: Unknown
<220> FEATURE:
<223> OTHER INFORMATION: Description of Unknown:
      ExoU/VipB toxin sequence

<400> SEQUENCE: 12

Met Lys Leu Ala Glu Ile Met Thr Lys Ser Arg Lys Leu Lys Arg Asn
1               5                   10                  15

Leu Leu Glu Ile Ser Lys Thr Glu Ala Gly Gln Tyr Ser Val Ser Ala
            20                  25                  30

Pro Glu His Lys Gly Leu Val Leu Ser Gly Gly Ala Lys Gly Ile
        35                  40                  45

Ser Tyr Leu Gly Met Ile Gln Ala Leu Gln Glu Arg Gly Lys Ile Lys
50                  55                  60

Asn Leu Thr His Val Ser Gly Ala Ser Ala Gly Ala Met Thr Ala Ser
65                  70                  75                  80

Ile Leu Ala Val Gly Met Asp Ile Lys Asp Ile Lys Lys Leu Ile Glu
                85                  90                  95

Gly Leu Asp Ile Thr Lys Leu Leu Asp Asn Ser Gly Val Gly Phe Arg
            100                 105                 110

Ala Arg Gly Asp Arg Phe Arg Asn Ile Leu Asp Val Ile Tyr Met Met
        115                 120                 125

Gln Met Lys Lys His Leu Glu Ser Val Gln Gln Pro Ile Pro Pro Glu
130                 135                 140

Gln Gln Met Asn Tyr Gly Ile Leu Lys Gln Lys Ile Ala Leu Tyr Glu
145                 150                 155                 160

Asp Lys Leu Ser Arg Ala Gly Ile Val Ile Asn Asn Val Asp Asp Ile
                165                 170                 175

Ile Asn Leu Thr Lys Ser Val Lys Asp Leu Glu Lys Leu Asp Lys Ala
            180                 185                 190

Leu Asn Ser Ile Pro Thr Glu Leu Lys Gly Ala Lys Gly Glu Gln Leu
        195                 200                 205

Glu Asn Pro Arg Leu Thr Leu Gly Asp Leu Gly Arg Leu Arg Glu Leu
210                 215                 220

Leu Pro Glu Glu Asn Lys His Leu Ile Lys Asn Leu Ser Val Val Val
225                 230                 235                 240

Thr Asn Gln Thr Lys His Glu Leu Glu Arg Tyr Ser Glu Asp Thr Thr
                245                 250                 255

Pro Gln Gln Ser Ile Ala Gln Val Val Gln Trp Ser Gly Ala His Pro
            260                 265                 270

Val Leu Phe Val Pro Gly Arg Asn Ala Lys Gly Glu Tyr Ile Ala Asp
        275                 280                 285
```

Gly Gly Ile Leu Asp Asn Met Pro Glu Ile Glu Gly Leu Asp Arg Glu
            290                 295                 300

Glu Val Leu Cys Val Lys Ala Glu Ala Gly Thr Ala Phe Glu Asp Arg
305                 310                 315                 320

Val Asn Lys Ala Lys Gln Ser Ala Met Glu Ala Ile Ser Trp Phe Lys
                325                 330                 335

Ala Arg Met Asp Ser Leu Val Glu Ala Thr Ile Gly Gly Lys Trp Leu
            340                 345                 350

His Ala Thr Ser Ser Val Leu Asn Arg Glu Lys Val Tyr Tyr Asn Ile
        355                 360                 365

Asp Asn Met Ile Tyr Ile Asn Thr Gly Glu Val Thr Thr Thr Asn Thr
    370                 375                 380

Ser Pro Thr Pro Glu Gln Arg Ala Arg Ala Val Lys Asn Gly Tyr Asp
385                 390                 395                 400

Gln Thr Met Gln Leu Leu Asp Ser His Lys Gln Thr Phe Asp His Pro
                405                 410                 415

Leu Met Ala Ile Leu Tyr Ile Gly His Asp Lys Leu Lys Asp Ala Leu
            420                 425                 430

Ile Asp Glu Lys Ser Glu Lys Glu Ile Phe Glu Ala Ser Ala His Ala
        435                 440                 445

Gln Ala Ile Leu His Leu Gln Glu Gln Ile Val Lys Glu Met Asn Asp
    450                 455                 460

Gly Asp Tyr Ser Ser Val Gln Asn Tyr Leu Asp Gln Ile Glu Asp Ile
465                 470                 475                 480

Leu Thr Val Asp Ala Lys Met Asp Asp Ile Gln Lys Glu Lys Ala Phe
                485                 490                 495

Ala Leu Cys Ile Lys Gln Val Asn Phe Leu Ser Glu Gly Lys Leu Glu
            500                 505                 510

Thr Tyr Leu Asn Lys Val Glu Ala Glu Ala Lys Ala Ala Glu Pro
        515                 520                 525

Ser Trp Ala Thr Lys Ile Leu Asn Leu Leu Trp Ala Pro Ile Glu Trp
    530                 535                 540

Val Val Ser Leu Phe Lys Gly Pro Ala Gln Asp Phe Lys Val Glu Val
545                 550                 555                 560

Gln Pro Glu Pro Val Lys Val Ser Thr Ser Glu Asn Gln Glu Thr Val
                565                 570                 575

Ser Asn Gln Lys Asp Ile Asn Pro Ala Val Glu Tyr Arg Lys Ile Ile
            580                 585                 590

Ala Glu Val Arg Arg Glu His Thr Asp Pro Ser Pro Ser Leu Gln Glu
        595                 600                 605

Lys Glu Arg Val Gly Leu Ser Thr Thr Phe Gly Gly His
    610                 615                 620

<210> SEQ ID NO 13
<211> LENGTH: 211
<212> TYPE: PRT
<213> ORGANISM: Pseudomonas syringae

<400> SEQUENCE: 13

Met Asn Arg Val Ser Gly Ser Ser Ser Ala Thr Trp Gln Ala Val Asn
1               5                   10                  15

Asp Leu Val Glu Gln Val Ser Glu Arg Thr Thr Leu Ser Thr Thr Gly
            20                  25                  30

Tyr Gln Thr Ala Met Gly Arg Leu Asn Lys Pro Glu Lys Ser Asp Ala

```
                35                  40                  45
Asp Ala Leu Met Thr Met Arg Arg Ala Gln Gln Tyr Thr Asp Ser Ala
 50                  55                  60

Lys Arg Thr Tyr Ile Ser Glu Thr Leu Met Asn Leu Ala Asp Leu Gln
 65                  70                  75                  80

Gln Arg Lys Ile Tyr Arg Thr Asn Ser Gly Asn Leu Arg Gly Ala Ile
                 85                  90                  95

Glu Met Thr Pro Thr Gln Leu Thr Asp Cys Val Gln Lys Cys Arg Glu
            100                 105                 110

Glu Gly Phe Ser Asn Cys Asp Ile Gln Ala Leu Glu Ile Gly Leu His
        115                 120                 125

Leu Arg His Lys Leu Gly Ile Ser Asp Phe Thr Ile Tyr Ser Asn Arg
    130                 135                 140

Lys Leu Ser His Asn Tyr Val Val Ile His Pro Ser Asn Ala Phe Pro
145                 150                 155                 160

Lys Gly Ala Ile Val Asp Ser Trp Thr Gly Gln Gly Val Val Glu Leu
                165                 170                 175

Asp Phe Lys Thr Arg Leu Lys Phe Lys His Arg Glu Glu Asn Tyr Ala
            180                 185                 190

Val Asn Ala Asn Met His Glu Trp Ile Glu Arg Tyr Gly Gln Ala His
        195                 200                 205

Val Ile Asp
    210

<210> SEQ ID NO 14
<211> LENGTH: 204
<212> TYPE: PRT
<213> ORGANISM: Pseudomonas syringae

<400> SEQUENCE: 14

Met Gly Asn Ile Cys Gly Thr Ser Gly Ser Arg His Val Tyr Ser Pro
 1               5                  10                  15

Ser His Thr Gln Arg Ile Thr Ser Ala Pro Ser Thr Ser Thr His Val
             20                  25                  30

Gly Gly Asp Thr Leu Thr Ser Ile His Gln Leu Ser His Ser Gln Arg
         35                  40                  45

Glu Gln Phe Leu Asn Met His Asp Pro Met Arg Val Met Gly Leu Asp
 50                  55                  60

His Asp Thr Glu Leu Phe Arg Thr Thr Asp Ser Arg Tyr Ile Lys Asn
 65                  70                  75                  80

Asp Lys Leu Ala Gly Asn Pro Gln Ser Met Ala Ser Ile Leu Met His
                 85                  90                  95

Glu Glu Leu Arg Pro Asn Arg Phe Ala Ser His Thr Gly Ala Gln Pro
            100                 105                 110

His Glu Ala Arg Ala Tyr Val Pro Lys Arg Ile Lys Ala Thr Asp Leu
        115                 120                 125

Gly Val Pro Ser Leu Asn Val Met Thr Gly Ser Leu Ala Arg Asp Gly
    130                 135                 140

Ile Arg Ala Tyr Asp His Met Ser Asp Asn Gln Val Ser Val Lys Met
145                 150                 155                 160

Arg Leu Gly Asp Phe Leu Glu Arg Gly Gly Lys Val Tyr Ala Asp Ala
                165                 170                 175

Ser Ser Val Ala Asp Asp Gly Glu Thr Ser Gln Ala Leu Ile Val Thr
            180                 185                 190
```

Leu Pro Lys Gly Gln Lys Val Pro Val Glu Arg Val
            195                 200

<210> SEQ ID NO 15
<211> LENGTH: 493
<212> TYPE: PRT
<213> ORGANISM: Pseudomonas syringae

<400> SEQUENCE: 15

Met Gln Ile Lys Asn Ser His Leu Tyr Ser Ala Ser Arg Met Val Gln
1               5                   10                  15

Asn Thr Phe Asn Ala Ser Pro Lys Met Glu Val Thr Asn Ala Ile Ala
            20                  25                  30

Lys Asn Asn Glu Pro Ala Ala Leu Ser Ala Thr Gln Thr Ala Lys Thr
        35                  40                  45

His Glu Gly Asp Ser Lys Gly Gln Ser Ser Asn Ser Lys Leu Pro
    50                  55                  60

Phe Arg Ala Met Arg Tyr Ala Ala Tyr Leu Ala Gly Ser Ala Tyr Leu
65                  70                  75                  80

Tyr Asp Lys Thr Ala Asn Asn Phe Phe Leu Ser Thr Thr Ser Leu His
                85                  90                  95

Asp Gly Lys Gly Gly Phe Thr Ser Asp Ala Arg Leu Asn Asp Ala Gln
            100                 105                 110

Asp Lys Ala Arg Lys Arg Tyr Gln Asn Asn His Ser Ser Thr Leu Glu
        115                 120                 125

Asn Lys Asn Ser Leu Leu Ser Pro Leu Arg Leu Cys Gly Glu Asn Gln
    130                 135                 140

Phe Leu Thr Met Ile Asp Tyr Arg Ala Ala Thr Lys Ile Tyr Leu Ser
145                 150                 155                 160

Asp Leu Val Asp Thr Glu Gln Ala His Thr Ser Ile Leu Lys Asn Ile
                165                 170                 175

Met Cys Leu Lys Gly Glu Leu Thr Asn Glu Glu Ala Ile Lys Lys Leu
            180                 185                 190

Asn Pro Glu Lys Thr Pro Lys Asp Tyr Asp Leu Thr Asn Ser Glu Ala
        195                 200                 205

Tyr Ile Ser Lys Asn Lys Tyr Ser Leu Thr Gly Val Lys Asn Glu Glu
    210                 215                 220

Thr Gly Ser Thr Gly Tyr Thr Ser Arg Ser Ile Thr Lys Pro Phe Val
225                 230                 235                 240

Glu Lys Gly Leu Lys His Phe Ile Lys Ala Thr His Gly Glu Lys Ala
                245                 250                 255

Leu Thr Pro Lys Gln Cys Met Glu Thr Leu Asp Asn Leu Leu Arg Lys
            260                 265                 270

Ser Ile Thr Leu Asn Ser Asp Ser Gln Phe Ala Ala Gly Gln Ala Leu
        275                 280                 285

Leu Val Phe Arg Gln Val Tyr Ala Gly Glu Asp Ala Trp Gly Asp Ala
    290                 295                 300

Glu Arg Val Ile Leu Lys Ser His Tyr Asn Arg Gly Thr Val Leu Gln
305                 310                 315                 320

Asp Glu Ala Asp Lys Ile Glu Leu Ser Arg Pro Phe Ser Glu Gln Asp
                325                 330                 335

Leu Ala Lys Asn Met Phe Lys Arg Asn Thr Ser Ile Ala Gly Pro Val
            340                 345                 350

Leu Tyr His Ala Tyr Ile Tyr Ile Gln Glu Lys Ile Phe Lys Leu Pro
        355                 360                 365

```
Pro Asp Lys Ile Glu Asp Leu Lys His Lys Ser Met Ala Asp Leu Lys
        370                 375                 380

Asn Leu Pro Leu Thr His Val Lys Leu Ser Asn Ser Gly Val Gly Phe
385                 390                 395                 400

Glu Asp Ala Ser Gly Leu Gly Asp Ser Phe Thr Ala Leu Asn Ala Thr
                405                 410                 415

Ser Cys Val Asn His Ala Arg Ile Met Ser Gly Glu Pro Pro Leu Ser
                420                 425                 430

Lys Asp Asp Val Val Ile Leu Ile Gly Cys Leu Asn Ala Val Tyr Asp
                435                 440                 445

Asn Ser Ser Gly Ile Arg His Ser Leu Arg Glu Ile Ala Arg Gly Cys
                450                 455                 460

Phe Val Gly Ala Gly Phe Thr Val Gln Asp Gly Asp Asp Phe Tyr Lys
465                 470                 475                 480

Gln Ile Cys Lys Asn Ala Ser Lys Gln Phe Tyr Asn Gly
                485                 490
```

<210> SEQ ID NO 16
<211> LENGTH: 530
<212> TYPE: PRT
<213> ORGANISM: Vibrio cholerae

<400> SEQUENCE: 16

```
Met Phe Lys Ile Ser Val Ser Gln Gln Ala Asn Val Met Ser Thr Ser
1               5                   10                  15

Asp Thr Ala Gln Arg Ser Ser Leu Lys Ile Ser Ile Lys Ser Ile Cys
                20                  25                  30

Asn Lys Ser Leu Ser Lys Lys Leu His Thr Leu Ala Glu Lys Cys Arg
            35                  40                  45

Arg Phe Ser Gln Glu Leu Lys Glu His Thr Ala Ser Lys Lys Gln Ile
        50                  55                  60

Val Glu Gln Ala Thr Thr Thr Val Arg Glu Ser Ser Leu Thr Lys Ser
65                  70                  75                  80

Asp Ser Glu Leu Gly Ser Ser Arg Ser Leu Leu Thr Ser Asp Val Leu
                85                  90                  95

Ser Ser Ser Ser His Glu Asp Leu Thr Ala Val Asn Leu Glu Asp
                100                 105                 110

Asn Asp Ser Val Phe Val Thr Ile Glu Ser Ser Glu Leu Ile Val
            115                 120                 125

Lys Gln Asp Gly Ser Ile Pro Pro Ala Pro Leu Pro Gly Asn Ile
130                 135                 140

Pro Pro Ala Pro Pro Leu Pro Ser Ala Gly Asn Ile Pro Thr Ala Pro
145                 150                 155                 160

Gly Leu Pro Lys Gln Lys Ala Thr Thr Glu Ser Val Ala Gln Thr Ser
                165                 170                 175

Asp Asn Arg Ser Lys Leu Met Glu Glu Ile Arg Gln Gly Val Lys Leu
                180                 185                 190

Arg Ala Thr Pro Lys Ser Ser Thr Glu Lys Ser Ala Ser Asp Pro
            195                 200                 205

His Ser Lys Leu Met Lys Glu Leu Ile Asn His Gly Ala Lys Leu Lys
        210                 215                 220

Lys Val Ser Thr Ser Asp Ile Pro Val Pro Pro Leu Pro Ala Ala
225                 230                 235                 240

Phe Ala Ser Lys Pro Thr Asp Gly Arg Ser Ala Leu Leu Ser Glu Ile
```

-continued

```
                245                 250                 255
Ala Gly Phe Ser Lys Asp Arg Leu Arg Lys Ala Gly Ser Ser Glu Thr
            260                 265                 270

Leu Asn Val Ser Gln Pro Thr Val Ala Glu Ser Ser Ile Pro Glu Ala
            275                 280                 285

Tyr Asp Leu Leu Leu Ser Asp Glu Met Phe Asn Leu Ser Pro Lys Leu
            290                 295                 300

Ser Glu Thr Glu Leu Asn Thr Leu Ala Asp Ser Leu Ala Asp Tyr Leu
305                 310                 315                 320

Phe Lys Ala Ala Asp Ile Asp Trp Met Gln Val Ile Ala Glu Gln Thr
                325                 330                 335

Lys Gly Ser Thr Gln Ala Thr Ser Leu Lys Ser Gln Leu Glu Gln Ala
            340                 345                 350

Pro Glu Tyr Val Lys Ala Phe Cys Asp Glu Ile Leu Lys Phe Pro Asp
            355                 360                 365

Cys Tyr Lys Ser Ala Asp Val Ala Ser Pro Glu Ser Pro Lys Ala Gly
            370                 375                 380

Pro Ser Val Ile Asp Val Ala Leu Lys Arg Leu Gln Ala Gly Arg
385                 390                 395                 400

Asn Arg Leu Phe Ser Thr Ile Asp Ala Lys Gly Thr Asn Glu Leu Lys
                405                 410                 415

Lys Gly Glu Ala Ile Leu Glu Ser Ala Ile Asn Ala Ala Arg Ser Val
            420                 425                 430

Met Thr Ala Glu Gln Lys Ser Ala Leu Leu Ser Ser Asn Val Lys Ser
            435                 440                 445

Ala Thr Phe Lys Val Phe Ser Glu Leu Pro Cys Met Glu Gly Phe Ala
450                 455                 460

Glu Gln Asn Gly Lys Ala Ala Phe Asn Ala Leu Arg Leu Ala Phe Tyr
465                 470                 475                 480

Ser Ser Ile Gln Ser Gly Asp Thr Ala Gln Gln Asp Ile Ala Arg Phe
                485                 490                 495

Met Lys Glu Asn Leu Ala Thr Gly Phe Ser Gly Tyr Ser Tyr Leu Gly
            500                 505                 510

Leu Thr Ser Arg Val Ala Gln Leu Glu Ala Gln Leu Ala Leu Ala Leu Thr
            515                 520                 525

Thr Lys
    530

<210> SEQ ID NO 17
<211> LENGTH: 288
<212> TYPE: PRT
<213> ORGANISM: Unknown
<220> FEATURE:
<223> OTHER INFORMATION: Description of Unknown:
      YopJ toxin sequence

<400> SEQUENCE: 17

Met Ile Gly Pro Ile Ser Gln Ile Asn Ile Ser Gly Gly Leu Ser Glu
1               5                   10                  15

Lys Glu Thr Ser Ser Leu Ile Ser Asn Glu Glu Leu Lys Asn Ile Ile
                20                  25                  30

Thr Gln Leu Glu Thr Asp Ile Ser Asp Gly Ser Trp Phe His Lys Asn
            35                  40                  45

Tyr Ser Arg Met Asp Val Glu Val Met Pro Ala Leu Val Ile Gln Ala
        50                  55                  60
```

```
Asn Asn Lys Tyr Pro Glu Met Asn Leu Asn Leu Val Thr Ser Pro Leu
 65                  70                  75                  80

Asp Leu Ser Ile Glu Ile Lys Asn Val Ile Glu Asn Gly Val Arg Ser
                 85                  90                  95

Ser Arg Phe Ile Ile Asn Met Gly Glu Gly Gly Ile His Phe Ser Val
            100                 105                 110

Ile Asp Tyr Lys His Ile Asn Gly Lys Thr Ser Leu Ile Leu Phe Glu
        115                 120                 125

Pro Ala Asn Phe Asn Ser Met Gly Pro Ala Met Leu Ala Ile Arg Thr
    130                 135                 140

Lys Thr Ala Ile Glu Arg Tyr Gln Leu Pro Asp Cys His Phe Ser Met
145                 150                 155                 160

Val Glu Met Asp Ile Gln Arg Ser Ser Glu Cys Gly Ile Phe Ser
                165                 170                 175

Phe Ala Leu Ala Lys Lys Leu Tyr Ile Glu Arg Asp Ser Leu Leu Lys
            180                 185                 190

Ile His Glu Asp Asn Ile Lys Gly Ile Leu Ser Asp Gly Glu Asn Pro
        195                 200                 205

Leu Pro His Asp Lys Leu Asp Pro Tyr Leu Pro Val Thr Phe Tyr Lys
    210                 215                 220

His Thr Gln Gly Lys Lys Arg Leu Asn Glu Tyr Leu Asn Thr Asn Pro
225                 230                 235                 240

Gln Gly Val Gly Thr Val Val Asn Lys Lys Asn Glu Thr Ile Val Asn
                245                 250                 255

Arg Phe Asp Asn Asn Lys Ser Ile Val Asp Gly Lys Glu Leu Ser Val
            260                 265                 270

Ser Val His Lys Lys Arg Ile Ala Glu Tyr Lys Thr Leu Leu Lys Val
        275                 280                 285

<210> SEQ ID NO 18
<211> LENGTH: 579
<212> TYPE: PRT
<213> ORGANISM: Pseudomonas sp.

<400> SEQUENCE: 18

Met Ala Gly Ile Asn Gly Ala Gly Pro Ser Gly Ala Tyr Phe Val Gly
 1                   5                  10                  15

His Thr Asp Pro Glu Pro Ala Ser Gly Gly Ala His Gly Ser Ser Ser
                 20                  25                  30

Gly Ala Ser Ser Ser Asn Ser Pro Arg Leu Pro Ala Pro Pro Asp Ala
            35                  40                  45

Pro Ala Ser Gln Ala Arg Asp Arg Arg Glu Met Leu Leu Arg Ala Arg
 50                  55                  60

Pro Leu Ser Arg Gln Thr Arg Glu Trp Val Ala Gln Gly Met Pro Pro
 65                  70                  75                  80

Thr Ala Glu Ala Gly Val Pro Ile Arg Pro Gln Glu Ser Ala Glu Ala
                 85                  90                  95

Ala Ala Pro Gln Ala Arg Ala Glu Glu Arg His Thr Pro Glu Ala Asp
            100                 105                 110

Ala Ala Ala Ser His Val Arg Thr Glu Gly Gly Arg Thr Pro Gln Ala
        115                 120                 125

Leu Ala Gly Thr Ser Pro Arg His Thr Gly Ala Val Pro His Ala Asn
    130                 135                 140

Arg Ile Val Gln Gln Leu Val Asp Ala Gly Ala Asp Leu Ala Gly Ile
145                 150                 155                 160
```

```
Asn Thr Met Ile Asp Asn Ala Met Arg Arg His Ala Ile Ala Leu Pro
            165                 170                 175
Ser Arg Thr Val Gln Ser Ile Leu Ile Glu His Phe Pro His Leu Leu
        180                 185                 190
Ala Gly Glu Leu Ile Ser Gly Ser Glu Leu Ala Thr Ala Phe Arg Ala
    195                 200                 205
Ala Leu Arg Arg Glu Val Arg Gln Gln Glu Ala Ser Ala Pro Pro Arg
210                 215                 220
Thr Ala Ala Arg Ser Ser Val Arg Thr Pro Glu Arg Ser Thr Val Pro
225                 230                 235                 240
Pro Thr Ser Thr Glu Ser Ser Ser Gly Ser Asn Gln Arg Thr Leu Leu
            245                 250                 255
Gly Arg Phe Ala Gly Leu Met Thr Pro Asn Gln Arg Arg Pro Ser Ser
        260                 265                 270
Ala Ser Asn Ala Ser Ala Ser Gln Arg Pro Val Asp Arg Ser Pro Pro
    275                 280                 285
Arg Val Asn Gln Val Pro Thr Gly Ala Asn Arg Val Val Met Arg Asn
290                 295                 300
His Gly Asn Asn Glu Ala Asp Ala Ala Leu Gln Gly Leu Ala Gln Gln
305                 310                 315                 320
Gly Val Asp Met Glu Asp Leu Arg Ala Ala Leu Glu Arg His Ile Leu
            325                 330                 335
His Arg Arg Pro Ile Pro Met Asp Ile Ala Tyr Ala Leu Gln Gly Val
        340                 345                 350
Gly Ile Ala Pro Ser Ile Asp Thr Gly Glu Ser Leu Met Glu Asn Pro
    355                 360                 365
Leu Met Asn Leu Ser Val Ala Leu His Arg Ala Leu Gly Pro Arg Pro
370                 375                 380
Ala Arg Ala Gln Ala Pro Arg Pro Ala Val Pro Val Ala Pro Ala Thr
385                 390                 395                 400
Val Ser Arg Arg Pro Asp Ser Ala Arg Ala Thr Arg Leu Gln Val Ile
            405                 410                 415
Pro Ala Arg Glu Asp Tyr Glu Asn Asn Val Ala Tyr Gly Val Arg Leu
        420                 425                 430
Leu Ser Leu Asn Pro Gly Ala Gly Val Arg Glu Thr Val Ala Ala Phe
    435                 440                 445
Val Asn Asn Arg Tyr Glu Arg Gln Ala Val Val Ala Asp Ile Arg Ala
450                 455                 460
Ala Leu Asn Leu Ser Lys Gln Phe Asn Lys Leu Arg Thr Val Ser Lys
465                 470                 475                 480
Ala Asp Ala Ala Ser Asn Lys Pro Gly Phe Lys Asp Leu Ala Asp His
            485                 490                 495
Pro Asp Asp Ala Thr Gln Cys Leu Phe Gly Glu Glu Leu Ser Leu Thr
        500                 505                 510
Ser Ser Val Gln Gln Val Ile Gly Leu Ala Gly Lys Ala Thr Asp Met
    515                 520                 525
Ser Glu Ser Tyr Ser Arg Glu Ala Asn Lys Asp Leu Val Phe Met Asp
530                 535                 540
Met Lys Lys Leu Ala Gln Phe Leu Ala Gly Lys Pro Glu His Pro Met
545                 550                 555                 560
Thr Arg Glu Thr Leu Asn Ala Glu Asn Ile Ala Lys Tyr Ala Phe Arg
            565                 570                 575
```

Ile Val Pro

<210> SEQ ID NO 19
<211> LENGTH: 1116
<212> TYPE: PRT
<213> ORGANISM: Unknown
<220> FEATURE:
<223> OTHER INFORMATION: Description of Unknown:
    SdbA toxin sequence

<400> SEQUENCE: 19

```
Met His Lys Lys Tyr Asn Tyr Ser Leu Glu Lys Glu Lys Lys Thr
1               5                   10                  15

Phe Trp Gln His Ile Leu Asp Ile Leu Lys Ala Pro Phe Arg Leu Pro
                20                  25                  30

Gly Trp Val Val Ser Phe Phe Leu Ala Arg Asn Ile Thr His Val Ala
            35                  40                  45

Leu Asn Pro Asn Asn Ile Pro Gln Gln Arg Leu Ile His Leu Thr Lys
    50                  55                  60

Thr Ser Asn Arg Pro Glu Asp Ile Val Val Ile Asn Phe Lys Lys
65                  70                  75                  80

Arg Pro Pro His Lys Trp Phe Asn Asp Thr Leu Ile Lys Ile Ala Asn
                85                  90                  95

Thr Ile Ala Ala Leu Pro Phe Val Thr Pro Arg Leu Arg Thr Arg Leu
            100                 105                 110

His Tyr Asp Asn Glu Asn Asp Ile Asn His Val Asn Lys Leu Leu Ala
            115                 120                 125

Glu Ile Asp Ala Leu Val Gln Gly Lys Ser Lys Gln Lys Tyr Cys Lys
130                 135                 140

Gly Arg Ala Phe Asp Trp Ser Lys Ile His Leu Lys Gly Leu Glu Phe
145                 150                 155                 160

Leu Asp Pro Lys Met Arg Gly Tyr Val Tyr Glu Gln Leu His Glu Lys
                165                 170                 175

Tyr Gly Tyr Val Ser Tyr Thr Thr Lys Arg Lys Pro Asn Ile Glu Phe
            180                 185                 190

Phe Thr Leu Lys Thr Pro Asp Gly Ser Glu Leu Asp Ser Val Gln Val
            195                 200                 205

Thr Gly Glu Asp Glu Glu Lys Lys Pro Met Gly Glu Arg Lys Phe Ile
210                 215                 220

Ile Thr Cys Ile Ala Arg Asp Gln Asn Phe Ile Asn Trp Ile Lys Asp
225                 230                 235                 240

Leu Asn Tyr Thr Ala Lys Asn Leu Gly Ala Thr Ala Ile Ser Phe Asn
                245                 250                 255

Tyr Arg Gly Val Asp Tyr Ser Arg Gly Leu Val Trp Thr Glu Asn Asn
            260                 265                 270

Leu Val Asp Asp Ile Leu Ala Gln Val Gln Arg Leu Ile Ser Leu Gly
            275                 280                 285

Ala Asp Pro Lys Asn Ile Cys Leu Asp Gly Met Cys Ile Gly Gly Ala
290                 295                 300

Val Ala Thr Ile Ala Ala Ala Lys Leu His Glu Lys Gly Met Lys Val
305                 310                 315                 320

Lys Leu Asn Asn Glu Arg Ser Phe Thr Ser Leu Ser Ser Leu Val Phe
                325                 330                 335

Gly Phe Ile Val Pro Glu Leu Gln Thr Ala Asn Trp Trp Ser Pro Leu
            340                 345                 350
```

```
Thr Tyr Gly Arg Phe Leu Leu Ala Gly Val Val Tyr Ala Leu Leu Thr
            355                 360                 365
Pro Leu Ile Trp Leu Ala Gly Trp Pro Val Asp Val Thr Lys Ala Trp
370                 375                 380
Asn Arg Ile Pro Ala Gln Asp Lys Met Tyr Ser Val Arg Asp Lys
385                 390                 395                 400
Asp Asn Gly Leu Tyr Asp Gly Val Ile His Asp His Phe Cys Ser Ile
                405                 410                 415
Ala Ser Leu Val Asp Ser Gln Ile Asn Ser Ile Leu Tyr Lys Leu Ser
            420                 425                 430
Thr Asp Gln Pro Leu Thr Glu Glu Lys Gln Ile Leu Cys Asp Asp
        435                 440                 445
Gln Phe Ser His His Phe Lys Pro Ser Gln Ser Val Leu Lys Asn Pro
    450                 455                 460
Lys Tyr Lys Gly Pro His Phe Ile Ser Arg Gln Asp Leu Val Ala Glu
465                 470                 475                 480
Leu Gly His Arg Glu Glu Tyr Thr Asn His Asp Tyr Phe Leu Asp Arg
                485                 490                 495
Leu Arg Glu Lys Phe Gln Leu Asp Arg Ala Thr Arg Pro Val Ala Leu
            500                 505                 510
Ala Glu Asp Gly Glu Lys Asp Ile Asp Gly Ile Ser Ser Gln Leu Ser
        515                 520                 525
Asn Asn Lys Glu Arg Pro Leu Ile Ala Ser Ser Gly Gly Thr Gly
    530                 535                 540
His Ile Ser Ala Thr His Gly Ile Ile Asn Asp Leu Gln Ser Lys Thr
545                 550                 555                 560
Asp Asn Val Val Ile Thr Gln His His Ala Glu Leu Tyr Lys Asn Lys
                565                 570                 575
Pro Phe Ser Ile Thr Ser Val Leu Ile Arg Ile Gly Val Trp Phe Thr
            580                 585                 590
Ser Leu Pro Ile Leu Glu Asp Ile Leu Lys Gly Val Met Arg Phe Ile
        595                 600                 605
Gly Tyr Pro Val Leu Pro Ser Ser Ser Ile Phe Trp Asp Gln Met Ser
    610                 615                 620
Lys Ile Gln Gln Ser Glu Thr Lys Lys Glu Asn Gly Ile Glu Thr Gly
625                 630                 635                 640
Arg Thr Arg Pro Tyr Val Asp Met Leu Leu Asp Ile Tyr Pro Glu Gly
                645                 650                 655
Tyr Glu Tyr Thr Ala Phe Asn Asn Ala Thr His Leu Thr Ser Ser Ile
            660                 665                 670
Glu Asp Ile Gln Thr Met Ile Ser Phe Lys Gly His Val Glu Glu Asp
        675                 680                 685
Asn Arg Asn Ile Val Tyr Gln Asn Ile Leu Gln Arg Leu Met His Ala
    690                 695                 700
Ala Lys Gln Asn Thr Pro Tyr Thr Arg Leu Ile Ser Thr Gln Ala Leu
705                 710                 715                 720
Ser Leu Gly Ala Ile Cys Asp Ala Val Lys Tyr Tyr Asn Thr Val Phe
                725                 730                 735
Leu Pro Val Tyr Asn Ala Glu Arg Gly Thr Ser Tyr Gln Pro Ile Ala
            740                 745                 750
Ile Asp Gln Tyr Met Thr Asp Leu Pro Ser Leu Gly Cys Ile His Phe
        755                 760                 765
Met Asn Asn Leu Glu Glu Leu Thr Ser Glu Gln Arg Gln Leu Met Glu
```

770                 775                 780
Ile His Ala Val Asn Met Ser Glu Pro Phe Lys Glu Ala His Phe Gly
785                 790                 795                 800

Lys Glu Gln Gly Phe Lys Ala Val His Asn Ile Asp Pro Arg Asn Asn
                805                 810                 815

Pro Met Ile Arg Asn Ala Phe Lys Asp Pro Ser Leu Thr Lys Tyr Leu
            820                 825                 830

Asp Lys Thr Gln Ser Phe Asp Leu His Phe Asn Val Tyr Lys Lys Glu
        835                 840                 845

Lys Gln Asn Ala Leu Pro Val Leu Asn Gly Lys Glu Lys Ile Thr Ile
    850                 855                 860

Lys Pro His Ala Lys Ile Ala Ser Ile Met Ile Gly Ser Leu Ala Ala
865                 870                 875                 880

Asn Ala Ser Ala Asp Tyr Ala Lys Tyr Leu Leu Asn Gln Gly Tyr Glu
                885                 890                 895

His Ile Phe Leu Phe Gly Gly Leu Asn Asp Ser Ile Ala Ala Arg Ile
            900                 905                 910

Asp Gln Ile Ile Asn Ser Tyr Pro Ala Pro Thr Arg Asp Glu Ile Arg
        915                 920                 925

Lys Lys Ile Ile Leu Leu Gly Asn Gln Ser Asp Val Glu Met Ala Pro
    930                 935                 940

Ile Met Thr Arg Ser Asn Cys Val Val Ile Arg Gly Gly Gly Leu Ser
945                 950                 955                 960

Val Met Glu Gln Met Ala Met Pro Ile Met Asp Asp Lys Ile Val Leu
                965                 970                 975

Leu His His Glu Asp Asn Glu Glu Gly Pro Leu Thr Ser Gly Leu Ser
            980                 985                 990

Trp Glu Asp Gly Asn Ser Asp Lys Leu Ile Glu Tyr Leu Ser Glu Lys
        995                 1000                1005

Gly Ala Tyr Ala Lys Lys Thr Ser Pro Gly Leu Cys Ser Gly His
    1010                1015                1020

Leu His Glu Ala Glu Lys Ser Phe Glu Lys Lys Tyr His Gly Gln
    1025                1030                1035

Leu Lys Ser Thr Glu Thr Lys Lys Lys Val Asp Leu Thr Ile Pro
    1040                1045                1050

Gln Gln Glu Thr Tyr Ser Leu Lys Lys Glu Trp Asp Arg Lys Thr
    1055                1060                1065

Gly Tyr Thr Glu Ser Gly His Ile Leu Ser His Gln His Arg Phe
    1070                1075                1080

Phe Asn Thr Ile Pro Glu Val Arg Glu Pro Phe Cys Ser Lys Glu
    1085                1090                1095

Asp Leu His His Asn Glu Leu Ser Ser Gln Ser Leu Val Ser Val
    1100                1105                1110

Ser Ala Gly
    1115

<210> SEQ ID NO 20
<211> LENGTH: 965
<212> TYPE: PRT
<213> ORGANISM: Legionella pneumophila

<400> SEQUENCE: 20

Met Ser Arg Ser Lys Asp Glu Val Leu Glu Ala Asn Asp Ser Leu Phe
1

```
Gly Ile Thr Val Gln Thr Trp Gly Thr Asn Asp Arg Pro Ser Asn Gly
             20                  25                  30

Met Met Asn Phe Ala Asp Gln Gln Phe Phe Gly Gly Asp Val Gly His
         35                  40                  45

Ala Ser Ile Asn Met Lys Leu Pro Val Thr Asp Lys Thr Lys Gln Trp
     50                  55                  60

Ile Glu Lys Tyr Cys Tyr Ser Gln Thr Tyr Asp Gln Phe Lys Lys Val
 65              70                  75                      80

Lys Gly Asn Glu Asp Lys Thr Tyr Glu Glu Tyr Leu Lys Thr Ala Lys
                 85                  90                  95

Arg Leu Ile Pro Val Glu Leu Lys Thr Gln Val Thr Arg Lys Ala Gln
                100                 105                 110

Tyr Asp Ser Asn Gly Asn Leu Val Thr Thr His Glu Lys Ala Tyr Glu
            115                 120                 125

Gln Ile Tyr Phe Asp Ile Asp Trp Ser Trp Trp Pro Gly Arg Leu Gln
        130                 135                 140

Asn Thr Glu Asp Asp Met Val Trp Glu Arg Glu Gly Lys His Phe Glu
145                 150                 155                 160

Tyr Asp Glu Lys Trp Lys Glu Tyr Leu Gln Pro Glu Gln Arg Val His
                165                 170                 175

Arg Gly Lys Leu Gly Ser Arg Lys Met Asp Tyr Ala Pro Thr Ser Ile
            180                 185                 190

Ile His Gln Arg Asp Ile Pro Thr Ser Glu Leu Glu Lys Ile Thr Arg
        195                 200                 205

Asp His Lys Ile His Thr Ile Glu Glu Lys Leu Asn Val Val Lys Leu
    210                 215                 220

Leu Gln Ser Lys Ile Asp Glu Met Pro His Thr Lys Met Ser Pro Ser
225                 230                 235                 240

Met Glu Leu Met Phe Lys Asn Leu Gly Ile Asn Val Glu Lys Leu Leu
                245                 250                 255

Asp Glu Thr Lys Asp Asn Gly Val Asp Pro Thr Asn Leu Glu Ala Met
            260                 265                 270

Arg Glu Tyr Leu Thr Asn Arg Leu Thr Glu Arg Lys Leu Glu Leu Glu
        275                 280                 285

Thr Glu Leu Ser Glu Ala Lys Lys Glu Val Asp Ser Thr Gln Val Lys
    290                 295                 300

Asn Lys Val Glu Asp Val Tyr Tyr Asp Phe Glu Tyr Lys Leu Asn Gln
305                 310                 315                 320

Val Arg Lys Lys Met Glu Glu Val Asn Ser Gln Leu Glu Lys Met Asp
                325                 330                 335

Ser Leu Leu His Lys Leu Glu Gly Asn Thr Ser Gly Pro Ile Pro Tyr
            340                 345                 350

Thr Ala Glu Ile Asp Glu Leu Met Ser Val Leu Pro Phe Leu Lys Glu
        355                 360                 365

Glu Leu Glu Leu Glu Asn Gly Thr Leu Ser Pro Lys Ser Ile Glu Asn
    370                 375                 380

Leu Ile Asp His Ile Asp Glu Leu Lys Asn Glu Leu Ala Ser Lys Gln
385                 390                 395                 400

Glu Lys Lys Asn Glu Arg Asn Leu Asn Leu Ile Lys Lys Tyr Glu Glu
                405                 410                 415

Leu Cys Glu Gln Tyr Lys Asp Asp Glu Glu Gly Leu Glu Glu Ala Leu
            420                 425                 430

Trp Glu Glu Gly Ile Asp Val Glu Glu Val Asn Ser Ala Lys Lys Asp
```

-continued

```
            435                 440                 445
Ile Ser Lys Pro Ala Pro Glu Ile Gln Lys Leu Thr Asp Leu Gln Glu
450                 455                 460

Gln Leu Arg Asn His Lys Glu Ser Gly Val Lys Leu Ser Ser Glu Leu
465                 470                 475                 480

Glu Glu Thr Leu Asn Ser Ser Val Lys Met Trp Lys Thr Lys Ile Asp
                    485                 490                 495

Ser Pro Cys Gln Val Ile Ser Glu Ser Ser Val Lys Ala Leu Val Ser
                500                 505                 510

Lys Ile Asn Ser Thr Arg Pro Glu Leu Val Lys Glu Lys Glu Gln Leu
            515                 520                 525

Pro Glu Gln Glu Glu Ser Leu Ser Lys Glu Ala Lys Lys Ala Gln Glu
530                 535                 540

Glu Leu Ile Lys Ile Gln Glu Phe Ser Gln Phe Tyr Ser Glu Asn Ser
545                 550                 555                 560

Ser Ala Tyr Met Val Ile Gly Leu Pro Pro His His Gln Val Ser Leu
                565                 570                 575

Pro Leu Ala Val Asn Gly Lys Arg Gly Leu His Pro Glu Ala Met Leu
                580                 585                 590

Lys Lys Met His Glu Leu Val Ala Gly Pro Glu Lys Lys Glu Phe Asn
            595                 600                 605

Leu His Thr Asn Cys Ser Leu Thr Ser Ile Glu Val Leu Ser Ala
610                 615                 620

Gly Ala Gln His Asp Pro Leu Leu His Ser Ile Met Gly Thr Arg Ala
625                 630                 635                 640

Leu Gly Phe Phe Gly Thr Pro Gln Gln Val Leu Glu Asn Ala Lys Leu
                645                 650                 655

Thr Ser Lys Thr Ile Asn Glu Gly Lys Lys Ser Asn Ile Phe Thr Pro
                660                 665                 670

Leu Val Thr Ala Ser Pro Leu Asp Arg Ala Leu Gly Tyr Ala Met Ser
            675                 680                 685

Ile Tyr Met Asp Pro Glu Ala Ser Lys Ala Lys Gln Asn Ala Gly Leu
690                 695                 700

Ala Leu Gly Val Leu Val Gly Leu Ala Lys Thr Pro Gly Ile Ile Ile
705                 710                 715                 720

Gly Ser Leu Leu Asn Pro Lys Gln Gly Phe Asn Asp Ile Leu Asn Thr
                725                 730                 735

Leu Asn Leu Val Tyr Ser Arg Asn Ser Thr Gly Leu Lys Val Gly Leu
                740                 745                 750

Thr Leu Met Ala Leu Pro Ala Met Ile Val Leu Ala Pro Leu Ala Ala
            755                 760                 765

Ile Gln Lys Gly Val Glu Val Ile Ala Glu Thr Ile Ala Lys Pro Phe
770                 775                 780

Lys Leu Ile Ala Asn Leu Phe Lys Gln Lys Pro Glu Ser Thr Asp Glu
785                 790                 795                 800

Ile Thr Val Ser Val Gly Ser Lys Lys Val Ala Glu Lys Glu Gly Ser
                805                 810                 815

Tyr Ser Asn Thr Ala Leu Ala Gly Leu Val Asn Ser Lys Ile Lys Ser
                820                 825                 830

Lys Ile Asp Glu Asn Thr Ile Thr Val Glu Phe Gln Lys Ser Pro Gln
            835                 840                 845

Lys Met Ile Glu Glu Phe Glu Ser Gln Leu Lys Glu Asn Pro Gly Lys
850                 855                 860
```

```
Val Val Val Leu Ser Glu Lys Ala His Asn Ala Val Leu Lys Phe Val
865                 870                 875                 880

Ser Lys Ser Asp Asp Glu Ala Leu Lys Gln Lys Phe Tyr Asp Cys Cys
                885                 890                 895

Asn Gln Ser Val Ala Arg Ser Gln Lys Phe Ala Pro Lys Thr Arg Asp
            900                 905                 910

Glu Ile Asp Glu Leu Val Glu Glu Val Thr Ser Thr Asp Lys Thr Glu
        915                 920                 925

Leu Thr Thr Ser Pro Arg Gln Glu Pro Ser Met Ser Ser Thr Ile Asp
    930                 935                 940

Glu Glu Glu Asn Ile Asp Ser Glu His Gln Ile Glu Thr Gly Thr Glu
945                 950                 955                 960

Ser Thr Met Arg Ile
                965

<210> SEQ ID NO 21
<211> LENGTH: 665
<212> TYPE: PRT
<213> ORGANISM: Legionella pneumophila

<400> SEQUENCE: 21

Met Lys Thr Lys Gln Glu Val Ser Gln Gln Asp Lys Leu Lys Asp Ser
1               5                   10                  15

Lys Ser Ser Thr Pro Leu Gln Thr Lys Glu Thr Trp Phe Ile Ser Asp
            20                  25                  30

Ala Leu Asn Ile Thr Phe Asp Pro Tyr Asp Phe Ser Ile Ser Val Thr
        35                  40                  45

Glu Gln Ala Pro Met Pro Tyr Arg Ile Val Phe Ser Gly Gly Gly Ser
    50                  55                  60

Arg Ile Leu Ala His Ile Gly Ala Leu Asp Glu Leu Thr Arg His Gly
65              70                  75                  80

Leu Lys Phe Thr Glu Phe Ser Gly Ser Ser Ala Gly Ala Met Val Ala
            85                  90                  95

Ala Phe Ala Tyr Leu Gly Tyr Asn Cys Ser Glu Ile Lys Gln Ile Ile
        100                 105                 110

Ser Trp Phe Asn Glu Asp Lys Leu Leu Asp Ser Pro Leu Ile Phe Asn
    115                 120                 125

Phe Asn Asn Ile Lys Gln Ile Phe Asn Lys Gly Gly Leu Ser Ser Ala
130                 135                 140

Lys Leu Met Arg Gln Ala Ala Asn Tyr Val Ile Leu Lys Lys Val Met
145                 150                 155                 160

Asp Ile Ile Ser Asp Glu Lys Phe Lys Thr Arg Phe Ala Lys Phe Gln
            165                 170                 175

Asn Phe Leu Glu Glu Asn Ile Tyr Arg Cys Pro Glu Asn Ile Thr Phe
        180                 185                 190

Gln Thr Leu Ala Arg Ile Lys Gly Ile Cys Pro Glu Cys Glu Leu Gly
    195                 200                 205

Glu Lys Leu Phe Ile Thr Gly Thr Asn Leu Ser Thr Gln Lys His Glu
210                 215                 220

Val Phe Ser Ile Asp Thr Thr Pro Ser Met Ala Leu Ala Asp Ala Ile
225                 230                 235                 240

Ile Ile Ser Ala Asn Leu Pro Ile Ala Phe Glu Arg Ile Cys Tyr Gln
            245                 250                 255

Gly Asn Val Tyr Ser Asp Gly Gly Ile Ser Asn Asn Leu Pro Ala His
```

```
            260                 265                 270
Cys Phe Ser Glu Lys Gly His Lys Thr Thr Phe Leu Lys His Lys Asp
            275                 280                 285

Asp Val Asp Phe Ser Val Leu Ala Leu Gln Phe Asp Asn Gly Leu Glu
            290                 295                 300

Glu Asn Ala Leu Tyr Ser Gln Asn Pro Ile Pro Lys Trp Ser Trp Leu
305                 310                 315                 320

Ser Asn Thr Phe Tyr Ser Leu Ile Thr Gly His Pro Asn Val Thr Glu
                        325                 330                 335

Asn Trp Tyr Glu Asp Leu Gln Ile Leu Arg Arg His Ala His Gln Ser
                340                 345                 350

Ile Leu Ile Lys Thr Pro Thr Ile Ala Leu Thr Asn Leu Thr Ile Ser
            355                 360                 365

Gln Asp Thr Lys Lys Ala Leu Val Glu Ser Gly Arg Thr Ala Ala Lys
            370                 375                 380

Thr Tyr Leu Glu Leu His Glu Phe Tyr Thr Asp Asp Tyr Gly Asn Ile
385                 390                 395                 400

Arg His Asn Glu Cys Leu His Glu Lys Phe Gln Lys Pro Glu Glu Leu
                        405                 410                 415

Leu Asp Tyr Cys Val Leu His Ser His Phe Glu Leu Leu Lys Lys Ile
                420                 425                 430

Lys Gln Ala Ile Ser Cys Ser Gln Tyr Leu Glu Lys Gly Tyr Lys His
            435                 440                 445

Tyr Leu Cys Glu Leu Cys Asp Asn Leu Leu Pro Pro Gln Leu Lys Cys
450                 455                 460

Pro Asn Glu Gly Ser Gly Thr Glu Gln Pro Glu Ile Lys Leu Glu Lys
465                 470                 475                 480

Asp Thr Ile Ile Cys Glu Lys Asn Asn Ser Gly Leu Thr Phe Ser
                        485                 490                 495

Met Thr Phe Phe Gly Val Pro Ser Pro Leu Val Lys Thr Leu Asn Gln
                500                 505                 510

Asp Ser Pro Glu Leu Lys Ile Lys Leu Phe Thr Gly Leu Tyr Pro Ile
            515                 520                 525

Leu Ile Gln Asn Trp Gln Asn Leu Cys Pro Val Ser Gly Ile Ser Gly
            530                 535                 540

Ile Leu Asn Ser Ile Arg Met Ser Phe Val Glu Ile Ser Ser Thr Asp
545                 550                 555                 560

Thr Cys Ile Lys Thr Leu Ile Asp Lys Leu Asn Glu Ile Glu Ile Gly
                        565                 570                 575

His Phe Leu Ile Phe Val Phe Lys Ala Ala Leu Lys Asn Tyr Asp Lys
                580                 585                 590

His Asp Phe Ile Leu Leu Lys Asn Leu Lys His Leu His His Ser
            595                 600                 605

Ile Glu Leu Ile Arg Asn Lys Pro Phe His Ser Asp Asp Arg Phe Tyr
            610                 615                 620

Gly Gln Trp Ser Phe Glu Gly His Asp Pro Lys Arg Ile Leu Glu Phe
625                 630                 635                 640

Ile Lys Ser Asp Asp Ile Ser Gly Leu Met Thr Ile Leu Glu Asp Lys
                        645                 650                 655

Lys Ala Leu Pro Asn Asn Lys Pro Asn
                660                 665

<210> SEQ ID NO 22
```

```
<211> LENGTH: 246
<212> TYPE: PRT
<213> ORGANISM: Legionella pneumophila

<400> SEQUENCE: 22
```

Met Val Ser Leu Glu His Ile Gln Lys Leu Ile Ser Glu Cys Arg Lys
1 5 10 15

Leu Gly Lys Asp Gly Leu Asp Asn Gly Thr Asn Gly Leu Ile Pro Glu
20 25 30

Leu Glu Ile Asp Val Val Pro Pro Ser Ala Phe Leu Gly Val Gly Asn
35 40 45

Asn Pro Ala Ile Phe Val Asn Ser Lys Thr Tyr Lys Leu Met Arg Thr
50 55 60

Thr His Glu Lys Trp Val Glu Asn Lys Thr Ile Val Phe Lys Ser Tyr
65 70 75 80

Leu Leu Ser Gln Pro Ala Ile Lys Ile Ile Gly Ala Ile Val His Glu
85 90 95

Thr Gly His Ala Phe Asn Val Ala Ala Lys Ile Pro Asn Thr Glu Ala
100 105 110

Asn Ala Cys Ile Phe Glu Ile Glu Val Leu Met Arg Leu Phe Gln Val
115 120 125

Lys Ser Pro Leu Leu Leu Gly Cys Thr Glu Leu Asp Met Gln Ser Tyr
130 135 140

Phe Lys Ser Arg Leu Thr Asp Tyr Asn Lys Cys Val Lys Asp Cys Gln
145 150 155 160

Cys Leu Ala Glu Met Val Glu Phe Ile Thr His Gln Phe Lys Leu Asp
165 170 175

Glu Val Ser Ile Ser Glu Lys Glu Asn Gln Ile Pro Leu Leu Ser Ile
180 185 190

Ser Asn Lys Trp Pro Gly Leu Phe Ala Lys Lys Gln Ile Ala Pro Asp
195 200 205

Met Asp Lys Leu Leu Thr Ser Pro Val Thr Ile Thr Pro Glu Val Lys
210 215 220

Ile Leu Phe Tyr Gln Leu Val Lys Glu His Phe His Ser Pro Glu Thr
225 230 235 240

Glu Ile Lys Leu Asp Ile
245

<210> SEQ ID NO 23
<211> LENGTH: 644
<212> TYPE: PRT
<213> ORGANISM: Legionella pneumophila

<400> SEQUENCE: 23

Met Tyr Lys Ile Tyr Ser Tyr Leu Gly Trp Arg Ile Asp Met Lys Thr
1 5 10 15

Glu Asn Leu Pro Gln Ala Gly Gln Glu Ala Gln Ile Asp Lys Lys Ile
20 25 30

His Phe Ile Trp Val Gly His Ile Met Pro Gln Lys Asn Ile Gln Val
35 40 45

Val Ser Glu Trp Ala Glu Lys Asn Pro Gly Tyr Glu Thr Ile Ile Trp
50 55 60

Val Asp Lys Lys Ile Ala Pro Ala Lys Glu Leu Asp Leu Phe Ile Leu
65 70 75 80

Asp Met Lys Ser Lys Gly Ile Thr Val Lys Asp Ile Asn Glu Glu Gly
85 90 95

```
Val Cys Arg Asp Ser Ile Arg His Glu Leu Asp Gln Glu Ser Pro Asn
                100                 105                 110

Tyr Gly Met Val Ser Asp Met Leu Arg Leu Asn Ile Leu Ala Ala Glu
            115                 120                 125

Gly Gly Ile Tyr Leu Asp Ser Asp Ile Leu Cys Ser Ala Pro Phe Pro
        130                 135                 140

Asp Glu Ile Tyr Ala Pro Phe Gly Phe Leu Leu Ser Pro Trp Ser Gln
145                 150                 155                 160

Gly Ala Asn Asn Thr Leu Cys Asn Asp Ile Ile Leu Cys Ser Lys Gly
                165                 170                 175

Asn Gln Ile Ile Gln Gln Leu Ala Asp Ala Ile Glu Gln Ser Tyr Ile
            180                 185                 190

Ala Arg Asp Ser Phe Glu Phe Thr His Glu Tyr Ala Ser Met Lys Glu
            195                 200                 205

Thr Lys Gly Glu Arg Ile Ala Lys Thr Leu Gly Val Thr Gly Pro Gly
        210                 215                 220

Phe Leu Phe His Gln Leu Lys Lys Met Gly Ile Leu Asn Asp Lys Ser
225                 230                 235                 240

Glu Met Glu Ala Ile His Trp Glu Leu Gln Asp Gln Arg Tyr Leu Ile
                245                 250                 255

Asp Gly Ser Val Lys Glu Pro Asp Tyr Phe Tyr Val Pro Gln Asn Asn
            260                 265                 270

Thr Asn Asp Ala Ser Trp Val Pro Ser Ile Lys Arg Pro Gly Ile Glu
            275                 280                 285

Asn Met Ser Phe Gln Glu Arg Leu Glu Asn Ala Val Gln Leu Ile Ala
        290                 295                 300

Phe Asp Ile Gln Lys Thr Gly Leu Phe Asn Leu Asp His Tyr Ala Asn
305                 310                 315                 320

Glu Leu Lys Val Lys Gln Asn Ser Trp Cys Ile Ala Ala Glu Thr Ser
                325                 330                 335

Pro Glu Leu Lys Pro Asp Ser Tyr Leu Leu Ile Arg Pro Arg Asp Lys
            340                 345                 350

Thr Gly Glu Trp Thr Leu Tyr Tyr Val Asp Asp Lys Lys Leu Asn
            355                 360                 365

Pro Val Thr Leu Pro Val Ile Lys Gly Ala Ile Lys Leu Ser Glu Val
        370                 375                 380

Ser Asp Pro Leu Arg Lys Phe His Thr Leu Leu Ser Gln Val Ser Asp
385                 390                 395                 400

Pro Val Asn Pro Thr Ala His Glu Leu Lys Gln Ile Gly Arg Ala Leu
                405                 410                 415

Ile Glu Leu Lys Pro Arg Gln Asp Glu Trp His Cys Lys Asn Lys Trp
            420                 425                 430

Ser Gly Ala Glu Glu Ile Ala Gln Glu Leu Trp Gln Arg Ile Thr Ser
        435                 440                 445

Asn Glu Thr Leu Arg Ala Gln Ile Lys Gln Cys Phe Thr Gln Phe Glu
        450                 455                 460

Ser Leu Lys Pro Arg Val Ala Glu Leu Gly Leu Thr Arg Ala Ser Gly
465                 470                 475                 480

Ala Gly Thr Glu Val Glu Ala His Glu Ser Thr Val Lys Glu Gln Glu
                485                 490                 495

Ile Ile Ser Gln Asn Thr Val Gly Glu Glu Gly Thr Lys Glu Lys Asn
            500                 505                 510
```

```
Ser Val Gln Leu Ala Ser Glu Asn Ser Ser Asp Glu Lys Ile Lys Thr
    515                 520                 525

Ala His Asp Leu Ile Asp Glu Ile Ile Gln Asp Val Ile Gln Leu Asp
    530                 535                 540

Gly Lys Leu Gly Leu Leu Gly Gly Asn Thr Arg Gln Leu Glu Asp Gly
545                 550                 555                 560

Arg Val Ile Asn Ile Pro Asn Gly Ala Ala Met Ile Phe Asp Asp Tyr
                565                 570                 575

Lys Lys Tyr Lys Gln Gly Glu Leu Thr Ala Glu Ser Ala Leu Glu Ser
            580                 585                 590

Met Ile Lys Ile Ala Lys Leu Ser Asn Gln Leu Asn Arg His Thr Phe
        595                 600                 605

Phe Asn Gln Arg Gln Pro Glu Thr Gly Gln Phe Tyr Lys Lys Val Ala
    610                 615                 620

Ala Ile Asp Leu Gln Thr Thr Ile Ala Ala Glu Tyr Asp Asn Asn His
625                 630                 635                 640

Gly Leu Arg Ile

<210> SEQ ID NO 24
<211> LENGTH: 219
<212> TYPE: PRT
<213> ORGANISM: Yersinia sp.

<400> SEQUENCE: 24

Met Lys Ile Ser Ser Phe Ile Ser Thr Ser Leu Pro Leu Pro Thr Ser
1               5                   10                  15

Val Ser Gly Ser Ser Val Gly Glu Met Ser Gly Arg Ser Val Ser
            20                  25                  30

Gln Gln Thr Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Val Ala His Ser Val Ile Gly Phe Ile Gln Arg Met Phe Ser Glu
65                  70                  75                  80

Gly Ser His Lys Pro Val Val Thr Pro Ala Pro Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Asn Ser Leu Asp Ala Glu Met
        115                 120                 125

Leu Gln Lys Asn His Asp Gln Phe Ala Thr Gly Ser Gly Pro Leu Arg
    130                 135                 140

Gly Ser Ile Thr Gln Cys Gln Gly Leu Met Gln Phe Cys Gly Gly Glu
145                 150                 155                 160

Leu Gln Ala Glu Ala Ser Ala Ile Leu Asn Thr Pro Val Cys Gly Ile
                165                 170                 175

Pro Phe Ser Gln Trp Gly Thr Ile Gly Gly Ala Ala Ser Ala Tyr Val
            180                 185                 190

Ala Ser Gly Val Asp Leu Thr Gln Ala Ala Asn Glu Ile Lys Gly Leu
        195                 200                 205

Ala Gln Gln Met Gln Lys Leu Leu Ser Leu Met
    210                 215

<210> SEQ ID NO 25
<211> LENGTH: 543
```

<212> TYPE: PRT
<213> ORGANISM: Salmonella sp.

<400> SEQUENCE: 25

```
Met Leu Lys Tyr Glu Glu Arg Lys Leu Asn Asn Leu Thr Leu Ser Ser
1               5                   10                  15

Phe Ser Lys Val Gly Val Ser Asn Asp Ala Arg Leu Tyr Ile Ala Lys
            20                  25                  30

Glu Asn Thr Asp Lys Ala Tyr Val Ala Pro Glu Lys Phe Ser Ser Lys
        35                  40                  45

Val Leu Thr Trp Leu Gly Lys Met Pro Leu Phe Lys Asn Thr Glu Val
    50                  55                  60

Val Gln Lys His Thr Glu Asn Ile Arg Val Gln Asp Gln Lys Ile Leu
65                  70                  75                  80

Gln Thr Phe Leu His Ala Leu Thr Glu Lys Tyr Gly Glu Thr Ala Val
                85                  90                  95

Asn Asp Ala Leu Leu Met Ser Arg Ile Asn Met Asn Lys Pro Leu Thr
            100                 105                 110

Gln Arg Leu Ala Val Gln Ile Thr Glu Cys Val Lys Ala Ala Asp Glu
        115                 120                 125

Gly Phe Ile Asn Leu Ile Lys Ser Lys Asp Asn Val Gly Val Arg Asn
    130                 135                 140

Ala Ala Leu Val Ile Lys Gly Asp Thr Lys Val Ala Glu Lys Asn
145                 150                 155                 160

Asn Asp Val Gly Ala Glu Ser Lys Gln Pro Leu Leu Asp Ile Ala Leu
                165                 170                 175

Lys Gly Leu Lys Arg Thr Leu Pro Gln Leu Glu Gln Met Asp Gly Asn
            180                 185                 190

Ser Leu Arg Glu Asn Phe Gln Glu Met Ala Ser Gly Asn Gly Pro Leu
        195                 200                 205

Arg Ser Leu Met Thr Asn Leu Gln Asn Leu Asn Lys Ile Pro Glu Ala
    210                 215                 220

Lys Gln Leu Asn Asp Tyr Val Thr Thr Leu Thr Asn Ile Gln Val Gly
225                 230                 235                 240

Val Ala Arg Phe Ser Gln Trp Gly Thr Cys Gly Gly Glu Val Glu Arg
                245                 250                 255

Trp Val Asp Lys Ala Ser Thr His Glu Leu Thr Gln Ala Val Lys Lys
            260                 265                 270

Ile His Val Ile Ala Lys Glu Leu Lys Asn Val Thr Ala Glu Leu Glu
        275                 280                 285

Lys Ile Glu Ala Gly Ala Pro Met Pro Gln Thr Met Ser Gly Pro Thr
    290                 295                 300

Leu Gly Leu Ala Arg Phe Ala Val Ser Ser Ile Pro Ile Asn Gln Gln
305                 310                 315                 320

Thr Gln Val Lys Leu Ser Asp Gly Met Pro Val Pro Val Asn Thr Leu
                325                 330                 335

Thr Phe Asp Gly Lys Pro Val Ala Leu Ala Gly Ser Tyr Pro Lys Asn
            340                 345                 350

Thr Pro Asp Ala Leu Glu Ala His Met Lys Met Leu Leu Glu Lys Glu
        355                 360                 365

Cys Ser Cys Leu Val Val Leu Thr Ser Glu Asp Gln Met Gln Ala Lys
    370                 375                 380

Gln Leu Pro Pro Tyr Phe Arg Gly Ser Tyr Thr Phe Gly Glu Val His
385                 390                 395                 400
```

-continued

```
Thr Asn Ser Gln Lys Val Ser Ala Ser Gln Gly Glu Ala Ile Asp
            405                 410                 415

Gln Tyr Asn Met Gln Leu Ser Cys Gly Glu Lys Arg Tyr Thr Ile Pro
            420                 425                 430

Val Leu His Val Lys Asn Trp Pro Asp His Gln Pro Leu Pro Ser Thr
            435                 440                 445

Asp Gln Leu Glu Tyr Leu Ala Asp Arg Val Lys Asn Ser Asn Gln Asn
450                 455                 460

Gly Ala Pro Gly Arg Ser Ser Asp Lys His Leu Pro Met Ile His
465                 470                 475                 480

Cys Leu Gly Gly Val Gly Arg Thr Gly Thr Met Ala Ala Ala Leu Val
            485                 490                 495

Leu Lys Asp Asn Pro His Ser Asn Leu Glu Gln Val Arg Ala Asp Phe
            500                 505                 510

Arg Asp Ser Arg Asn Asn Arg Met Leu Glu Asp Ala Ser Gln Phe Val
            515                 520                 525

Gln Leu Lys Ala Met Gln Ala Gln Leu Leu Met Thr Thr Ala Ser
            530                 535                 540
```

<210> SEQ ID NO 26
<211> LENGTH: 240
<212> TYPE: PRT
<213> ORGANISM: Salmonella typhimurium

<400> SEQUENCE: 26

```
Met Thr Asn Ile Thr Leu Ser Thr Gln His Tyr Arg Ile His Arg Ser
1               5                   10                  15

Asp Val Glu Pro Val Lys Glu Lys Thr Thr Glu Lys Asp Ile Phe Ala
            20                  25                  30

Lys Ser Ile Thr Ala Val Arg Asn Ser Phe Ile Ser Leu Ser Thr Ser
            35                  40                  45

Leu Ser Asp Arg Phe Ser Leu His Gln Gln Thr Asp Ile Pro Thr Thr
50                  55                  60

His Phe His Arg Gly Asn Ala Ser Glu Gly Arg Ala Val Leu Thr Ser
65                  70                  75                  80

Lys Thr Val Lys Asp Phe Met Leu Gln Lys Leu Asn Ser Leu Asp Ile
            85                  90                  95

Lys Gly Asn Ala Ser Lys Asp Pro Ala Tyr Ala Arg Gln Thr Cys Glu
            100                 105                 110

Ala Ile Leu Ser Ala Val Tyr Ser Asn Asn Lys Asp Gln Cys Cys Lys
            115                 120                 125

Leu Leu Ile Ser Lys Gly Val Ser Ile Thr Pro Phe Leu Lys Glu Ile
130                 135                 140

Gly Glu Ala Ala Gln Asn Ala Gly Leu Pro Gly Glu Ile Lys Asn Gly
145                 150                 155                 160

Val Phe Thr Pro Gly Gly Ala Gly Ala Asn Pro Phe Val Val Pro Leu
            165                 170                 175

Ile Ala Ser Ala Ser Ile Lys Tyr Pro His Met Phe Ile Asn His Asn
            180                 185                 190

Gln Gln Val Ser Phe Lys Ala Tyr Ala Glu Lys Ile Val Met Lys Glu
            195                 200                 205

Val Thr Pro Leu Phe Asn Lys Gly Thr Met Pro Thr Pro Gln Gln Phe
            210                 215                 220

Gln Leu Thr Ile Glu Asn Ile Ala Asn Lys Tyr Leu Gln Asn Ala Ser
```

225          230          235          240

<210> SEQ ID NO 27
<211> LENGTH: 561
<212> TYPE: PRT
<213> ORGANISM: Salmonella typhimurium

<400> SEQUENCE: 27

Met Gln Ile Gln Ser Phe Tyr His Ser Ala Ser Leu Lys Thr Gln Glu
1               5                   10                  15

Ala Phe Lys Ser Leu Gln Lys Thr Leu Tyr Asn Gly Met Gln Ile Leu
            20                  25                  30

Ser Gly Gln Gly Lys Ala Pro Ala Lys Ala Pro Asp Ala Arg Pro Glu
        35                  40                  45

Ile Ile Val Leu Arg Glu Pro Gly Ala Thr Trp Gly Asn Tyr Leu Gln
    50                  55                  60

His Gln Lys Ala Ser Asn His Ser Leu His Asn Leu Tyr Asn Leu Gln
65                  70                  75                  80

Arg Asp Leu Leu Thr Val Ala Ala Thr Val Leu Gly Lys Gln Asp Pro
                85                  90                  95

Val Leu Thr Ser Met Ala Asn Gln Met Glu Leu Ala Lys Val Lys Ala
            100                 105                 110

Asp Arg Pro Ala Thr Lys Gln Glu Ala Ala Lys Ala Leu Lys
        115                 120                 125

Lys Asn Leu Ile Glu Leu Ile Ala Ala Arg Thr Gln Gln Asp Gly
    130                 135                 140

Leu Pro Ala Lys Glu Ala His Arg Phe Ala Ala Val Ala Phe Arg Asp
145                 150                 155                 160

Ala Gln Val Lys Gln Leu Asn Asn Gln Pro Trp Gln Thr Ile Lys Asn
                165                 170                 175

Thr Leu Thr His Asn Gly His His Tyr Thr Asn Thr Gln Leu Pro Ala
            180                 185                 190

Ala Glu Met Lys Ile Gly Ala Lys Asp Ile Phe Pro Ser Ala Tyr Glu
        195                 200                 205

Gly Lys Gly Val Cys Ser Trp Asp Thr Lys Asn Ile His His Ala Asn
    210                 215                 220

Asn Leu Trp Met Ser Thr Val Ser Val His Glu Asp Gly Lys Asp Lys
225                 230                 235                 240

Thr Leu Phe Cys Gly Ile Arg His Gly Val Leu Ser Pro Tyr His Glu
                245                 250                 255

Lys Asp Pro Leu Leu Arg His Val Gly Ala Glu Asn Lys Ala Lys Glu
            260                 265                 270

Val Leu Thr Ala Ala Leu Phe Ser Lys Pro Glu Leu Leu Asn Lys Ala
        275                 280                 285

Leu Ala Gly Glu Ala Val Ser Leu Lys Leu Val Ser Val Gly Leu Leu
    290                 295                 300

Thr Ala Ser Asn Ile Phe Gly Lys Glu Gly Thr Met Val Glu Asp Gln
305                 310                 315                 320

Met Arg Ala Trp Gln Ser Leu Thr Gln Pro Gly Lys Met Ile His Leu
                325                 330                 335

Lys Ile Arg Asn Lys Asp Gly Asp Leu Gln Thr Val Lys Ile Lys Pro
            340                 345                 350

Asp Val Ala Ala Phe Asn Val Gly Val Asn Glu Leu Ala Leu Lys Leu
        355                 360                 365

-continued

```
Gly Phe Gly Leu Lys Ala Ser Asp Ser Tyr Asn Ala Glu Ala Leu His
    370                 375                 380

Gln Leu Leu Gly Asn Asp Leu Arg Pro Glu Ala Arg Pro Gly Gly Trp
385                 390                 395                 400

Val Gly Glu Trp Leu Ala Gln Tyr Pro Asp Asn Tyr Glu Val Val Asn
                405                 410                 415

Thr Leu Ala Arg Gln Ile Lys Asp Ile Trp Lys Asn Asn Gln His His
                420                 425                 430

Lys Asp Gly Gly Glu Pro Tyr Lys Leu Ala Gln Arg Leu Ala Met Leu
                435                 440                 445

Ala His Glu Ile Asp Ala Val Pro Ala Trp Asn Cys Lys Ser Gly Lys
450                 455                 460

Asp Arg Thr Gly Met Met Asp Ser Glu Ile Lys Arg Glu Ile Ile Ser
465                 470                 475                 480

Leu His Gln Thr His Met Leu Ser Ala Pro Gly Ser Leu Pro Asp Ser
                485                 490                 495

Gly Gly Gln Lys Ile Phe Gln Lys Val Leu Leu Asn Ser Gly Asn Leu
                500                 505                 510

Glu Ile Gln Lys Gln Asn Thr Gly Gly Ala Gly Asn Lys Val Met Lys
                515                 520                 525

Asn Leu Ser Pro Glu Val Leu Asn Leu Ser Tyr Gln Lys Arg Val Gly
530                 535                 540

Asp Glu Asn Ile Trp Gln Ser Val Lys Gly Ile Ser Ser Leu Ile Thr
545                 550                 555                 560

Ser
```

<210> SEQ ID NO 28
<211> LENGTH: 685
<212> TYPE: PRT
<213> ORGANISM: Salmonella typhimurium

<400> SEQUENCE: 28

```
Met Val Thr Ser Val Arg Thr Gln Pro Pro Val Ile Met Pro Gly Met
1               5                   10                  15

Gln Thr Glu Ile Lys Thr Gln Ala Thr Asn Leu Ala Ala Asn Leu Ser
                20                  25                  30

Ala Val Arg Glu Ser Ala Thr Thr Thr Leu Ser Gly Glu Ile Lys Gly
            35                  40                  45

Pro Gln Leu Glu Asp Phe Pro Ala Leu Ile Lys Gln Ala Ser Leu Asp
        50                  55                  60

Ala Leu Phe Lys Cys Gly Lys Asp Ala Glu Ala Leu Lys Glu Val Phe
65                  70                  75                  80

Thr Asn Ser Asn Asn Val Ala Gly Lys Lys Ala Ile Met Glu Phe Ala
                85                  90                  95

Gly Leu Phe Arg Ser Ala Leu Asn Ala Thr Ser Asp Ser Pro Glu Ala
                100                 105                 110

Lys Thr Leu Leu Met Lys Val Gly Ala Glu Tyr Thr Ala Gln Ile Ile
            115                 120                 125

Lys Asp Gly Leu Lys Glu Lys Ser Ala Phe Gly Pro Trp Leu Pro Glu
        130                 135                 140

Thr Lys Lys Ala Glu Ala Lys Leu Glu Asn Leu Glu Lys Gln Leu Leu
145                 150                 155                 160

Asp Ile Ile Lys Asn Asn Thr Gly Gly Glu Leu Ser Lys Leu Ser Thr
                165                 170                 175
```

-continued

```
Asn Leu Val Met Gln Glu Val Met Pro Tyr Ile Ala Ser Cys Ile Glu
            180                 185                 190

His Asn Phe Gly Cys Thr Leu Asp Pro Leu Thr Arg Ser Asn Leu Thr
            195                 200                 205

His Leu Val Asp Lys Ala Ala Lys Ala Val Glu Ala Leu Asp Met
            210                 215                 220

Cys His Gln Lys Leu Thr Gln Glu Gln Gly Thr Ser Val Gly Arg Glu
225                 230                 235                 240

Ala Arg His Leu Glu Met Gln Thr Leu Ile Pro Leu Leu Leu Arg Asn
                245                 250                 255

Val Phe Ala Gln Ile Pro Ala Asp Lys Leu Pro Asp Pro Lys Ile Pro
            260                 265                 270

Glu Pro Ala Ala Gly Pro Val Pro Asp Gly Lys Lys Ala Glu Pro
275                 280                 285

Thr Gly Ile Asn Ile Asn Ile Asn Ile Asp Ser Ser Asn His Ser Val
            290                 295                 300

Asp Asn Ser Lys His Ile Asn Asn Ser Arg Ser His Val Asp Asn Ser
305                 310                 315                 320

Gln Arg His Ile Asp Asn Ser Asn His Asp Asn Ser Arg Lys Thr Ile
                325                 330                 335

Asp Asn Ser Arg Thr Phe Ile Asp Asn Ser Gln Arg Asn Gly Glu Ser
            340                 345                 350

His His Ser Thr Asn Ser Ser Asn Val Ser His Ser His Ser Arg Val
            355                 360                 365

Asp Ser Thr Thr His Gln Thr Glu Thr Ala His Ser Ala Ser Thr Gly
370                 375                 380

Ala Ile Asp His Gly Ile Ala Gly Lys Ile Asp Val Thr Ala His Ala
385                 390                 395                 400

Thr Ala Glu Ala Val Thr Asn Ala Ser Ser Glu Ser Lys Asp Gly Lys
                405                 410                 415

Val Val Thr Ser Glu Lys Gly Thr Thr Gly Glu Thr Thr Ser Phe Asp
            420                 425                 430

Glu Val Asp Gly Val Thr Ser Lys Ser Ile Ile Gly Lys Pro Val Gln
            435                 440                 445

Ala Thr Val His Gly Val Asp Asp Asn Lys Gln Gln Ser Gln Thr Ala
450                 455                 460

Glu Ile Val Asn Val Lys Pro Leu Ala Ser Gln Leu Ala Gly Val Glu
465                 470                 475                 480

Asn Val Lys Thr Asp Thr Leu Gln Ser Asp Thr Thr Val Ile Thr Gly
                485                 490                 495

Asn Lys Ala Gly Thr Thr Asp Asn Asp Asn Ser Gln Thr Asp Lys Thr
            500                 505                 510

Gly Pro Phe Ser Gly Leu Lys Phe Lys Gln Asn Ser Phe Leu Ser Thr
            515                 520                 525

Val Pro Ser Val Thr Asn Met His Ser Met His Phe Asp Ala Arg Glu
530                 535                 540

Thr Phe Leu Gly Val Ile Arg Lys Ala Leu Glu Pro Asp Thr Ser Thr
545                 550                 555                 560

Pro Phe Pro Val Arg Arg Ala Phe Asp Gly Leu Arg Ala Glu Ile Leu
                565                 570                 575

Pro Asn Asp Thr Ile Lys Ser Ala Ala Leu Lys Ala Gln Cys Ser Asp
            580                 585                 590

Ile Asp Lys His Pro Glu Leu Lys Ala Lys Met Glu Thr Leu Lys Glu
```

```
                595                 600                 605
Val Ile Thr His His Pro Gln Lys Glu Lys Leu Ala Glu Ile Ala Leu
            610                 615                 620

Gln Phe Ala Arg Glu Ala Gly Leu Thr Arg Leu Lys Gly Glu Thr Asp
625                 630                 635                 640

Tyr Val Leu Ser Asn Val Leu Asp Gly Leu Ile Gly Asp Gly Ser Trp
            645                 650                 655

Arg Ala Gly Pro Ala Tyr Glu Ser Tyr Leu Asn Lys Pro Gly Val Asp
                660                 665                 670

Arg Val Ile Thr Thr Val Asp Gly Leu His Met Gln Arg
            675                 680                 685

<210> SEQ ID NO 29
<211> LENGTH: 732
<212> TYPE: PRT
<213> ORGANISM: Yersinia pseudotuberculosis

<400> SEQUENCE: 29

Met Lys Ser Val Lys Ile Met Gly Thr Met Pro Ser Ile Ser Leu
1               5                   10                  15

Ala Lys Ala His Glu Arg Ile Ser Gln His Trp Gln Asn Pro Val Gly
            20                  25                  30

Glu Leu Asn Ile Gly Gly Lys Arg Tyr Arg Ile Ile Asp Asn Gln Val
        35                  40                  45

Leu Arg Leu Asn Pro His Ser Gly Phe Ser Leu Phe Arg Glu Gly Val
    50                  55                  60

Gly Lys Ile Phe Ser Gly Lys Met Phe Asn Phe Ser Ile Ala Arg Asn
65                  70                  75                  80

Leu Thr Asp Thr Leu His Ala Ala Gln Lys Thr Thr Ser Gln Glu Leu
                85                  90                  95

Arg Ser Asp Ile Pro Asn Ala Leu Ser Asn Leu Phe Gly Ala Lys Pro
            100                 105                 110

Gln Thr Glu Leu Pro Leu Gly Trp Lys Gly Glu Pro Leu Ser Gly Ala
        115                 120                 125

Pro Asp Leu Glu Gly Met Arg Val Ala Glu Thr Asp Lys Phe Ala Glu
    130                 135                 140

Gly Glu Ser His Ile Ser Ile Ile Glu Thr Lys Asp Lys Gln Arg Leu
145                 150                 155                 160

Val Ala Lys Ile Glu Arg Ser Ile Ala Glu Gly His Leu Phe Ala Glu
                165                 170                 175

Leu Glu Ala Tyr Lys His Ile Tyr Lys Thr Ala Gly Lys His Pro Asn
            180                 185                 190

Leu Ala Asn Val His Gly Met Ala Val Val Pro Tyr Gly Asn Arg Lys
        195                 200                 205

Glu Glu Ala Leu Leu Met Asp Glu Val Asp Gly Trp Arg Cys Ser Asp
    210                 215                 220

Thr Leu Arg Thr Leu Ala Asp Ser Trp Lys Gln Gly Lys Ile Asn Ser
225                 230                 235                 240

Glu Ala Tyr Trp Gly Thr Ile Lys Phe Ile Ala His Arg Leu Leu Asp
                245                 250                 255

Val Thr Asn His Leu Ala Lys Ala Gly Val Val His Asn Asp Ile Lys
            260                 265                 270

Pro Gly Asn Val Val Phe Asp Arg Ala Ser Gly Glu Pro Val Val Ile
        275                 280                 285
```

```
Asp Leu Gly Leu His Ser Arg Ser Gly Glu Gln Pro Lys Gly Phe Thr
    290                 295                 300

Glu Ser Phe Lys Ala Pro Glu Leu Gly Val Gly Asn Leu Gly Ala Ser
305                 310                 315                 320

Glu Lys Ser Asp Val Phe Leu Val Val Ser Thr Leu Leu His Cys Ile
                325                 330                 335

Glu Gly Phe Glu Lys Asn Pro Glu Ile Lys Pro Asn Gln Gly Leu Arg
            340                 345                 350

Phe Ile Thr Ser Glu Pro Ala His Val Met Asp Glu Asn Gly Tyr Pro
        355                 360                 365

Ile His Arg Pro Gly Ile Ala Gly Val Glu Thr Ala Tyr Thr Arg Phe
370                 375                 380

Ile Thr Asp Ile Leu Gly Val Ser Ala Asp Ser Arg Pro Asp Ser Asn
385                 390                 395                 400

Glu Ala Arg Leu His Glu Phe Leu Ser Asp Gly Thr Ile Asp Glu Glu
                405                 410                 415

Ser Ala Lys Gln Ile Leu Lys Asp Thr Leu Thr Gly Glu Met Ser Pro
            420                 425                 430

Leu Ser Thr Asp Val Arg Arg Ile Thr Pro Lys Lys Leu Arg Glu Leu
        435                 440                 445

Ser Asp Leu Leu Arg Thr His Leu Ser Ser Ala Ala Thr Lys Gln Leu
450                 455                 460

Asp Met Gly Gly Val Leu Ser Asp Leu Asp Thr Met Leu Val Ala Leu
465                 470                 475                 480

Asp Lys Ala Glu Arg Glu Gly Gly Val Asp Lys Asp Gln Leu Lys Ser
                485                 490                 495

Phe Asn Ser Leu Ile Leu Lys Thr Tyr Arg Val Ile Glu Asp Tyr Val
            500                 505                 510

Lys Gly Arg Glu Gly Asp Thr Lys Asn Ser Ser Thr Glu Val Ser Pro
        515                 520                 525

Tyr His Arg Ser Asn Phe Met Leu Ser Ile Val Glu Pro Ser Leu Gln
530                 535                 540

Arg Ile Gln Lys His Leu Asp Gln Thr His Ser Phe Ser Asp Ile Gly
545                 550                 555                 560

Ser Leu Val Arg Ala His Lys His Leu Glu Thr Leu Glu Val Leu
                565                 570                 575

Val Thr Leu Ser Gln Gln Gly Gln Pro Val Ser Ser Glu Thr Tyr Gly
            580                 585                 590

Phe Leu Asn Arg Leu Ala Glu Ala Lys Ile Thr Leu Ser Gln Gln Leu
        595                 600                 605

Asn Thr Leu Gln Gln Gln Glu Ser Ala Lys Ala Gln Leu Ser Ile
610                 615                 620

Leu Ile Asn Arg Ser Gly Ser Trp Ala Asp Val Ala Arg Gln Ser Leu
625                 630                 635                 640

Gln Arg Phe Asp Ser Thr Arg Pro Val Lys Phe Gly Thr Glu Gln
                645                 650                 655

Tyr Thr Ala Ile His Arg Gln Met Met Ala Ala His Ala Ala Ile Thr
            660                 665                 670

Leu Gln Glu Val Ser Glu Phe Thr Asp Asp Met Arg Asn Phe Thr Val
        675                 680                 685

Asp Ser Ile Pro Leu Leu Ile Gln Leu Gly Arg Ser Ser Leu Met Asp
690                 695                 700

Glu His Leu Val Glu Gln Arg Glu Lys Leu Arg Glu Leu Thr Thr Ile
```

```
                705                 710                 715                 720

Ala Glu Arg Leu Asn Arg Leu Glu Arg Glu Trp Met
                725                 730

<210> SEQ ID NO 30
<211> LENGTH: 529
<212> TYPE: PRT
<213> ORGANISM: Yersinia sp.

<400> SEQUENCE: 30

Met Phe Ile Asn Pro Arg Asn Val Ser Asn Thr Phe Leu Gln Glu Pro
1               5                   10                  15

Leu Arg His Ser Ser Asn Leu Thr Glu Met Pro Val Glu Ala Glu Asn
            20                  25                  30

Val Lys Ser Lys Thr Glu Tyr Tyr Asn Ala Trp Ser Glu Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro His Leu Glu Ser Leu
            85                  90                  95

Val Ala Ser Cys Asn Ser Leu Thr Glu Leu Pro Glu Leu Pro Gln Ser
        100                 105                 110

Leu Lys Ser Leu Gln Val Glu Asn Asn Asn Leu Lys Ala Leu Pro Asp
    115                 120                 125

Leu Pro Pro Ser Leu Lys Lys Leu His Val Arg Glu Asn Asp Leu Thr
130                 135                 140

Asp Leu Pro Glu Leu Pro Gln Ser Leu Glu Ser Leu Arg Val Asp Asn
145                 150                 155                 160

Asn Asn Leu Lys Ala Leu Ser Asp Leu Pro Pro Ser Leu Glu Tyr Leu
                165                 170                 175

Thr Ala Ser Ser Asn Lys Leu Glu Glu Leu Pro Glu Leu Gln Asn Leu
            180                 185                 190

Pro Phe Leu Ala Ala Ile Tyr Ala Asp Asn Leu Leu Glu Thr Leu
        195                 200                 205

Pro Asp Leu Pro Pro Ser Leu Lys Lys Leu His Val Arg Glu Asn Asp
    210                 215                 220

Leu Thr Asp Leu Pro Glu Leu Pro Gln Ser Leu Glu Ser Leu Gln Val
225                 230                 235                 240

Asp Asn Asn Asn Leu Lys Ala Leu Ser Asp Leu Pro Pro Ser Leu Glu
                245                 250                 255

Tyr Leu Thr Ala Ser Ser Asn Lys Leu Glu Glu Leu Pro Glu Leu Gln
            260                 265                 270

Asn Leu Pro Phe Leu Ala Ala Ile Tyr Ala Asp Asn Leu Leu Glu
        275                 280                 285

Thr Leu Pro Asp Leu Pro Pro His Leu Glu Ile Leu Val Ala Ser Tyr
    290                 295                 300

Asn Ser Leu Thr Glu Leu Pro Glu Leu Pro Gln Ser Leu Lys Ser Leu
305                 310                 315                 320

Arg Val Asp Asn Asn Asn Leu Lys Ala Leu Ser Asp Leu Pro Pro Ser
                325                 330                 335

Leu Glu Tyr Leu Thr Ala Ser Ser Asn Lys Leu Glu Glu Leu Pro Glu
            340                 345                 350
```

-continued

```
Leu Gln Asn Leu Pro Phe Leu Ala Ile Tyr Ala Asp Asn Asn Leu
            355                 360                 365
Leu Glu Thr Leu Pro Asp Leu Pro Ser Leu Lys Lys Leu His Val
    370                 375                 380
Arg Glu Asn Asp Leu Thr Asp Leu Pro Glu Leu Pro Gln Ser Leu Thr
385                 390                 395                 400
Phe Leu Asp Val Ser Asp Asn Ile Ser Gly Leu Ser Glu Leu Pro
                405                 410                 415
Pro Asn Leu Tyr Tyr Leu Asp Ala Ser Ser Asn Glu Ile Arg Ser Leu
            420                 425                 430
Cys Asp Leu Pro Pro Ser Leu Val Asp Leu Asn Val Lys Ser Asn Gln
            435                 440                 445
Leu Ser Glu Leu Pro Ala Leu Pro Pro His Leu Glu Arg Leu Ile Ala
    450                 455                 460
Ser Phe Asn Tyr Leu Ala Glu Val Pro Glu Leu Pro Gln Asn Leu Lys
465                 470                 475                 480
Gln Leu His Val Glu Gln Asn Ala Leu Arg Glu Phe Pro Asp Ile Pro
                485                 490                 495
Glu Ser Leu Glu Glu Leu Glu Met Asp Ser Glu Arg Val Val Asp Pro
            500                 505                 510
Tyr Glu Phe Ala His Glu Thr Thr Asp Lys Leu Glu Asp Asp Val Phe
            515                 520                 525
Glu

<210> SEQ ID NO 31
<211> LENGTH: 35
<212> TYPE: PRT
<213> ORGANISM: Unknown
<220> FEATURE:
<223> OTHER INFORMATION: Description of Unknown:
      Amatoxin sequence

<400> SEQUENCE: 31

Met Ser Asp Ile Asn Ala Thr Arg Leu Pro Ile Trp Gly Ile Gly Cys
1               5                   10                  15
Asn Pro Cys Val Gly Asp Asp Val Thr Thr Leu Leu Thr Arg Gly Glu
                20                  25                  30
Ala Leu Cys
        35

<210> SEQ ID NO 32
<211> LENGTH: 34
<212> TYPE: PRT
<213> ORGANISM: Amanita phalloides

<400> SEQUENCE: 32

Met Ser Asp Ile Asn Ala Thr Arg Leu Pro Ala Trp Leu Val Asp Cys
1               5                   10                  15
Pro Cys Val Gly Asp Asp Val Asn Arg Leu Leu Thr Arg Gly Glu Ser
            20                  25                  30
Leu Cys

<210> SEQ ID NO 33
<211> LENGTH: 291
<212> TYPE: PRT
<213> ORGANISM: Ustilago maydis

<400> SEQUENCE: 33
```

-continued

```
Met Ile Lys Pro Glu Arg Ser Ile Leu Thr Ile Leu Ile Gly Ile Leu
1               5                   10                  15

Cys Leu Leu Ala Tyr Val Leu Ala Asn Gly Glu Pro His Asp Gly Asp
            20                  25                  30

Asn Glu Trp Ser Ser Tyr Cys Ser Asp Gln Gly Phe Arg Arg Ser Asp
        35                  40                  45

Asp Gly Leu Val Thr Thr Pro Asp Val Gly Gln Glu Ser Ile Gly Lys
50                  55                  60

Asn Ser Ile Asn Gly Ser Glu Leu Val Asp Tyr Leu Gln Cys Leu Lys
65              70                  75                  80

Val Arg Leu Asn Gly Gln Lys Gln Val Ser Asn Asp Gly Trp Leu
                85                  90                  95

Leu Leu Leu Val Gln Glu Pro Ser Val Asn Val Thr Gln Lys Ala Met
            100                 105                 110

Ser Glu Cys Asn Tyr Asn Val Ser Ser Gly His Lys Ala Gly Ser Tyr
        115                 120                 125

Ile Gln Val Thr Asn Thr Pro Ala Asp Tyr Lys Val Ile Ser Arg Arg
    130                 135                 140

Gly Ser Tyr Glu Gly Asp Gln Leu Pro Glu Asp Val Lys Pro Tyr Phe
145                 150                 155                 160

Gly Val Gln Lys Thr Ser Asp Tyr Arg Pro Ile Ser Lys Arg Ile Asn
                165                 170                 175

Pro Asn Leu Thr Leu Arg Gln Leu Ala Tyr Asn Phe Ala Ala Leu Asn
            180                 185                 190

Met Cys Ser Leu Trp Cys Asn Ser Cys Ile Ser Arg Ser Cys Pro Tyr
        195                 200                 205

Tyr Ile Ala Glu Leu Thr Val His Val Asn Asn Ile His His Gly Thr
    210                 215                 220

Val Trp Leu His His Phe Cys Arg Asn Ala Ser Pro Gln Gly Gly Asn
225                 230                 235                 240

Leu Tyr Ser Thr Leu Thr Ile Ser His Lys Asp Thr Ala Tyr Tyr Val
                245                 250                 255

Gly Thr Gly Trp Trp Lys Val Arg Ser Thr Ala Ala Thr Thr Asn Asp
            260                 265                 270

Val Ala Gly Asp Trp Tyr Pro Ala Ser Trp Asn Gln Tyr Trp Cys Gly
        275                 280                 285

Pro His Tyr
    290

<210> SEQ ID NO 34
<211> LENGTH: 219
<212> TYPE: PRT
<213> ORGANISM: Ustilago maydis

<400> SEQUENCE: 34

Met Leu Ile Phe Ser Val Leu Met Tyr Leu Gly Leu Leu Ala Gly
1               5                   10                  15

Ala Ser Ala Leu Pro Asn Gly Leu Ser Pro Arg Asn Asn Ala Phe Cys
            20                  25                  30

Ala Gly Phe Gly Leu Ser Cys Lys Trp Glu Cys Trp Cys Thr Ala His
        35                  40                  45

Gly Thr Gly Asn Glu Leu Arg Tyr Ala Thr Ala Ala Gly Cys Gly Asp
    50                  55                  60

His Leu Ser Lys Ser Tyr Tyr Asp Ala Arg Ala Gly His Cys Leu Phe
65              70                  75                  80
```

```
Ser Asp Asp Leu Arg Asn Gln Phe Tyr Ser His Cys Ser Ser Leu Asn
                85                  90                  95

Asn Asn Met Ser Cys Arg Ser Leu Ser Lys Arg Thr Ile Gln Asp Ser
            100                 105                 110

Ala Thr Asp Thr Val Asp Leu Gly Ala Glu Leu His Arg Asp Asp Pro
        115                 120                 125

Pro Pro Thr Ala Ser Asp Ile Gly Lys Arg Gly Lys Arg Pro Arg Pro
    130                 135                 140

Val Met Cys Gln Cys Val Asp Thr Thr Asn Gly Gly Val Arg Leu Asp
145                 150                 155                 160

Ala Val Thr Arg Ala Ala Cys Ser Ile Asp Ser Phe Ile Asp Gly Tyr
                165                 170                 175

Tyr Thr Glu Lys Asp Gly Phe Cys Arg Ala Lys Tyr Ser Trp Asp Leu
            180                 185                 190

Phe Thr Ser Gly Gln Phe Tyr Gln Ala Cys Leu Arg Tyr Ser His Ala
        195                 200                 205

Gly Thr Asn Cys Gln Pro Asp Pro Gln Tyr Glu
    210                 215
```

<210> SEQ ID NO 35
<211> LENGTH: 316
<212> TYPE: PRT
<213> ORGANISM: Saccharomyces cerevisiae

<400> SEQUENCE: 35

```
Met Thr Lys Pro Thr Gln Val Leu Val Arg Ser Val Ser Ile Leu Phe
1               5                   10                  15

Phe Ile Thr Leu Leu His Leu Val Val Ala Leu Asn Asp Val Ala Gly
            20                  25                  30

Pro Ala Glu Thr Ala Pro Val Ser Leu Leu Pro Arg Glu Ala Pro Trp
        35                  40                  45

Tyr Asp Lys Ile Trp Glu Val Lys Asp Trp Leu Leu Gln Arg Ala Thr
    50                  55                  60

Asp Gly Asn Trp Gly Lys Ser Ile Thr Trp Gly Ser Phe Val Ala Ser
65                  70                  75                  80

Asp Ala Gly Val Val Ile Phe Gly Ile Asn Val Cys Lys Asn Cys Val
                85                  90                  95

Gly Glu Arg Lys Asp Asp Ile Ser Thr Asp Cys Gly Lys Gln Thr Leu
            100                 105                 110

Ala Leu Leu Val Ser Ile Phe Val Ala Val Thr Ser Gly His His Leu
        115                 120                 125

Ile Trp Gly Gly Asn Arg Pro Val Ser Gln Ser Asp Pro Asn Gly Ala
    130                 135                 140

Thr Val Ala Arg Arg Asp Ile Ser Thr Val Ala Asp Gly Asp Ile Pro
145                 150                 155                 160

Leu Asp Phe Ser Ala Leu Asn Asp Ile Leu Asn Glu His Gly Ile Ser
                165                 170                 175

Ile Leu Pro Ala Asn Ala Ser Gln Tyr Val Lys Arg Ser Asp Thr Ala
            180                 185                 190

Glu His Thr Thr Ser Phe Val Val Thr Asn Asn Tyr Thr Ser Leu His
        195                 200                 205

Thr Asp Leu Ile His His Gly Asn Gly Thr Tyr Thr Thr Phe Thr Thr
    210                 215                 220

Pro His Ile Pro Ala Val Ala Lys Arg Tyr Val Tyr Pro Met Cys Glu
```

225                 230                 235                 240

His Gly Ile Lys Ala Ser Tyr Cys Met Ala Leu Asn Asp Ala Met Val
                245                 250                 255

Ser Ala Asn Gly Asn Leu Tyr Gly Leu Ala Glu Lys Leu Phe Ser Glu
                260                 265                 270

Asp Glu Gly Gln Trp Glu Thr Asn Tyr Tyr Lys Leu Tyr Trp Ser Thr
                275                 280                 285

Gly Gln Trp Ile Met Ser Met Lys Phe Ile Glu Ser Ile Asp Asn
                290                 295                 300

Ala Asn Asn Asp Phe Glu Gly Cys Asp Thr Gly His
305                 310                 315

<210> SEQ ID NO 36
<211> LENGTH: 296
<212> TYPE: PRT
<213> ORGANISM: Saccharomyces cerevisiae

<400> SEQUENCE: 36

Met Gly His Leu Ala Ile Leu Phe Ser Ile Ile Ala Val Leu Asn Ile
1               5                   10                  15

Ala Thr Ala Val Ala Ser Ser Asp Ser Ile Tyr Leu Lys Gly His Arg
                20                  25                  30

Val Gly Gln Asp Ile Asp Ser Leu Tyr Arg Val Tyr Asp Asn Gly Thr
            35                  40                  45

Met Tyr Pro Val Thr Phe Asn Glu Trp Leu Asn Asp Leu Thr Gly Met
        50                  55                  60

Asn Asp Leu Ala Thr Asn Ala Thr Ile Leu Lys Arg Asp Ser Ser
65                  70                  75                  80

Asp Val Ser Cys Val Thr Glu Thr Cys Gln Tyr Val Asp Tyr His Val
                85                  90                  95

Asp Asp Glu Gly Val Ile Thr Ile Asp Ile Ser Thr Tyr Arg Ile Pro
                100                 105                 110

Val Glu Trp Asp Ser Gly Ser Ala Gly Asn Ala Ser Tyr Gly Val Ser
            115                 120                 125

Lys Arg Asp Thr Lys Tyr Glu Thr Phe Cys Lys Lys Ile Cys Gly
            130                 135                 140

Ile Asn Val Ser Gly Phe Cys Asn Ala Tyr Asp Phe Ala Val His Ala
145                 150                 155                 160

Phe Asp Phe Gly Gly Ser Val Tyr Asn Pro Val Ser Gly Ile Thr Asp
                165                 170                 175

Arg Ile Lys Glu Ala Thr Lys Arg Asp Lys Thr Glu Cys Leu Gly Tyr
                180                 185                 190

Glu Leu Asp His Val Arg Ile Asp Pro Ala Val Asp Trp Ser Ile Ser
            195                 200                 205

Ile Ser Thr Trp Lys Gln Gly Ser Ala Asn Cys Asp Thr Gln Ala Ser
210                 215                 220

Ala Asp Ser Leu Lys Cys Ala Ala Gln Lys Ala Leu Glu Ser Glu His
225                 230                 235                 240

Asn His Gln Lys Thr Ala Phe Cys Ile His Leu Asp Asn Gly Gly Ser
                245                 250                 255

Phe Asn Leu Asp Ile Arg Leu Ile Ser Glu Leu Ser Phe Ser Lys Tyr
                260                 265                 270

Asn Pro Trp Ala Leu Pro Cys Pro Lys Tyr Lys Gly Ser Asn Ser Trp
            275                 280                 285

```
Gln Val Val Ser Asp Cys Phe Gln
    290                 295
```

<210> SEQ ID NO 37
<211> LENGTH: 708
<212> TYPE: PRT
<213> ORGANISM: Saccharomyces cerevisiae

<400> SEQUENCE: 37

```
Met Pro Arg Phe Ala Ile Ile Phe Ala Leu Leu Ile Ala Tyr Ser Leu
1               5                   10                  15

Phe Leu Ser Thr Leu Phe Thr Gly Ser Ile Pro Asp Arg Ala Asn Thr
            20                  25                  30

Val Thr Ser Asn Ala Pro Cys Gln Val Val Ile Trp Asp Trp Ile Arg
        35                  40                  45

Thr Arg Arg Ile Cys Asn Cys Cys Ser Arg Leu Cys Tyr Ser Leu Leu
    50                  55                  60

Gly Arg Ser Asn Leu Ser Arg Thr Ala Lys Arg Gly Val Cys Thr Ile
65                  70                  75                  80

Ala Gly Ala Val Leu Ala Thr Ala Ala Val Ile Val Ala Ala Val Leu
                85                  90                  95

Val Gly Lys Ser Ser Gly Ser Ala Thr Lys Arg Gly Leu Thr Lys Thr
            100                 105                 110

Ile Ser Val Leu Asn His Thr Ile Pro Phe Thr Asp His Ile Leu Asn
        115                 120                 125

Gly Gln Thr Leu Ser Asn Gly Thr Gly Ser Asn Phe Val Thr Ile Gly
    130                 135                 140

Phe Ser Gly Tyr Ala Val His Ala Thr Ile Lys Arg Ala Ser Thr Thr
145                 150                 155                 160

Asp Ile Ile Ser Trp Val Pro Glu Ser Met Glu Pro Thr Leu Ala
                165                 170                 175

Arg Val Ala Ser Tyr Val Ser Ser Ser Ile Asn Leu Ala Ala Val
            180                 185                 190

Pro Asp Thr Gly Gly Asn Ala Ser Ala Leu Ser Phe Gln Asn Ala Val
        195                 200                 205

Gln Glu Phe Ala Thr Ser Trp Val Ser Met Thr Tyr Asp Gln Ser Tyr
    210                 215                 220

Gly Asp Leu Arg Asn Val Ala Asn Asp Glu Gly Gly Glu Glu Ile Leu
225                 230                 235                 240

Ile Leu Met Arg Lys Arg Ser Tyr Arg Ile Ser Phe Gln Val Ile Glu
                245                 250                 255

Thr Gly Ser Thr Ala Leu Leu Leu Arg Thr Arg Arg Val Val Ser Gln
            260                 265                 270

Leu Ile Thr Met Thr Tyr Leu Val Thr Val Gln Ala Arg Val Gly Ile
        275                 280                 285

Gln Ile Gly Asp Ile Phe Gln His Tyr Gly Gly Ile Asp Asn Tyr Val
    290                 295                 300

Met Thr Ser Ile Ser Val Leu Arg Thr Leu Glu Asp Lys Ala Phe His
305                 310                 315                 320

Glu Asn Lys Leu Leu Ile Val Arg Glu Pro Asn Lys Ser Asn Gln
                325                 330                 335

Asp Ala Asn Gln Ser Tyr Arg Leu Arg Pro Phe Ser Ala Asn Asp Leu
            340                 345                 350

Ile Gln Asn Leu Lys Ser Val Asp Ile Gly Phe Leu Ala Phe Cys Ser
        355                 360                 365
```

```
Phe Phe Asp Lys Tyr Ala His Tyr Pro Glu Ile Ile Met Met Lys Ile
    370                 375                 380

Thr Ile Phe Ile Ser Lys Gly Asn Leu Trp Ser Ile Ile Tyr Val Ile
385                 390                 395                 400

Gln Ala Arg Tyr Val Arg Lys Arg Val Met Lys Val Arg Gly Gln Met
                405                 410                 415

Pro Gly Gly Leu Leu Thr Asn Met Glu Ser Leu Leu Asn Ile Val Ser
                420                 425                 430

Thr Pro Asn Leu Asn Ile Ser Glu Phe His Ile Gln Thr His Ser Met
            435                 440                 445

Ser Gln Ser Lys Pro Met Tyr Phe Gln Lys Gln Cys Tyr Ser Ser Gln
    450                 455                 460

Asn Asn Ile Ile Tyr Ile Tyr Asn Ser Ile His Ile Thr Cys Gly Ala
465                 470                 475                 480

Val Tyr Val Ile Val His Asp Val Arg Thr Pro Ser Val Phe Val Leu
                485                 490                 495

Ile Glu Leu Arg Asn Cys Lys Pro Leu Lys Asn Ser Trp Cys Glu Thr
                500                 505                 510

Thr Lys Thr Ser Pro Arg Asp Thr Lys Ile Lys Lys Asn Glu Tyr Asn
    515                 520                 525

Glu Thr Val Cys Arg Arg Ala Gly Ala Leu Leu Asp Gly Arg Val Arg
    530                 535                 540

Thr Ile Arg Phe Leu Met Met Arg Thr His Trp Ser Arg Val Lys Gly
545                 550                 555                 560

Val Ser Cys Asn Thr Ala Asn Arg Leu Ser Arg Phe Cys Asn His Val
                565                 570                 575

Val Ser Tyr Tyr Pro Ser Gln Asn Ala Thr Ile His Leu Leu Pro Thr
                580                 585                 590

Ser Leu Arg Ala Glu Ser Leu Glu Gln Gln Tyr Thr Thr Arg Pro Leu
                595                 600                 605

Ser Ser Ser Asn Asn Arg Phe Cys Cys Leu Lys Ser Ile Phe Ile Asn
    610                 615                 620

Asn Cys Lys Lys Ala Cys Glu Ser Pro Ser Leu Val Ser Cys Asn Leu
625                 630                 635                 640

Gln Gln Thr Ala Glu Leu Leu Met Val Tyr Tyr Leu Tyr Ile Cys Glu
                645                 650                 655

Ala Cys Tyr Val Ser Arg Asn His Asp Leu Leu Ser Lys Gln Cys Met
                660                 665                 670

Ser Thr Val Arg Ala Val Tyr Val Ala Arg Met Arg Leu Pro Lys Phe
            675                 680                 685

Arg Ser Thr Phe Pro Cys Met Pro Arg Leu Cys Trp Leu Val Asn Gly
    690                 695                 700

Val Val Val Val
705

<210> SEQ ID NO 38
<211> LENGTH: 768
<212> TYPE: PRT
<213> ORGANISM: Bacillus anthracis

<400> SEQUENCE: 38

Met His Val Lys Glu Lys Glu Lys Asn Lys Asp Glu Asn Lys Arg Lys
1               5                   10                  15

Asp Glu Glu Arg Asn Lys Thr Gln Glu Glu His Leu Lys Glu Ile Met
```

-continued

```
                20                  25                  30
Lys His Ile Val Lys Ile Glu Val Lys Gly Glu Ala Val Lys Lys
                35                  40                  45
Glu Ala Ala Glu Lys Leu Leu Glu Lys Val Pro Ser Asp Val Leu Glu
 50                  55                  60
Met Tyr Lys Ala Ile Gly Gly Lys Ile Tyr Ile Val Asp Gly Asp Ile
 65                  70                  75                  80
Thr Lys His Ile Ser Leu Glu Ala Leu Ser Glu Asp Lys Lys Lys Ile
                85                  90                  95
Lys Asp Ile Tyr Gly Lys Asp Ala Leu Leu His Glu His Tyr Val Tyr
                100                 105                 110
Ala Lys Glu Gly Tyr Glu Pro Val Leu Val Ile Gln Ser Ser Glu Asp
                115                 120                 125
Tyr Val Glu Asn Thr Glu Lys Ala Leu Asn Val Tyr Tyr Glu Ile Gly
                130                 135                 140
Lys Ile Leu Ser Arg Asp Ile Leu Ser Lys Ile Asn Gln Pro Tyr Gln
145                 150                 155                 160
Lys Phe Leu Asp Val Leu Asn Thr Ile Lys Asn Ala Ser Asp Ser Asp
                165                 170                 175
Gly Gln Asp Leu Leu Phe Thr Asn Gln Leu Lys Glu His Pro Thr Asp
                180                 185                 190
Phe Ser Val Glu Phe Leu Glu Gln Asn Ser Asn Glu Val Gln Glu Val
                195                 200                 205
Phe Ala Lys Ala Phe Ala Tyr Tyr Ile Glu Pro Gln His Arg Asp Val
                210                 215                 220
Leu Gln Leu Tyr Ala Pro Glu Ala Phe Asn Tyr Met Asp Lys Phe Asn
225                 230                 235                 240
Glu Gln Glu Ile Asn Leu Ser Leu Glu Glu Leu Lys Asp Gln Arg Met
                245                 250                 255
Leu Ser Arg Tyr Glu Lys Trp Glu Lys Ile Lys Gln His Tyr Gln His
                260                 265                 270
Trp Ser Asp Ser Leu Ser Glu Glu Gly Arg Gly Leu Leu Lys Lys Leu
                275                 280                 285
Gln Ile Pro Ile Glu Pro Lys Lys Asp Asp Ile Ile His Ser Leu Ser
                290                 295                 300
Gln Glu Glu Lys Glu Leu Leu Lys Arg Ile Gln Ile Asp Ser Ser Asp
305                 310                 315                 320
Phe Leu Ser Thr Glu Glu Lys Glu Phe Leu Lys Lys Leu Gln Ile Asp
                325                 330                 335
Ile Arg Asp Ser Leu Ser Glu Glu Lys Glu Leu Leu Asn Arg Ile
                340                 345                 350
Gln Val Asp Ser Ser Asn Pro Leu Ser Glu Lys Glu Lys Glu Phe Leu
                355                 360                 365
Lys Lys Leu Lys Leu Asp Ile Gln Pro Tyr Asp Ile Asn Gln Arg Leu
                370                 375                 380
Gln Asp Thr Gly Gly Leu Ile Asp Ser Pro Ser Ile Asn Leu Asp Val
385                 390                 395                 400
Arg Lys Gln Tyr Lys Arg Asp Ile Gln Asn Ile Asp Ala Leu Leu His
                405                 410                 415
Gln Ser Ile Gly Ser Thr Leu Tyr Asn Lys Ile Tyr Leu Tyr Glu Asn
                420                 425                 430
Met Asn Ile Asn Asn Leu Thr Ala Thr Leu Gly Ala Asp Leu Val Asp
                435                 440                 445
```

-continued

Ser Thr Asp Asn Thr Lys Ile Asn Arg Gly Ile Phe Asn Glu Phe Lys
    450                 455                 460

Lys Asn Phe Lys Tyr Ser Ile Ser Ser Asn Tyr Met Ile Val Asp Ile
465                 470                 475                 480

Asn Glu Arg Pro Ala Leu Asp Asn Glu Arg Leu Lys Trp Arg Ile Gln
                485                 490                 495

Leu Ser Pro Asp Thr Arg Ala Gly Tyr Leu Glu Asn Gly Lys Leu Ile
            500                 505                 510

Leu Gln Arg Asn Ile Gly Leu Glu Ile Lys Asp Val Gln Ile Ile Lys
        515                 520                 525

Gln Ser Glu Lys Glu Tyr Ile Arg Ile Asp Ala Lys Val Val Pro Lys
    530                 535                 540

Ser Lys Ile Asp Thr Lys Ile Gln Glu Ala Gln Leu Asn Ile Asn Gln
545                 550                 555                 560

Glu Trp Asn Lys Ala Leu Gly Leu Pro Lys Tyr Thr Lys Leu Ile Thr
                565                 570                 575

Phe Asn Val His Asn Arg Tyr Ala Ser Asn Ile Val Glu Ser Ala Tyr
            580                 585                 590

Leu Ile Leu Asn Glu Trp Lys Asn Asn Ile Gln Ser Asp Leu Ile Lys
        595                 600                 605

Lys Val Thr Asn Tyr Leu Val Asp Gly Asn Gly Arg Phe Val Phe Thr
    610                 615                 620

Asp Ile Thr Leu Pro Asn Ile Ala Glu Gln Tyr Thr His Gln Asp Glu
625                 630                 635                 640

Ile Tyr Glu Gln Val His Ser Lys Gly Leu Tyr Val Pro Glu Ser Arg
                645                 650                 655

Ser Ile Leu Leu His Gly Pro Ser Lys Gly Val Glu Leu Arg Asn Asp
            660                 665                 670

Ser Glu Gly Phe Ile His Glu Phe Gly His Ala Val Asp Asp Tyr Ala
        675                 680                 685

Gly Tyr Leu Leu Asp Lys Asn Gln Ser Asp Leu Val Thr Asn Ser Lys
    690                 695                 700

Lys Phe Ile Asp Ile Phe Lys Glu Glu Gly Ser Asn Leu Thr Ser Tyr
705                 710                 715                 720

Gly Arg Thr Asn Glu Ala Glu Phe Phe Ala Glu Ala Phe Arg Leu Met
                725                 730                 735

His Ser Thr Asp His Ala Glu Arg Leu Lys Val Gln Lys Asn Ala Pro
            740                 745                 750

Lys Thr Phe Gln Phe Ile Asn Asp Gln Ile Lys Phe Ile Asn Ser
        755                 760                 765

<210> SEQ ID NO 39
<211> LENGTH: 319
<212> TYPE: PRT
<213> ORGANISM: Unknown
<220> FEATURE:
<223> OTHER INFORMATION: Description of Unknown:
      Shiga toxin sequence

<400> SEQUENCE: 39

Met Lys Cys Ile Leu Leu Lys Trp Val Leu Cys Leu Leu Leu Gly Phe
1               5                   10                  15

Ser Ser Val Ser Tyr Ser Arg Glu Phe Thr Ile Asp Phe Ser Thr Gln
                20                  25                  30

Gln Ser Tyr Val Ser Ser Leu Asn Ser Ile Arg Thr Glu Ile Ser Thr

```
            35                  40                  45
Pro Leu Glu His Ile Ser Gln Gly Thr Thr Ser Val Ser Val Ile Asn
 50                  55                  60

His Thr Pro Pro Gly Ser Tyr Phe Ala Val Asp Ile Arg Gly Leu Asp
 65                  70                  75                  80

Val Tyr Gln Ala Arg Phe Asp His Leu Arg Leu Ile Ile Glu Gln Asn
                 85                  90                  95

Asn Leu Tyr Val Ala Gly Phe Val Asn Thr Ala Thr Asn Thr Phe Tyr
                100                 105                 110

Arg Phe Ser Asp Phe Ala His Ile Ser Val Pro Gly Val Thr Thr Val
            115                 120                 125

Ser Met Thr Thr Asp Ser Ser Tyr Thr Thr Leu Gln Arg Val Ala Ala
130                 135                 140

Leu Glu Arg Ser Gly Met Gln Ile Ser Arg His Ser Leu Val Ser Ser
145                 150                 155                 160

Tyr Leu Ala Leu Met Glu Phe Ser Gly Asn Thr Met Thr Arg Asp Ala
                165                 170                 175

Ser Arg Ala Val Leu Arg Phe Val Thr Val Thr Ala Glu Ala Leu Arg
            180                 185                 190

Phe Arg Gln Ile Gln Arg Glu Phe Arg Gln Ala Leu Ser Glu Thr Ala
            195                 200                 205

Pro Val Tyr Thr Met Thr Pro Gly Asp Val Asp Leu Thr Leu Asn Trp
210                 215                 220

Gly Arg Ile Ser Asn Val Leu Pro Glu Tyr Arg Gly Glu Asp Gly Val
225                 230                 235                 240

Arg Val Gly Arg Ile Ser Phe Asn Asn Ile Ser Ala Ile Leu Gly Thr
                245                 250                 255

Val Ala Val Ile Leu Asn Cys His His Gln Gly Ala Arg Ser Val Arg
            260                 265                 270

Ala Val Asn Glu Glu Ser Gln Pro Glu Cys Gln Ile Thr Gly Asp Arg
            275                 280                 285

Pro Val Ile Lys Ile Asn Asn Thr Leu Trp Glu Ser Asn Thr Ala Ala
290                 295                 300

Ala Phe Leu Asn Arg Lys Ser Gln Ser Leu Tyr Thr Thr Gly Glu
305                 310                 315

<210> SEQ ID NO 40
<211> LENGTH: 299
<212> TYPE: PRT
<213> ORGANISM: Saponaria officinalis

<400> SEQUENCE: 40

Met Lys Ser Trp Ile Met Leu Val Val Thr Trp Leu Ile Ile Leu Gln
  1               5                  10                  15

Thr Thr Val Thr Ala Val Ile Ile Tyr Glu Leu Asn Leu Gln Gly Thr
                 20                  25                  30

Thr Lys Ala Gln Tyr Ser Thr Phe Leu Lys Gln Leu Arg Asp Asp Ile
             35                  40                  45

Lys Asp Pro Asn Leu His Tyr Gly Gly Thr Asn Leu Pro Val Ile Lys
 50                  55                  60

Arg Pro Val Gly Pro Pro Lys Phe Leu Arg Val Asn Leu Lys Ala Ser
 65                  70                  75                  80

Thr Gly Thr Val Ser Leu Ala Val Gln Arg Ser Asn Leu Tyr Val Ala
                 85                  90                  95
```

```
Ala Tyr Leu Ala Lys Asn Asn Asn Lys Gln Phe Arg Ala Tyr Tyr Phe
                100                 105                 110

Lys Gly Phe Gln Ile Thr Thr Asn Gln Leu Asn Asn Leu Phe Pro Glu
            115                 120                 125

Ala Thr Gly Val Ser Asn Gln Gln Glu Leu Gly Tyr Gly Glu Ser Tyr
        130                 135                 140

Pro Gln Ile Gln Asn Ala Ala Gly Val Thr Arg Gln Gln Ala Gly Leu
145                 150                 155                 160

Gly Ile Lys Lys Leu Ala Glu Ser Met Thr Lys Val Asn Gly Val Ala
                165                 170                 175

Arg Val Glu Lys Asp Glu Ala Leu Phe Leu Ile Val Val Gln Met
                180                 185                 190

Val Gly Glu Ala Ala Arg Phe Lys Tyr Ile Glu Asn Leu Val Leu Asn
            195                 200                 205

Asn Phe Asp Thr Ala Lys Glu Val Glu Pro Val Pro Asp Arg Val Ile
        210                 215                 220

Ile Leu Glu Asn Asn Trp Gly Leu Leu Ser Arg Ala Ala Lys Thr Ala
225                 230                 235                 240

Asn Asn Gly Val Phe Gln Thr Pro Leu Val Leu Thr Ser Tyr Ala Val
                245                 250                 255

Pro Gly Val Glu Trp Arg Val Thr Thr Val Ala Glu Val Glu Ile Gly
            260                 265                 270

Ile Phe Leu Asn Val Asp Asn Asn Gly Leu Pro Ser Ile Ile Tyr Asn
        275                 280                 285

Asn Ile Ile Ser Gly Ala Phe Gly Asp Thr Tyr
290                 295

<210> SEQ ID NO 41
<211> LENGTH: 565
<212> TYPE: PRT
<213> ORGANISM: Saponaria officinalis

<400> SEQUENCE: 41

Met Tyr Ala Val Ala Thr Trp Leu Cys Phe Gly Ser Thr Ser Gly Trp
1               5                   10                  15

Ser Phe Thr Leu Glu Asp Asn Asn Ile Phe Pro Lys Gln Tyr Pro Ile
            20                  25                  30

Ile Asn Phe Thr Thr Ala Gly Ala Thr Val Gln Ser Tyr Thr Asn Phe
        35                  40                  45

Ile Arg Ala Val Arg Gly Arg Leu Thr Thr Gly Ala Asp Val Arg His
    50                  55                  60

Asp Ile Pro Val Leu Pro Asn Arg Val Gly Leu Pro Ile Asn Gln Arg
65                  70                  75                  80

Phe Ile Leu Val Glu Leu Ser Asn His Ala Glu Leu Ser Val Thr Leu
                85                  90                  95

Ala Leu Asp Val Thr Asn Ala Tyr Val Val Gly Tyr Arg Ala Gly Asn
            100                 105                 110

Ser Ala Tyr Phe Phe His Pro Asp Asn Gln Glu Asp Ala Glu Ala Ile
        115                 120                 125

Thr His Leu Phe Thr Asp Val Gln Asn Arg Tyr Thr Phe Ala Phe Gly
    130                 135                 140

Gly Asn Tyr Asp Arg Leu Glu Gln Leu Ala Gly Asn Leu Arg Glu Asn
145                 150                 155                 160

Ile Glu Leu Gly Asn Gly Pro Leu Glu Glu Ala Ile Ser Ala Leu Tyr
                165                 170                 175
```

```
Tyr Tyr Ser Thr Gly Thr Gln Leu Pro Thr Leu Ala Arg Ser Phe
            180                 185                 190

Ile Ile Cys Ile Gln Met Ile Ser Glu Ala Ala Arg Phe Gln Tyr Ile
        195                 200                 205

Glu Gly Glu Met Arg Thr Arg Ile Arg Tyr Asn Arg Arg Ser Ala Pro
    210                 215                 220

Asp Pro Ser Val Ile Thr Leu Glu Asn Ser Trp Gly Arg Leu Ser Thr
225                 230                 235                 240

Ala Ile Gln Glu Ser Asn Gln Gly Ala Phe Ala Ser Pro Ile Gln Leu
                245                 250                 255

Gln Arg Arg Asn Gly Ser Lys Phe Ser Val Tyr Asp Val Ser Ile Leu
            260                 265                 270

Ile Pro Ile Ile Ala Leu Met Val Tyr Arg Cys Ala Pro Pro Pro Ser
        275                 280                 285

Ser Gln Phe Ser Leu Leu Ile Arg Pro Val Val Pro Asn Phe Asn Ala
    290                 295                 300

Asp Val Cys Met Asp Pro Glu Pro Ile Val Arg Ile Val Gly Arg Asn
305                 310                 315                 320

Gly Leu Cys Val Asp Val Arg Asp Gly Arg Phe His Asn Gly Asn Ala
                325                 330                 335

Ile Gln Leu Trp Pro Cys Lys Ser Asn Thr Asp Ala Asn Gln Leu Trp
            340                 345                 350

Thr Leu Lys Arg Asp Asn Thr Ile Arg Ser Asn Gly Lys Cys Leu Thr
        355                 360                 365

Thr Tyr Gly Tyr Ser Pro Gly Val Tyr Val Met Ile Tyr Asp Cys Asn
    370                 375                 380

Thr Ala Ala Thr Asp Ala Thr Arg Trp Gln Ile Trp Asp Asn Gly Thr
385                 390                 395                 400

Ile Ile Asn Pro Arg Ser Ser Leu Val Leu Ala Ala Thr Ser Gly Asn
                405                 410                 415

Ser Gly Thr Thr Leu Thr Val Gln Thr Asn Ile Tyr Ala Val Ser Gln
            420                 425                 430

Gly Trp Leu Pro Thr Asn Asn Thr Gln Pro Phe Val Thr Thr Ile Val
        435                 440                 445

Gly Leu Tyr Gly Leu Cys Leu Gln Ala Asn Ser Gly Gln Val Trp Ile
    450                 455                 460

Glu Asp Cys Ser Ser Glu Lys Ala Glu Gln Gln Trp Ala Leu Tyr Ala
465                 470                 475                 480

Asp Gly Ser Ile Arg Pro Gln Gln Asn Arg Asp Asn Cys Leu Thr Ser
                485                 490                 495

Asp Ser Asn Ile Arg Glu Thr Val Val Lys Ile Leu Ser Cys Gly Pro
            500                 505                 510

Ala Ser Ser Gly Gln Arg Trp Met Phe Lys Asn Asp Gly Thr Ile Leu
        515                 520                 525

Asn Leu Tyr Ser Gly Leu Val Leu Asp Val Arg Arg Ser Asp Pro Ser
    530                 535                 540

Leu Lys Gln Ile Ile Leu Tyr Pro Leu His Gly Asp Pro Asn Gln Ile
545                 550                 555                 560

Trp Leu Pro Leu Phe
                565

<210> SEQ ID NO 42
<211> LENGTH: 730
```

<212> TYPE: PRT
<213> ORGANISM: Galerina marginata

<400> SEQUENCE: 42

```
Met Ser Ser Val Thr Trp Ala Pro Gly Asn Tyr Pro Ser Thr Arg Arg
1               5                   10                  15

Ser Asp His Val Asp Thr Tyr Gln Ser Ala Ser Lys Gly Glu Val Pro
            20                  25                  30

Val Pro Asp Pro Tyr Gln Trp Leu Glu Glu Ser Thr Asp Glu Val Asp
        35                  40                  45

Lys Trp Thr Thr Ala Gln Ala Asp Leu Ala Gln Ser Tyr Leu Asp Gln
    50                  55                  60

Asn Ala Asp Ile Gln Lys Leu Ala Glu Lys Phe Arg Ala Ser Arg Asn
65                  70                  75                  80

Tyr Ala Lys Phe Ser Ala Pro Thr Leu Leu Asp Asp Gly His Trp Tyr
                85                  90                  95

Trp Phe Tyr Asn Arg Gly Leu Gln Ser Gln Ser Val Leu Tyr Arg Ser
            100                 105                 110

Lys Glu Pro Ala Leu Pro Asp Phe Ser Lys Gly Asp Asn Val Gly
        115                 120                 125

Asp Val Phe Asp Pro Asn Val Leu Ala Ala Asp Gly Ser Ala Gly
    130                 135                 140

Met Val Leu Cys Lys Phe Ser Pro Asp Gly Lys Phe Phe Ala Tyr Ala
145                 150                 155                 160

Val Ser His Leu Gly Gly Asp Tyr Ser Thr Ile Tyr Val Arg Ser Thr
                165                 170                 175

Ser Ser Pro Leu Ser Gln Ala Ser Val Ala Gln Gly Val Asp Gly Arg
            180                 185                 190

Leu Ser Asp Glu Val Lys Trp Phe Lys Phe Ser Thr Ile Ile Trp Thr
        195                 200                 205

Lys Asp Ser Lys Gly Phe Leu Tyr Gln Arg Tyr Pro Ala Arg Glu Arg
    210                 215                 220

His Glu Gly Thr Arg Ser Asp Arg Asn Ala Met Met Cys Tyr His Lys
225                 230                 235                 240

Val Gly Thr Thr Gln Glu Asp Ile Ile Val Tyr Gln Asp Asn Glu
                245                 250                 255

His Pro Glu Trp Ile Tyr Gly Ala Asp Thr Ser Glu Asp Gly Lys Tyr
            260                 265                 270

Leu Tyr Leu Tyr Gln Phe Lys Asp Thr Ser Lys Lys Asn Leu Leu Trp
        275                 280                 285

Val Ala Glu Leu Asp Glu Asp Gly Val Lys Ser Gly Ile His Trp Arg
    290                 295                 300

Lys Val Val Asn Glu Tyr Ala Ala Asp Tyr Asn Ile Ile Thr Asn His
305                 310                 315                 320

Gly Ser Leu Val Tyr Ile Lys Thr Asn Leu Asn Ala Pro Gln Tyr Lys
                325                 330                 335

Val Ile Thr Ile Asp Leu Ser Lys Asp Glu Pro Glu Ile Arg Asp Phe
            340                 345                 350

Ile Pro Glu Glu Lys Asp Ala Lys Leu Ala Gln Val Asn Cys Ala Asn
        355                 360                 365

Glu Glu Tyr Phe Val Ala Ile Tyr Lys Arg Asn Val Lys Asp Glu Ile
    370                 375                 380

Tyr Leu Tyr Ser Lys Ala Gly Val Gln Leu Thr Arg Leu Ala Pro Asp
385                 390                 395                 400
```

```
Phe Val Gly Ala Ala Ser Ile Ala Asn Arg Gln Lys Gln Thr His Phe
                405                 410                 415
Phe Leu Thr Leu Ser Gly Phe Asn Thr Pro Gly Thr Ile Ala Arg Tyr
            420                 425                 430
Asp Phe Thr Ala Pro Glu Thr Gln Arg Phe Ser Ile Leu Arg Thr Thr
        435                 440                 445
Lys Val Asn Glu Leu Asp Pro Asp Phe Glu Ser Thr Gln Val Trp
    450                 455                 460
Tyr Glu Ser Lys Asp Gly Thr Lys Ile Pro Met Phe Ile Val Arg His
465                 470                 475                 480
Lys Ser Thr Lys Phe Asp Gly Thr Ala Ala Ile Gln Tyr Gly Tyr
                485                 490                 495
Gly Gly Phe Ala Thr Ser Ala Asp Pro Phe Ser Pro Ile Ile Leu
            500                 505                 510
Thr Phe Leu Gln Thr Tyr Gly Ala Ile Phe Ala Val Pro Ser Ile Arg
        515                 520                 525
Gly Gly Gly Glu Phe Gly Glu Glu Trp His Lys Gly Arg Arg Glu
    530                 535                 540
Thr Lys Val Asn Thr Phe Asp Asp Phe Ile Ala Ala Gln Phe Leu
545                 550                 555                 560
Val Lys Asn Lys Tyr Ala Ala Pro Gly Lys Val Ala Ile Asn Gly Ala
                565                 570                 575
Ser Asn Gly Gly Leu Leu Val Met Gly Ser Ile Val Arg Ala Pro Glu
            580                 585                 590
Gly Thr Phe Gly Ala Ala Val Pro Glu Gly Gly Val Ala Asp Leu Leu
        595                 600                 605
Lys Phe His Lys Phe Thr Gly Gly Gln Ala Trp Ile Ser Glu Tyr Gly
    610                 615                 620
Asn Pro Ser Ile Pro Glu Glu Phe Asp Tyr Ile Tyr Pro Leu Ser Pro
625                 630                 635                 640
Val His Asn Val Arg Thr Asp Lys Val Met Pro Ala Thr Leu Ile Thr
                645                 650                 655
Val Asn Ile Gly Asp Gly Arg Val Val Pro Met His Ser Phe Lys Phe
            660                 665                 670
Ile Ala Thr Leu Gln His Asn Val Pro Gln Asn Pro His Pro Leu Leu
        675                 680                 685
Ile Lys Ile Asp Lys Ser Trp Leu Gly His Gly Met Gly Lys Pro Thr
    690                 695                 700
Asp Lys Asn Val Lys Asp Ala Ala Asp Lys Trp Gly Phe Ile Ala Arg
705                 710                 715                 720
Ala Leu Gly Leu Glu Leu Lys Thr Val Glu
                725                 730

<210> SEQ ID NO 43
<211> LENGTH: 730
<212> TYPE: PRT
<213> ORGANISM: Amanita bisporigera

<400> SEQUENCE: 43

Met Pro Pro Thr Pro Trp Ala Pro His Ser Tyr Pro Thr Arg Arg
1               5                   10                  15
Ser Asp His Val Asp Val Tyr Gln Ser Ala Ser Arg Gly Glu Val Pro
                20                  25                  30
Val Pro Asp Pro Tyr Gln Trp Leu Glu Glu Asn Ser Asn Glu Val Asp
```

-continued

```
                35                  40                  45
Glu Trp Thr Thr Ala Gln Thr Ala Phe Thr Gln Gly Tyr Leu Asp Lys
 50                  55                  60

Asn Ala Asp Arg Gln Lys Leu Glu Glu Lys Phe Arg Ala Ser Lys Asp
 65                  70                  75                  80

Tyr Val Lys Phe Ser Ala Pro Thr Leu Leu Asp Ser Gly His Trp Tyr
                 85                  90                  95

Trp Phe Tyr Asn Ser Gly Val Gln Ser Gln Ala Val Leu Tyr Arg Ser
                100                 105                 110

Lys Lys Pro Val Leu Pro Asp Phe Gln Arg Gly Thr Arg Lys Val Gly
            115                 120                 125

Glu Val Tyr Phe Asp Pro Asn Val Leu Ser Ala Asp Gly Thr Ala Ile
            130                 135                 140

Met Gly Thr Cys Arg Phe Ser Pro Ser Gly Glu Tyr Phe Ala Tyr Ala
145                 150                 155                 160

Val Ser His Leu Gly Val Asp Tyr Phe Thr Ile Tyr Val Arg Pro Thr
                165                 170                 175

Ser Ser Ser Leu Ser Gln Ala Pro Glu Ala Glu Gly Gly Asp Gly Arg
            180                 185                 190

Leu Ser Asp Gly Val Lys Trp Cys Lys Phe Thr Thr Ile Thr Trp Thr
            195                 200                 205

Lys Asp Ser Lys Gly Phe Leu Tyr Gln Arg Tyr Pro Ala Arg Glu Ser
210                 215                 220

Leu Val Ala Lys Asp Arg Asp Lys Asp Ala Met Val Cys Tyr His Arg
225                 230                 235                 240

Val Gly Thr Thr Gln Leu Glu Asp Ile Ile Val Gln Asp Lys Glu
                245                 250                 255

Asn Pro Asp Trp Thr Tyr Gly Thr Asp Ala Ser Glu Asp Gly Lys Tyr
            260                 265                 270

Ile Tyr Leu Val Val Tyr Lys Asp Ala Ser Lys Gln Asn Leu Leu Trp
            275                 280                 285

Val Ala Glu Phe Asp Lys Asp Gly Val Lys Pro Glu Ile Pro Trp Arg
290                 295                 300

Lys Val Ile Asn Glu Phe Gly Ala Asp Tyr His Val Ile Thr Asn His
305                 310                 315                 320

Gly Ser Leu Ile Tyr Val Lys Thr Asn Val Asn Ala Pro Gln Tyr Lys
                325                 330                 335

Val Val Thr Ile Asp Leu Ser Thr Gly Glu Pro Glu Ile Arg Asp Phe
            340                 345                 350

Ile Pro Glu Gln Lys Asp Ala Lys Leu Thr Gln Val Lys Cys Val Asn
            355                 360                 365

Lys Gly Tyr Phe Val Ala Ile Tyr Lys Arg Asn Val Lys Asp Glu Ile
            370                 375                 380

Tyr Leu Tyr Ser Lys Ala Gly Asp Gln Leu Ser Arg Leu Ala Ser Asp
385                 390                 395                 400

Phe Ile Gly Val Ala Ser Ile Thr Asn Arg Glu Lys Gln Pro His Ser
                405                 410                 415

Phe Leu Thr Phe Ser Gly Phe Asn Thr Pro Gly Thr Ile Ser Arg Tyr
            420                 425                 430

Asp Phe Thr Ala Pro Asp Thr Gln Arg Leu Ser Ile Leu Arg Thr Thr
            435                 440                 445

Lys Leu Asn Gly Leu Asn Ala Asp Asp Phe Glu Ser Thr Gln Val Trp
450                 455                 460
```

```
Tyr Lys Ser Lys Asp Gly Thr Lys Val Pro Met Phe Ile Val Arg His
465                 470                 475                 480

Lys Ser Thr Lys Phe Asp Gly Thr Ala Pro Ala Ile Gln Asn Gly Tyr
                485                 490                 495

Gly Gly Phe Ala Ile Thr Ala Asp Pro Phe Phe Ser Pro Ile Met Leu
            500                 505                 510

Thr Phe Met Gln Thr Tyr Gly Ala Ile Leu Ala Val Pro Asn Ile Arg
        515                 520                 525

Gly Gly Gly Glu Phe Gly Gly Glu Trp His Lys Ala Gly Arg Arg Glu
    530                 535                 540

Thr Lys Gly Asn Thr Phe Asp Asp Phe Ile Ala Ala Gln Phe Leu
545                 550                 555                 560

Val Lys Asn Lys Tyr Ala Ala Pro Gly Lys Val Ala Ile Thr Gly Ala
                565                 570                 575

Ser Asn Gly Gly Phe Leu Val Cys Gly Ser Val Val Arg Ala Pro Glu
            580                 585                 590

Gly Thr Phe Gly Ala Ala Val Ser Glu Gly Gly Val Ala Asp Leu Leu
        595                 600                 605

Lys Phe Asn Lys Phe Thr Gly Gly Met Ala Trp Thr Ser Glu Tyr Gly
    610                 615                 620

Asn Pro Phe Ile Lys Glu Asp Phe Asp Phe Val Gln Ala Leu Ser Pro
625                 630                 635                 640

Val His Asn Val Pro Lys Asp Arg Val Leu Pro Ala Thr Leu Leu Met
                645                 650                 655

Thr Asn Ala Gly Asp Asp Arg Val Val Pro Met His Ser Leu Lys Phe
            660                 665                 670

Val Ala Asn Leu Gln Tyr Asn Val Pro Gln Asn Pro His Pro Leu Leu
        675                 680                 685

Ile Arg Val Asp Lys Ser Trp Leu Gly His Gly Phe Gly Lys Thr Thr
    690                 695                 700

Asp Lys His Thr Lys Asp Ala Ala Asp Lys Trp Ser Phe Val Ala Gln
705                 710                 715                 720

Ser Leu Gly Leu Glu Trp Lys Thr Val Asp
                725                 730

<210> SEQ ID NO 44
<211> LENGTH: 734
<212> TYPE: PRT
<213> ORGANISM: Hypsizygus marmoreus

<400> SEQUENCE: 44

Met Ala Ile Ser Pro Thr Pro Trp Thr Pro Asn Thr Tyr Pro Pro Thr
1               5                   10                  15

Arg Arg Ser Ser His Val Asp Ile Tyr Lys Ser Ala Thr Arg Gly Glu
                20                  25                  30

Val Arg Val Ala Asp Pro Tyr Gln Trp Leu Glu Glu Asn Thr Glu Glu
            35                  40                  45

Thr Asp Lys Trp Thr Thr Ala Gln Glu Glu Phe Thr Arg Ser Tyr Leu
        50                  55                  60

Asp Lys Asn Thr Asp Arg Gln Arg Leu Glu Asp Ala Phe Arg Thr Ser
65                  70                  75                  80

Thr Asp Tyr Ala Lys Phe Ser Ser Pro Thr Leu Tyr Glu Asp Gly Arg
                85                  90                  95

Trp Tyr Trp Phe Tyr Asn Ser Gly Leu Gln Pro Gln Pro Leu Ile Tyr
```

```
            100                 105                 110
Arg Ser Lys Gly Lys Thr Leu Pro Asp Phe Ser Gln Asp Asp Asn Val
        115                 120                 125

Val Gly Glu Val Phe Phe Asp Pro Asn Leu Leu Ser Asp Asp Gly Thr
    130                 135                 140

Ala Ala Leu Ser Ile Tyr Asp Phe Ser Asp Cys Gly Lys Tyr Phe Ala
145                 150                 155                 160

Tyr Gly Ile Ser Phe Ser Gly Ser Asp Phe Ser Thr Ile Tyr Val Arg
                165                 170                 175

Ser Thr Glu Ser Pro Leu Ala Lys Lys Asn Ser Gly Ser Thr Asp Asp
            180                 185                 190

Asp Arg Leu Ser Asp Glu Ile Lys His Val Lys Phe Ser Ala Val Thr
        195                 200                 205

Trp Thr Lys Asp Ser Lys Gly Phe Phe Tyr Gln Arg Tyr Pro Ala His
    210                 215                 220

Glu Asn Ala Lys Glu Gly Ile Glu Thr Gly Gly Asp Val Asp Ala Met
225                 230                 235                 240

Ile Tyr Tyr His Val Ile Gly Thr Ser Gln Ser Glu Asp Ile Leu Val
                245                 250                 255

His Ser Asp Lys Ser Asn Pro Glu Trp Met Trp Ser Ile Asp Ile Thr
            260                 265                 270

Glu Asp Gly Lys Tyr Leu Ile Leu Tyr Thr Met Lys Asp Ser Ser Arg
        275                 280                 285

Lys Asn Leu Met Trp Ile Ala Glu Leu Ser Lys Asn Glu Ile Gly Pro
    290                 295                 300

Asn Ile Gln Trp Asn Lys Ile Ile Asp Val Phe Asp Ala Glu Tyr His
305                 310                 315                 320

Leu Ile Thr Asn Asp Gly Pro Ile Leu Tyr Val Lys Thr Asn Ala Asp
                325                 330                 335

Ala Pro Gln Tyr Lys Leu Val Thr Met Asp Ile Ser Gly Asp Lys Asp
            340                 345                 350

Ile Ser Arg Asp Leu Ile Pro Glu Asp Lys Asn Ala Asn Leu Val Gln
        355                 360                 365

Val Asp Cys Val Asn Arg Asp Thr Phe Ala Val Ile Tyr Lys Arg Asn
    370                 375                 380

Val Lys Asp Glu Ile Tyr Leu Tyr Ser Lys Thr Gly Ile Gln Leu Ser
385                 390                 395                 400

Arg Leu Ala Ser Asp Phe Val Gly Ala Ala Ser Ile Ser Ser Arg Glu
                405                 410                 415

Lys Gln Pro His Phe Phe Val Thr Met Thr Gly Phe Ser Thr Pro Gly
            420                 425                 430

Thr Val Ala Arg Tyr Asp Phe Gly Ala Pro Glu Glu Gln Arg Trp Ser
        435                 440                 445

Ile Tyr Arg Ser Val Lys Val Asn Gly Leu Asn Pro Asp Asp Phe Glu
    450                 455                 460

Ser Lys Gln Val Trp Tyr Glu Ser Lys Asp Gly Thr Lys Ile Pro Met
465                 470                 475                 480

Phe Ile Val Arg His Lys Ala Thr Lys Phe Asp Gly Thr Ala Pro Ala
                485                 490                 495

Ile Gln Tyr Gly Tyr Gly Gly Phe Ser Ile Ser Ile Asn Pro Phe Phe
            500                 505                 510

Ser Pro Thr Ile Leu Thr Phe Leu Gln Thr Tyr Gly Ala Val Leu Ala
        515                 520                 525
```

-continued

```
Val Pro Asn Ile Arg Gly Gly Ala Glu Phe Gly Asp Trp His Lys
            530                 535                 540
Ala Gly Thr Arg Glu Lys Lys Gly Asn Val Phe Asp Asp Phe Val Ala
545                 550                 555                 560
Ala Thr Gln Tyr Leu Val Lys Asn Lys Tyr Ala Gly Glu Gly Lys Val
                565                 570                 575
Ala Ile Asn Gly Gly Ser Asn Gly Gly Leu Leu Val Gly Ala Cys Ile
            580                 585                 590
Asn Arg Ala Pro Glu Gly Thr Phe Gly Ala Ala Val Ala Glu Val Gly
        595                 600                 605
Val Met Asp Leu Leu Lys Phe Ser Lys Phe Thr Ile Gly Lys Ala Trp
    610                 615                 620
Thr Ser Asp Tyr Gly Asp Pro Asp Pro Lys Asp Phe Asp Phe Ile
625                 630                 635                 640
Cys Pro Leu Ser Pro Leu His Asn Ile Pro Thr Asp Arg Val Leu Pro
                645                 650                 655
Pro Thr Met Leu Leu Thr Ala Asp His Asp Asp Arg Val Val Pro Met
            660                 665                 670
His Ser Phe Lys His Ala Ala Thr Leu Gln Tyr Thr Leu Pro His Asn
        675                 680                 685
Pro His Pro Leu Val Ile Arg Ile Asp Lys Lys Ala Gly His Gly Ala
    690                 695                 700
Gly Lys Ser Thr Glu Lys Arg Ile Lys Glu Ser Ala Asp Lys Trp Gly
705                 710                 715                 720
Phe Val Ala Gln Ser Leu Gly Leu Val Trp Gln Glu Pro Ala
                725                 730
```

<210> SEQ ID NO 45
<211> LENGTH: 733
<212> TYPE: PRT
<213> ORGANISM: Conocybe apala

<400> SEQUENCE: 45

```
Met Pro Pro Ser Thr Pro Asn Glu Tyr Pro Pro Thr Arg Arg Ser Asp
1               5                   10                  15
Asp Val Leu Thr Tyr Arg Ser Glu Lys Asn Gly Glu Val Val Val Pro
            20                  25                  30
Asp Pro Tyr Gln Trp Leu Glu His Asn Thr Glu Thr Asp Lys Trp
        35                  40                  45
Thr Thr Ala Gln Ala Ala Phe Thr Arg Ala His Leu Asp Lys Asn Pro
    50                  55                  60
Lys Arg Asn Ala Leu Glu Glu Ala Phe Thr Ala Ala Asn Asp Tyr Ala
65                  70                  75                  80
Lys Phe Ser Ala Pro Gln Leu His Asp Asp Gly Arg Trp Tyr Trp Tyr
                85                  90                  95
Tyr Asn Thr Gly Leu Gln Ala Gly Thr Cys Leu Trp Arg Thr Arg Asp
            100                 105                 110
Asp Thr Ile Pro Asp Phe Ser Lys Gln Leu Asp Glu Asp Val Gly Glu
        115                 120                 125
Ile Phe Phe Asp Pro Asn Ala Leu Ser Lys Asp Gly Thr Ala Ala Leu
    130                 135                 140
Ser Thr Tyr Arg Phe Ser Arg Asp Gly Lys Tyr Phe Ala Tyr Ala Ile
145                 150                 155                 160
Ala Gln Ser Gly Ser Asp Phe Asn Thr Ile Tyr Val Arg Pro Thr Asp
```

```
            165                 170                 175
Ser Pro Leu Thr Lys Arg Asp Glu Ser Gly Arg Asp Pro Ser Arg Leu
            180                 185                 190

Ala Asp Glu Val Lys Phe Val Lys Phe Ser Gly Ile Thr Trp Ala Pro
            195                 200                 205

Asn Ser Glu Gly Phe Phe Tyr Gln Arg Tyr Pro His Ile Asp Gly Ala
            210                 215                 220

Thr Leu Glu Glu Gly Gly Ile Ala Thr Arg Arg Asp Leu His Ala Met
225                 230                 235                 240

Val Tyr Tyr His Arg Val Gly Thr Pro Gln Ser Glu Asp Ile Leu Ile
            245                 250                 255

His Arg Asp Pro Ala Asn Pro Glu Trp Met Phe Gly Val Asn Val Thr
            260                 265                 270

Asp Asn Gly Glu Tyr Ile Glu Leu Tyr Ile Ser Lys Asp Ser Ser Arg
            275                 280                 285

Lys Asn Met Leu Trp Val Ala Asn Phe Ala Met Asn Lys Ile Gly Glu
            290                 295                 300

Gln Phe Gln Trp Arg Lys Val Ile Asn Asp Phe Ala Ala Glu Tyr Asp
305                 310                 315                 320

Val Ile Thr Asn His Gly Pro Val Tyr Tyr Phe Arg Thr Asp Asp Gly
            325                 330                 335

Ala Pro Lys His Lys Ile Leu Ser Ile Asn Ile Asp Thr Asn Glu Arg
            340                 345                 350

Lys Leu Leu Val Pro Glu Ser Glu Asp Ala Ala Leu Phe Ser Thr Val
            355                 360                 365

Cys Val Asn Lys Asn Tyr Met Ala Leu Ile Tyr Lys Arg Asn Val Lys
            370                 375                 380

Asp Glu Val His Leu Tyr Thr Leu Glu Gly Lys Pro Val Arg Arg Leu
385                 390                 395                 400

Ala Glu Asp Phe Val Gly Ala Cys Thr Ile Ser Gly Lys Glu Lys Gln
            405                 410                 415

Pro Trp Phe Phe Val Thr Met Ser Gly Phe Thr Ser Pro Ser Thr Val
            420                 425                 430

Gly Arg Tyr Asn Phe Gln Ile Pro Glu Glu Asn Arg Trp Ser Ile
            435                 440                 445

Phe Arg Ala Ala Lys Ile Lys Asn Leu Asn Pro Asn Asp Phe Glu Ala
            450                 455                 460

Ser Gln Val Trp Tyr Lys Ser Lys Asp Gly Thr Asn Val Pro Met Phe
465                 470                 475                 480

Ile Val Arg His Lys Ser Thr Gln Phe Asp Gly Thr Ala Pro Ala Leu
            485                 490                 495

Gln Tyr Gly Tyr Gly Gly Phe Ser Ile Ser Ile Asp Pro Phe Phe Ser
            500                 505                 510

Ala Ser Ile Leu Thr Phe Leu Lys Val Tyr Gly Ala Ile Leu Val Val
            515                 520                 525

Pro Ser Ile Arg Gly Gly Asn Glu Phe Gly Glu Glu Trp His Arg Gly
            530                 535                 540

Gly Met Lys Gln Asn Lys Val Asn Cys Phe Asp Asp Phe Ile Ala Ala
545                 550                 555                 560

Thr Asn His Leu Val Glu His Lys Tyr Ala Ala Pro Gly Lys Val Ala
            565                 570                 575

Ile Asn Gly Gly Ser Asn Gly Gly Leu Leu Val Ala Ala Cys Ile Asn
            580                 585                 590
```

-continued

```
Arg Ala Pro Glu Gly Thr Phe Gly Ala Ala Ile Ala Glu Val Gly Val
            595                 600                 605

His Asp Met Leu Lys Phe His Lys Phe Thr Ile Gly Lys Ala Trp Thr
610                 615                 620

Ser Asp Tyr Gly Asn Pro Asp Pro His Asp Phe Asp Tyr Ile Tyr
625                 630                 635                 640

Pro Ile Ser Pro Val His Asn Val Pro Thr Asp Lys Ile Leu Pro Pro
                645                 650                 655

Thr Leu Leu Leu Thr Ala Asp His Asp Asp Arg Val Val Pro Met His
                660                 665                 670

Thr Phe Lys Leu Ala Ala Thr Leu Gln His Thr Leu Pro His Asn Pro
            675                 680                 685

His Pro Leu Leu Leu Arg Val Asp Lys Lys Ala Gly His Gly Ala Gly
        690                 695                 700

Lys Pro Leu Gln Leu Lys Ile Arg Glu Gln Ala Asp Lys Trp Gly Phe
705                 710                 715                 720

Val Ala Gln Ser Phe Gln Leu Val Trp Arg Asp Gly Val
                725                 730
```

<210> SEQ ID NO 46
<211> LENGTH: 730
<212> TYPE: PRT
<213> ORGANISM: Amanita bisporigera

<400> SEQUENCE: 46

```
Met Pro Pro Thr Pro Trp Ala Pro His Ser Tyr Pro Pro Thr Arg Arg
1               5                   10                  15

Ser Asp His Val Asp Val Tyr Gln Ser Ala Ser Arg Gly Glu Val Pro
                20                  25                  30

Val Pro Asp Pro Tyr Gln Trp Leu Glu Glu Asn Ser Asn Glu Val Asp
            35                  40                  45

Glu Trp Thr Thr Ala Gln Thr Ala Phe Thr Gln Gly Tyr Leu Asp Lys
    50                  55                  60

Asn Ala Asp Arg Gln Lys Leu Glu Glu Lys Phe Arg Ala Ser Lys Asp
65                  70                  75                  80

Tyr Val Lys Phe Ser Ala Pro Thr Leu Leu Asp Ser Gly His Trp Tyr
                85                  90                  95

Trp Phe Tyr Asn Ser Gly Val Gln Ser Gln Ala Val Leu Tyr Arg Ser
                100                 105                 110

Lys Lys Pro Val Leu Pro Asp Phe Gln Arg Gly Thr Arg Lys Val Gly
            115                 120                 125

Glu Val Tyr Phe Asp Pro Asn Val Leu Ser Ala Asp Gly Thr Ala Ile
    130                 135                 140

Met Gly Thr Cys Arg Phe Ser Pro Ser Gly Glu Tyr Phe Ala Tyr Ala
145                 150                 155                 160

Val Ser His Leu Gly Val Asp Tyr Phe Thr Ile Tyr Val Arg Pro Thr
                165                 170                 175

Ser Ser Ser Leu Ser Gln Ala Pro Glu Ala Glu Gly Gly Asp Gly Arg
            180                 185                 190

Leu Ser Asp Gly Val Lys Trp Cys Lys Phe Thr Thr Ile Thr Trp Thr
        195                 200                 205

Lys Asp Ser Lys Gly Phe Leu Tyr Gln Arg Tyr Pro Ala Arg Glu Ser
    210                 215                 220

Leu Val Ala Lys Asp Arg Asp Lys Asp Ala Met Val Cys Tyr His Arg
```

```
                225                 230                 235                 240
Val Gly Thr Thr Gln Leu Glu Asp Ile Ile Val Gln Gln Asp Lys Glu
                    245                 250                 255

Asn Pro Asp Trp Thr Tyr Gly Thr Asp Ala Ser Glu Asp Gly Lys Tyr
                    260                 265                 270

Ile Tyr Leu Val Val Tyr Lys Asp Ala Ser Lys Gln Asn Leu Leu Trp
                    275                 280                 285

Val Ala Glu Phe Asp Lys Asp Gly Val Lys Pro Glu Ile Pro Trp Arg
                290                 295                 300

Lys Val Ile Asn Glu Phe Gly Ala Asp Tyr His Val Ile Thr Asn His
305                 310                 315                 320

Gly Ser Leu Ile Tyr Val Lys Thr Asn Val Asn Ala Pro Gln Tyr Lys
                    325                 330                 335

Val Val Thr Ile Asp Leu Ser Thr Gly Glu Pro Glu Ile Arg Asp Phe
                    340                 345                 350

Ile Pro Glu Gln Lys Asp Ala Lys Leu Thr Gln Val Lys Cys Val Asn
                    355                 360                 365

Lys Gly Tyr Phe Val Ala Ile Tyr Lys Arg Asn Val Lys Asp Glu Ile
    370                 375                 380

Tyr Leu Tyr Ser Lys Ala Gly Asp Gln Leu Ser Arg Leu Ala Ser Asp
385                 390                 395                 400

Phe Ile Gly Val Ala Ser Ile Thr Asn Arg Glu Lys Gln Pro His Ser
                    405                 410                 415

Phe Leu Thr Phe Ser Gly Phe Asn Thr Pro Gly Thr Ile Ser Arg Tyr
                    420                 425                 430

Asp Phe Thr Ala Pro Asp Thr Gln Arg Leu Ser Ile Leu Arg Thr Thr
                    435                 440                 445

Lys Leu Asn Gly Leu Asn Ala Asp Asp Phe Glu Ser Thr Gln Val Trp
    450                 455                 460

Tyr Lys Ser Lys Asp Gly Thr Lys Val Pro Met Phe Ile Val Arg His
465                 470                 475                 480

Lys Ser Thr Lys Phe Asp Gly Thr Ala Pro Ala Ile Gln Asn Gly Tyr
                    485                 490                 495

Gly Gly Phe Ala Ile Thr Ala Asp Pro Phe Phe Ser Pro Ile Met Leu
                    500                 505                 510

Thr Phe Met Gln Thr Tyr Gly Ala Ile Leu Ala Val Pro Asn Ile Arg
                    515                 520                 525

Gly Gly Gly Glu Phe Gly Gly Glu Trp His Lys Ala Gly Arg Arg Glu
    530                 535                 540

Thr Lys Gly Asn Thr Phe Asp Asp Phe Ile Ala Ala Ala Gln Phe Leu
545                 550                 555                 560

Val Lys Asn Lys Tyr Ala Ala Pro Gly Lys Val Ala Ile Thr Gly Ala
                    565                 570                 575

Ser Asn Gly Gly Phe Leu Val Cys Gly Ser Val Arg Ala Pro Glu
                580                 585                 590

Gly Thr Phe Gly Ala Ala Val Ser Glu Gly Gly Val Ala Asp Leu Leu
                    595                 600                 605

Lys Phe Asn Lys Phe Thr Gly Gly Met Ala Trp Thr Ser Glu Tyr Gly
    610                 615                 620

Asn Pro Phe Ile Lys Glu Asp Phe Asp Phe Val Gln Ala Leu Ser Pro
625                 630                 635                 640

Val His Asn Val Pro Lys Asp Arg Val Leu Pro Ala Thr Leu Leu Met
                    645                 650                 655
```

```
Thr Asn Ala Gly Asp Asp Arg Val Val Pro Met His Ser Leu Lys Phe
            660                 665                 670
Val Ala Asn Leu Gln Tyr Asn Val Pro Gln Asn Pro His Pro Leu Leu
            675                 680                 685
Ile Arg Val Asp Lys Ser Trp Leu Gly His Gly Phe Gly Lys Thr Thr
            690                 695                 700
Asp Lys His Thr Lys Asp Ala Ala Asp Lys Trp Ser Phe Val Ala Gln
705                 710                 715                 720
Ser Leu Gly Leu Glu Trp Lys Thr Val Asp
            725                 730

<210> SEQ ID NO 47
<211> LENGTH: 738
<212> TYPE: PRT
<213> ORGANISM: Lentinula edodes

<400> SEQUENCE: 47

Met Phe Ser Ala Thr Gln Glu Ser Pro Thr Met Ser Val Pro Gln Trp
1               5                   10                  15
Asp Pro Tyr Pro Pro Val Ser Arg Asp Glu Thr Ser Ala Ile Thr Tyr
            20                  25                  30
Gln Ser Lys Leu Cys Gly Ser Val Thr Val Arg Asp Pro Tyr Ser Ala
        35                  40                  45
Leu Glu Val Pro Phe Asp Asp Ser Glu Thr Lys Ala Phe Val His
    50                  55                  60
Ala Gln Arg Lys Phe Ala Arg Thr Tyr Leu Asp Glu Ile Pro Asp Arg
65                  70                  75                  80
Glu Thr Trp Leu Gln Thr Leu Lys Glu Ser Trp Asn Tyr Arg Arg Phe
                85                  90                  95
Thr Val Pro Lys Arg Glu Ser Asp Gly Tyr Thr Tyr Phe Glu Tyr Asn
            100                 105                 110
Asp Gly Leu Gln Ser Gln Met Ser Leu Arg Arg Val Lys Val Ser Glu
        115                 120                 125
Glu Asp Thr Ile Leu Thr Glu Ser Gly Pro Gly Gly Glu Leu Phe Phe
    130                 135                 140
Asp Pro Asn Leu Leu Ser Leu Asp Gly Asn Ala Ala Leu Thr Gly Ser
145                 150                 155                 160
Met Met Ser Pro Cys Gly Lys Tyr Trp Ala Tyr Gly Val Ser Glu His
                165                 170                 175
Gly Ser Asp Trp Met Thr Thr Tyr Val Arg Lys Thr Ser Pro His
            180                 185                 190
Met Pro Ser Gln Glu Lys Gly Lys Asp Pro Gly Arg Met Asp Asp Val
        195                 200                 205
Ile Arg Tyr Ser Arg Phe Phe Ile Val Tyr Trp Ser Ser Asp Ser Lys
    210                 215                 220
Gly Phe Pro Tyr Ser Arg Tyr Pro Pro Glu Asp Asp Glu Gly Lys Gly
225                 230                 235                 240
Asn Thr Pro Ala Gln Asn Cys Met Val Tyr Tyr His Arg Leu Gly Glu
                245                 250                 255
Lys Gln Glu Lys Asp Thr Leu Val Tyr Glu Asp Pro Glu His Pro Phe
            260                 265                 270
Trp Leu Trp Ala Leu Gln Leu Ser Pro Ser Gly Arg Tyr Ala Leu Leu
        275                 280                 285
Thr Ala Ser Arg Asp Ala Ser His Thr Gln Leu Ala Lys Ile Ala Asp
```

```
              290                 295                 300
Ile Gly Thr Ser Asp Ile Gln Asn Gly Ile Gln Trp Leu Thr Ile His
305                 310                 315                 320

Asp Gln Trp Gln Ala Arg Phe Val Ile Ile Gly Asp Asp Ser Thr
                325                 330                 335

Ile Tyr Phe Met Thr Asn Leu Glu Ala Lys Asn Tyr Leu Val Ala Thr
                340                 345                 350

Leu Asp Ile Arg His Ser Glu Ala Gly Val Lys Thr Leu Val Ala Glu
                355                 360                 365

Asn Pro Asp Ala Leu Leu Ile Ser Ala Ser Ile Leu Ser Thr Asp Lys
370                 375                 380

Leu Val Leu Val Tyr Leu His Asn Ala Arg His Glu Ile His Val His
385                 390                 395                 400

Asp Leu Asn Thr Gly Lys Pro Ile Arg Gln Ile Phe Asp Asn Leu Ile
                405                 410                 415

Gly Gln Phe Ser Leu Ser Gly Arg Arg Asp Asp Asn Asp Met Phe Val
                420                 425                 430

Phe His Ser Gly Phe Thr Ser Pro Gly Thr Ile Tyr Arg Phe Arg Leu
                435                 440                 445

Asn Glu Asp Ser Asn Lys Gly Thr Leu Phe Arg Ala Val Gln Val Pro
450                 455                 460

Gly Leu Asn Leu Ser Asp Phe Thr Thr Glu Ser Val Phe Tyr Pro Ser
465                 470                 475                 480

Lys Asp Gly Thr Pro Ile His Met Phe Ile Thr Arg Leu Lys Asp Thr
                485                 490                 495

Pro Val Asp Gly Thr Ala Pro Val Tyr Ile Tyr Gly Tyr Gly Gly Phe
                500                 505                 510

Ala Leu Ala Met Leu Pro Thr Phe Ser Val Ser Thr Leu Leu Phe Cys
                515                 520                 525

Lys Ile Tyr Arg Ala Met Tyr Val Val Pro Asn Ile Arg Gly Gly Ser
530                 535                 540

Glu Phe Gly Glu Ser Trp His Arg Glu Gly Met Leu Asp Lys Lys Gln
545                 550                 555                 560

Asn Val Phe Asp Asp Phe Asn Ala Ala Thr Lys Trp Leu Val Ala Asn
                565                 570                 575

Lys Tyr Ala Asn Lys Tyr Asn Val Ala Ile Arg Gly Gly Ser Asn Gly
                580                 585                 590

Gly Val Leu Thr Thr Ala Cys Ala Asn Gln Ala Pro Glu Leu Tyr Arg
                595                 600                 605

Cys Val Ile Thr Ile Gly Gly Ile Ile Asp Met Leu Arg Phe Pro Lys
610                 615                 620

Phe Thr Phe Gly Ala Leu Trp Arg Ser Glu Tyr Gly Asp Pro Glu Asp
625                 630                 635                 640

Pro Glu Asp Phe Asp Phe Ile Tyr Lys Tyr Ser Pro Tyr His Asn Ile
                645                 650                 655

Pro Ser Gly Asp Val Val Leu Pro Ala Met Leu Phe Phe Thr Ala Ala
                660                 665                 670

Tyr Asp Asp Arg Val Ser Pro Leu His Ser Phe Lys His Val Ala Ala
                675                 680                 685

Leu Gln Tyr Asn Phe Pro Asn Gly Pro Asn Pro Val Leu Met Arg Ile
                690                 695                 700

Asp Leu Asn Thr Gly His Phe Ala Gly Lys Ser Thr Gln Lys Met Leu
705                 710                 715                 720
```

Glu Glu Thr Ala Asp Glu Tyr Arg Cys Asp Leu Leu Cys Cys Asn Leu
                725                 730                 735

Gln Leu

<210> SEQ ID NO 48
<211> LENGTH: 723
<212> TYPE: PRT
<213> ORGANISM: Omphalotacae olearis

<400> SEQUENCE: 48

Met Ser Phe Pro Gly Trp Gly Pro Tyr Pro Val Glu Arg Asp Glu
1               5                   10                  15

Thr Ser Ala Ile Thr Tyr Ser Ser Lys Leu His Gly Ser Val Thr Val
                20                  25                  30

Arg Asp Pro Tyr Ser Gln Leu Glu Val Pro Phe Glu Asp Ser Glu Glu
            35                  40                  45

Thr Lys Ala Phe Val His Ser Gln Arg Lys Phe Ala Arg Thr Tyr Leu
        50                  55                  60

Asp Glu Asn Pro Asp Arg Glu Ala Trp Leu Glu Thr Leu Lys Lys Ser
65                  70                  75                  80

Trp Asn Tyr Arg Arg Phe Ser Ala Leu Lys Pro Glu Ser Asp Gly His
                85                  90                  95

Tyr Tyr Phe Glu Tyr Asn Asp Gly Leu Gln Ser Gln Leu Ser Leu Tyr
            100                 105                 110

Arg Val Arg Met Gly Glu Glu Asp Thr Val Leu Thr Glu Ser Gly Pro
        115                 120                 125

Gly Gly Glu Leu Phe Phe Asn Pro Asn Leu Leu Ser Leu Asp Gly Asn
130                 135                 140

Ala Ala Leu Thr Gly Phe Val Met Ser Pro Cys Gly Asn Tyr Trp Ala
145                 150                 155                 160

Tyr Gly Val Ser Glu His Gly Ser Asp Trp Met Ser Ile Tyr Val Arg
                165                 170                 175

Lys Thr Ser Ser Pro His Leu Pro Ser Gln Glu Arg Gly Lys Asp Pro
            180                 185                 190

Gly Arg Met Asn Asp Lys Ile Arg His Val Arg Phe Phe Ile Val Ser
        195                 200                 205

Trp Thr Ser Asp Ser Lys Gly Phe Phe Tyr Ser Arg Tyr Pro Pro Glu
        210                 215                 220

Asp Asp Glu Gly Lys Gly Asn Ala Pro Ala Met Asn Cys Met Val Tyr
225                 230                 235                 240

Tyr His Arg Ile Gly Glu Asp Gln Glu Ser Asp Val Leu Val His Glu
                245                 250                 255

Asp Pro Glu His Pro Phe Trp Ile Ser Ser Val Gln Leu Thr Pro Ser
            260                 265                 270

Gly Arg Tyr Ile Leu Phe Ala Ala Ser Arg Asp Ala Ser His Thr Gln
        275                 280                 285

Leu Val Lys Ile Ala Asp Leu His Glu Asn Asp Ile Gly Thr Asn Met
        290                 295                 300

Lys Trp Lys Asn Leu His Asp Pro Trp Glu Ala Arg Phe Thr Ile Val
305                 310                 315                 320

Gly Asp Glu Gly Ser Lys Ile Tyr Phe Met Thr Asn Leu Lys Ala Lys
                325                 330                 335

Asn Tyr Lys Val Ala Thr Phe Asp Ala Asn His Pro Asp Glu Gly Leu
            340                 345                 350

Thr Thr Leu Ile Ala Glu Asp Pro Asn Ala Phe Leu Val Ser Ala Ser
        355                 360                 365

Ile His Ala Gln Asp Lys Leu Leu Val Tyr Leu Arg Asn Ala Ser
370                 375                 380

His Glu Ile His Ile Arg Asp Leu Thr Thr Gly Lys Pro Leu Gly Arg
385                 390                 395                 400

Ile Phe Glu Asp Leu Leu Gly Gln Phe Met Val Ser Gly Arg Arg Gln
                405                 410                 415

Asp Asn Asp Ile Phe Val Leu Phe Ser Ser Phe Leu Ser Pro Gly Thr
            420                 425                 430

Val Tyr Arg Tyr Thr Phe Gly Glu Glu Lys Gly His Ser Ser Leu Phe
        435                 440                 445

Arg Ala Ile Ser Ile Pro Gly Leu Asn Leu Asp Asp Phe Met Thr Glu
    450                 455                 460

Ser Val Phe Tyr Pro Ser Lys Asp Gly Thr Ser Val His Met Phe Ile
465                 470                 475                 480

Thr Arg Pro Lys Asp Val Leu Leu Asp Gly Thr Ser Pro Val Leu Gln
                485                 490                 495

Tyr Gly Tyr Gly Gly Phe Ser Leu Ala Met Leu Pro Thr Phe Ser Leu
            500                 505                 510

Ser Thr Leu Leu Phe Cys Lys Ile Tyr Arg Ala Ile Tyr Ala Ile Pro
        515                 520                 525

Asn Ile Arg Gly Gly Ser Glu Tyr Gly Glu Ser Trp His Arg Glu Gly
    530                 535                 540

Met Leu Asp Lys Lys Gln Asn Val Phe Asp Phe Asn Ala Ala Thr
545                 550                 555                 560

Glu Trp Leu Ile Ala Asn Lys Tyr Ala Ser Lys Asp Arg Ile Ala Ile
                565                 570                 575

Arg Gly Gly Ser Asn Gly Gly Val Leu Thr Thr Ala Cys Ala Asn Gln
            580                 585                 590

Ala Pro Gly Leu Tyr Arg Cys Val Ile Thr Ile Glu Gly Ile Ile Asp
        595                 600                 605

Met Leu Arg Phe Pro Lys Phe Thr Phe Gly Ala Ser Trp Arg Ser Glu
    610                 615                 620

Tyr Gly Asp Pro Glu Asp Pro Glu Asp Phe Asp Phe Ile Phe Lys Tyr
625                 630                 635                 640

Ser Pro Tyr His Asn Ile Pro Pro Gly Asp Thr Ile Met Pro Ala
                645                 650                 655

Met Leu Phe Phe Thr Ala Ala Tyr Asp Asp Arg Val Ser Pro Leu His
            660                 665                 670

Thr Phe Lys His Val Ala Ala Leu Gln His Asn Phe Pro Lys Gly Pro
        675                 680                 685

Asn Pro Cys Leu Met Arg Ile Asp Leu Asn Ser Gly His Phe Ala Gly
    690                 695                 700

Lys Ser Thr Gln Glu Met Leu Glu Glu Thr Ala Asp Glu Tyr Arg Leu
705                 710                 715                 720

Lys Val Gln

<210> SEQ ID NO 49
<211> LENGTH: 417
<212> TYPE: PRT
<213> ORGANISM: Lentinula edodes

<400> SEQUENCE: 49

-continued

```
Met Glu Thr Pro Thr Leu Asn Lys Ser Gly Ser Leu Thr Ile Val Gly
1               5                   10                  15

Thr Gly Ile Glu Ser Ile Gly Gln Met Thr Leu Gln Thr Leu Ser Tyr
            20                  25                  30

Ile Glu Ala Ala Asp Lys Val Phe Tyr Cys Val Ile Asp Pro Ala Thr
        35                  40                  45

Glu Ala Phe Ile Leu Thr Lys Asn Lys Asp Cys Val Asp Leu Tyr Gln
    50                  55                  60

Tyr Tyr Asp Asn Gly Lys Ser Arg Met Asp Thr Tyr Thr Gln Met Ser
65                  70                  75                  80

Glu Val Met Leu Arg Glu Val Arg Lys Gly Leu Asp Val Val Gly Val
                85                  90                  95

Phe Tyr Gly His Pro Gly Val Phe Val Asn Pro Ser Leu Arg Ala Leu
            100                 105                 110

Ala Ile Ala Lys Ser Glu Gly Phe Lys Ala Arg Met Leu Pro Gly Val
        115                 120                 125

Ser Ala Glu Asp Cys Leu Tyr Ala Asp Leu Cys Ile Asp Pro Ser Asn
    130                 135                 140

Pro Gly Cys Leu Thr Tyr Glu Ala Ser Asp Phe Leu Ile Arg Glu Arg
145                 150                 155                 160

Pro Thr Asn Ile Tyr Ser His Phe Ile Leu Phe Gln Val Gly Cys Val
                165                 170                 175

Gly Ile Ala Asp Phe Asn Phe Thr Gly Phe Glu Asn Ser Lys Phe Gly
            180                 185                 190

Ile Leu Val Asp Arg Leu Glu Lys Glu Tyr Gly Ala Glu His Pro Val
        195                 200                 205

Val His Tyr Ile Ala Ala Met Leu Pro His Glu Asp Pro Val Thr Asp
210                 215                 220

Gln Trp Thr Ile Gly Gln Leu Arg Glu Pro Glu Phe Tyr Lys Arg Val
225                 230                 235                 240

Gly Gly Val Ser Thr Phe Tyr Ile Pro Pro Lys Glu Arg Lys Glu Ile
                245                 250                 255

Asn Val Asp Ile Ile Arg Glu Leu Lys Phe Leu Pro Glu Gly Lys Val
            260                 265                 270

Pro Asp Thr Arg Thr Gln Ile Tyr Pro Pro Asn Gln Trp Glu Pro Glu
        275                 280                 285

Val Pro Thr Val Pro Ala Tyr Gly Ser Asn Glu His Ala Ala Ile Ala
    290                 295                 300

Gln Leu Asp Thr His Thr Pro Pro Glu Gln Tyr Gln Pro Leu Ala Thr
305                 310                 315                 320

Ser Lys Ala Met Thr Asp Val Met Thr Lys Leu Ala Leu Asp Pro Lys
                325                 330                 335

Ala Leu Ala Glu Tyr Lys Ala Asp His Arg Ala Phe Ala Gln Ser Val
            340                 345                 350

Pro Asp Leu Thr Ala Asn Glu Arg Thr Ala Leu Glu Ile Gly Asp Ser
        355                 360                 365

Trp Ala Phe Arg Cys Ala Met Lys Glu Met Pro Ile Ser Leu Leu Asp
370                 375                 380

Asn Ala Lys Gln Ser Met Glu Glu Ala Ser Glu Gln Gly Phe Pro Trp
385                 390                 395                 400

Ile Ile Val Val Gly Val Val Gly Val Val Gly Ser Val Ser Ser
            405                 410                 415
```

Ala

<210> SEQ ID NO 50
<211> LENGTH: 417
<212> TYPE: PRT
<213> ORGANISM: Omphalotacae olearis

<400> SEQUENCE: 50

Met Glu Thr Ser Thr Gln Thr Lys Ala Gly Ser Leu Thr Ile Val Gly
1               5                   10                  15

Thr Gly Ile Glu Ser Ile Gly Gln Met Thr Leu Gln Ala Leu Ser Tyr
            20                  25                  30

Ile Glu Ala Ala Ala Lys Val Phe Tyr Cys Val Ile Asp Pro Ala Thr
        35                  40                  45

Glu Ala Phe Ile Leu Thr Lys Asn Lys Asn Cys Val Asp Leu Tyr Gln
50                  55                  60

Tyr Tyr Asp Asn Gly Lys Ser Arg Leu Asn Thr Tyr Thr Gln Met Ser
65                  70                  75                  80

Glu Leu Met Val Arg Glu Val Arg Lys Gly Leu Asp Val Val Gly Val
                85                  90                  95

Phe Tyr Gly His Pro Gly Val Phe Val Asn Pro Ser His Arg Ala Leu
            100                 105                 110

Ala Ile Ala Lys Ser Glu Gly Tyr Arg Ala Arg Met Leu Pro Gly Val
        115                 120                 125

Ser Ala Glu Asp Cys Leu Phe Ala Asp Leu Cys Ile Asp Pro Ser Asn
130                 135                 140

Pro Gly Cys Leu Thr Tyr Glu Ala Ser Asp Phe Leu Ile Arg Asp Arg
145                 150                 155                 160

Pro Val Ser Ile His Ser His Leu Val Leu Phe Gln Val Gly Cys Val
                165                 170                 175

Gly Ile Ala Asp Phe Asn Phe Thr Gly Phe Asp Asn Asn Lys Phe Gly
            180                 185                 190

Val Leu Val Asp Arg Leu Glu Gln Glu Tyr Gly Ala Glu His Pro Val
        195                 200                 205

Val His Tyr Ile Ala Ala Met Met Pro His Gln Asp Pro Val Thr Asp
210                 215                 220

Lys Tyr Thr Val Ala Gln Leu Arg Glu Pro Glu Ile Ala Lys Arg Val
225                 230                 235                 240

Gly Gly Val Ser Thr Phe Tyr Ile Pro Pro Lys Ala Arg Lys Ala Ser
                245                 250                 255

Asn Leu Asp Ile Ile Arg Arg Leu Glu Leu Leu Pro Ala Gly Gln Val
            260                 265                 270

Pro Asp Lys Lys Ala Arg Ile Tyr Pro Ala Asn Gln Trp Glu Pro Asp
        275                 280                 285

Val Pro Glu Val Glu Pro Tyr Arg Pro Ser Asp Gln Ala Ala Ile Ala
290                 295                 300

Gln Leu Ala Asp His Ala Pro Pro Glu Gln Tyr Gln Pro Leu Ala Thr
305                 310                 315                 320

Ser Lys Ala Met Ser Asp Val Met Thr Lys Leu Ala Leu Asp Pro Lys
                325                 330                 335

Ala Leu Ala Asp Tyr Lys Ala Asp His Arg Ala Phe Ala Gln Ser Val
            340                 345                 350

Pro Asp Leu Thr Pro Gln Glu Arg Ala Ala Leu Glu Leu Gly Asp Ser
        355                 360                 365

```
Trp Ala Ile Arg Cys Ala Met Lys Asn Met Pro Ser Ser Leu Leu Asp
        370                 375                 380

Ala Ala Arg Glu Ser Gly Glu Glu Ala Ser Gln Asn Gly Phe Pro Trp
385                 390                 395                 400

Val Ile Val Val Gly Val Ile Gly Val Ile Gly Ser Val Met Ser Thr
                405                 410                 415

Glu

<210> SEQ ID NO 51
<211> LENGTH: 417
<212> TYPE: PRT
<213> ORGANISM: Dendrothele bispora

<400> SEQUENCE: 51

Met Glu Ser Ser Thr Gln Thr Lys Pro Gly Ser Leu Ile Val Val Gly
1               5                   10                  15

Thr Gly Ile Glu Ser Ile Gly Gln Met Thr Leu Gln Ala Leu Ser Tyr
            20                  25                  30

Ile Glu Ala Ala Ser Lys Val Phe Tyr Cys Val Ile Asp Pro Ala Thr
        35                  40                  45

Glu Ala Phe Ile Leu Thr Lys Asn Lys Asn Cys Val Asp Leu Tyr Gln
50                  55                  60

Tyr Tyr Asp Asn Gly Lys Ser Arg Met Asp Thr Tyr Thr Gln Met Ala
65                  70                  75                  80

Glu Leu Met Leu Lys Glu Val Arg Asn Gly Leu Asp Val Val Gly Val
                85                  90                  95

Phe Tyr Gly His Pro Gly Val Phe Val Asn Pro Ser His Arg Ala Leu
            100                 105                 110

Ala Ile Ala Arg Ser Glu Gly Tyr Gln Ala Arg Met Leu Pro Gly Val
        115                 120                 125

Ser Ala Glu Asp Cys Leu Phe Ala Asp Leu Cys Ile Asp Pro Ser Asn
130                 135                 140

Pro Gly Cys Leu Thr Tyr Glu Ala Ser Asp Phe Leu Ile Arg Glu Arg
145                 150                 155                 160

Pro Val Asn Val His Ser His Leu Ile Leu Phe Gln Val Gly Cys Val
                165                 170                 175

Gly Ile Ala Asp Phe Asn Phe Ser Gly Phe Asp Asn Ser Lys Phe Thr
            180                 185                 190

Ile Leu Val Asp Arg Leu Glu Gln Glu Tyr Gly Pro Asp His Thr Val
        195                 200                 205

Val His Tyr Ile Ala Ala Met Met Pro His Gln Asp Pro Val Thr Asp
210                 215                 220

Lys Phe Thr Ile Gly Gln Leu Arg Glu Pro Glu Ile Ala Lys Arg Val
225                 230                 235                 240

Gly Gly Val Ser Thr Phe Tyr Ile Pro Pro Lys Ala Arg Lys Asp Ile
                245                 250                 255

Asn Thr Asp Ile Ile Arg Leu Leu Glu Phe Leu Pro Ala Gly Lys Val
            260                 265                 270

Pro Asp Lys His Thr Gln Ile Tyr Pro Pro Asn Gln Trp Glu Pro Asp
        275                 280                 285

Val Pro Thr Leu Pro Pro Tyr Gly Gln Asn Glu Gln Ala Ala Ile Thr
290                 295                 300

Arg Leu Glu Ala His Ala Pro Pro Glu Glu Tyr Gln Pro Leu Ala Thr
305                 310                 315                 320
```

```
Ser Lys Ala Met Thr Asp Val Met Thr Lys Leu Ala Leu Asp Pro Lys
                325                 330                 335

Ala Leu Ala Glu Tyr Lys Ala Asp His Arg Ala Phe Ala Gln Ser Val
            340                 345                 350

Pro Asp Leu Thr Pro Gln Glu Arg Ala Ala Leu Glu Leu Gly Asp Ser
        355                 360                 365

Trp Ala Ile Arg Cys Ala Met Lys Asn Met Pro Ser Ser Leu Leu Glu
370                 375                 380

Ala Ala Ser Gln Ser Val Glu Glu Ala Ser Met Asn Gly Phe Pro Trp
385                 390                 395                 400

Val Ile Val Thr Gly Ile Val Gly Val Ile Gly Ser Val Val Ser Ser
                405                 410                 415

Ala

<210> SEQ ID NO 52
<211> LENGTH: 410
<212> TYPE: PRT
<213> ORGANISM: Rhizopogon vinicolor

<400> SEQUENCE: 52

Met Thr Thr Asp Thr Lys Arg Gly Thr Leu Thr Ile Ala Gly Ser Gly
1               5                   10                  15

Ile Ala Ser Ile Ala His Ile Thr Leu Glu Thr Leu Ser Tyr Ile Lys
            20                  25                  30

Glu Ser Asp Lys Leu Phe Tyr Leu Val Cys Asp Pro Val Thr Glu Ala
        35                  40                  45

Phe Ile Gln Asp Asn Ala Thr Gly Asp Phe Phe Asp Leu Ser Val Phe
    50                  55                  60

Tyr Asp Lys Asn Lys Ser Arg Tyr Asp Ser Tyr Ile Gln Met Cys Glu
65                  70                  75                  80

Ile Met Leu Arg Ala Val Arg Ala Gly His Ser Val Leu Gly Ile Phe
                85                  90                  95

Tyr Gly His Pro Gly Val Phe Val Ser Pro Ser His Arg Ala Ile Ala
            100                 105                 110

Val Ala Arg Glu Glu Gly Tyr Lys Ala Arg Met Leu Pro Gly Val Ser
        115                 120                 125

Ala Glu Asp Tyr Met Phe Ala Asp Leu Glu Phe Asp Pro Ser Gln Ser
    130                 135                 140

Thr Cys Asn Thr Tyr Glu Ala Thr Glu Leu Leu Leu Arg Asp Arg Pro
145                 150                 155                 160

Leu Asp Pro Ala Ile Gln Asn Ile Ile Trp Gln Val Gly Ser Val Gly
                165                 170                 175

Val Val Asp Met Glu Phe Glu Lys Ser Lys Phe His Leu Leu Val Asp
            180                 185                 190

Arg Leu Glu Gln Asp Phe Gly Pro Asp His Lys Val Val His Tyr Ile
        195                 200                 205

Gly Ala Val Leu Pro Gln Ser Thr Thr Thr Met Asp Ile Phe Thr Ile
    210                 215                 220

Ser Asp Leu Arg Lys Glu Asn Val Ala Lys Gln Phe Gly Thr Ile Ser
225                 230                 235                 240

Thr Leu Tyr Ile Pro Pro Arg Asp Glu Gly Pro Val Ser Ser Ser Met
                245                 250                 255

Thr Gln Ala Phe Asp Phe Lys Ala Gly Ala Met Val Tyr Ser Pro Val
            260                 265                 270
```

```
Lys Trp Ala Gly Pro Lys Leu Asn Ile Val Ser Ala Leu Ser Pro Tyr
            275                 280                 285

Glu Arg Asp Val Ile Ser Gln Ile Asp Thr His Val Ala Pro Glu Gly
        290                 295                 300

Tyr Lys Ile Leu His Thr Ser Ala Ala Met Asn Lys Phe Met Thr Asp
305                 310                 315                 320

Leu Ser Leu Lys Pro Lys Phe Leu Glu Glu Tyr Lys Leu Tyr Pro Glu
                325                 330                 335

Ala Val Val Glu Ser Ala Glu Gly Leu Ser Asn Leu Glu Lys Phe Gly
            340                 345                 350

Leu Lys Phe Gly Ser Asp Gly Ala Val Tyr Ile Leu Met Lys Ala Thr
        355                 360                 365

Glu Ser Asp Ile Ala Ser Gly Arg Gln Leu Thr Glu Asp Glu Ile Ala
370                 375                 380

Lys Ala His Lys Ser Val Gly Phe Pro Thr Val Leu Val Ile Leu Pro
385                 390                 395                 400

Thr Val Ile Val Val Leu Ile Gly Arg Glu
                405                 410

<210> SEQ ID NO 53
<211> LENGTH: 413
<212> TYPE: PRT
<213> ORGANISM: Rhizopogon vinicolor

<400> SEQUENCE: 53

Met Ser Thr Lys Arg Gly Thr Leu Thr Ile Ala Gly Ser Gly Ile Ala
1               5                   10                  15

Ser Val Gly His Ile Thr Leu Gly Thr Leu Ser Tyr Ile Lys Glu Ser
            20                  25                  30

Asp Lys Ile Phe Tyr Leu Val Cys Asp Pro Val Thr Glu Ala Phe Ile
        35                  40                  45

Tyr Asp Asn Ser Thr Ala Asp Cys Phe Asp Leu Ser Val Phe Tyr Asp
50                  55                  60

Lys Thr Lys Gly Arg Tyr Asp Ser Tyr Ile Gln Met Cys Glu Val Met
65                  70                  75                  80

Leu Lys Ala Val Arg Ala Gly His Asp Val Leu Gly Val Phe Tyr Gly
                85                  90                  95

His Pro Gly Val Phe Val Ser Pro Ser His Arg Ala Ile Ala Val Ala
            100                 105                 110

Arg Gln Glu Gly Tyr Lys Ala Lys Met Leu Pro Gly Ile Ser Ala Glu
        115                 120                 125

Asp Tyr Met Phe Ala Asp Leu Glu Phe Asp Pro Ser Val Ser Gly Cys
130                 135                 140

Lys Thr Cys Glu Ala Thr Glu Ile Leu Leu Arg Asp Lys Pro Leu Asp
145                 150                 155                 160

Pro Thr Ile Gln Asn Ile Ile Trp Gln Val Gly Ser Val Gly Val Val
                165                 170                 175

Asp Met Glu Phe Ser Lys Ser Lys Phe Gln Leu Leu Val Asp Arg Leu
            180                 185                 190

Glu Lys Asp Phe Gly Pro Asp His Lys Val Val His Tyr Ile Gly Ala
        195                 200                 205

Val Leu Pro Gln Ser Thr Thr Thr Met Asp Thr Phe Thr Ile Ala Asp
210                 215                 220

Leu Arg Lys Glu Asp Val Ala Lys Gln Phe Gly Thr Ile Ser Thr Leu
225                 230                 235                 240
```

```
Tyr Ile Pro Pro Arg Asp Glu Gly His Val Asn Leu Ser Met Ala Lys
                245                 250                 255

Val Phe Gly Gly Pro Gly Ala Ser Val Lys Leu Asn Asp Ser Ile Lys
            260                 265                 270

Trp Ala Gly Pro Lys Leu Asn Ile Val Ser Ala Asn Asp Pro His Glu
            275                 280                 285

Arg Asp Val Ile Ala Gln Val Asp Thr His Val Ala Pro Glu Gly His
        290                 295                 300

Lys Lys Leu Arg Val Ser Ala Ala Met Lys Lys Phe Met Thr Asp Leu
305                 310                 315                 320

Ala Leu Lys Pro Lys Phe Leu Glu Glu Tyr Lys Leu Asp Pro Val Ala
                325                 330                 335

Val Val Glu Ser Ala Glu Gly Leu Ser Asn Leu Glu Arg Phe Gly Leu
            340                 345                 350

Lys Phe Ala Arg Ser Gly Pro Ala Asp Ala Leu Met Lys Ala Thr Glu
        355                 360                 365

Ser Asp Ile Ala Ser Gly Arg Gln Leu Thr Glu Glu Ile Ala Gln
        370                 375                 380

Gly Thr Gly Pro Val Gly Leu Gln Thr Ala Leu Ala Leu Leu Val Leu
385                 390                 395                 400

Leu Gly Leu Gly Val Ala Ile Val Thr Arg Pro Asp Asp
                405                 410

<210> SEQ ID NO 54
<211> LENGTH: 569
<212> TYPE: PRT
<213> ORGANISM: Rhizophogun vinicolor

<400> SEQUENCE: 54

Met Ala Lys Val Phe Gly Leu Val Leu Gly Phe Leu Ser Gln Thr Phe
1               5                   10                  15

Thr Tyr Pro Ser Gln Val Trp Phe Ser Pro Val Gly Ala Asn Asn Gly
            20                  25                  30

Gln Val Ile Thr Pro Glu Leu Ser Asn Ser Ile Gln Glu Thr Leu Asp
        35                  40                  45

Val Trp Asn Ile Thr Gly Leu Ser Val Ala Ile Ile Pro Lys Ser Gly
    50                  55                  60

Glu Pro Glu Tyr His Ser Trp Gly Asp Arg Thr Glu Asp Gly Glu Ser
65                  70                  75                  80

Val Thr Gln Asp Thr Leu Phe His Met Ala Ser Val Ser Lys Ala Phe
                85                  90                  95

Cys Val Ser Ala Leu Gly Ile Leu Met Asp Asp Phe Glu His Gly Arg
            100                 105                 110

Asn Val Thr Pro Leu Pro Pro Ala Leu Thr Glu Phe Asn Trp His Thr
        115                 120                 125

Ser Ile Gln Asp Leu Leu Pro Gly Glu Trp Gln Leu Met Asp Glu Trp
    130                 135                 140

Ala Ser Arg Lys Ala Asn Met Lys Asp Ile Leu Ser His Val Ser Gly
145                 150                 155                 160

Leu Pro Arg His Asp Phe Ala Phe Gly Pro Tyr Glu Ser Pro Lys Glu
                165                 170                 175

Ala Val Ser Arg Leu Arg Tyr Leu Arg Pro Ala Phe Glu Leu Arg Glu
            180                 185                 190

Gln Trp Ser Tyr Asn Asn Gln Met Phe Met Val Ala Gly His Ile Val
```

```
            195                 200                 205
Glu Thr Tyr Ser Gly Lys Thr Tyr Thr Ser Phe Val Glu Asp Arg Ile
    210                 215                 220

Phe Thr Pro Leu Gly Met Ser Ser Thr Phe Ser Pro Ala Lys Ala
225                 230                 235                 240

Ala Lys Thr Gly Lys Phe Thr Gln Gly Trp Thr Ser Ser Gly Arg Leu
                245                 250                 255

Leu Pro Glu Leu Phe Pro Glu Asp Met Val Met Leu Met Ala Gly Ala
                260                 265                 270

Gly Gly Val Ile Ser Ser Ala Val Asp Met Ser Lys Trp Val Ala Leu
                275                 280                 285

Trp Leu Asn Lys Gly Val Tyr Asp Asn Val Thr Val Ile Pro Ser Ser
    290                 295                 300

Val Tyr Gly Asn Ala Ser Gln Ser Tyr Ala Val Ser Ile Ser Thr Pro
305                 310                 315                 320

Val Asp Ser Glu His Ser Ile Gln Gly Tyr Gly Leu Gly Trp Phe Gln
                325                 330                 335

Asn Ser Tyr Leu Gly His Asn Val Val Tyr His Ser Gly Ser Ile Pro
                340                 345                 350

Gly Leu Ser Met Leu Val Ser Phe Leu Pro Asp Asp Val Gly Phe
                355                 360                 365

Val Val Phe Ala Asn Gly Gly Asp Lys Ala Ala Pro Val Met Asn Ile
370                 375                 380

Ser Asn Ser Ile Ile Asp Ala Ala Leu His Leu Arg Ser Gly Pro Ala
385                 390                 395                 400

Pro Pro Ile Met Pro Glu Lys Lys Ala Val Thr Ser Pro Ser Glu Asp
                405                 410                 415

Ile Val Asn Leu Glu Leu Pro Leu Glu Glu Phe Ser Gly Thr Tyr Thr
                420                 425                 430

Asp Pro Gly Tyr Gly Thr Phe Thr Phe Cys Ser Pro Ser Ser Ser
                435                 440                 445

Ser Tyr Cys Gln Gln Val Met Thr Asp Phe Thr Ala Val Asp Ser Val
    450                 455                 460

His Pro Ser Ala Pro Ser Pro Leu Gln Leu Leu Ala Ala Trp Pro Arg
465                 470                 475                 480

Met Gly Ser Ser His Ile Arg Ala Val His Gln Ser Gly Asn Lys Phe
                485                 490                 495

Leu Leu Leu Cys Thr Ala Leu Phe Pro Glu Gly Tyr Gly Arg Asp Ser
                500                 505                 510

Thr Pro Phe Glu Thr Ala Glu Ile Gly Thr Pro Gly Ala Thr Ala Glu
                515                 520                 525

Phe Val Val Glu Asp Gly Lys Val Gly Phe Gly Leu Phe Gly Leu
                530                 535                 540

Val Asp Gln Val Thr Glu Arg Glu Arg Thr Gln Thr Thr Val Lys Asp
545                 550                 555                 560

Arg Ala Glu Val Trp Phe Asp Lys Val
                565
```

<210> SEQ ID NO 55
<211> LENGTH: 571
<212> TYPE: PRT
<213> ORGANISM: Rhizophogun vinicolor

<400> SEQUENCE: 55

```
Met Ile Met Ala Lys Val Phe Gly Leu Val Leu Gly Phe Leu Ser Gln
1               5                   10                  15

Thr Phe Thr Tyr Pro Ser Gln Ile Arg Leu Ser Pro Val Gly Val Asn
            20                  25                  30

Asn Gly Gln Val Ile Thr Pro Glu Leu Ser Asn Ser Ile Gln Glu Thr
        35                  40                  45

Leu Asp Val Trp Asn Ile Thr Gly Leu Ser Val Ala Ile Ile Pro Lys
    50                  55                  60

Ser Gly Glu Pro Glu Tyr His Ser Trp Gly Asp Arg Thr Glu Asp Gly
65                  70                  75                  80

Glu Ser Val Thr Gln Asp Thr Leu Phe His Met Ala Ser Val Ser Lys
                85                  90                  95

Ala Phe Cys Val Ser Ala Leu Gly Ile Leu Met Asp Asp Phe Glu His
            100                 105                 110

Gly Arg Asn Val Thr Pro Leu Pro Pro Ala Leu Thr Glu Phe Asn Trp
            115                 120                 125

His Thr Ser Ile Gln Asp Leu Leu Pro Gly Glu Trp Gln Leu Met Asp
    130                 135                 140

Glu Trp Ala Ser Arg Lys Ala Asn Val Lys Asp Ile Leu Ser His Val
145                 150                 155                 160

Ser Gly Leu Pro Ser His His Phe Ala Phe Gly Pro Tyr Glu Ser Pro
                165                 170                 175

Lys Glu Val Val Ser Arg Leu Arg Tyr Leu Arg Pro Ala Phe Glu Leu
            180                 185                 190

Arg Glu Gln Trp Ser Tyr Asn Asn Gln Met Phe Thr Val Ala Gly His
            195                 200                 205

Ile Val Glu Thr Tyr Ser Gly Lys Thr Tyr Thr Ser Phe Val Glu Asp
    210                 215                 220

Arg Ile Phe Thr Pro Leu Gly Met Phe Ser Ser Thr Phe Ser Pro Ala
225                 230                 235                 240

Lys Ala Val Lys Thr Gly Lys Phe Thr Gln Gly Trp Thr Ser Ser Gly
            245                 250                 255

Arg Leu Leu Pro Glu Phe Phe Gln Glu Asp Met Ile Met Pro Met Ala
            260                 265                 270

Gly Pro Gly Gly Val Ile Ser Ser Ala Val Asp Met Ser Lys Trp Val
            275                 280                 285

Ala Leu Trp Leu Asn Lys Gly Val His Asp Asn Val Thr Ile Ile Pro
            290                 295                 300

Ser Ser Val Tyr Gly Asn Ala Ser Gln Ser Tyr Ala Val Ser Ile Ser
305                 310                 315                 320

Thr Pro Val Asp Ser Glu His Ser Ile Leu Gly Tyr Gly Leu Gly Trp
                325                 330                 335

Phe Arg Asn Ser Tyr Leu Gly His Asp Val Val Tyr His Ser Gly Ser
            340                 345                 350

Ile Pro Gly Leu Ser Thr Leu Val Ser Phe Leu Pro Asp Asp Val
            355                 360                 365

Gly Phe Val Val Phe Ala Asn Gly Asp Asn Lys Ala Ala Pro Val Met
            370                 375                 380

Asn Ile Ser Asn Arg Ile Ile Asp Ala Ala Leu His Leu Arg Ser Gly
385                 390                 395                 400

Pro Ala Pro Pro Ile Met Pro Glu Lys Lys Ala Val Thr Ser Pro Ser
                405                 410                 415

Glu Asp Ile Val Asn Leu Glu Leu Pro Leu Glu Glu Phe Ser Gly Thr
```

```
                420             425             430
Tyr Thr Asp Pro Gly Tyr Gly Thr Phe Thr Phe Cys Ser Pro Ser Ser
            435             440             445

Ser Ser Pro Tyr Cys Gln Gln Val Ile Ala Asn Phe Thr Thr Val Asp
            450             455             460

Ser Val Arg Pro Ser Ala Pro Ser Ser Leu Gln Leu Leu Ala Ala Trp
465             470             475             480

Pro Arg Val Gly Ser Ser His Ile Arg Thr Val His Gln Ser Gly Asn
            485             490             495

Lys Phe Met Leu Leu Pro Thr Ala Leu Phe Pro Glu Gly Tyr Gly Arg
            500             505             510

Asp Ser Thr Pro Phe Glu Thr Ala Glu Ile Gly Thr Arg Gly Ala Pro
            515             520             525

Val Glu Phe Val Val Glu Asp Gly Arg Val Val Gly Phe Gly Leu Phe
            530             535             540

Gly Leu Val Gly Gln Val Thr Glu Arg Glu Arg Thr Gln Thr Thr Val
545             550             555             560

Lys Asp Arg Ala Gly Val Trp Phe Asp Lys Val
            565             570

<210> SEQ ID NO 56
<211> LENGTH: 413
<212> TYPE: PRT
<213> ORGANISM: Rhizophogun vinicolor

<400> SEQUENCE: 56

Met Ser Thr Lys Arg Gly Thr Leu Thr Ile Ala Gly Ser Gly Ile Ala
1               5                   10                  15

Ser Val Gly His Ile Thr Leu Gly Thr Leu Ser Tyr Ile Lys Glu Ser
            20                  25                  30

Asp Lys Ile Phe Tyr Leu Val Cys Asp Pro Val Thr Glu Ala Phe Ile
            35                  40                  45

Tyr Asp Asn Ser Thr Ala Asp Cys Phe Asp Leu Ser Val Phe Tyr Asp
        50                  55                  60

Lys Thr Lys Gly Arg Tyr Asp Ser Tyr Ile Gln Met Cys Glu Val Met
65                  70                  75                  80

Leu Lys Ala Val Arg Ala Gly His Asp Val Leu Gly Val Phe Tyr Gly
                85                  90                  95

His Pro Gly Val Phe Val Ser Pro Ser His Arg Ala Ile Ala Val Ala
            100                 105                 110

Arg Gln Glu Gly Tyr Lys Ala Lys Met Leu Pro Gly Ile Ser Ala Glu
            115                 120                 125

Asp Tyr Met Phe Ala Asp Leu Glu Phe Asp Pro Ser Val Ser Gly Cys
        130                 135                 140

Lys Thr Cys Glu Ala Thr Glu Ile Leu Leu Arg Asp Lys Pro Leu Asp
145                 150                 155                 160

Pro Thr Ile Gln Asn Ile Ile Trp Gln Val Gly Ser Val Gly Val Val
                165                 170                 175

Asp Met Glu Phe Ser Lys Ser Lys Phe Gln Leu Leu Val Asp Arg Leu
            180                 185                 190

Glu Lys Asp Phe Gly Pro Asp His Lys Val Val His Tyr Ile Gly Ala
            195                 200                 205

Val Leu Pro Gln Ser Thr Thr Thr Met Asp Thr Phe Thr Ile Ala Asp
        210                 215                 220
```

```
Leu Arg Lys Glu Asp Val Ala Lys Gln Phe Gly Thr Ile Ser Thr Leu
225                 230                 235                 240

Tyr Ile Pro Pro Arg Asp Glu Gly His Val Asn Leu Ser Met Ala Lys
            245                 250                 255

Val Phe Gly Gly Pro Gly Ala Ser Val Lys Leu Asn Asp Ser Ile Lys
            260                 265                 270

Trp Ala Gly Pro Lys Leu Asn Ile Val Ser Ala Asn Asp Pro His Glu
            275                 280                 285

Arg Asp Val Ile Ala Gln Val Asp Thr His Val Ala Pro Glu Gly His
            290                 295                 300

Lys Lys Leu Arg Val Ser Ala Ala Met Lys Lys Phe Met Thr Asp Leu
305                 310                 315                 320

Ala Leu Lys Pro Lys Phe Leu Glu Glu Tyr Lys Leu Asp Pro Val Ala
                325                 330                 335

Val Val Glu Ser Ala Glu Gly Leu Ser Asn Leu Glu Arg Phe Gly Leu
            340                 345                 350

Lys Phe Ala Arg Ser Gly Pro Ala Asp Ala Leu Met Lys Ala Thr Glu
            355                 360                 365

Ser Asp Ile Ala Ser Gly Arg Gln Leu Thr Glu Glu Ile Ala Gln
370                 375                 380

Gly Thr Gly Pro Val Gly Leu Gln Thr Ala Leu Ala Leu Val Leu
385                 390                 395                 400

Leu Gly Leu Gly Val Ala Ile Val Thr Arg Pro Asp Asp
                405                 410

<210> SEQ ID NO 57
<211> LENGTH: 598
<212> TYPE: PRT
<213> ORGANISM: Rhizophogun vinicolor

<400> SEQUENCE: 57

Met Thr Ser Asp Asn Leu Gln Pro Glu Val Ile Ser Ala Asn Trp Leu
1               5                   10                  15

Lys Ser Leu Glu Ala Ala Ser Ser Thr Gly Asp Thr Ala Ser Phe Val
                20                  25                  30

Ser His Phe Leu Pro Asp Gly Trp Phe Arg Asp Met Leu Cys Phe Thr
            35                  40                  45

Trp Asn Phe Arg Thr Leu Ser Gly Gln Glu Lys Ile His Gly Phe Ile
        50                  55                  60

Ser Glu Val Val Asp Gly Gln Ser Arg Leu Ser Tyr Ser His Leu His
65                  70                  75                  80

Asp Phe Lys Leu Asp Asp His Ser Val Asn Ala Pro Ser Pro Phe Lys
                85                  90                  95

Leu Pro Gly Pro Pro Asp Ile Glu Gly Val Gln Gly Ala Phe Thr Phe
            100                 105                 110

Ser Ile Thr Lys Pro Ala Ala Tyr Gly Arg Gly Phe Phe Arg Leu Thr
        115                 120                 125

Gln Asp Val His Gly Asn Trp Lys Ala Leu Thr Leu Phe Thr Asn Met
    130                 135                 140

Gln Asp Leu Val Gly His Glu Glu Ser Ser Ala Asp Glu Tyr Asp Pro
145                 150                 155                 160

His Glu Lys Ala Asn Pro Thr Val Val Ile Val Lys Val Gly Gly
                165                 170                 175

Gly Gln Ser Gly Leu Ile Cys Ala Ala Arg Leu Gly Lys Leu Gly Ile
            180                 185                 190
```

```
Arg Ala Leu Val Ile Asp Lys Asn Ala Arg Val Gly Asp Ile Trp Arg
            195                 200                 205

Gln Arg Tyr Ala Glu Ala Leu Pro Ser Phe Ala Val Leu Ser Arg Gln
        210                 215                 220

Glu Thr Gln Val Pro Glu Pro Tyr Ala Ala Tyr Ser Gln Ile Ser Lys
225                 230                 235                 240

Leu Leu Pro Tyr Pro Ser Asn Phe Pro Lys Tyr Leu Pro Lys Gly Lys
                245                 250                 255

Leu Ala Asn Phe Leu Glu Ser Tyr Ala Ile Asn Gln Glu Leu Cys Ile
            260                 265                 270

Trp Leu Ser Ser Thr Val Ser Pro Ser Pro Val Tyr Asp Ser Phe Ser
        275                 280                 285

Ala Arg Trp Thr Val Glu Val Glu His Glu Asn Arg Lys Val Ile Leu
        290                 295                 300

His Pro Lys His Leu Val Leu Ala Thr Gly His Gly Arg Pro Arg Ile
305                 310                 315                 320

Pro Thr Trp Asn Gly Met Asp Asp Phe Gln Gly Thr Leu Tyr His Ser
                325                 330                 335

Asp Phe His Arg Asp Ala Glu Lys Phe Arg Gly Lys Cys Val Val Val
            340                 345                 350

Ile Gly Ala Gly Asn Ala Ser Gly Asp Ile Cys Glu Asp Phe Val Ala
            355                 360                 365

Gln Gly Ala Ala Glu Val Thr Ile Val Gln Arg Ser Ala Thr Cys Val
        370                 375                 380

Val Ser Ser Ala Thr Ala Asp Ala Phe Val Phe Lys Leu Pro Phe Ser
385                 390                 395                 400

Asp Lys Thr Pro Ile Glu Glu Leu Asp Phe Arg His Asn Ser Met Pro
                405                 410                 415

Leu Ala Phe Val Leu Gln Leu Met Lys Ser Gly Gly Thr Gln His Met
            420                 425                 430

Lys Ala His Asp Lys Glu His His Glu Gly Leu Arg Lys Ala Gly Phe
        435                 440                 445

Asn Leu Thr Trp Glu Pro Ser Pro Gly Ser Gly Glu Val Gly Leu Leu
        450                 455                 460

Gly Phe Val Phe Glu Arg Ala Gly Ser Gly Thr Met Ile Asp Thr Gly
465                 470                 475                 480

Phe Gly Lys Leu Ile Val Glu Gly Thr Val Lys Val Lys Gln Gly Gln
                485                 490                 495

Asn Ile Ser His Phe Asp Lys Glu Gly Ile Thr Phe Lys Asp Gly Ser
            500                 505                 510

Lys Leu Pro Ala Asp Val Ile Val Ala Ala Thr Gly Asn Glu Leu Thr
        515                 520                 525

Met Asp Ala Ile Arg Ala Val Leu Gly Asp Thr Ile Ala Glu Gln Leu
530                 535                 540

Pro Pro Lys Val Trp Gly Leu Asp Ala Glu Gly Leu Asn Gln Met
545                 550                 555                 560

Tyr Arg Pro Ser Gly His Pro Gly Leu Trp Phe Ala Val Gly Ser Leu
                565                 570                 575

Gly Met Thr Arg Phe Cys Ser Lys His Leu Gly Leu Gln Ile Leu Ala
            580                 585                 590

Gln Glu Val Gly Ile Ala
        595
```

<210> SEQ ID NO 58
<211> LENGTH: 515
<212> TYPE: PRT
<213> ORGANISM: Galerina marginata

<400> SEQUENCE: 58

| | | | | | | | | | | | | | | | |
|---|---|---|---|---|---|---|---|---|---|---|---|---|---|---|---|
| Met | Gly | Lys | Met | Ala | Tyr | His | Thr | Val | Leu | Asp | Asp | Ile | Ala | Leu | Tyr |
| 1 | | | | 5 | | | | | 10 | | | | | 15 | |
| Leu | Leu | Gly | Ser | Ala | Ala | Leu | Val | Ile | Phe | Tyr | Arg | Ser | Phe | Phe | Tyr |
| | | | 20 | | | | | 25 | | | | | 30 | | |
| Pro | Tyr | Phe | Leu | Ser | Gly | Arg | Arg | Leu | Ala | Pro | Gly | Pro | Thr | Lys | Gly |
| | | 35 | | | | | 40 | | | | | 45 | | | |
| Glu | Leu | Ser | Lys | Glu | Leu | Lys | Gln | Phe | Asn | Asn | Glu | Ile | Asn | Val | His |
| | 50 | | | | | 55 | | | | | 60 | | | | |
| Phe | Leu | Arg | His | Met | Val | Lys | Glu | Tyr | Gly | Pro | Ile | Phe | Arg | Leu | Val |
| 65 | | | | 70 | | | | | 75 | | | | | 80 | |
| Gly | Ala | Pro | Met | Ile | Pro | Gly | Pro | Gly | Leu | Val | Val | Cys | Thr | Pro | Thr |
| | | | 85 | | | | | 90 | | | | | 95 | | |
| Ala | Gln | Gln | Arg | Ile | Leu | Val | Ser | Asn | Ser | Ile | Asn | Tyr | Gly | Gln | Pro |
| | | | 100 | | | | | 105 | | | | | 110 | | |
| Arg | Leu | Ala | Phe | Phe | Arg | Trp | Val | Thr | Gly | Gly | Leu | Phe | Thr | Leu | Pro |
| | | 115 | | | | | 120 | | | | | 125 | | | |
| Glu | Arg | Glu | His | Arg | Gly | Met | Arg | Lys | Ile | Leu | Asp | Pro | Val | Phe | Ser |
| | 130 | | | | | 135 | | | | | 140 | | | | |
| Phe | Arg | Asn | Leu | Ile | Ser | Thr | Thr | Gly | Val | Tyr | Tyr | Asn | Thr | Val | Gln |
| 145 | | | | 150 | | | | | 155 | | | | | 160 | |
| Ser | Leu | Ile | Thr | Ile | Phe | Arg | Ser | Lys | Ile | Asp | Gly | Glu | Asn | Gly | Ala |
| | | | 165 | | | | | 170 | | | | | 175 | | |
| Lys | Asp | Gly | Asp | Val | Ile | Leu | Val | Tyr | Glu | Trp | Leu | Ala | Arg | Leu | Ala |
| | | | 180 | | | | | 185 | | | | | 190 | | |
| Ile | Asp | Asn | Val | Ser | Glu | Ala | Ile | Leu | Gly | Phe | Lys | Leu | Asp | Thr | Leu |
| | | 195 | | | | | 200 | | | | | 205 | | | |
| His | Asp | Pro | Asn | Asn | Glu | Leu | Ile | Thr | Thr | Leu | Asp | Glu | Leu | Ser | Arg |
| | 210 | | | | | 215 | | | | | 220 | | | | |
| Ile | Pro | Thr | Ala | Ala | Phe | Glu | Leu | Leu | Val | Arg | Val | Pro | Gly | Phe | Leu |
| 225 | | | | 230 | | | | | 235 | | | | | 240 | |
| Arg | Leu | Val | Thr | Phe | Asp | Ser | Val | Arg | His | Ser | Thr | Leu | Trp | Gln | Arg |
| | | | 245 | | | | | 250 | | | | | 255 | | |
| Arg | Val | Pro | Gly | Arg | Leu | Gly | Val | Phe | Phe | Thr | Phe | Met | Arg | Cys | Leu |
| | | | 260 | | | | | 265 | | | | | 270 | | |
| Ser | Thr | Ile | Arg | Lys | Asn | Ala | Leu | Ala | Ile | Lys | Ala | Thr | Ile | Leu | Gln |
| | | 275 | | | | | 280 | | | | | 285 | | | |
| Glu | Asp | Ser | Ala | Asn | Arg | Asp | Leu | Asn | Val | Ile | Ser | Val | Leu | Gln | His |
| | 290 | | | | | 295 | | | | | 300 | | | | |
| Met | Gln | Ser | Ser | Asp | Glu | Thr | Ala | Asn | Ala | Asp | Ile | Ala | Gly | Asn | Ile |
| 305 | | | | 310 | | | | | 315 | | | | | 320 | |
| Ile | Met | Leu | Trp | Met | Ser | Gly | Arg | Ala | Thr | Ile | Ala | Thr | Arg | Ile | Ser |
| | | | 325 | | | | | 330 | | | | | 335 | | |
| Trp | Leu | Leu | Trp | Leu | Leu | Ala | Lys | Asp | Gln | Gln | Cys | Gln | Gln | Gln | Leu |
| | | | 340 | | | | | 345 | | | | | 350 | | |
| Arg | Asp | Glu | Ile | Ala | Pro | Leu | Phe | Ser | Arg | Asp | Pro | Arg | Pro | Asp | Tyr |
| | | 355 | | | | | 360 | | | | | 365 | | | |
| Arg | Ser | Leu | Asp | Lys | Leu | Gln | Trp | Leu | Asp | Ser | Val | Ile | Met | Glu | Ser |
| | 370 | | | | | 375 | | | | | 380 | | | | |

```
Ile Arg Leu Phe Leu Phe Gly Pro Asn Ile Arg Val Ala Leu Asn Asp
385                 390                 395                 400

Asp Tyr Ile Asp Gly Val Phe Val Pro Lys Gly Thr Val Val Val Ile
            405                 410                 415

Pro Leu Asp Leu Phe Thr Arg Gly Asp Ile Trp Gly Glu Asp Pro Asp
        420                 425                 430

Gln Phe Lys Pro Ala Arg Trp Leu Asp Ser Thr Lys Arg Tyr Lys Ile
        435                 440                 445

Ser Pro Pro Phe Leu Ser Phe Leu Thr Gly Pro His Arg Cys Ile Ala
    450                 455                 460

Lys Gly Met Ala Ile Met Gln Thr Lys Ile Val Ile Ala Ser Leu Ile
465                 470                 475                 480

Ala Asn Phe Glu Phe Lys Pro Ala Tyr Glu Gly Gln His Val Glu Gly
                485                 490                 495

Asn Pro Ser Ile Ile Gly His Gly Met Pro Leu His Val Lys Pro Ile
            500                 505                 510

Arg Pro Ser
        515

<210> SEQ ID NO 59
<211> LENGTH: 1318
<212> TYPE: PRT
<213> ORGANISM: Galerina marginata

<400> SEQUENCE: 59

Met Pro Tyr Val Pro Asp Pro Lys Tyr Phe Glu His Arg Glu Gln Ser
1               5                   10                  15

Ser Gly Ala Thr Leu Tyr Tyr Cys Leu Val Cys Arg Asp Gly Arg Glu
            20                  25                  30

Arg Gln Pro His His Ile Lys Thr His Glu Ala Ser Gln Ala His Arg
        35                  40                  45

Thr Ala Leu Ser Val Phe Asp Ser Gln Ala Glu Ser Ser Ser Gln Gln
    50                  55                  60

Thr His Gly Asn Pro Thr Gln Pro Gly Tyr Phe Asp Pro Val Ile Asp
65                  70                  75                  80

Asp Ala Val Arg Ala Leu Leu Val Ser Gly Ser Gly Asp Pro His Gln
                85                  90                  95

Pro Leu Tyr Pro Ala Gly His Pro Asn Val Tyr Gly Glu Pro Asn Phe
            100                 105                 110

Thr Asp Ser Arg Arg Thr Ser Pro Val Thr Gly Ile Asp Trp Asp
        115                 120                 125

Gln Phe Glu Ala Gln Glu Asp Thr His Ala Val Pro Ser Ala Gln Asp
    130                 135                 140

Gln Leu Arg Ala Asp Ile Cys Gln Ala Thr Leu Asp Trp Leu Asn Asp
145                 150                 155                 160

Asp Ile Ser Asp Asp Glu Arg Glu Pro Ser Glu Val Asp Ser Val
                165                 170                 175

Asp Ser Asp Ala Glu Ser Asp Arg Glu Pro Ile Pro Asp Asp Gln Pro
            180                 185                 190

Arg Lys Arg Ala Arg Thr Asn Arg Asn Pro Ile Ser Glu Asp Trp
        195                 200                 205

Tyr Pro Trp Gln Asp Lys Ile Thr Cys Thr Leu Asp Ile Leu Met His
    210                 215                 220

Leu Pro Arg Ser Val Phe Ser Arg Lys Gln Leu Asp Leu Phe Leu Trp
```

-continued

```
             225                 230                 235                 240
Leu Leu Arg Val Asn Asn Val Asp Asp Val Pro Thr Gly Lys Ser Met
             245                 250                 255
Lys Met Leu Asn Lys Ile Leu Gln Gly Met Cys Gly Ile Glu Thr Ile
             260                 265                 270
Ala Tyr Glu Gly Lys Leu Gly His Asn Tyr His Val Asn Asn Ile Ala
             275                 280                 285
Gln Ile Leu Ala Gln Glu Leu Cys Asn Pro Lys Val Gly Pro His Ile
             290                 295                 300
Tyr Phe Tyr Pro Glu Asp Ser Gly Asp Asn Leu Ala Glu Ala Arg Gln
305                  310                 315                 320
Ala Ala Arg Trp Leu His Glu Leu Arg Pro Glu Thr Thr Pro Met
             325                 330                 335
Ile His Leu Pro Ser Gly Asp Tyr Tyr Ile Tyr Glu Pro Ala Met Leu
             340                 345                 350
Ser Asn Arg Ser Phe Cys Ile Pro Phe Arg Trp Phe Thr Arg Asn Gly
             355                 360                 365
Lys Phe His Ala Arg Ala Trp Ser Leu Glu Thr Gly Val Val Asp Asn
             370                 375                 380
Thr Leu Gly Trp Ile Val His Lys Glu Asn Glu Val Glu Ile Ser Glu
385                  390                 395                 400
Asp Asp Leu Leu Lys Asp Phe Thr Arg Phe Ser Ser Asp Cys Glu Ala
             405                 410                 415
Tyr Asn Val Pro His Pro Ser Arg Ile Leu Gly Val Ser Cys Ala Asp
             420                 425                 430
Ser Gly Asn Leu Leu Pro Trp Asn His Thr Asn Pro Val Leu Gly Asn
             435                 440                 445
Arg Trp Arg Gln Leu Ala Lys Gly His Arg Thr Leu Cys Leu Pro Leu
             450                 455                 460
Trp Met Tyr Cys Asp Asp Thr Ser Gly Asn Thr Ser Lys Lys Trp Asn
465                  470                 475                 480
Glu His Asn Ser Phe Leu Phe Thr Leu Ala Gly Leu Pro Arg Glu His
             485                 490                 495
Thr Ala Lys Glu Tyr Asn Ile His Phe Leu Cys Thr Ser Asn Leu Ala
             500                 505                 510
Pro Pro Leu Glu Met Met Asp Gly Val Val Ser Gln Ile Glu Ala Ala
             515                 520                 525
Gln Gln Asn Gly Ile Trp Ala Trp Asp Cys Val Arg Lys Glu Pro Val
             530                 535                 540
Leu Ile Phe Pro Thr Ile Leu Ala Leu Leu Gly Asp Asn Pro Met His
545                  550                 555                 560
Ser Glu Phe Ala Cys His Ile Gly Leu Arg Gly Lys Phe Phe Cys Arg
             565                 570                 575
Thr Cys Trp Val Lys Gly Ser Asp Ala Gln Asp Asp Ala Asn Ile Val
             580                 585                 590
Thr Pro Gly Leu His Glu Thr Pro Glu Asn Ser Pro Ala Pro Ser Pro
             595                 600                 605
Ala Pro Ser Pro Ala Pro Ser Pro Ala Pro Ser Pro Ala Pro Ser Pro
             610                 615                 620
Ala Leu Ser Met Ala Pro Gln Ser Gln Pro Thr Pro Ser Glu Pro
625                  630                 635                 640
Ser Met Gln Val Pro Ala Pro Pro Ser Thr Ala Ala Pro Thr Lys Ala
             645                 650                 655
```

-continued

Arg Gly Lys Lys Lys Glu Thr Met Ser Ala Met Leu Asn Arg Ile Thr
        660                 665                 670

Ala Phe Ile Lys Pro Gly Arg Leu Arg Asn Lys Ser Glu Thr Gln Lys
        675                 680                 685

Thr Leu Gln Asn Phe Lys Glu Gln Ala Gln Thr Ile Gly Ala Lys Thr
    690                 695                 700

Lys Leu Lys Thr Ala Arg Thr Glu Thr Gly Ile Lys Asp Thr Val Gln
705                 710                 715                 720

Glu Phe Phe Phe Glu Lys Leu Phe Ser Ser Tyr Lys Asn Lys Arg Gly
                725                 730                 735

Pro Gln Ala Lys Gln Glu Ala Leu Asp Gln Ala Val Asn Gln Leu Pro
            740                 745                 750

Ser Asp Ile Thr Ser Pro Val Trp Arg Leu Lys Gly Leu Asp Pro His
        755                 760                 765

Gln Asp Thr Pro Val Glu Ile Leu His Val Val Leu Leu Gly Phe Ile
    770                 775                 780

Lys Tyr Phe Trp Arg Asp Leu Val Gln Asn Gln Ile Asn Asp Asp Gln
785                 790                 795                 800

Lys Gln Thr Leu Ile Gln Arg Leu Asn Ser Phe Asp Val Thr Gly Leu
                805                 810                 815

Gly Ile Thr Gln Leu Gly Gly Glu Thr Leu Val Asn Tyr Ala Gly Ser
            820                 825                 830

Leu Thr Gly Arg Asp Phe Arg Ala Val Ala Gln Val Ala Pro Phe Val
        835                 840                 845

Ile Tyr Asp Met Val Pro Ala Asp Val Phe Asp Ala Trp Leu Ala Leu
    850                 855                 860

Ser Lys Leu Val Pro Leu Val Trp Gln Pro Tyr Ile Glu Asn Val Ala
865                 870                 875                 880

Gln Tyr Leu Thr Thr Leu Glu His Glu Ile His Val Phe Leu Leu Arg
                885                 890                 895

Thr Ala Arg Trp Thr Thr Gly Trp Phe Asn Lys Ser Lys Phe His Ile
            900                 905                 910

Ile Leu His Leu Pro Ser His Ile Arg Arg Phe Gly Pro Ala Ile Leu
        915                 920                 925

Phe Ala Thr Glu Ala Phe Glu Ser Phe Asn Ala Val Ile Arg Ala Lys
    930                 935                 940

Ser Val His Ser Asn Arg Gln Ala Pro Ser Arg Asp Ile Ala Leu Ala
945                 950                 955                 960

Phe Ala Gln Gly Asn Arg Ile Arg His Leu Leu Ser Gly His Phe
                965                 970                 975

Leu Ser Ala Asp Thr His Met Val Val Asp Pro Asp Gln Pro Gln Leu
            980                 985                 990

Gly Gln Tyr Glu Arg Leu Ala Arg Gly Arg Trp Arg Ser Val Gly Pro
        995                 1000                1005

Gly Pro Gly His Leu Val Ser Ala Glu Pro Ile Leu Pro Ser Tyr
    1010                1015                1020

Leu Gly Ile Pro Pro Gln Ser Thr Thr Ser Ser Ala Gly Leu Cys
    1025                1030                1035

Lys Arg Thr Lys Thr Pro Pro Gln Thr Phe Leu Gln Thr Leu Thr
    1040                1045                1050

Gly Leu Lys Leu Pro Asn Val Ser Arg Pro Gly Ala Arg Glu Leu
    1055                1060                1065

-continued

```
Trp Gln Thr Cys Ser Glu Val Tyr Leu Leu Asn Asp Asp Lys Cys
   1070                1075                1080

Leu Ile Gly His His Val Ile Val Gln Arg Gln Ser Glu Gln Ala
   1085                1090                1095

Ser Phe Val Ser Pro Pro Phe Ile Ala Arg Ile Gly Glu Ile Leu
   1100                1105                1110

Gln Lys Val Gly Ser Ala Asn His Ala His Asp Lys Pro Asp Gly
   1115                1120                1125

Ile Leu Val Gln Thr Leu Lys Ser Ser Glu Val Ala Asp Lys Phe
   1130                1135                1140

Gln Met Pro Arg Leu Val Pro Gln Asn Glu Trp Ser Phe Val Pro
   1145                1150                1155

Leu Ala Asp Ile Leu Cys Thr Val Asn Ala Gln His Asp Cys Asp
   1160                1165                1170

Arg Asn Gly Cys Thr Ala Ser Gly Phe Arg Tyr Val Tyr Gln Glu
   1175                1180                1185

Arg Ile Gln Thr Asn Asp Gln Arg Pro Val Val Glu His Val Asn
   1190                1195                1200

Gln Pro Glu Asp Phe Ile Leu Asn Thr Ala Gln Met Arg Asp Ala
   1205                1210                1215

Leu His Leu Gln Lys Phe Arg Ile Arg Ser Arg Ser Leu Asp Glu
   1220                1225                1230

Gln Thr Ile Ile His Glu Ser Val Ala Arg Thr Ile Asn Gln Arg
   1235                1240                1245

Lys Ala Gln Asp Asn Ser Ser Ser Gly Thr Gly Gly Ala Gly Val
   1250                1255                1260

Ser Gly Arg Gly Arg Gly Arg Gly Arg Gly Arg Gly Gly Gly Val
   1265                1270                1275

Glu Gly Pro Ser Thr Ser Arg Gly Arg Gly Gly Gly Ile Glu Gly
   1280                1285                1290

Arg Gly Ala Ser Ser Ser Ser Gly Asn Gly Arg Gly Arg Gly Arg
   1295                1300                1305

Gly Ala Arg Ser Ala Gln Ser Val Pro Phe
   1310                1315

<210> SEQ ID NO 60
<211> LENGTH: 1262
<212> TYPE: PRT
<213> ORGANISM: Galerina marginata

<400> SEQUENCE: 60

Met Pro Arg Lys Lys Pro Ala Pro Glu Cys Phe Glu Thr Asp Glu Ala
1               5                   10                  15

Ser Lys Met Ile Arg Cys Leu Ile Cys Lys Glu Asn Asp Thr Val Gln
            20                  25                  30

Gln Gly Thr Trp Ile Lys His Gly Ser Ala Ser Gln His Ile Glu Thr
        35                  40                  45

Asn Ala His Lys Leu Ala Val Ala Arg Arg Glu Gln Leu Leu Gln Val
    50                  55                  60

Gln Gln Glu Glu Glu Arg Arg Leu Gln Glu Ile Tyr Gly Gly Asn Thr
65                  70                  75                  80

Ile Pro Leu Ser Gly Asn Ala Gln Leu Tyr Pro Thr Tyr Pro Arg Ala
                85                  90                  95

Asn Met Tyr Gly Asn Gln Asp Ala Val Asp Thr Asp Met Asp Asn Gln
            100                 105                 110
```

```
Asn Ser Pro Pro Gln Ala Tyr Met Leu Cys Asp Ala Asp Ile Pro Asp
        115                 120                 125

Leu Gly Ile Lys Pro Ile Glu Arg Pro Asp Pro Ser Gln Glu Arg Glu
130                 135                 140

Arg Leu Arg Gln Gln Val Glu Gln Leu Leu Gln Ala Glu His Glu
145                 150                 155                 160

Asp Glu Phe Gly Ser Pro Asp Pro Asp Asp Leu Thr Ser Thr Asn
                165                 170                 175

Ile Ala Gln Ala Phe Ala Asp Leu Asp Leu Glu Glu Met Leu Asp Glu
            180                 185                 190

Glu Glu Val Phe Asp Tyr Phe Asn Gln Val Ser Pro Glu His Asp Tyr
                195                 200                 205

Tyr Pro Tyr Pro Asn Lys Thr Thr Met Leu Leu Asp Ile Leu Asp Asn
210                 215                 220

Leu Pro Arg Leu Arg Met Ser Ser Asn Gln Leu Arg Leu Ile Leu Trp
225                 230                 235                 240

Leu Leu Lys Gln Thr Gly Val Ser Asn Val Pro Ser Phe Ser Gly Phe
                245                 250                 255

Arg Asn Met Gln Thr His Leu Arg Asn Met Cys Gly Thr Thr Pro Lys
                260                 265                 270

Gln His Val Ser Ser Leu Gly Asn Ile Phe Tyr Ser Asn Asn Ile Gly
            275                 280                 285

Glu Ser Val Met Arg Asp Phe Ala Asn Pro Glu Val Ala Lys His Leu
            290                 295                 300

His Leu Tyr Pro Glu Glu Thr Glu Gly Pro Ile Ser Glu Val Trp Gln
305                 310                 315                 320

Ala Glu Arg Trp Lys Glu Phe Ala Pro Ser Glu Leu Thr Pro Met Phe
                325                 330                 335

Ser Gln Gly His Arg Gln Phe Ile Asp Glu Val Ala Gln Leu Gln
                340                 345                 350

Asp Gly Gln Tyr Val Ile Pro Arg Asn Trp Val Met Arg Lys Gly Lys
            355                 360                 365

Leu Thr Ser Asp Cys His Ile Val Thr Val Asn Pro Val Arg Phe Ser
            370                 375                 380

Lys Leu His Gly Ser Leu Val Leu Val Leu Lys Gln Cys Phe Gln Ser
385                 390                 395                 400

Gly Trp Thr Leu Leu Ser Glu Thr Gln Ile Phe His Ala Asp Asp Phe
                405                 410                 415

Gln Phe Asn Tyr Phe Asp Val Val Ser Arg Ile Arg Gly Pro Ile Ser
            420                 425                 430

Trp Ser Glu Gly Thr Glu Val Pro Ala Met Pro Asn Asn Leu Arg Glu
            435                 440                 445

Leu Ala Gly Asp Asp Asp Leu Val Val Ile Met Val Pro Leu Trp Cys
450                 455                 460

Asp Asp Val Ser Gly Asn Lys Ser Lys Gln Tyr Asn Lys His Ile Asn
465                 470                 475                 480

Val Tyr Met Ala Asn Ser Asn Ile Pro Gly Arg Leu Leu Gln Gln Glu
            485                 490                 495

Tyr Phe Val Arg Phe Val Ser Thr Ser Pro Asn Ala Thr Ser Pro Glu
                500                 505                 510

Gln Phe Ser Ala Leu Lys Asp Gln Ile Asn Glu Thr Gln Lys Lys Pro
            515                 520                 525
```

-continued

```
Ile Gln Cys Tyr Asn Ala His Thr Asn Lys Lys Thr Arg Ala Ile Leu
    530                 535                 540

Arg Val Pro Gly Leu Pro Ala Asp Asn Pro Gln Gln Ser Glu Glu Ser
545                 550                 555                 560

Cys His Met Gly Gly Asn Ala Asn Cys Lys Cys Arg Lys Cys His Val
                565                 570                 575

Gly Gly Pro His Glu Lys Lys Glu Ser Asn Glu Gly Tyr His Glu His
                580                 585                 590

Tyr Leu Thr Gly Ile Lys Arg Ser Ala Glu Glu Thr Arg Leu Glu Leu
                595                 600                 605

Glu Lys Gln Ile Lys Leu Ala Met Tyr Gly Val Glu Lys Pro Ile Asn
    610                 615                 620

Glu Thr Gln Thr Asn Thr Gly Thr Lys Asp Lys Val Ala Gln His Trp
625                 630                 635                 640

Ile Asp Ile Leu Leu Ala Lys Ser Arg Glu Leu Lys Ser Ala Asn Pro
                645                 650                 655

Ser Arg Ser Val Glu Glu Ile Ala Gln Glu Leu Gln Thr Trp Phe Asp
                660                 665                 670

Glu Gln Pro Gly Asp Lys Ile Asn Pro Leu Leu Ser Ile Ala Gly Leu
                675                 680                 685

Asp Pro Thr Gln Asp Thr Pro Val Glu Ile Leu His Thr Ile Leu Leu
    690                 695                 700

Gly Ile Val Lys Tyr Ala Trp His His Leu His Ser Asn Trp Thr Glu
705                 710                 715                 720

Ala Glu Gln Asn Leu Phe Thr Val Arg Leu Gln Ser Thr Asp Ile Asp
                725                 730                 735

Gly Leu Ser Val Pro Pro Ile Arg Val Ala Tyr Met Met Gln Tyr Arg
                740                 745                 750

Asn Gly Leu Ile Gly Lys His Phe Lys Thr Leu Met Gln Thr Leu Pro
                755                 760                 765

Phe His Val His Gly Thr Val Ser Asp Ala Gln Phe Lys Leu Val Lys
    770                 775                 780

Ala Ile Gly Glu Leu Gly Ser Val Leu Trp Val His Glu Ile Gly Asp
785                 790                 795                 800

Met Glu Lys Tyr Leu Ser Asp Leu Glu Ile Leu Ile Gly Asn Val Leu
                805                 810                 815

Asp Ala Phe Ala Glu Ile Asp Pro Ser Thr Ala Met Tyr Ala Arg Phe
                820                 825                 830

Ile Tyr Glu Pro Met Pro Val Pro Ser Lys Ile Ile Val Lys Leu Lys
                835                 840                 845

Leu His Met Leu Pro His Leu Ile Glu Asp Ile Lys Arg Phe Gly Pro
    850                 855                 860

Ala Ile Arg Asn Ser Thr Glu Val Phe Glu Cys Phe Asn Ala Ile Phe
865                 870                 875                 880

Arg Leu Cys Ser Ile Leu Ser Asn His Gln Ala Ala Ser Arg Asp Ile
                885                 890                 895

Ala Leu Lys Phe Ala Ser Met Asp Arg Leu Lys His Met Leu Ser Gly
                900                 905                 910

Gly Tyr Trp Leu Ser Glu Val Glu Glu Gly Lys Phe Glu Trp Ile Arg
                915                 920                 925

Ala Gly Glu Asn Val Arg Asn Ile Leu Gln Ser Glu Pro Thr Ile Gln
    930                 935                 940

Arg His Leu Gly Trp Ala Pro Ser Ala Lys Phe Gln Ser Gly Arg Lys
```

```
            945                 950                 955                 960
        Arg Thr Pro Pro Thr Ser Trp Glu Asn Thr Lys Ala Ser Gln Phe Met
                        965                 970                 975
        Asp Ser Glu Glu Thr Ala Ala Ile Gly Phe Pro Asn Pro Arg Leu Leu
                        980                 985                 990
        Ser Trp Arg Lys Gly Val Thr Thr Thr Ala Gln Ser Gly Asp Arg Cys
                    995                 1000                1005
        Ser Thr Gly Ser Trp Val Val Ala Arg Asn His Lys Val Cys Tyr
                1010                1015                1020
        Ile Leu Ala Ser His Tyr Cys Ser Ile Ala Lys Asn Asp Gln Gly
                1025                1030                1035
        Glu Ser Cys Ile Gly Arg Ile His Glu Ile Ile Gly Pro Asp Glu
                1040                1045                1050
        Lys Ser Ala Ser Ser Thr Gly Ile Ile Thr Leu Glu Cys Phe Gln
                1055                1060                1065
        Leu Gly Lys Glu His His Pro Asp Phe Gly Leu Pro Thr Leu Gln
                1070                1075                1080
        Arg Pro Gln Ala Asp Leu Pro Lys Tyr Ile Leu Lys Ala Trp Gln
                1085                1090                1095
        Asp Pro Leu Phe Ile Phe Ser Ala His His Asp Cys His Thr Ala
                1100                1105                1110
        Ser Cys Gln Ala Thr Ala Leu Gln Pro Gln Leu Gln Glu Arg Gln
                1115                1120                1125
        Leu Thr Ser Arg Met Asn Lys Leu Ile Ala His Asn Asp Ser Asp
                1130                1135                1140
        His Phe Ile Ile Asn Leu Tyr Gly Leu His Asn Ala Ile Leu Leu
                1145                1150                1155
        Arg Glu Phe Leu Pro Arg Leu Thr Ala Pro Gln Pro Leu His
                1160                1165                1170
        Gln Asp Arg Lys Ala Phe His Tyr Glu Val Ala Ala Lys Leu Arg
                1175                1180                1185
        Val Gln Gln Ala Glu Lys Arg Ala Lys Thr Asn Ala Arg Arg Lys
                1190                1195                1200
        Ala Thr Arg Ala Ala Asn Lys Ala Lys Gln Val Glu Arg Gln Lys
                1205                1210                1215
        Gln Asn Pro Asp His Glu Gln Glu Ser Glu Gln Glu Met Asp Glu
                1220                1225                1230
        Arg Pro Asn Ser Glu Asn Gly Ser Asp Ile Glu Leu Gly Gly Asp
                1235                1240                1245
        Asp Asp Ile Glu Val Glu Thr Arg Arg Lys Arg Arg Asn
                1250                1255                1260

<210> SEQ ID NO 61
<211> LENGTH: 1206
<212> TYPE: PRT
<213> ORGANISM: Hypsizygus marmoreus

<400> SEQUENCE: 61

Met Gly Arg Arg Ala Glu Glu Leu Pro Ala Tyr Val Glu Leu Ser Glu
1               5                   10                  15

Asp Gly Thr Leu Val Arg Cys Asn Leu Cys Leu Met His Asn Arg Leu
                20                  25                  30

Asp Tyr Ser Lys Glu Trp Ile Gln Arg Lys Gly Trp Arg Ser His Lys
        35                  40                  45
```

Gly Ser Gly Ile His Asp Arg Ser Glu Ala Lys Gln Arg Val Leu Asp
    50                  55                  60

Asp Ala Ala Met Asp Leu Gln Glu Pro Ala Ser Ala Glu Val Glu Val
65                  70                  75                  80

Val Thr Phe Asn Asp Ile Leu Ile Ile Asn Ala Pro Lys Thr Pro Thr
                85                  90                  95

Gly Asn Met Gln Ser Glu Glu Gln Ala Met Trp Asp His Phe Asp Ala
                100                 105                 110

Gly Ser Phe Thr Leu Glu Ala Gly Glu Asp Pro Asn His Ser Ser Gln
                115                 120                 125

Arg Leu Tyr Gln Asp Leu Ala Arg Lys Ala Asp Ala Tyr Gly Ala Trp
    130                 135                 140

Asp Gly Thr Glu Ala Leu Pro Glu Tyr Arg Asp Leu Asp Asp Val Ser
145                 150                 155                 160

Gln Phe Leu Asp Glu Asp Glu Glu Asp Leu Leu Ser Glu Ile Leu
                165                 170                 175

Arg Gly Leu Gly Leu Glu Glu Glu His Glu Asp Ser Ser Asp Arg Asn
                180                 185                 190

Pro Ala Glu Glu Leu Asn Ser Pro Trp Tyr Pro Tyr Gly Ser Lys Leu
    195                 200                 205

Met Phe Leu Leu Asp Thr Ile Asp Asn Leu Pro Arg Leu Arg Ile Ser
    210                 215                 220

Gly Ala Met Met Arg Val Phe Leu Trp Leu Leu Arg Glu Val Gly Val
225                 230                 235                 240

Arg Gln Val Pro Ser Phe Asp Lys Leu Arg Lys Ile Gln Arg Lys Leu
                245                 250                 255

Arg Glu Gly Ser Gly Val Pro Thr Val His Trp Met Ser Pro Lys Gly
                260                 265                 270

Asn Ala Tyr Ser Phe Asn Asp Pro Ala Val Ile Val Ala Asn Asp Trp
    275                 280                 285

Ala Ser Pro Ile Thr Arg Pro His Leu Arg Arg Tyr Pro Val Ile Pro
    290                 295                 300

Lys Asp Gly Val Ile Thr Glu Val Tyr His Ala Glu Lys Trp His Arg
305                 310                 315                 320

Glu Ile Asn Arg His Phe Leu Thr Pro Met Tyr Asp Asp Gly Phe Arg
                325                 330                 335

His Tyr Phe Ile Asp Glu Leu Ala Gln Leu Lys Asp Gly Arg Tyr Ala
                340                 345                 350

Val Pro Val Arg Trp Leu Glu Asp Val Asp Gly Arg Ile Val Ala Asp
                355                 360                 365

Ala Trp Arg Val Glu Leu Glu Asp Asp Asn Arg Ala Thr Ile Ile Asp
    370                 375                 380

Thr Ala Thr Val Arg Ile His Ser Gln Glu Leu Ala Leu Asn Phe Glu
385                 390                 395                 400

Glu Ile Ile Glu Ser Asn Leu Met Pro Glu Trp Ser Asp Thr Thr Thr
                405                 410                 415

Glu Ala Gly His Pro Ser Arg Met Pro Asn Pro Asp Arg Ala Leu Ala
                420                 425                 430

Glu Gly Asp Pro Ile Tyr Thr Ser Phe Ile Asp Ile Phe Gly Asp Asp
                435                 440                 445

Val Ser Gly Asn Arg Ser Lys Ser Trp Asn Lys His Trp Asn Met Tyr
450                 455                 460

Ile Ser His Arg Asn Leu Pro Arg Lys Leu Leu His Gln Gln Tyr His

```
            465                 470                 475                 480
Thr His Phe Val Ser Thr Ser Thr Phe Ala Ser Ile Pro Glu Gln Phe
                        485                 490                 495

Val Gly Val Lys Glu Ala Ile Glu Ser Thr His Ser Lys Pro Val Lys
            500                 505                 510

Val Arg Asp Ala Asp Thr Gly Lys Gln Ile Arg Leu Lys Ile Tyr Cys
            515                 520                 525

Asn Cys Gly Pro Gly Asp Asn Pro Ser Gln Ser Glu Thr Ser Gly His
            530                 535                 540

Ile Gly Gly Asn Gly Asn Tyr Pro Cys Arg Lys Cys His Thr Gly Gly
545                 550                 555                 560

Thr Gln Lys Ser Lys Glu Thr Asp Glu Gly Phe Tyr Lys Met Phe Thr
                565                 570                 575

Ala Gly Glu Ala Arg Ser Ser Lys Glu Thr Leu Ala Glu Val Lys Ser
            580                 585                 590

Gln Val Glu Ala Ala Cys Thr Gly Val Ala Lys Thr Val Ala Asp Ala
            595                 600                 605

Gln Ser Asp Thr Gly Val Lys Asp Ala Tyr Thr Gln Tyr Trp Ile Asp
            610                 615                 620

Ala Ile Ile Glu Lys Ala Arg Ala Met Gln Lys Glu Asn Pro Gly Met
625                 630                 635                 640

Pro Thr Thr Thr Ile Gln Ala Thr Leu Ile Lys Trp Val Tyr Asp His
                645                 650                 655

Glu Glu Ala Ile Tyr Asn Ser Phe Leu Thr Leu Asp Gly Phe Asp Ala
            660                 665                 670

Ser Arg Asp Thr Pro Val Glu Ile Leu His Thr Ile Leu Leu Gly Ile
            675                 680                 685

Val Lys Tyr Leu Trp His Arg Ser His Thr Ser Trp Asn Ala Ala Gln
            690                 695                 700

Lys Lys Ile Tyr Ser Thr Arg Leu Gln Gly Thr Asn Thr Gln Gly Leu
705                 710                 715                 720

Ser Ile His His Ile Arg Ala Asn Tyr Ile Met Gln Tyr Ala Asn Ser
                725                 730                 735

Leu Ile Gly Arg Gln Leu Lys Thr Leu Ala Gln Val Asn Val Phe His
            740                 745                 750

Val Tyr Asp Leu Val Asp Pro Leu Arg Phe Leu Phe Thr Lys Ala Thr
            755                 760                 765

Gly Glu Leu Cys Ala Leu Leu Trp Phe Thr Glu Ile Arg Asp Leu Glu
            770                 775                 780

Glu Tyr Leu Ser Asp Val Asp Ile Ala Ala Asn Val Leu Asp Ile
785                 790                 795                 800

Ala Ala Val Ile Asp Pro Ser Lys Ile Val Ser Lys Ile Lys Tyr His
                805                 810                 815

Leu Leu Ser His Leu Arg Glu Asp Ile Ile Arg Phe Gly Pro Leu Val
            820                 825                 830

Gly Val Ala Thr Glu Val Phe Glu Cys Phe Asn Ala Val Phe Arg Tyr
            835                 840                 845

Cys Ser Ile Leu Ser Asn His Leu Ala Pro Ser Arg Asp Ile Ala Tyr
            850                 855                 860

Lys Leu Ala Ala Gln Glu Thr Met Lys His Phe Leu Ser Gly Gly Trp
865                 870                 875                 880

Trp His Val Lys Asp Ser Val Asp Leu Gln Gly Asn Pro Lys Trp Val
                885                 890                 895
```

```
Gln Pro Gly Pro Ser Val Arg Thr Phe Met Ala Ser Asn Pro Val Leu
                900                 905                 910

His Thr Leu Cys Gly Trp Thr Arg Asn Asn Asp Ser Thr Pro Gly Thr
            915                 920                 925

Val Lys Ser Glu Pro Arg Lys Arg Gly Pro Asp Lys Gln Thr Leu Leu
    930                 935                 940

Pro Leu Val Arg Leu Ala Trp Leu Glu Thr Gln Gly Ser Arg Ala Leu
945                 950                 955                 960

Asn Asn Thr Ser Pro Asn Asn Glu Thr Gln Trp Gln Arg Cys Lys Tyr
                965                 970                 975

Val Ile Ala Glu Thr Gln Asp Gln Cys Asn Val Gly Ser Trp Val Phe
            980                 985                 990

Ala Arg Ser Pro Leu Leu Glu Asn Ile Pro Ile Pro Gly Arg Ile Val
        995                 1000                1005

Glu Ile Leu Gln Asp Thr Ser Ala Ser Pro Ser Ala Phe Val Val
    1010                1015                1020

Ile Asp Val Phe Gln Val Ser Ala Thr Arg Asp Glu Val Phe Gly
    1025                1030                1035

Met Pro Val Leu Leu Arg Arg Phe Asn Glu Cys Cys Leu His Val
    1040                1045                1050

Ile Pro Ala Ser Ser Val Ile Phe Asp Phe Asn Ala Gln His Asp
    1055                1060                1065

Cys Arg Tyr Ala Lys Cys Glu Ala Thr Gly Glu Gln Pro Leu Ile
    1070                1075                1080

Gln Glu Arg Val Pro Ser Gly Val Thr Glu Asn Phe Val Val His
    1085                1090                1095

Lys Ala Ile Asp Arg Tyr Leu Ile Asn Ile His Ala Leu His Asn
    1100                1105                1110

Ala His Leu Ile Arg Ala Thr Leu Pro Arg Asp Leu Thr Ala Pro
    1115                1120                1125

Ile Pro Tyr Ala Pro Asn Arg Glu Ala His His Ser Ala Ile Ala
    1130                1135                1140

Ala Glu Leu Arg Ser Ala Gln Asp Thr Lys Arg Ala Lys Thr Ala
    1145                1150                1155

Ala Lys Thr Ala Ala Asn Ala Ala Ala Lys Lys Ala Glu Ala Ala
    1160                1165                1170

Leu Lys Asp Thr Thr Ser Gly Pro Ala Ala Lys Arg Arg Arg Val
    1175                1180                1185

Asp Asp Glu Gly Ser Gly Glu Asp Asn Arg Asp Val Asp Met
    1190                1195                1200

Val Ser Val
    1205

<210> SEQ ID NO 62
<211> LENGTH: 1213
<212> TYPE: PRT
<213> ORGANISM: Galerina marginata

<400> SEQUENCE: 62

Met Ala Lys Gly Arg Lys Leu Asn Asn Pro Leu Pro Asp Phe Ile Glu
1               5                   10                  15

Ile Ser Asn Asp Gly Leu Gln Val Arg Cys Thr Leu Cys Leu Ala Ala
            20                  25                  30

Arg Gln His Asn Gly Ser Gly Trp Ile Lys Arg Gly Ser Val Ser Asn
```

```
                35                  40                  45
His Leu Lys Ser Asp Asn His Thr Asn Ser Leu Glu Ala His Glu Met
 50                  55                  60

Lys Lys Ser Ala Glu Lys Ala Glu Gly Arg Ser Val Gln Glu Glu Ile
 65                  70                  75                  80

Ala Met Glu Glu Gly Met Asp Phe Val Ile Leu Ser Ser Lys Ile Gln
                 85                  90                  95

Pro Glu Ile Thr Ala Pro Ala Arg Ala Pro Arg Arg Ser Asn Glu Glu
                100                 105                 110

Gln Glu Met Trp Asp Arg Tyr Thr Leu Gly Gly Glu Val Phe Asp Ala
                115                 120                 125

Gly Val Asp His Thr Leu Val Glu Ala Glu Arg Lys Arg Leu Glu
                130                 135                 140

Arg Glu Ala Thr Asp Phe Asp Leu Trp His Gly Ala Asp Phe Leu Pro
145                 150                 155                 160

Glu Glu Asp Pro Asn Asp Gly Glu Leu Leu Asp Glu Leu Glu Gln
                165                 170                 175

Asp Asp Ile Leu Ser Glu Leu Leu Arg Asn Ala His Leu Asn Ala Pro
                180                 185                 190

Asp Ala Ala Asp Val Leu Thr Glu Glu Pro Arg Ala Ala Ala Asp Pro
                195                 200                 205

Arg Ile Cys Asp Ala Trp Ser Pro Tyr Glu Ser Lys Met Met Phe Leu
210                 215                 220

Leu Asp Thr Leu Asp Asn Leu Pro Arg Leu Arg Ile Ser Asn Ser Leu
225                 230                 235                 240

Met Asn Val Phe Leu Trp Ile Leu Arg Glu Gly Gly Ala Arg Asp Val
                245                 250                 255

Pro Ser Leu Tyr His Leu Arg Gln Val Gln Thr Thr Leu Arg Lys Ser
                260                 265                 270

Thr Gly Val Pro Thr Thr Gln His Lys Ser Pro Lys Gly Asn Val Tyr
                275                 280                 285

Ser Met Asn Asp Pro Arg Thr Leu Val Ala Met Asp Trp Ala Asn Pro
290                 295                 300

Val Ile Cys Asp His Ile Arg Arg Tyr Pro Val Ile Pro Arg Asn Gly
305                 310                 315                 320

Val Ile Ser Glu Val Tyr His Ala Gln Lys Trp Arg Lys Asp Val Asp
                325                 330                 335

Pro His Thr Leu Ser Pro Met Tyr Asp Ala Gly Asn Cys His Tyr Tyr
                340                 345                 350

Ile Asp Glu Val Ala Arg Leu Lys Asn Gly Thr Phe Ile Ile Pro Val
                355                 360                 365

Arg Trp Leu Glu Asp Glu Asp Arg Asn Val Cys Ala Asp Ala Tyr Val
                370                 375                 380

Val Gln Phe Asp Asp Gln Phe Ile Ala Ser Val Val Asp Gly Glu Thr
385                 390                 395                 400

Ile Ile Val Gln Ala Ser Asp Leu Gln Asn Asn Phe Leu Asp Leu Lys
                405                 410                 415

Asp Met Gly Leu Leu Pro Thr Trp Gly Asn Gln Thr Ile Glu Ser Gly
                420                 425                 430

His Pro Ala Arg Met Pro Asn Pro Asp Arg Ala Leu Ala Glu Gly Asp
                435                 440                 445

Pro Leu Tyr Thr Ser Trp Ile Asp Val Phe Gly Asp Asp Val Ser Gly
                450                 455                 460
```

```
Asn Arg Ser Lys Asn Trp Asn Lys His Trp Asn Ile Tyr Ile Ser His
465                 470                 475                 480

Arg Asn Leu Pro Arg Lys Leu Leu Gln Gln Glu Phe His Thr His Phe
                485                 490                 495

Val Ser Thr Ser Pro Val Ala Ser Val Thr Glu Gln Phe His Gly Ile
            500                 505                 510

Lys Gln Val Ile Glu Leu Thr His Lys Ser Pro Val Lys Val Arg His
            515                 520                 525

Gly Thr Ser Gly Ala Gln Ile Arg Phe Lys Ile Asn Val Asn Cys Gly
530                 535                 540

Pro Gly Asp Asn Pro Ala Gln Ser Glu Val Cys Gly His Ile Gly Val
545                 550                 555                 560

Asn Gly Asn Lys Leu Cys Arg Lys Cys His Thr Gly Thr His Glu
                565                 570                 575

Val Lys Glu Ser Asp Glu Gly Phe Asn Ser Leu Phe Glu Pro Gly Asp
            580                 585                 590

Ala Arg Ser Ala Gln Glu Ile Val Ala Asp Val Glu Ser Gln Val Gln
            595                 600                 605

Leu Ala Cys Leu Gly Ile Ala Gln His Val Gln Asn Gln Gln Thr Lys
610                 615                 620

Asn Gly Ile Lys Asp Ala Tyr Thr Gln Tyr Trp Ile Asp Tyr Leu Ile
625                 630                 635                 640

Asn Arg Ala Arg Thr Leu Arg Lys Glu Gln Pro Arg Arg Thr Thr Ala
                645                 650                 655

Asp Ile Gln Ser Glu Leu Leu Val Trp Val Gln Glu His Lys Asp Glu
            660                 665                 670

Ile Tyr Asn Pro Phe Leu Lys Leu Asp Gly Phe Asp Ala Ala Val Asp
            675                 680                 685

Thr Pro Val Glu Ile Leu His Thr Ile Leu Gly Ile Val Lys Tyr
690                 695                 700

Leu Trp His Gly Ser His Thr Ser Trp Thr Ala Ile Gln Lys Gln Thr
705                 710                 715                 720

Tyr Ser Val Arg Leu Gln Ser Thr Asp Thr Ser Gly Leu Ser Ile His
                725                 730                 735

Ala Ile Arg Ala Asn Tyr Ile Met Gln Tyr Ala Asn Ser Leu Ile Gly
            740                 745                 750

Arg Gln Phe Lys Thr Ile Ala Gln Val Asn Val Phe His Val Tyr Asp
            755                 760                 765

Leu Val Asp Thr Thr Gln Phe Leu Leu Thr Lys Ala Val Gly Glu Leu
        770                 775                 780

Thr Ala Leu Leu Trp Ile Pro Glu Ile Ala Asn Met Glu Glu Tyr Leu
785                 790                 795                 800

Leu Asp Val Glu Ala Ala Ala Asn Val Leu Asp Leu Phe Ala Leu
                805                 810                 815

Ile Asp Pro Ser Lys Met Thr Asn Lys Leu Lys Leu His Leu Leu Val
                820                 825                 830

His Leu Lys Ala Asp Ile Leu Arg Phe Gly Pro Leu Val Gly Val Ala
                835                 840                 845

Thr Glu Thr Phe Glu Cys Phe Asn Ala Ile Phe Arg Phe Cys Ser Ile
        850                 855                 860

Tyr Ser Asn His Leu Ala Pro Ser Arg Asp Ile Ala Phe Gln Leu Ala
865                 870                 875                 880
```

```
Ser Gln Glu Val Leu Lys Tyr Arg Leu Thr Gly Gly Trp Trp Pro Ala
                885                 890                 895

Ser Asp Gly Glu Trp Lys Arg Pro Gly Pro Ser Val Arg Asn Phe Ile
        900                 905                 910

His Asp His Pro Thr Leu Gln Ala Leu Leu Gly Trp Thr Lys Glu Glu
            915                 920                 925

Lys Leu Val Asn Gly Ser Phe Arg Leu Glu Pro Leu Lys Arg Asp Ala
        930                 935                 940

Ser Gln Lys Ile Glu Ser Arg Lys His Leu Pro Trp Leu Gln Thr Gln
945                 950                 955                 960

Gly Ala Lys Ala Val Asn Ser Ser Glu Asp Asn Asp Ser Lys Trp Thr
                965                 970                 975

Ala Cys Arg Phe Ala Val Ala Asn Ser Gly Asp Lys Cys Ser Val Gly
            980                 985                 990

Ser Trp Val Phe Ala Thr Ser Pro Phe Asn Ser Asn Gln Ser Val Thr
        995                 1000                1005

Gly Arg Ile Val Glu Val Leu Ala Glu Ser Glu Gly Lys Arg Ala
    1010                1015                1020

Val Val Val Leu Asp Ile Phe Glu Val Cys Ser Thr Arg His Lys
    1025                1030                1035

Ile Phe Gly Met Pro Met Leu Ala Arg Arg His Glu Glu Pro Val
    1040                1045                1050

Tyr Ala Val Ile Ala Ser Thr Asn Ile Glu Phe Leu Tyr Asn Val
    1055                1060                1065

Gln His Asp Cys Pro Leu Ala Lys Cys Thr Ala Ser Gly Lys Gln
    1070                1075                1080

Pro Leu Ile Gln Glu Arg Val Glu Ser Gly Leu Phe Lys Thr Tyr
    1085                1090                1095

Ile Glu His Lys Pro Ile Glu Arg Phe Val Ile Asn Thr His Ala
    1100                1105                1110

Phe His Asn Ala His Arg Leu Arg Ala Val Leu Gln Arg Ser Leu
    1115                1120                1125

Val Val Pro Ile Pro Leu Tyr Pro Pro Glu Ile Arg Lys Thr Lys
    1130                1135                1140

His Ala Glu Phe Ala His Asn Leu Gln Ala Thr Gln Lys Val Lys
    1145                1150                1155

Leu Glu Ala Arg Ala Ala Gln Lys Ala Lys Glu Ile Ile Thr Pro
    1160                1165                1170

Ala Asp Lys Thr Asp Ser Thr Ile Pro Lys Lys Arg Thr Arg Ser
    1175                1180                1185

Glu Met Glu Thr Glu Thr Asp Asp Thr Ala Ile Ala Thr Gln Ala
    1190                1195                1200

Asp Val Phe Phe Asn Ala Gln Gly Cys Pro
    1205                1210

<210> SEQ ID NO 63
<211> LENGTH: 517
<212> TYPE: PRT
<213> ORGANISM: Galerina marginata

<400> SEQUENCE: 63

Met Val Gln Ile Lys Arg Leu Leu Gly Phe Leu Ser Ser Pro Ser
1               5                   10                  15

Gln Thr Pro Leu Glu Ser Asn His Gly Pro Val Pro Ser Lys Ser Ile
            20                  25                  30
```

Ala Val Val Gly Ala Gly Ser Ala Gly Leu Ala Met Leu Arg Thr Leu
            35                  40                  45

Val Glu Leu Glu Ala Phe Ser Arg Asn Asn Trp Glu Val Val Leu Tyr
 50                  55                  60

Glu Glu Arg Glu Ser Val Gly Gly Ile Trp Leu Pro Asp Asn Asn Asp
 65                  70                  75                  80

Val Phe Pro Pro Glu Ile Pro Lys Thr Pro Leu Tyr Pro Leu Leu Arg
                 85                  90                  95

Thr Asn Thr Pro Val Pro Ser Met Thr Tyr Pro Gly Phe Pro Phe Pro
            100                 105                 110

Pro Ser Thr Pro Leu Tyr Pro Arg His Asp His Val Glu Ala Tyr His
            115                 120                 125

Leu Arg Tyr Ala Arg Arg His Asn Leu Leu Asp Phe Ile Lys Phe Asp
            130                 135                 140

Thr Met Val Glu Lys Ala Phe Trp Asn Gly Thr Pro Glu Glu Gly Tyr
145                 150                 155                 160

Trp Asn Leu Thr Leu Ser Ser Lys Glu Gly Arg Met Arg Tyr Lys Thr
                165                 170                 175

Phe Asp His Leu Val Val Ala Thr Gly Asn Asn His Ile Pro His Ile
            180                 185                 190

Pro Val Trp Lys Gly Gln Glu Asp Trp Leu Ala Ser Pro Ala Asn His
            195                 200                 205

Ser Arg Lys Ile Ile His Ser Val Tyr Tyr Arg Gly Pro Glu Ala Phe
210                 215                 220

Ser Asn Gln Thr Val Leu Ile Val Gly Asn Gly Gly Ser Gly Arg Asp
225                 230                 235                 240

Ala Ala Thr Gln Ile Leu Gly Tyr Ala Ser Gln Thr Phe Met Ser Ile
                245                 250                 255

Arg Arg Ser Tyr Gly Pro Val Asp Asp Gly Val Ile Val Lys Pro Asp
            260                 265                 270

Ile Ser His Phe Thr Glu Ala Gly Val Val Phe Val Asp Gly Thr Ile
            275                 280                 285

Leu Asp Pro Asp Val Ile Leu Leu Gly Thr Gly Tyr Glu Met Gln Lys
            290                 295                 300

Pro Leu Leu Ser Glu Gly Gly Glu Leu Ser Phe Asp Pro Thr Ala Lys
305                 310                 315                 320

Asp Asn Ser Ser Val Arg Gly Thr Leu Val Thr Asn Gly His Tyr Ile
                325                 330                 335

Phe Pro Leu His Arg His Ile Phe Ser Leu Ser Pro Arg Tyr Pro Pro
            340                 345                 350

Asn Ala Leu Ala Phe Ile Gly Leu Leu Ser Phe Ile Ala Ser Cys Pro
            355                 360                 365

Ser Asp Ile Ala Gln Ser Leu Phe Ala Ala His Ala Ile Leu Asp Pro
            370                 375                 380

Ser Ile Leu Pro Pro Arg His Leu Leu Leu Glu Gly Leu Ala Ser Tyr
385                 390                 395                 400

Glu Asp Lys Ala Arg Arg Gln Gly Leu Asp Pro Tyr Leu Lys Gly Pro
                405                 410                 415

Ile Met Leu Asn Asn Thr Ser Asn Asp Tyr Gln Asp Glu Leu Val Glu
            420                 425                 430

Tyr Leu Lys Gln Lys Asn Ala Ile Pro Asp Asp Gly Lys Lys Phe Val
            435                 440                 445

-continued

```
Glu Glu Trp Arg Arg Glu Ile Leu Ala Tyr His Tyr Leu Gln Arg Gly
    450                 455                 460

Trp Ser Arg Ile Glu Lys Leu Gly Met Gly Pro Ala Trp Thr Glu Gly
465                 470                 475                 480

Val Lys Thr Glu Ala Gln Trp Phe Asp Leu Met Thr Arg Val Asn Glu
                485                 490                 495

Trp Gln Lys Asn Trp Glu Thr Glu Asn Gly Ile Ala Phe Arg Val Asp
            500                 505                 510

Leu Asp Leu Thr Gly
        515
```